US010793498B2

(12) United States Patent
Jansen et al.

(10) Patent No.: US 10,793,498 B2
(45) Date of Patent: Oct. 6, 2020

(54) PROCESSES AND APPARATUS FOR EXTRACTION OF SUBSTANCES AND ENRICHED EXTRACTS FROM PLANT MATERIAL

(71) Applicant: BIOMASS OIL SEPARATION SOLUTIONS, LLC, Roscoe, IL (US)

(72) Inventors: Robert Patrick Jansen, Collinsville, IL (US); Neta Matis, Hod Hasharon (IL); Noa Lapidot, Mevaseret Zion (IL); Adam F. Tracy, Roscoe, IL (US); Lucas A. Burke, South Beloit, IL (US)

(73) Assignee: BIOMASS OIL SEPARATION SOLUTIONS, LLC, Roscoe, IL (US)

( * ) Notice: Subject to any disclaimer, the term of this patent is extended or adjusted under 35 U.S.C. 154(b) by 0 days.

(21) Appl. No.: 16/742,722

(22) Filed: Jan. 14, 2020

(65) Prior Publication Data
US 2020/0199055 A1 Jun. 25, 2020

Related U.S. Application Data

(63) Continuation of application No. PCT/US2019/043795, filed on Jul. 26, 2019.

(60) Provisional application No. 62/714,513, filed on Aug. 3, 2018, provisional application No. 62/742,139, filed on Oct. 5, 2018, provisional application No. 62/795,773, filed on Jan. 23, 2019, provisional application No. 62/789,117, filed on Jan. 7, 2019, provisional application No. 62/788,271, filed on Jan. 4, 2019.

(51) Int. Cl.
| | |
|---|---|
| C07C 37/00 | (2006.01) |
| C07D 311/72 | (2006.01) |
| C07D 311/78 | (2006.01) |
| B01J 20/281 | (2006.01) |
| B01D 5/00 | (2006.01) |
| B01D 3/14 | (2006.01) |
| B01D 15/18 | (2006.01) |
| B01D 11/02 | (2006.01) |
| B01D 3/40 | (2006.01) |
| B01J 8/10 | (2006.01) |
| B01J 8/08 | (2006.01) |
| A61K 31/05 | (2006.01) |
| A61K 31/352 | (2006.01) |
| A61K 31/192 | (2006.01) |
| A61K 31/015 | (2006.01) |
| A61K 31/01 | (2006.01) |
| A61K 31/336 | (2006.01) |
| A61K 36/185 | (2006.01) |
| B01J 31/04 | (2006.01) |
| B01J 31/08 | (2006.01) |
| B01J 31/10 | (2006.01) |

(52) U.S. Cl.
CPC .......... *C07C 37/004* (2013.01); *C07D 311/72* (2013.01); *C07D 311/78* (2013.01)

(58) Field of Classification Search
CPC ... C07C 37/004; C07D 311/78; C07D 311/72; B01J 20/281; B01J 8/10; B01J 8/087; B01J 2208/00805; B01J 31/04; B01J 31/08; B01J 31/10; B01J 20/20; B01J 2220/56; B01J 2220/60; B01D 5/0048; B01D 3/143; B01D 15/1821; B01D 11/0207; B01D 11/0226; B01D 11/0284; B01D 11/0288; B01D 11/0296; B01D 3/40; B01D 3/14; A61K 31/05; A61K 31/352; A61K 31/192; A61K 31/015; A61K 31/01; A61K 31/336; A61K 36/185
See application file for complete search history.

(56) References Cited

U.S. PATENT DOCUMENTS

| | | | |
|---|---|---|---|
| 2,769,787 A | 11/1956 | Diamond | |
| 2,985,589 A | 5/1961 | Broughton et al. | |
| 4,048,205 A | 9/1977 | Neuzil et al. | |
| 4,049,688 A | 9/1977 | Neuzil et al. | |
| 4,066,677 A | 1/1978 | De Rosset et al. | |
| 4,305,882 A | 12/1981 | Emken et al. | |
| 4,332,623 A | 6/1982 | Ando et al. | |
| 4,379,751 A | 4/1983 | Yoritomi et al. | |
| 4,379,784 A | 4/1983 | Maier et al. | |
| 4,529,551 A | 7/1985 | Cleary et al. | |
| 4,617,177 A | 10/1986 | Schumacher | |
| 4,721,584 A | 1/1988 | Arai et al. | |
| 4,961,881 A | 10/1990 | Ou | |
| 4,970,002 A | 11/1990 | Ando et al. | |

(Continued)

FOREIGN PATENT DOCUMENTS

| | | |
|---|---|---|
| CN | 104194920 A | 12/2014 |
| CN | 106860492 A | 6/2017 |

(Continued)

OTHER PUBLICATIONS

Karlsson, S., "Optimizing the operation of a sequential-simulated moving-bed separation process using MINLP." Computer Aided Chemical Engineering. vol. 8. Elsevier, 2000. 463-468.*

(Continued)

*Primary Examiner* — John M Mauro
(74) *Attorney, Agent, or Firm* — Wilson Sonsini Goodrich & Rosati

(57) ABSTRACT

The present disclosure relates to scalable processes for extracting, refining and fracationating extracts of natural products, such as plant material and for providing well controlled refined extracts.

25 Claims, 35 Drawing Sheets

(56) References Cited

U.S. PATENT DOCUMENTS

| | | |
|---|---|---|
| 5,064,539 A | 11/1991 | Tanimura et al. |
| 5,102,553 A | 4/1992 | Kearney et al. |
| 5,556,546 A | 9/1996 | Tanimura et al. |
| 6,033,706 A | 3/2000 | Silkeberg et al. |
| 6,093,326 A | 7/2000 | Heikkila et al. |
| 6,187,204 B1 | 2/2001 | Heikkild et al. |
| 6,254,734 B1 | 7/2001 | Sephton |
| 6,365,416 B1 | 4/2002 | Elsohly et al. |
| 6,379,554 B1 | 4/2002 | Kearney et al. |
| 6,403,126 B1 | 6/2002 | Webster et al. |
| 6,482,268 B2 | 11/2002 | Hyoky et al. |
| 6,482,323 B2 | 11/2002 | Tanimura et al. |
| 6,685,781 B2 | 2/2004 | Hyoky et al. |
| 7,595,070 B2 | 9/2009 | Olansky et al. |
| 7,667,061 B2 | 2/2010 | Binder et al. |
| 7,700,368 B2 | 4/2010 | Flockhart et al. |
| 8,088,710 B2 | 1/2012 | Binder et al. |
| 8,415,285 B2 | 4/2013 | Develter et al. |
| 8,846,409 B2 | 9/2014 | Flockhart et al. |
| 8,937,191 B2 | 1/2015 | Oroskar et al. |
| 9,034,395 B2 | 5/2015 | Whittle et al. |
| 9,199,960 B2 | 12/2015 | Ferri |
| 9,295,810 B2 | 3/2016 | Hicks et al. |
| 9,340,475 B2 | 5/2016 | Mona et al. |
| 9,937,218 B2 | 4/2018 | Towle |
| 9,950,976 B1 | 4/2018 | Keller |
| 9,956,498 B1 | 5/2018 | Tucker |
| 9,987,567 B1 | 6/2018 | Ko |
| 10,143,706 B2 | 12/2018 | Kotra et al. |
| 10,155,176 B1 | 12/2018 | Feuer et al. |
| 10,189,762 B1 | 1/2019 | Oroskar et al. |
| 10,195,159 B2 | 2/2019 | Whittle et al. |
| 10,207,199 B2 | 2/2019 | Nadal Roura |
| 10,246,431 B2 | 4/2019 | Changoer et al. |
| 10,301,242 B2 | 5/2019 | Zhang et al. |
| 10,406,453 B2 | 9/2019 | Ko et al. |
| 10,413,845 B1 | 9/2019 | Tegen et al. |
| 10,414,709 B1 | 9/2019 | Tegen et al. |
| 10,507,407 B2 | 12/2019 | Galyuk |
| 10,583,160 B2 | 3/2020 | Raderman |
| 10,604,464 B2 | 3/2020 | Oroskar et al. |
| 10,610,805 B1 | 4/2020 | Metcalf |
| 10,611,713 B2 | 4/2020 | Chen et al. |
| 10,624,872 B1 | 4/2020 | McCorkle et al. |
| 10,647,691 B2 | 5/2020 | Erfurt et al. |
| 10,662,137 B2 | 5/2020 | Qu et al. |
| 10,669,248 B2 | 6/2020 | Thomas et al. |
| 2004/0143126 A1 | 7/2004 | Webster et al. |
| 2005/0266108 A1 | 12/2005 | Flockhart et al. |
| 2006/0167283 A1 | 7/2006 | Flockhart et al. |
| 2007/0093665 A1 | 4/2007 | Burdick et al. |
| 2008/0103193 A1 | 5/2008 | Castor et al. |
| 2010/0298579 A1 | 11/2010 | Steup et al. |
| 2013/0146542 A1 | 6/2013 | Huang et al. |
| 2015/0126754 A1 | 5/2015 | Fernandez et al. |
| 2015/0203434 A1 | 7/2015 | Flockhart et al. |
| 2016/0002133 A1 | 1/2016 | Mona, III et al. |
| 2016/0228787 A1 | 8/2016 | Payack |
| 2017/0020944 A1 | 1/2017 | Towle |
| 2017/0022132 A1 | 1/2017 | Mona, III et al. |
| 2017/0051231 A1 | 2/2017 | Mancosky |
| 2017/0071992 A1 | 3/2017 | Tomaso |
| 2017/0266153 A1 | 9/2017 | Levy et al. |
| 2017/0312651 A1 | 11/2017 | Galyuk |
| 2018/0010066 A1 | 1/2018 | Stantchev |
| 2018/0147247 A1 | 5/2018 | Ivanov |
| 2018/0162828 A1 | 6/2018 | Nadal |
| 2018/0282250 A1 | 10/2018 | Rutz et al. |
| 2018/0361271 A1 | 12/2018 | Galyuk |
| 2019/0010106 A1 | 1/2019 | Oroskar et al. |
| 2019/0010107 A1 | 1/2019 | Oroskar et al. |
| 2019/0010110 A1 | 1/2019 | Oroskar et al. |
| 2019/0099697 A1 | 4/2019 | Sibal |
| 2019/0276420 A1 | 9/2019 | Tegen et al. |
| 2020/0038777 A1 | 2/2020 | Galyuk |
| 2020/0048215 A1 | 2/2020 | Thomas et al. |
| 2020/0071285 A1 | 3/2020 | Tegen et al. |
| 2020/0108044 A1 | 4/2020 | Hur |
| 2020/0164012 A1 | 5/2020 | Raderman |
| 2020/0165219 A1 | 5/2020 | Changoer et al. |
| 2020/0172503 A1 | 6/2020 | Oroskar et al. |
| 2020/0181050 A1 | 6/2020 | Cipolletti et al. |
| 2020/0188812 A1 | 6/2020 | Galyuk |
| 2020/0190002 A1 | 6/2020 | Tegen et al. |

FOREIGN PATENT DOCUMENTS

| | | |
|---|---|---|
| CN | 107365622 A | 11/2017 |
| GB | 2240053 A | 7/1991 |
| GB | 2400320 A | 10/2004 |
| GB | 2408978 B | 4/2006 |
| WO | WO-9636684 A1 | 11/1996 |
| WO | WO-2004026857 A2 | 4/2004 |
| WO | WO-2006053766 A1 | 5/2006 |
| WO | WO-2007075499 A3 | 9/2007 |
| WO | WO-2014072862 A1 | 5/2014 |
| WO | WO-2015032519 A1 | 3/2015 |
| WO | WO-2016004410 A1 | 1/2016 |
| WO | WO-2017040938 A1 | 3/2017 |
| WO | WO-2017194173 A1 | 11/2017 |
| WO | WO-2018187500 A1 | 10/2018 |
| WO | WO-2018190935 A1 | 10/2018 |
| WO | WO-2019010419 A1 | 1/2019 |
| WO | WO-2019087074 A2 | 5/2019 |
| WO | WO-2019100172 A1 | 5/2019 |
| WO | WO-2019113187 A1 | 6/2019 |
| WO | WO-2019119153 A1 | 6/2019 |
| WO | WO-2019130201 A1 | 7/2019 |
| WO | WO-2019156931 A1 | 8/2019 |
| WO | WO-2019173582 A1 | 9/2019 |
| WO | WO-2020018453 A1 | 1/2020 |
| WO | WO-2020028198 A1 | 2/2020 |
| WO | WO-2019207319 A9 | 3/2020 |
| WO | WO-2020046822 A1 | 3/2020 |
| WO | WO-2020084412 A1 | 4/2020 |
| WO | WO-2020084427 A1 | 4/2020 |
| WO | WO-2020117688 A2 | 6/2020 |
| WO | WO-2020124014 A1 | 6/2020 |

OTHER PUBLICATIONS

710SPIRITS. 710 Spirits Solubility Parameter. Northwest Scientific, Inc. (Dec. 20, 2018). Retrieved Jan. 23, 2020 from URL: <https://www.nwsci.com/customer/docs/SKUDocs/RMR/710%20Solubility%20Parameter.pdf>. 3 Pages.

Amirav, et al. Approaching a Step Forward Towards the CSI Vision—Cannabis Seeds Identification with the 5975-SMB GC-MS and Cold EI. Webpage. blog.avivanalytical.com/2012/12/approaching-step-forward-towards-csi.html. 2012. Accessed on Nov. 22, 2018. 6 Pages.

Angelova et al. Bio-accumulation and distribution of heavy metals in fibre crops (flax, cotton and hemp). Industrial Crops and Products 19(3):197-205 (2004).

Atkins, et al. Analysis of Cannabis and Hemp Products for Heavy Metals. Poster. SPEX CertiPrep (2017). 1 Page.

Atkins, P. Analysis of Heavy Metal Concentrations and Human Exposure from Hemp Oils and Hemp Products. Poster. SPEX CertiPrep (2017). 1 Page.

Baram et al.: The Heterogeneity and Complexity of Cannabis Extracts as Antitumor Agents. Oncotarget 10(41): 4091-4106 (2019).

Brooks, et al. Optimization of the Bleaching Process. AOCS Lipid Library. (2013). 13 Pages.

Burke, J. Solubility parameters: theory and application. (Aug. 1984).The Oakland Museum of California. Part 2—The Hildebrand Solubility Parameter. 5 Pages.

Cochran, J.: Medical Marijuana Solvent Extraction Efficiency—Potency Determinations with GC-FID. https://blog.restek.com/?p=3018. 19 pages (2011).

Curran, et al. Argentation resin chromatography of diterpene resin acids. Journal of the American Oil Chemists Society 58.11 (1981): 980-982.

(56) References Cited

OTHER PUBLICATIONS

Davis et al.: The Preparation and Analysis of Enriched and Pure Cannabinoids from Marihuana and Hashish. Chemistry and Life Sciences Laboratory, Research Triangle Institute. 33(4): 453-460 (1970).
Eboh, et al. Analysis of heavy metal content in canabis leaf and seed cultivated in southern part of Nigeria. Pakistan J Nutr 4 (2005): 349-351.
Food Fats and Oils. Institute of Shortening and Edible Oils. (2016). 30 pages.
Gauvin, et al. Marijuana Toxicity: Heavy Metal Exposure Through State-Sponsored Access to "la Fee Verte". Pharmaceut Reg Affairs. 2018. 7:1. 10 Pages.
Glod, B. Principles and applications of ion-exclusion chromatography. Acta Chromatographica, No. 7, 1997. pp. 72-88.
Hamm, et al. Edible oil processing. John Wiley & Sons, 2013. 340 Pages.
Hong, et al. A review size-exclusion chromatography for the analysis of protein biotherapeutics and their aggregates. Journal of liquid chromatography & related technologies 35.20 (2012): 2923-2950.
Iffland et al.: Decarboxylation of Tetrahydrocannabinolic acid (THCA) to active THC. European Industrial Hemp Association (EIHA). 3 pages (2016).
Jukes et al. The Combination of Certain Fatty Acids with Lysine, Arginine and Salamine. J Biol Chem 110:9-16 (1935).
Juza et al.: Simulated moving-bed chromatography and its application to chirotechnology. Trends in Biotechnology. 18(3): 108-118 (2000).
Lewis et al.: Chemical Profiling of Medical Cannabis Extracts. ACS Omega 2: 6091-6103 (2017).
Marican, et al. A review on pesticide removal through different processes. Environmental Science and Pollution Research 25.3 (Nov. 28, 2017): 2051-2064.
Munch, E. Degumming of Plants Oils for different applications. Society of Chemical Industry, Cairo (Mar. 20, 2007). 30 Pages.
Nevada State Division of Public and Behavioral Health Policy #MME005 titled "Medical Marijuana Establishment Heavy Metals Testing Standards" effective as of Feb. 18, 2015.
Pavlovic et al.: Quality Traits of "Cannabidiol Oils": Cannabinoids Content, Terpene Fingerprint and Oxidation Stability of European Commercially Available Preparations. Molecules 23: 1230. 22 pages (2018).
PCT/US2019/043795 International Search Report and Written Opinion dated Oct. 29, 2019.
Powers, D.: Remediation of Pesticides from First Pass Distillate via Liquid/Liquid Ex-traction and Chromatographic Adsorption. ARCON Journal. 3 pages.
Purolite. Purolite Product Information. Chromalite Resins for Reverse-Phase Chromatography, Adsorption and Spe. 24 pages (2014).
Rajendran et al.: Simulated Moving Bed Chromatography for the Separation of Enantiomers. Journal of Chromatography A. 1216: 709-738 (2009).
Romano et al.: Cannabis Oil: Chemical Evaluation of an Upcoming Cannabis-Based Medicine. Cannabinoids 1(1): 1-11 (2013).
U.S. Department of Health and Human Services Food and Drug Administration, Center for Drug Evaluation and Research (CDER), Center for Biologics Evaluation and Research (CBER). Q3C—Tables and List Guidance for Industry. [Jun. 2017] ICH. Revision 3. 10 pages.
Brian Windsor, Purolite International Ltd. Resin Types and Production (presentation). Society of Chemical Industry (SCI) (2012). 35 pages.
CBD Purification with Chromalite Chromatographic Resins (poster). Purolite Life Sciences (Apr. 25, 2020).
Chloride in Drinking-water. Background document for development WHO Guidelines for Drinking-water Quality. WHO/SDE/WSH/03. 04/03. World Health Organization (2003). 9 pages. Originally published in Guidelines for drinking-water quality, 2nd ed. vol. 2. Health criteria and other supporting information, World Health Organization, Geneva, 1996.
Chojnacka et al. Bio-based Fertilizers: A Practical Approach Towards Circular Economy. Bioresour Technol Jan. 2020;295:122223.doi: 10.1016/j.biortech.2019.122223. Epub Oct. 3, 2019. 11 pages.
Derler. Master Thesis: Screening of organic acids suitable for stimulation treatments. OMV, Leoben, Austria (2018). 85 pages.
Engelhardt. Lead in Water—Significance, Sources, and Test Methods. Application Note: Lead Sources, Effects, and Test Methods. Hach (2015). 2 pages.
Engineering Bulletin: C104Plus and C104EPlus Hydrogen Cycle Operation Hydrochloric or Sulfuric Acid Regeneration. Purolite (2014). 16 pages.
Greenwald. The Dissociation of Some Calcium Salts. J Biol Chem 124:437-452 (1938).
Lead DOC316.53.01054. LeadTrak Fast Column Extraction Method (Method 8317). Hach Company (2007). Edition 7. 8 pages.
Mark Slagt, Dow Company. Ion Exchange Resin Selection (presentation). Society of Chemical Industry (SCI) (2012). 38 pages.
Purolite C104Plus (Product Data Sheet). Purolite (2020). Retrieved May 21, 2020 from URL: https://www.purolite.com/product-pdf/C104PLUS.pdf.2 pages.
Technical Data: C104Plus Weak Acid Cation Resin. Purolite Ion Exchange Resins. May 3, 2012. 6 pages.
Toth et al. Comprehensive evaluation and comparison of advanced separation methods on the separation of ethyl acetate-ethanol-water highly non-ideal mixture. Separation and Purification Technology 224 (2019) 490-508. Available online May 14, 2019.
Yang et al. Simulation of Pressure-swing Distillation for Separation of Ethyl Acetate-Ethanol-Water. IOP Conf. Series: Materials Science and Engineering 274 (2017) 012026 doi:10.1088/1757-899X/274/1/012026. 8 pages.

* cited by examiner

PROCESSES AND APPARATUS FOR EXTRACTION OF SUBSTANCES AND ENRICHED EXTRACTS FROM PLANT MATERIAL

CROSS-REFERENCE TO RELATED APPLICATION

The present application is a continuation of International Patent Application No. PCT/US2019/043795, filed Jul. 26, 2019, which claims the benefit of U.S. Provisional Patent Application No. 62/714,513, filed Aug. 3, 2018, U.S. Provisional Patent Application No. 62/742,139, filed Oct. 5, 2018, U.S. Provisional Patent Application No. 62/795,773, filed Jan. 23, 2019, 62/789,117, filed Jan. 7, 2019, and U.S. Provisional Patent Application No. 62/788,271, filed Jan. 4, 2019, each of which is incorporated herein by reference in its entirety.

BACKGROUND

The therapeutic activity of plant medicines is attributed to the active constituents that they contain. In some cases, the intrinsic activity of natural products has been linked to specific chemical species, but in other cases the activity of the plant medicine is considered to be due to a combination of constituents acting in concert. The active constituents may be present at varying concentrations in different plant strains and may depend on growing conditions. Furthermore, active constituents may be present at varying amounts in different parts of the plant.

*Cannabis* is a genus of plants that include three species: *Cannabis sativa*, *Cannabis indica*, and *Cannabis ruderalis*. This genus has long been in use for its hemp fiber material, and the active constituents have been used as milk, seeds and oils, for medicinal purposes and for recreational use. Recent years have seen a surge in research and development directed to utilization of the constituents of this genus for therapeutic purposes.

There is great need for generating a large variety of *cannabis* compositions to help find the most desired effect for every indication and every patient. The industry typically addresses this need by genetically developing more and more strains in order to increase the selection. Such development of strains is expensive, complicated and takes time to form the required product.

Many of the *cannabis*-derived products utilize the primary psychoactive component of the *Cannabis* plant, tetrahydrocannabinol (THC). *Cannabis* plants initially contain tetrahydrocannabinolic acid (THCA) and cannabidiolic acid (CBDA); these compounds break down to THC and cannabindiol (CBD) when exposed to UV light and/or heat. THC belongs to the larger family of cannabinoids. CBD is a non-psychoactive cannabinoid that is used in medicinal preparations. According to Handbook of *Cannabis* (R. G. Partwee (Ed.), Oxford Univ. Press 2014, Ch. 1), by 2012, a total of 545 chemical compounds have been identified as constituents of *Cannabis Sativa* L, out of which 104 were classified as cannabinoids and 441 classified as non-cannabinoids. With much research in this area in recent years, the number of identified compounds continues to grow. The identified cannabinoids were classified into 11 types: (−)-Δ-9-trans-tetrahydrocannabinol (Δ9-THC), (−)-delta-8-trans-tetrahydrocannabinol (Δ8-THC), cannabigerol (CBG), cannabichromene (CBC), cannabidiol (CBD), cannabinodiol (CBND), cannabielsoin (CBE), cannabicyclol (CBL), cannabinol (CBN), cannabitriol (CBT), and miscellaneous-type cannabinoids. Some of the identified cannabinoids may undergo chemical transformation under certain conditions. Currently, the cannabinoids of greatest commercial interest are Δ9-tetrahydrocannabinol carboxylic acid A (Δ9-THC acid A), Δ9-tetrahydrocannabinol carboxylic acid B (Δ9-THC acid B) and the decarboxylated form Δ9-THC, as well as cannabidiolic acid (CBDA) and the decarboxylated form cannabidiol (CBD).

In addition, it is suggested that terpenes extracted from *Cannabis Sativa* L have some effects, including therapeutic effects, and may alter the effects of cannabinoids in certain indications. The most common terpenes that have been identified include α-pinene, myrcene, limonene, β-caryophyllene, linalool, humulene, ocimene, and terpinolene, each of which can be isolated from other herbal plants or industrially produced by fermentation.

SUMMARY

The present disclosure relates to refining processes for extracts of naturally-occurring compounds, which are extracted from biomass. In particular, systems and processes for providing highly refined cannabinoids and terpenes are described.

In certain aspects, the present disclosure provides an integrated modular system for extracting, refining, and fractionating plant constituents, the system comprising: (a) a biomass feeding unit; (b) at least one solvent extraction unit; (c) a first refining unit; (d) a second refining unit; (e) at least one chemical conversion unit; and (f) a third refining unit. In some embodiments, the biomass feeding unit further comprises a biomass grinding unit, sizing unit, sorting unit, or any combination thereof. In some embodiments, the sizing unit comprises a screen that the plant material passes through. In some embodiments, the sorting unit separates the plant material by density. In some embodiments, the system further comprises at least one solvent recycling unit. In some embodiments, the system further comprises pumps, pipes, and conveyors for transferring the biomass. In some embodiments, the system is designed and constructed for continuous extracting, refining and fractionating high purity constituents from plant material. In some embodiments, the system further comprises a central computer control; control valves; monitors and sensors for continuously monitoring temperature, pressure, or flow.

In some embodiments, the at least one solvent recycling unit comprises: (i) at least one decanting tank; (ii) at least one evaporating system equipped with barometric condensers, wherein solvent and, optionally, water vapors are collected and transferred to the decanting tank; (iii) at least one stripper distillation system, wherein a distillate is collected and transferred to the decanting tank; (iv) at least one decanting system, wherein an aqueous phase is transferred to the at least one stripper distillation system to recover a solvent; (v) at least one press, wherein a pressed depleted biomass is transferred to a dryer, wherein subsequent liquids are transferred for further refining; (vi) at least one dryer, wherein solvent and, optionally, water vapors are collected and transferred to the decanting tank, wherein the solids comprise (a) depleted plant material after extraction and (b) loaded solid adsorbents; (vii) at least one chiller, wherein a solvent is chilled to a temperature; and (viii) at least one pump and piping system.

In some embodiments, the plant biomass comprises *cannabis*.

In some embodiments, the first refining unit comprises: at least one column of granulated activated carbon (GAC); and at least one barometric evaporator.

In some embodiments, the second refining unit comprises: (i) at least one temperature-controlled stirring tank; (ii) at least one filter; (iii) at least one decanting tank; (iv) at least one buffering tank; (v) at least one ion exchange column; (vi) at least one barometric evaporator; (vii) at least one decanter tank; and (viii) at least one settler. In some embodiments, the system further comprises at least a second temperature-controlled stirring tank, a second filter, or any combination thereof.

In some embodiments, the at least one chemical conversion unit comprises a stirred heating tank. In some embodiments, the third refining unit comprises a distillation unit. In some embodiments, the distillation unit comprises a short path distillation unit.

In certain aspects, the present disclosure provides a method of preparing at least one plant-extracted constituent, the method comprising: (i) extracting a constituent from the plant material with a first solvent to obtain a first loaded extractant; (ii) contacting the first loaded extractant with an adsorbent, a desorbant, or a combination thereof to obtain a first refined extractant; (iii) concentrating the first refined extractant to obtain a first refined oil; (iv) contacting the first refined oil with at least one substance selected from the group consisting of a basic amino acid, a protamine, clay, water, activated carbon, filter aid, and ion exchange resin, or a combination thereof to obtain a second refined extractant; and (v) concentrating the second refined extractant to obtain a second refined oil. In some embodiments, prior to (iv), the first refined oil is contacted with a second solvent to obtain a second loaded extractant, wherein the second loaded extractant is subsequently contacted with at least one substance selected from the group consisting of a basic amino acid, a protamine, clay, water, activated carbon, filter aid, and ion exchange resin, or a combination thereof to obtain a second refined extractant.

In some embodiments, the method further comprises distilling the second refined oil to obtain a purified oil. In some embodiments, further comprises fractionating the purified oil by chromatography to obtain at least one fractionated plant-extracted constituent. In some embodiments, the chromatography is simulated moving bed (SMB) chromatography.

In some embodiments, the method further comprises treating the second refined oil with heat, a catalyst, or a combination thereof, thereby de-carboxylating at least one carboxylic acid containing constituent of the second refined oil. In some embodiments, the second refined oil is heated under vacuum at a temperature ranging from 105° C. to 170° C. In some embodiments, the catalyst is a dicarboxylic acid, a tricarboxylic acid, an ion exchange resin, or any combination thereof. In some embodiments, the catalyst is selected from the group consisting of citric acid, oxalic acid, malic acid, ascorbic acid, tartaric acid, Amberlite, Amberlyst, Smopex, or Dowex.

In some embodiments, at least 85% (% mol) of the cannabinoid constituents of the plant material are de-carboxylated in the purified oil. In some embodiments, the method further comprises prior to (i), feeding a plant material into a biomass feeding unit. In some embodiments, the biomass feeding unit further comprises a biomass grinding unit, sizing unit, sorting unit, or any combination thereof.

In some embodiments, the adsorbent is selected from the group consisting of silica gel, alumina, zeolites, polymers, resins, clay, clay minerals, ores, charcoal, activated carbon, or metals, such as Ni, Cu, Ag, Pt and colloids. In some embodiments, the adsorbent is activated carbon. In some embodiments, the activated carbon is granulated activated carbon (GAC). In some embodiments, contacting with GAC removes at least 10% of the tetrahydrocannabinoids present in the loaded extractant.

In some embodiments, the desorbent is selected from the group consisting of 1-butanol, ethyl acetate, ethyl formate, 2-methyl-1-butanol, ethanol, heptane, cyclohexane, 2-butanone, 2-propanol, or propylene glycol.

In some embodiments, the method further comprises (a) contacting the first refined oil or the second loaded extractant with a solution of the basic amino acid, the protamine, or a combination thereof; (b) further contacting the first refined oil or the second loaded extractant with the clay, thereby obtaining a first slurry; (c) filtering at least one solid from the first slurry, thereby obtaining a first mother liquor comprising an aqueous phase and an organic phase; (d) separating the aqueous phase and the organic phase; (e) contacting the organic phase with an ion exchange resin, thereby obtaining a deionized organic phase; (f) contacting the deionized organic phase with activated carbon, thereby obtaining a second slurry; (g) filtering at least one solid from the second slurry, thereby obtaining a second mother liquor comprising an aqueous phase and an organic phase; (h) adding brine to the second mother liquor; (i) concentrating the second mother liquor, thereby obtaining an aqueous phase and a concentrated organic phase; and (j) separating the aqueous phase and the concentrated organic phase, thereby obtaining the second refined extract.

In some embodiments, the clay is selected from the group consisting of Fuller's Earth, Kaolin clay, bentonite, diatomaceous earth, magnesium silicate (such as Florisil), or a mixture thereof. In some embodiments, the ion exchange resin is a strong acid ion exchange resin (SAC), a weak acid ion exchange resin (WAC), or a powdered activated carbon (PAC) resin, or any combination thereof, and the temperature is from 45° C. to 60° C. In some embodiments, the brine is a solution of a salt that is selected from the group consisting of sodium chloride, sodium acetate, sodium formate, or any mixture thereof.

In some embodiments, the plant material comprises *cannabis*. In some embodiments, the extracted constituents comprise cannabinoids and terpenes. In some embodiments, the plant material comprises green, dried, or pelletized material.

In some embodiments, the solvent: is categorized as class 3 according to Q3C—Table and Lists Guidance for Industry (US Department of Health and Human Services, FDA, CDER, CBER), June 2017 ICH rev. 3 and/or forms a heterogeneous azeotrope with water, wherein the solvent and the azeotrope have a boiling point lower than the boiling point of water. In some embodiments, the first solvent, second solvent, or a combination thereof comprises a mixture of solvents. In some embodiments, the solvent forms a heterogeneous azeotrope with water, wherein the heterogeneous azeotrope has a boiling point lower than the boiling point of the solvent. In some embodiments, the solvent is selected from the group consisting of 1-butanol, ethyl acetate, ethyl formate, 2-methyl-1-butanol, ethanol, heptane, cyclohexane, 2-butanone, 2-propanol, or propylene glycol.

In some embodiments, the method is a continuous process at industrial or semi-industrial scale. In some embodiments, the method is an integrated process for preparing at least one plant-extracted constituent.

In some embodiments, the constituents of the purified oil comprises any of the characteristics, or any combination thereof, selected from: (i) at least 85% wt cannabinoids; (ii) at most 1% wt/wt fatty acids; (iii) at most 30 ppm heavy metals; (iv) at most 5000 μg/g ethanol; (v) at most 3000 μg/g methanol; (vi) at most 5000 μg/g ethyl acetate; (vii) at most 5000 μg/g butane; and (viii) at most 290 μg/g hexane.

In some embodiments, the concentration of THC in the at least one fractionated plant-extracted constituent is controlled to 0.001% to 0.3% wt/wt. In some embodiments, at least one fractionated plant-extracted constituent comprises at least 95% of the THC present in the purified oil, thereby forming a THC-enriched fraction. In some embodiments, the THC-enriched fraction comprises at most 15% of the CBD present in the purified oil. In some embodiments, the at least one fractionated plant-extracted constituent comprises at most 0.300% THC in the purified oil, thereby forming a THC-depleted fraction. In some embodiments, the purified oil further comprises at most 0.05 mg/kg pesticides as analyzed by Official Methods of Analysis, AOAC Official Method 2007.01, Pesticide Residues in Foods by Acetonitrile Extraction and Partitioning with Magnesium Sulfate, AOAC INTERNATIONAL (modified) or CEN Standard Method EN 15662: Food of plant origin—Determination of pesticide residues using GC-MS and/or LC-MS/MS following acetonitrile extraction/partitioning and clean-up by dispersive SPE—QuEChERS method.

In certain aspects, the present disclosure provides a system for continuously extracting herbal constituents from a plant material, wherein the system comprises at least two conveyors and at least two mixing tanks, wherein each conveyor comprises: (a) an internal screw for propagating plant material and at least one solvent from an upstream end to a downstream end of at least one of the conveyors of the at least two conveyors; (b) a wire screen for separating liquids from the plant material; and (c) an inlet for the plant material comprising at least one inlet for solvent, wherein the inlet is adjacent to at least one of the at least two conveyors, wherein a flow direction for each conveyor is co-current.

In some embodiments, each conveyor is inclined, such that the plant material is fed at the downstream end and propagated out of the upstream end. In some embodiments, the at least two conveyors are arranged in a substantially opposing arrangement such that a stream of solvent can flow between the at least two conveyors. In some embodiments, the at least two mixing tanks are connected with the at least two conveyors via conduits equipped with pumps for pumping a plant material slurry and a partially loaded extractant to the at least two conveyors, wherein the overall flow of the system is in counter-current orientation. In some embodiments, the tanks and pumps process the plant material in the at least two conveyors. In some embodiments, a residence time of plant material in the extractor and the ratio of liquid to plant material in each conveyor is controlled by the angle of inclination, the pitch of the screw, the turning speed of the screw, the pumping speed of the solvent and plant material.

In some embodiments, the system further comprises: (a) an uppermost conveyor or a plurality of uppermost conveyors is fed with plant material and at least one solvent, thereby producing a loaded extractant; (b) a middle conveyor or a plurality of middle conveyors is fed with partially extracted plant material from the uppermost conveyor or the plurality of uppermost conveyors and at least one solvent; and (c) the lowermost conveyor or a plurality of lowermost conveyors is fed with extracted biomass from the middle conveyor the plurality of middle conveyors and freshly regenerated solvent.

In some embodiments, the plurality of middle converters comprises two conveyors in parallel. In some embodiments, the plurality of middle converters comprises two conveyors in series. In some embodiments, wherein the two conveyors in series are operated in a counter-current mode with respect to each other.

In some embodiments, plant material and liquids are separated in the conveyor over the wire screen, wherein the through stream comprises a loaded extractant and water and the retained stream comprises a loaded extractant, water and plant material. In some embodiments, the plant material is separated by density.

In some embodiments, the system further comprises a screw press, wherein the screw press receives the retained stream from the uppermost conveyor and removes liquids to provide a concentrated plant material stream, comprising 50 to 80% solids.

In certain aspects, the disclosure provides a method for fractionating a *cannabis* extract, the method comprising (1) fractionating a *cannabis* extract using a continuous simulated moving bed method (2) collecting a fraction enriched in a first cannabinoid relative to the *cannabis* extract and (3) collecting a fraction enriched in at least a second cannabinoid relative to the *cannabis* extract. In some embodiments, the fractionating is carried out in a sequential simulated moving bed chromatography. In some embodiments, the sequential simulated moving bed chromatography sequence comprises: (1) passing a feed stream comprising *cannabis* extract into an adsorbent, thereby flushing a first raffinate stream comprising THCA and decarboxylated cannabinoids from the adsorbent; (2) flushing an extract stream enriched in CBDA relative to the feed stream with a desorbent stream; and (3) recycling the desorbent stream back to the adsorbent. In some embodiments, the chromatography media is a cross-linked dextran polymer, a non-ionic acrylic polymer, a macroporous resin, or any combination thereof.

In certain aspects, the disclosure provides a composition of *cannabis*-derived extract substantially free of heavy metals. In some embodiments, the composition comprises: (i) at least 85% wt cannabinoids; (ii) at most 1% wt/wt fatty acids; (iii) at most 30 ppm heavy metals; (iv) at most 5000 μg/g ethanol; (v) at most 3000 μg/g methanol; (vi) at most 5000 μg/g ethyl acetate; (vii) at most 5000 μg/g butane; and (viii) at most 290 μg/g hexane.

INCORPORATION BY REFERENCE

All publications, patents, and patent applications mentioned in this specification are herein incorporated by reference to the same extent as if each individual publication, patent, or patent application was specifically and individually indicated to be incorporated by reference. To the extent publications and patents or patent applications incorporated by reference contradict the disclosure contained in the specification, the specification is intended to supersede and/or take precedence over any such contradictory material.

BRIEF DESCRIPTION OF THE FIGURES

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings (also "Figure" and "Fig." herein), of which:

DETAILED DESCRIPTION

Figure 1A:
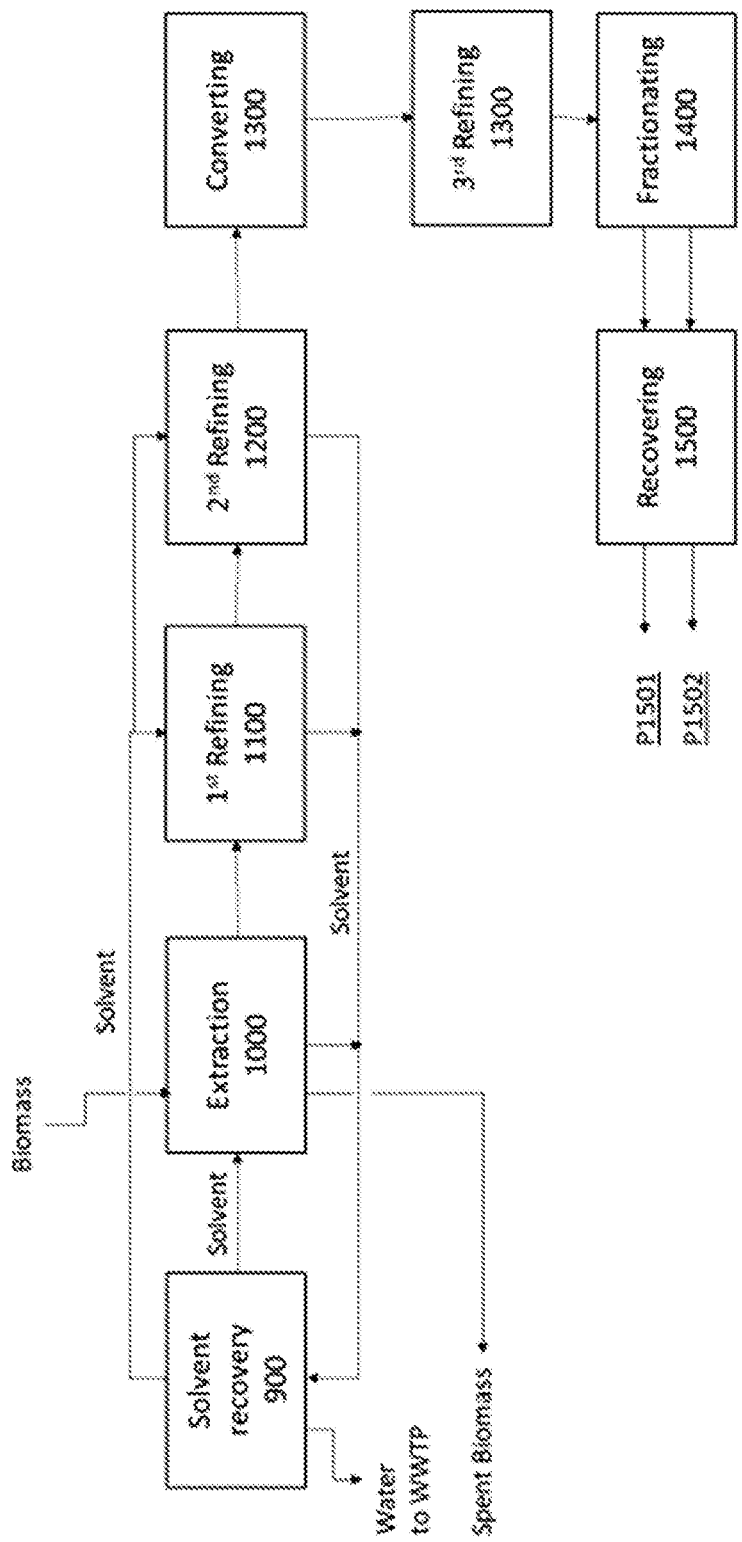
FIG. 1A illustrates a schematic diagram of a modular process to extract, refine and fractionate constituents from plant material, to provide products enriched with a certain constituent or group of constituents, and to convert carboxylic acid constituents to their respective de-carboxylated constituents.

While various embodiments of the invention have been shown and described herein, it will be obvious to those skilled in the art that such embodiments are provided by way of example. Numerous variations, changes, and substitutions may occur to those skilled in the art without departing from the invention. It should be understood that various alternatives to the embodiments of the invention described herein may be employed.

As used herein, the singular forms "a," "an," and "the" include plural references unless the context clearly dictates otherwise. Any reference to "or" herein is intended to encompass "and/or" unless otherwise stated.

As used herein, the term "about" or "approximately" means within 10%, preferably within 10%, and more preferably within 5% of a given value or range.

The term "plant material", as used herein, generally refers to materials derived from plants. At least a portion of the plant material may be in the form of grass, rush, bark, wood, gourds, stems, roots, seeds, leaves, or flowers. In some embodiments, the plant material may be in the form of *cannabis*.

The terms "*cannabis*", "*cannabis* plant material", or "*cannabis* biomass", as used herein, may refer to whole *cannabis* plants and also parts thereof. In some embodiments, at least a portion of the *cannabis* (e.g., the aerials, stems, leaves, flowering heads, or any combination thereof) may contain bioactive constituent(s). The terms "*cannabis*", "*cannabis* plant material", and "*cannabis* biomass" may encompass freshly harvested plant material, and also plant material which has been subjected to a pre-treatment step (e.g., dried material). The terms "*cannabis*", "*cannabis* plant material", or "*cannabis* biomass" can refer to any strain or combination of strains (i.e., Cannabis sativa, *cannabis* indica, or cannibis *ruderalis*).

The term "cannabinoid" refers to both its carboxylic acid form and its decarboxylated form. THC refers to tetrahydrocannabinol, while THCA refers to the carboxylated form of THC (tetrahydrocannabinolic acid). CBD refers to cannabidiol, while CBDA (cannabidiolic acid) refers to the carboxylated form of CBD. Other cannabinoid constituents may be: (−)-Δ-9-trans-tetrahydrocannabinol (Δ9-THC), (−)-delta-8-trans-tetrahydrocannabinol (Δ8-THC), cannabigerol (CBG), cannabichromene (CBC), cannabinodiol (CBND), cannabielsoin (CBE), cannabicyclol (CBL), cannabinol (CBN), cannabitriol (CBT).

Any strain of *cannabis* plant is suitable to be extracted by the processes disclosed herein. The term "strain" refers to different varieties of a particular plant genus. For example, the term strain can refer to different varieties of *cannabis* plants. Different *cannabis* strains often exhibit distinct chemical compositions with characteristic levels of cannabinoids and terpenes, as well as other components. Differing cannabinoid and terpene profiles associated with different *cannabis* strains can be useful for the treatment of different diseases, or for treating different subjects with the same disease. In some embodiments, the *cannabis* plant is a hemp plant. In some embodiments, the *cannabis* plant is a hybrid *cannabis* plant, or an asexual clone of said hybrid *cannabis* plant. In some embodiments, the *cannabis* plant is naturally bred or genetically engineered to express specifically high or specifically low concentration of at least one cannabinoid and/or at least one terpene. Any organ of a *cannabis* plant may be utilized in the subject methods, including but not limited to flowers, buds, kernel, leaves, stem, stalk, and roots.

The term "constituent" or "plant extracted constituent", as used herein, may refer to a(n) unaltered or altered component present within the plant material. In some embodiments, at least one constituent may be isolated from the plant material. The "constituents" may refer to pharmaceutically active ingredients, pharmaceutically inactive ingredients, flavor and aroma compounds, and any other chemical species that may be extracted from plant material.

The term "loaded extractant", as used herein, may refer to a solution comprising at least one solute dissolved in a substance. In some embodiments, a loaded extractant may comprise at least one impurity. The term "loaded solvent" and "loaded extractant" are used interchangeably, and refer to solvent comprising constituents extracted from a plant material.

The term "refined extractant", as used herein, may refer to a solution comprising at least one solute dissolved in a substance, wherein the solution has at least one less impurity present. In some embodiments, a refined extractant may comprise at least one impurity.

The term "refined oil", as described herein, may refer to an oil comprising at least one constituent extracted from a plant material, wherein the oil has at least one less impurity present. In some embodiments, a refined oil may comprise at least one impurity.

The term "basic amino acid", as described herein, may refer to as any amino acid containing a side chain that has a pKa in water of greater than about 6 (e.g., arginine, lysine, or histidine).

The term "protamine", as used herein, may refer to an arginine rich, nuclear protein.

The term "filter aid", as used herein, may refer to a group of inert materials that can be used in filtration pretreatment. In certain embodiments, filter aids may be used to aid filtration.

The term "stream", as described herein, may refer to a flow of solid, liquid, gas, or any combination thereof.

The term "effluent", as described herein, may refer to a solid, liquid, gas, or any combination thereof that may exit or enter a system.

The term "feeding unit" or "biomass feeding unit", as described herein, may refer to a receptacle that holds particulate matter. In some embodiments, the feeding unit can transfer the particulate matter to an extracting unit. In some embodiments, the feeding unit is equipped with a grinding unit. In some embodiments, the feeding unit is equipped with a sizing unit. In some embodiments, the feeding unit is equipped with a grinding and sizing unit. In some embodiments, the grinding unit produces biomass particulate less than about 12 mm. In some embodiments, the grinding unit produces biomass particulate less than about 6 mm.

The term "brine", as used herein, may refer to a solution of salt dissolved in water. In some embodiments, the salt may comprise $Na^+$, $K^+$, $Li^+$, $Cs^+$, or $Ca^{2+}$. In some embodiments, the salt may comprise, for example, sodium chloride, sodium acetate, potassium chloride, potassium acetate, lithium chloride, lithium acetate, cesium chloride, cesium acetate, calcium chloride, calcium acetate, sodium sulfate, potassium sulfate, lithium sulfate, calcium sulfate, or any combination thereof.

A "bleaching agent" refers to solids used by the edible oil industry as part of refining edible oils and fats for the purpose of removing some color, residual chlorophyll, residual soaps, gums and waxes, trace metal, various oxidation products and peroxides.

All percent numbers are weight to weight percent, unless specifically detailed differently.

When referring to the composition of a complex extract, it is useful to refer to the concentration of a specific component with reference to "Solvent Removed Base", SRB, i.e. the concentration of the specific component with respect to the total mass that is left once all solvents have been evaporated from the mass.

The present disclosure provides processes, methods and systems for extracting plant material. Further, the disclosure provides processes for refining crude oil to provide a least one constituent with a purity that may be sufficient for human consumption. Further, the disclosure provides processes, methods, and systems for fractionating extractants from plant material into product streams enriched with at least one constituent. In some embodiments, the process comprises units that may be integrated to provide an efficient, high yielding, and well-controlled continuous process. In some embodiments, process units may be applied separately, or in combination, with different extraction or refining processes.

Active substances may be extracted from plant material by a solvent, wherein the solvent may comprise a solvent or a mixture of solvents, wherein the solvent or mixture of solvents: (i) may be categorized as class 3 according to Q3C—Table and Lists Guidance for Industry (US Department of Health and Human Services, FDA, CDER, CBER), June 2017 ICH rev. 3; (ii) may form a heterogeneous azeotrope with water, wherein the solvent and the azeotrope may have a boiling point lower than the boiling point of water; and/or (iii) may form a heterogeneous azeotrope with water, wherein the solvent and the azeotrope may have a boiling point lower than the boiling point of water. In some embodiments, the ratio of water to solvent, Rw/Rs, may be greater in the vapor phase of the azeotrope than in the solvent liquid phase. In some embodiments, the solvent may be selected from, for example, 1-butanol, ethyl acetate, ethyl format, 2-methyl-1-butanol, ethanol, heptane, cyclohexane, 2-butanone, 2-propanol, propylene glycol, and mixtures thereof (e.g., ethyl acetate and ethyl formate).

In some embodiments, the clay may be Fuller's Earth, Kaolin clay, bentonite, diatomaceous earth, magnesium silicate (such as Florisil®) and mixtures thereof.

In some embodiments, the ion exchange resin may be, for example, a strong acid cation (SAC) resin, a weak acid cation (WAC) resin, a chelating resin, a strong base anion (SBA) resin, or a weak base anion (WBA) resin. In some embodiments, the ion exchange resin may have functional groups, for example, comprising sulfonic acid, carboxylic acid, aminophosphonic acid, Type I quaternary ammonium, quaternary ammonium, or any combination thereof. In some embodiments, the ion exchange resin may be in the form of, for example, $H^+$, $Na^+$, $Cl^-$, or $SO_4^{2-}$. In some embodiments, the ion exchange resin may comprise a resin that is, for example, agarose, cellulose, dextran, or polystyrene. In some embodiments, the ion exchange resin may be, for example, Amberj et 1600 H, PPC100H, Purolite 5950, Puromet MTS9500, Purolite 5940, Puromet MTA5012, MTA8000PPSO4, or Purolite A500.

The product obtained after extraction and after the removal of the extractant is a refined oil, comprising the target constituents, as well as many other compounds or families of compounds that are co-extracted with the target constituents. Extraction of *cannabis* or hemp plants can provide a refined oil comprising about 60 to 85% cannabinoids, about 2-5% terpenes and a mixture of triglycerides, free fatty acids, phospholipids, waxes and gums, and many other compounds. In some embodiments, it is important to further purify the refine oil by applying process steps for the removal of at least some waxes and gums, since they increase viscosity and adherence properties of the mixture such that it is very difficult to filter or flow. In some embodiments, it is important to remove any substances that may have adverse impact on the use of the product, such as pesticides and herbicides, aflatoxins and mycotoxins, volatile organic solvents and heavy metals. In some embodiments, the purified oil can be fractionated to enhance the concentration of a certain constituent of a group of constituents.

Furthermore, the present disclosure provides a system and process that facilitates meeting various anti-static electricity measures and other requirements of local Fire Marshal; VOC (volatile organic carbon) emissions and other EPA requirements; controls applied by BATF (Bureau of Alcohol, Tobacco and Firearms) in the case of non-denatured ethanol as a component in the solvent; the system design can meet Good Manufacturing Practice requirement as required for the production of food or drugs ingredients. In some embodiments, the system is designed with integrated process control logic to manage critical process parameters which are typically not used in batch processes; controls are monitored by a computer for process history and interlocks that minimize unsafe conditions; the system is capable of product accounting from beginning to end so is suitable for handling of restricted materials.

In some embodiments, the system is equipped with an inert gas purge, for example nitrogen, to fill the headspace of the vessels and/or equipment. In some embodiments, the purged gas from the system of integrated vessels and equipment are vented through a scrubber with a high boiling point solvent, for example cold mineral oil, that is capable of adsorbing the volatile organic compounds travelling with the gas stream. In some embodiments, the solvent is stripped of these volatiles and recycled to the scrubber.

A schematic integrated process for providing extracted, refined and fractionated products from plant material is shown in FIG. 1A. In some embodiments, the integrated process comprises an extraction unit (1000), a first refining unit (1100), and a second refining unit (1200), that receives regenerated, recycled solvent from the solvent recovery system (900). Fresh or dried plant material is fed into the extraction unit, where the solvent extracts the plant material to provide a loaded extractant comprising plant constituents and water. Solvent is recovered at each refining unit and transferred to recovery (900) for removal of excess water and impurities it may carry and recycling it for further use. The refined oil is further refined at third refining (1300), to provide purified oil. In some embodiments, subsequent to the third refining, the refined oil can be treated by heat and/or catalyst to convert carboxylic acid constituents to their respective de-carboxylated form. In some embodiments, the refined oil is treated by heat under vacuum to convert carboxylic acid constituents to their respective de-carboxylated form. In some embodiments, the purified oil can be fractionated by a chromatography process to at least two fractions, wherein one fraction is enriched with a specific constituent and the other fraction is depleted of the specific constituent. For example, if the plant is a *cannabis* plant, one fraction is enriched with THC and the other fraction is depleted of THC. The fractioned streams are recovered by evaporating to provide the products, these products being of high purity and controlled composition of constituents.

Figure 1B:
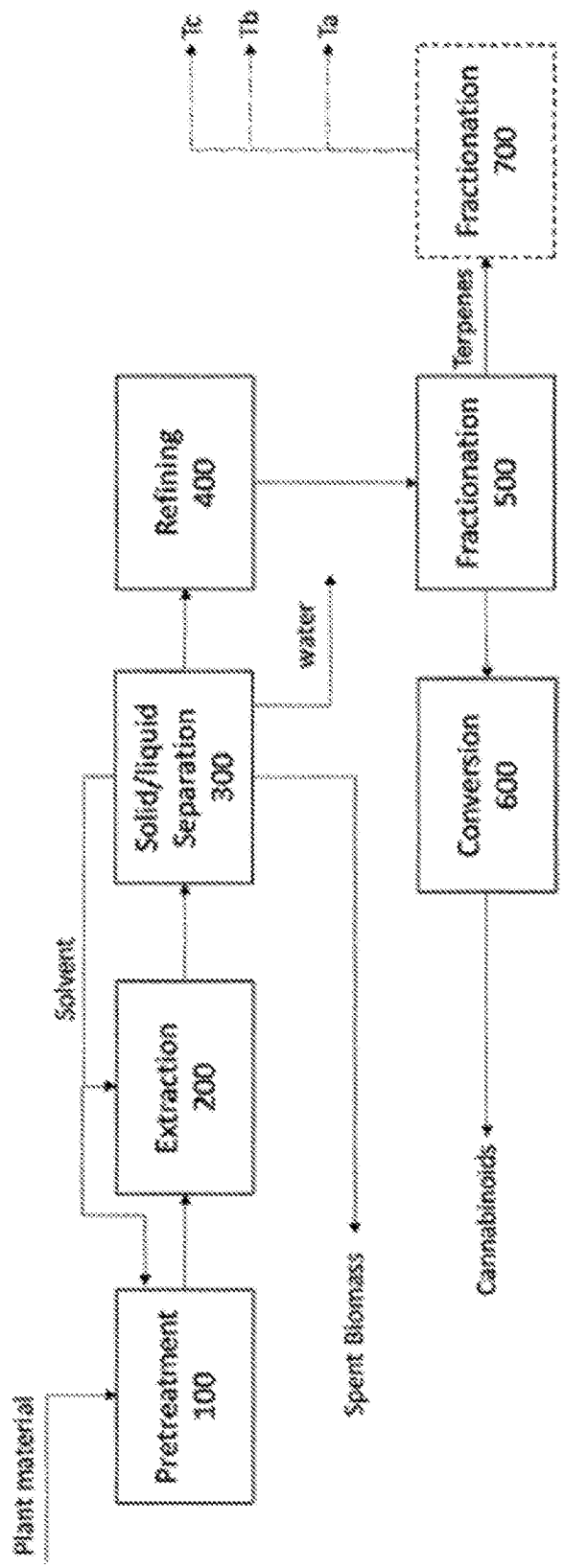
FIG. 1B illustrates a schematic diagram of a process to extract and refine cannabinoids and terpenes from plant material, to provide products enriched with a certain constituent or group of constituents, and to convert cannabinoids to their active form by decarboxylating them.

A schematic for providing fractionated and refined products from plant material is shown in FIG. 1B. In certain aspects, plant material may be pretreated (100) prior to extraction (200). Pretreatment may comprise separating the different parts of the plants, i.e. buds, leaves, stalk, etc., such that each part can be treated separately. Pretreatment may comprise a reduction in plant material size (e.g. mechanical breaking, milling, grinding). Size reduction may be done on the plant material before adding a solvent, during mixing with the solvent or after adding a solvent. The sized plant material may then be extracted in the extraction unit (200). The streams exiting the extraction unit may be separated at the solid/liquid separation unit (300) to provide a stream of solvent loaded with extractives, a stream of water that is directed to waste treatment, and a stream of dried, spent biomass. The loaded solvent can then be refined (400) and fractionated (500) to provide a first stream comprising terpenes and a second stream comprising cannabinoids, mostly still in their carboxylic acid form. The cannabinoids can be converted (600) to their decarboxylated form. In some embodiments, the terpenes may be further fractionated (700) to obtain fractions of terpenes separated by their boiling point range or by other physical properties.

In certain aspects, the plant material is ground, chopped, milled, or sheared such that the average size of the resulting particles is at least about 0.01 mm, 0.1 mm, 1 mm, 10 mm, 100 mm, or 1,000 mm, or more. In some embodiments, the average size of the resulting particles is at most about 1,000 mm, 100 mm, 10 mm, 1 mm, 0.1 mm, 0.01 mm, or less. In some embodiments, the average size of the resulting particles is about 0.01 mm to about 1,000 mm, such as about 0.01 to about 100 mm, about 0.01 to about 10 mm, about 0.05 to about 8 mm, about 0.1 to about 5 mm, or about 0.5 to about 3 mm.

In some aspects, the harvested plant material is chilled prior to extraction to prevent degradation of the plant material. In some aspect, the harvested plant material is kept at a temperature above freezing to prevent cell rupture by forming water crystallites. In some embodiments, the temperature of the harvested plant material prior to extraction is controlled to be higher than about 0° C., such as higher than about 10, 20, 30, 40, or 50° C., or more. In some embodiments, the temperature of the harvested plant material is controlled to be at most about 50° C., such about 40, 35, 30, 25, 20, 15, 12, 10, 9, 8, 7, or 6° C., or less.

In some embodiments, extraction is conducted at temperature of at most about 0° C., −5° C., −10° C., −15° C., −20° C., −25° C., −35° C., −45° C., or less. In some embodiments, extraction is conducted at a temperature of at least about −45° C., −35° C., −25° C., −20° C., −15° C., −10° C., −5° C., 0° C., 10° C., 20° C., or more. In some embodiments, the extraction is conducted at about −25° C. In some embodiments, the solvent is chilled to about −25° C. prior to contacting with the plant material to provide rapid chilling of the plant material by mixing with the cold solvent. In some embodiments, the ratio of solvent to plant material is about 10:1, 15:1, 20:1, 25:1, 30:1, 35:1, 40:1 wt/wt, or more, with respect to the plant materials feed. In some aspects, the solvent is degassed and/or purged with an inert gas.

Figure 2A:
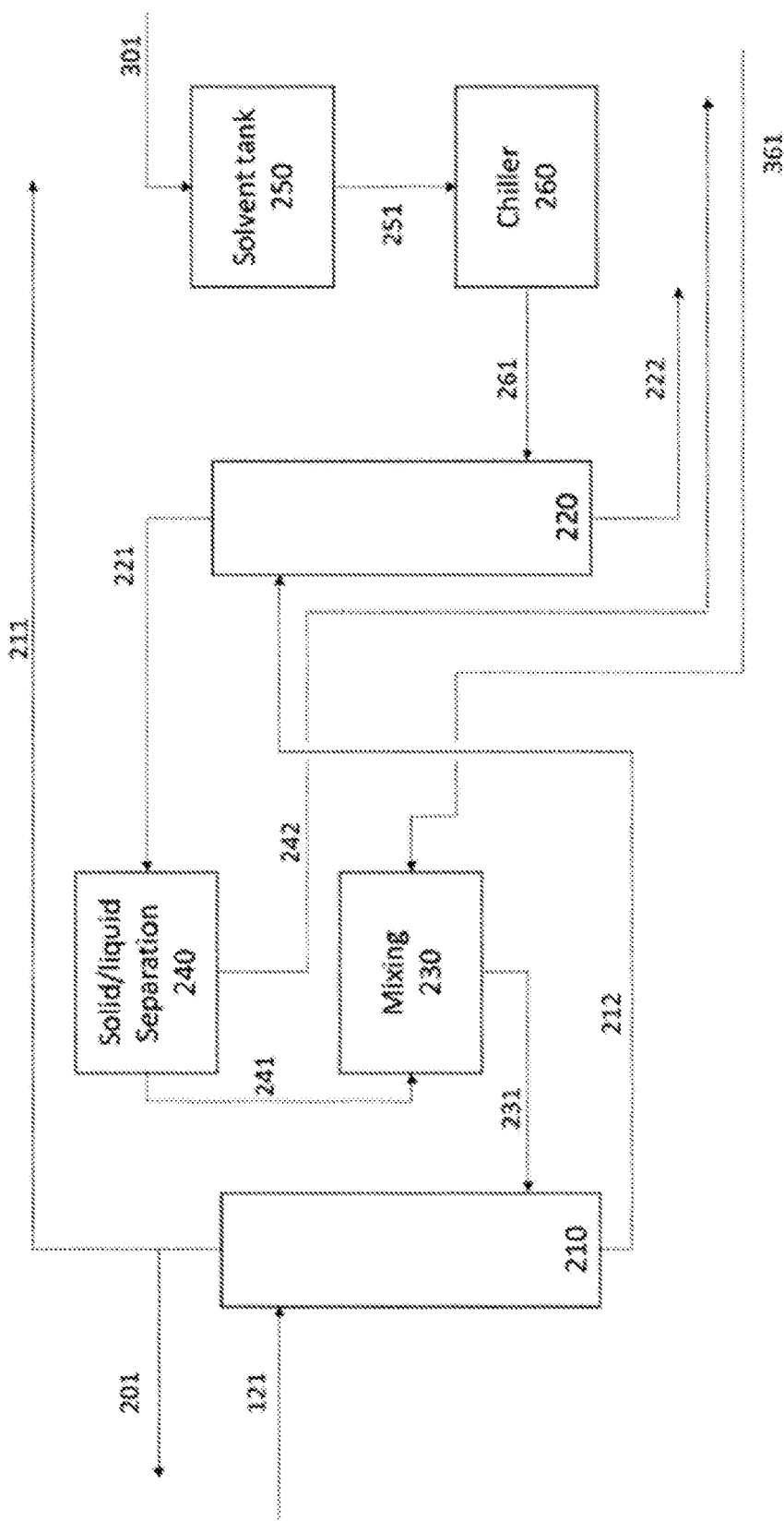
FIG. 2A illustrates a schematic diagram of a process for extracting the constituents of interest from the plant material. The figure demonstrates the configuration utilizing two extracting columns in a counter current set up for clarity. The scheme may be reduced to applying a single column, depending on the number of stages achieved in a single column, or to applying more columns in a counter current mode.

FIG. 2A illustrates extraction unit 200 in more detail. In some embodiments, the extraction unit may comprise at least one extractor 210. In some embodiments, the extraction unit may comprise two extractors 210 and 220. In some embodiments, extractors 210 and 220 may be arranged in a counter current mode. In some embodiments, the extraction system may comprise more than two extractors operating in a counter current mode. In some embodiments, each extractor may comprise a pulse extraction column, wherein such column may be pulsated by inert gas (e.g. nitrogen) wave action or a mechanical pulsator. A properly sized pulsed column (length/diameter) can provide multiple extraction stages. Control of the solid to liquid ratio may allow separation of the extracted solid that precipitates from the loaded solvent which carries the extracted oil at the top. Such extractors are commercially available from multiple extraction equipment suppliers, including, for example, Tenova Advance Technologies, De Dietrich Process Systems, Koch Modular Process Systems and others.

FIG. 2A may demonstrate the configuration utilizing two extracting columns in a counter current set up. FIG. 2A may be readily modified to apply a single column or to apply more than two columns in a counter current mode. In some embodiments, multiple stages of extraction are achieved in a single column. In some embodiments, 1 to 3 columns are applied to achieve sufficient extraction stages. In some embodiments, the overall contact time of the counter-current streams (i.e., the stream of plant material and the stream of extracting solvent) is for at least about 120 minutes, or more. In some embodiments, the overall contact time of the counter-current streams (i.e., the stream of plant material and the stream of extracting solvent) is from about 5 minutes to about 120 minutes, such as from about 10 minutes to about 60 minutes, or about 20 minutes to about 40 minutes.

In some aspects, extraction unit 200 is designed to extract constituents from plant material at high efficiency. In some embodiments, extraction unit 200 is capable of extracting at least 50%, such as at least 60, 70, 80, 90, 95%, or more, of the amount present of each constituent of interest in the plant material. Provided that the different chemical character of multiple extracted constituents, it may be preferred to set the extraction yield at different efficiency values for different components. In some embodiments, the efficiency for each constituent may be altered by changing operating parameters of the pulsed extractor(s), e.g. the in-flow rates of top stream feeding plant material and the bottom stream feeding extracting solvent, the pulse mode and rate, plant material particle size, solvent to solid ratio and temperature of each extractor. Operation parameters of the extractor can be modified to allow for optimal yields.

In some embodiments, extractor 210 can be fed via conduit 121 by fresh slurry, comprising solvent and plant material from mixer 120. The slurry may be fed to the upper part of the pulse extractor, while the solvent may be fed via conduit 231 in a counter current fashion to the lower part of the column, thus forming a highly efficient contact between solvent and plant material for effective extraction. The solvent fed via conduit 231 may comprise low levels of extracted constituents. In some embodiments, the solids can travel down to the bottom of the column and are then pumped via conduit 212 to extractor 220. The liquid can travel to the top end of the pulse extractor, where it is split to stream 201, which is transferred via conduit 201 to the pretreatment mixer to start the process with more fresh feed, while the loaded extractant can be transferred via conduit 211 for product refining.

In some aspects, the slurry exiting the bottom of extractor 210 can be fed to the top of extractor 220. Chilled solvent may be fed in a counter current fashion to the bottom of extractor 220 via conduit 261, which may be connected to chiller 260 that receives recycled solvent from solvent tank 250 via conduit 251. In some embodiments, the solvent exits extractor 220 from the top via conduit 221, any remaining solids are separated at solid/liquid separator 240, the clarified partially loaded solvent may be transferred to mixing 230 via conduit 241, mixed with clarified solvent that is transferred from solid/liquid separation unit 300 via conduit 361, and is fed via conduit 231 to extractor 210. The solids collected at solid/liquid separator 240 may be transferred (242) to solid/liquid separation unit 300 for further recovery of loaded solvent and drying of the spent biomass. In some embodiments, the slurry comprising the extracted plant material exits extractor 220 from the bottom, and may be transferred (222) to solid/liquid separation unit 300 for recovery of the loaded solvent and drying of the spent biomass.

Figure 2B:
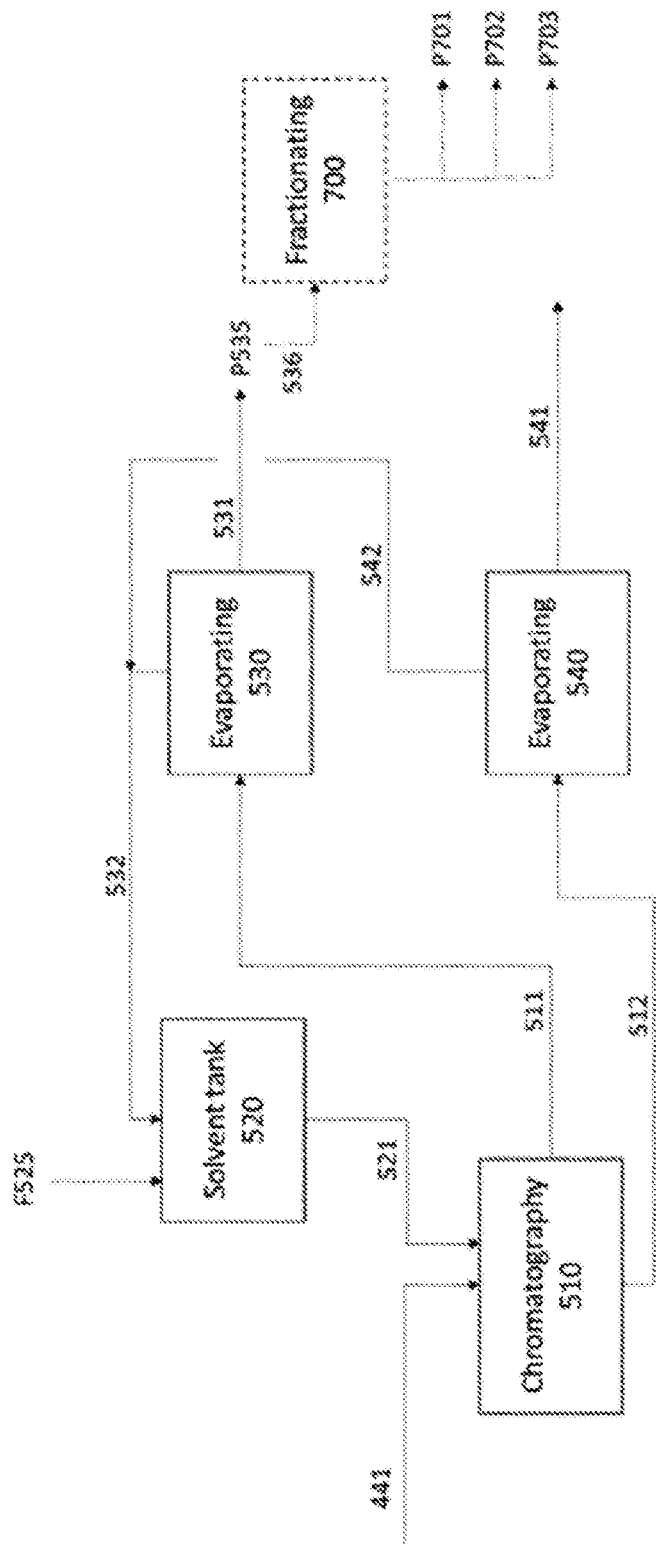
FIG. 2B illustrates a schematic diagram of a process for chromatographic separation of the extract to a stream rich in terpenes and a stream rich in cannabinoids in their carboxylic acid form (e.g. THCA, CBDA), and an exemplary process for further fractionating terpenes to two or more fractions based on their boiling point or on a different physical property.

FIG. 2B illustrates processes applied in fractionating unit 500. In certain aspects, refined oil stream 441 is fractionated in chromatography unit 510 to a fraction rich in terpenes (511) and a fraction rich in cannabinoids (512). In some embodiments, the cannabinoids comprise the carboxylic acid form of cannabinoids, as extracted from the plant material (also referred to as "phytocannabinoids"). In some embodiments, the decarboxylated cannabinoids are also recovered as a third separate fraction to avoid yield loss. In some embodiments, the decarboxylated cannabinoids fraction can be combined with the major phytocannabinoids fraction either before or after decarboxylation.

In certain aspects, chromatography can be carried out by any means. In some embodiments, the chromatography method is a simulated moving bed (SMB) or sequential simulated moving bed (SSMB). Examples of simulated moving bed processes are disclosed, for instance, in U.S. Pat. Nos. 6,379,554; 5,102,553; 6,093,326; and 6,187,204, and examples of sequential simulated moving bed processes can be found in GB 2,240,053; and U.S. Pat. Nos. 4,332,623; 4,379,751; and 4,970,002, each of which is incorporated herein by reference in its entirety. In certain aspects, the resin bed is divided into a series of discrete vessels, each of which sequence through a series of 4 zones (feed, separation, feed/separation/raffinate and safety) connected by a recirculation loop. In some embodiments, a manifold system connects the vessels and directs, in appropriate sequence to (or from) each vessel, each of the four media accommodated by the process. These media can be referred to as feed, eluent, extract and raffinate (e.g., a feed can be refined oil mixture 441, the eluent can be a solvent (521), the extract is a solution enriched with phytocannabinoids (512), one raffinate is a solution enriched with terpenes (511) and a second raffinate is a solution enriched with decarboxylated cannabinoids).

In some embodiments, the chromatographic fractionation can be carried out in a batch mode, a simulated moving bed (SMB) mode or a sequential simulated moving bed (SSMB) mode. The temperature of the chromatographic fractionation is typically in the range of about 20° C. to 90° C., or about 25° C. to 55° C. In some embodiments, the chromatographic fractionation can be carried out with a linear flow rate of at least about 0.25 ml/min, or more. In some embodiments, the chromatographic fractionation can be carried out with a linear flow rate of at least about 100 ml/min, or more. In some embodiments, the chromatographic fractionation can be carried out with a linear flow rate of about 0.25 ml/min to about 100 ml/min in the separation column.

In some embodiments, a method for medium and large-scale chromatographic separations is the sequential simulated moving bed (SSMB) mode, or a simulated moving bed (SMB) mode. Both methods may use a number of columns packed with a suitable sorbent and connected in series. There may be inlet ports for feed and solvent (which may include recycled solvent), and outlet ports for two or more products (or other separated fractions). The injection of the mixture solution to be separated may be periodically switched between the columns along the direction of the liquid flow, thereby simulating continuous motion of the sorbent relative to the ports and to the liquid. The SMB may be a continuous counter current type operation. SSMB is a more advanced method, requiring a sequential operation. Its advantages over SMB and over other older methods include: fewer columns are needed in the SSMB method versus the SMB, hence less resin is required and associated costs of installation are significantly reduced in large systems; the pressure profile is better controlled, facilitating the use of more sensitive resins; and the achievable recovery/purity is higher than obtained with SMB systems.

Fractionation of terpenes and cannabinoids from the refined extracted oil can be achieved using a strong base anion (SBA) resin. In some embodiments, the SBA resin may have a particle size of uniform size. In some embodiments. suitable commercial SBA resins are those typically with a bead size in the 200-400 micron range. The resin can be macroporous or gel type. Such resins can be sourced from several manufacturers, including Finex, Lanxess AG, Purolite, and Dow Chemicals Ltd. In some embodiments, the resin is made neutral by washing it with water or a solvent comprising a low concentration of an acid. In some embodiments, the acid is an organic acid. In some embodiments, the acid is selected from edible organic acids, including for example citric acid, acetic acid, lactic acid, citric acid, malic acid, benzoic acid, ascorbic acid, tartaric acid, oxalic acid, tannic acid, caffeotannic acid, butyric acid, fumaric acid, formic acid, folic acid, adipic acid, alginic acid, galic acid, glutamic acid, sorbic acid, succinic acid, phosphoric acid, and 2-aminoethanesulfonic acid. In some embodiments, the acid is acetic acid, formic acid or citric acid. In some embodiments, the resin is brought to acetic acid form by washing it with the solvent comprising about 0.0001 to about 1 M acetic acid. In some embodiments, the resin is brought to acetic acid form by washing it with the solvent comprising about 0.0001 to about 0.2 M acetic acid.

In some embodiments, the method of fractionating refined *cannabis* extract comprises a sequential simulated moving bed chromatography sequence, wherein the sequence comprises: (1) passing a feed stream comprising *cannabis* extract into an adsorbent, thereby flushing a first raffinate stream comprising terpenes from the adsorbent; (2) flushing an extract stream enriched in cannabinoids relative to the feed stream with a desorbent stream; and (3) recycling the desorbent stream back to the adsorbent. In some embodiments, the adsorbent comprises the solvent, wherein the solvent comprises 0.0001 to 0.2 M acetic acid. In some embodiments, the desorbent comprises the solvent, wherein the solvent comprises an increased amount of acetic acid, such as 0.01 to 1M acetic acid. In some embodiments, the fractionation method further comprises flushing a second raffinate stream comprising decarboxylated cannabinoids from the adsorbent.

In certain aspects, the terpene fraction can be transferred via conduit 511 to evaporation 530. In some embodiments, the fraction is washed with a slightly basic water solution to remove residual acetic acid prior to evaporation. In some embodiments, evaporator 530 comprises a wiped film evaporator. The vapors collected at evaporator 530 top may be condensed and transferred via 532 back to solvent tank 520. In some embodiments, additional amounts of solvent can be added to solvent tank 520 via F525. In some embodiments, the temperature of evaporation 530 is at least about 70° C., or more. In some embodiments, the temperature of evaporation 530 is at most about 20° C., or less. In some embodiments, the temperature of evaporation 530 is from about 20-70° C., such as about 30-60° C. or about 40-50° C. In some embodiments, evaporation is carried out at a temperature of at least about 100° C., or more. In some embodiments, evaporation is carried out at a temperature of at most about 100° C., such as about 90, 80, 70, 60, about 50° C., or less, such that only the solvent is evaporated, while terpenes remain at the bottom. In some embodiments, evaporation is carried out at about 45° C. In some embodiments, at least about 60%, such as about 70, 80, 85, 90, 95, 96, 97, 98, 99%, or more of the solvent is removed by evaporation. In some embodiments, concentrated product stream 531 comprises at least about 70%, such as about 80, 90, 95% wt/wt, or more, refined terpenes. In some embodiments, the concentrated terpene stream comprises at most about 1% wt/wt, such as about 0.9, 0.8, 0.7, 0.6, 0.5, 0.4, or 0.3% wt/wt solvent. In some embodiments, the concentrated terpene product stream comprises at most about 0.1% wt/wt, such as about 0.01 or 0.001% wt/wt water. The concentrated refined terpenes may be collected as product P535. In some embodiments, the terpenes may be transferred via conduit 536 and further fractionated (700) by fractional distillation to produce at least a fraction of low-boiling point terpenes (P701) and a fraction of high-boiling point terpenes (P703). In some embodiments, more than two fractions are produced. In some embodiments, a third fraction of mid-boiling point terpenes (P702) is collected.

In certain aspects, the cannabinoids fraction is transferred via conduit 512 to evaporating 540. In some embodiments, the fraction is washed with water to remove residual acetic acid prior to evaporation. In some embodiments, the acid is neutralized with minimal amounts of base to assist removal from the organic phase. In some embodiments, evaporator 540 comprises a wiped film evaporator. The vapors collected at evaporator 540 top may be condensed and transferred via 542 back to solvent tank 520. In some embodiment, the vapors collected at evaporator 540 top are condensed and transferred to liquid/liquid separation unit 330 to separate water from the solvent. In some embodiments, the temperature of evaporation 530 is at least about 70° C., or more. In some embodiments, the temperature of evaporation 530 is at most about 20° C., or more. In some embodiments, the temperature of evaporation 530 is from about 20-70° C., such as about 30-60° C. or about 40-50° C. In some embodiments, evaporation is carried out at a temperature of at least about 100° C., or more. In some embodiments, evaporation is carried out at a temperature of at most about 100° C., such as about 90, 80, 70, 60, about 50° C., or less, such that only the solvent is evaporated, while terpenes remain at the bottom. In some embodiments, evaporation is carried out at about 45° C. In some embodiments, at least about 60%, such as about 70, 80, 85, 90, 95, 96, 97, 98, 99%, or more of the solvent is removed by evaporation. In some embodiments, the concentrated product stream comprises at least about 70% wt/wt, such as about 80, 90 or even more than 95% wt/wt refined cannabinoids. The concentrated refined cannabinoids may be transferred via conduit 541 to converting unit 600.

Figure 6A:
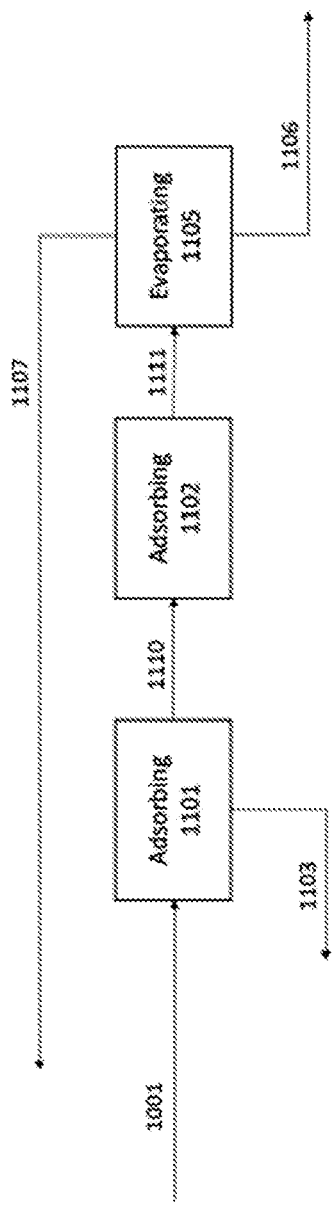
FIG. 6A illustrates a schematic diagram of a process unit for a first refining of the loaded solvent comprising extracted constituents to provide a first refined oil.
Figure 6B:
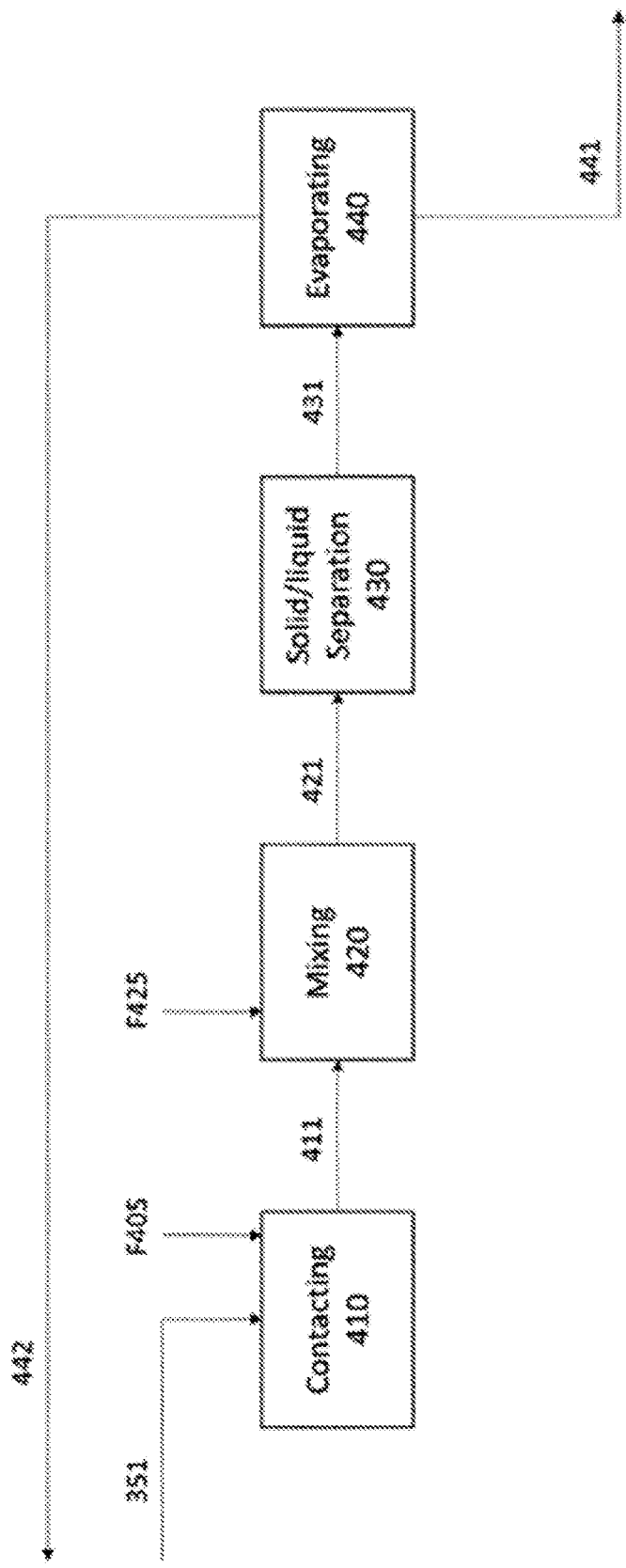
FIG. 6B illustrates a schematic diagram of a processes for refining the extract stream.

FIG. 6B illustrates processes applied in refining unit 400. In certain aspects, unit 400 comprises contacting 410 and mixing 420, where the concentrated product stream is contacted with absorbing agents that are capable of removing residues of impurities, color bodies and the like, followed by solid/liquid separation 430 to remove the loaded absorbing agents and recover refined product stream 431. In some embodiments, the refined product stream is colorless, or substantially colorless. In some aspects, the refining processes comprise a bleaching process, wherein the bleaching is part of the refining process of edible oils and fats, designed to remove contaminants which adversely impact the appearance or performance of these oils (see, e.g., U.S. Pat. No. 6,033,706 and WO 1996/036684). The primary object of bleaching of oil is to remove major portions of colored substances present. In some embodiments, alkaline or acid natural clays are used. In some embodiments, acid-activated clays are used. In some aspects, the clays, also referred to as "bleaching earth", tend to efficiently absorb color components. In some embodiments, bleaching earth not only removes color pigments but also trace metals and any residual soaps remaining from the neutralization process. The removing of trace metals may be important as such components act as catalysts for free radicals. Normal bleaching conditions can be 0.5 to 2% by weight activated bleaching earth, based on the weight of the oil. In some embodiments, such bleaching comprises contacting the oils with clays, preferably "acid activated" clays (i.e. clays that have been washed with acid). Bleaching processes can remove some of the color, residual chlorophyll, residual soaps, gums and waxes, trace metal, various oxidation products and peroxides.

In some embodiments, contacting 410 comprises contacting concentrated product stream 351 and F405 comprising activated carbon, preferably acid-washed activated carbon, wherein the contacting may be done by stirring and filtration or by flowing the product stream through a loaded column. In some embodiments, the ratio of activated carbon to extracted oil is about 0.01-1% wt/wt, such as 0.05-0.5% wt/wt. In some embodiments, contacting is conducted at about 30, 35, 40, 45, 50, 55, or 60° C. In some embodiments, contacting is conducted at about 30-60° C. In some embodiments, mixing 420 comprises mixing of product stream 411 and F425 comprising clays. In some embodiments, the clays comprise Fuller's Earth, Kaolin clay, bentonite, diatomaceous earth, or mixtures thereof. In some embodiments, the clay or clays are acid activated or partially activated by washing them with a suitable acid. In some embodiments, the ratio of clay mixture to extracted oil is about 0.01-1% wt/wt, such as about 0.05-0.5% wt/wt. In some embodiments, contacting is conducted at about 30, 35, 40, 45, 50, 55, or 60° C. In some embodiments, contacting is conducted at about 30-60° C. In some embodiments, the contacting is conducted under reduced pressure, e.g. 50-350 mm Hg, 50-125 mm Hg, or 300-760 mm Hg. In some embodiments, solid/liquid separation 430 removes at least a portion of solids from stream 421 by filtration, centrifugation or any other industrial method for the removal of suspended solids from liquid. In some embodiments, solid/liquid separation 430 removes all solids from stream 421 by filtration, centrifugation or any other industrial method for the removal of suspended solids from liquid. In some embodiments, the refined product is transferred via conduit 431 to evaporating 440.

In certain aspects, evaporator 440 comprises a wiped film evaporator (WFE). The vapors collected at evaporator 440 top are condensed and transferred back to liquid/liquid separation 330 via conduit 442. In some embodiments, evaporator 440 transfers oil stream 441 to fractionating unit 500 via conduit 441. In some embodiments, the temperature of evaporation 530 is at least about 70° C., or more. In some embodiments, the temperature of evaporation 530 is at most about 20° C., or less. In some embodiments, the temperature of evaporation 530 is from about 20-70° C., such as about 30-60° C. or about 40-50° C. In some embodiments, evaporation is carried out at a temperature of at least about 100° C., or more. In some embodiments, evaporation is carried out at a temperature of at most about 100° C., such as about 90, 80, 70, 60, about 50° C., or less, such that only the solvent is evaporated, while terpenes remain at the bottom. In some embodiments, evaporation is carried out at about 45° C. In some embodiments, at least about 60%, such as about 70, 80, 85, 90, 95, 96, 97, 98, 99%, or more of the solvent is removed by evaporation. In some embodiments, the viscosity of the concentrated solution is less than 5 mPa·s, such as less than 3, 2, or 1 mPa·s at 25° C. In some embodiments, the concentrated product stream comprises more than 30% wt/wt, such as more than 40, 50, 60, 70, 80, 90, or even more than 95% wt/wt extracted oil.

Figure 8A:
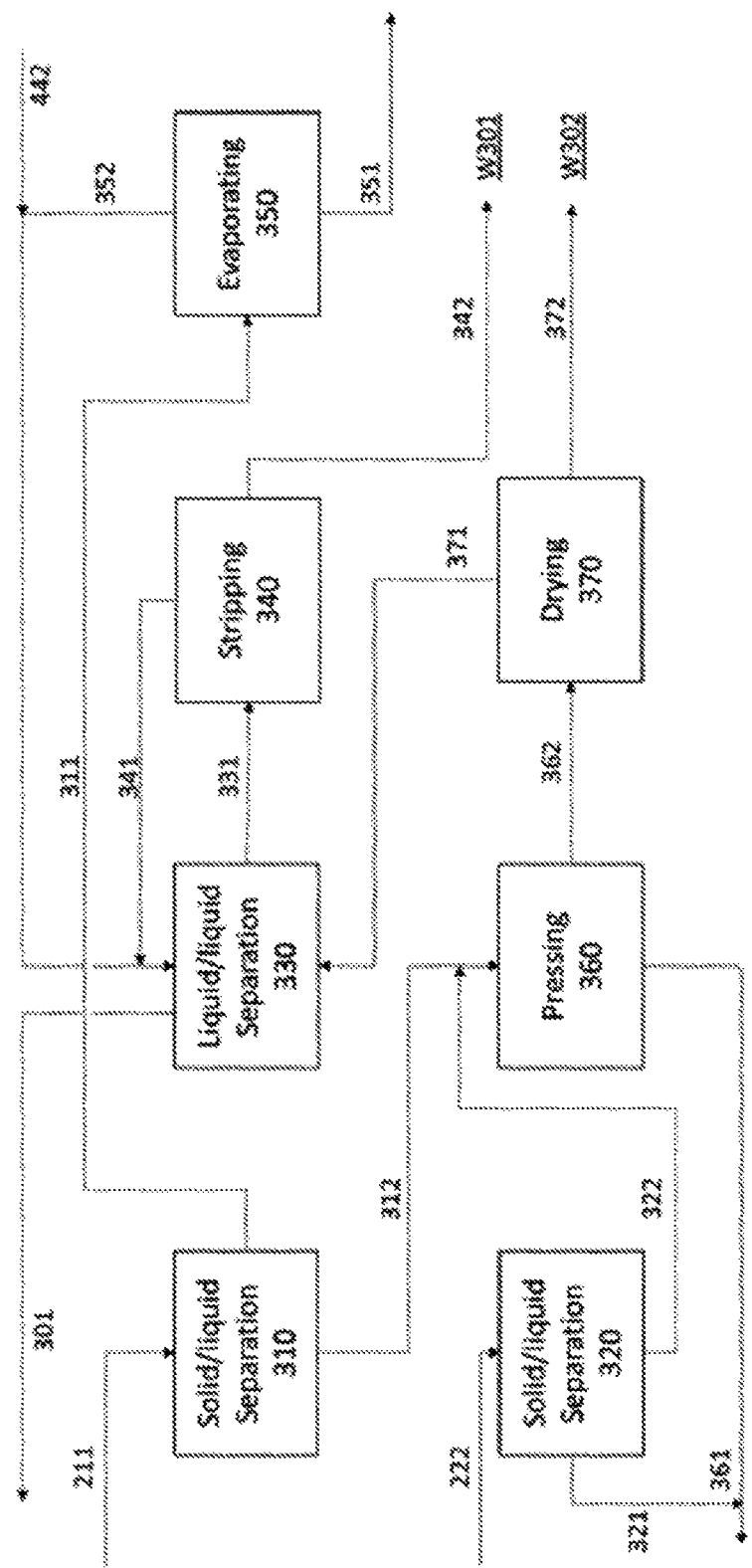
FIG. 8A illustrates a schematic diagram of a process for separating spent biomass and waste water from the solvent and recovering the solvent.

FIG. 8A illustrates various parts of solid/liquid separation unit 300. In some aspects, solid/liquid separation unit 300 is optimized to recover to maximum yield of the product stream, while maintaining temperatures at all stages at most about 100° C., such as about 90, 80, 70, 60, 50° C., or less to minimize product degradation. In some aspects, solid/liquid separation unit 300 is optimized to minimize solvent loss. In some embodiments, solvent loss of the entire extraction operation is at most about 10%, such as about 9, 8, 7, 6, 5, 4, 3, 2, 1, 0.1%, or less of the total solvent capacity of the entire operation. In some aspects, solid/liquid separation unit 300 is optimized to separate water from the solvent at minimal energy costs. In some embodiments, the energy requirement is at most about 2.5 times less than removing the same amount of water by direct evaporation.

In some aspects, solid/liquid separator 310 receives loaded solvent from the top of extractor 210 via conduit 211 and removes any carryover solids. The solids are transferred via conduit 312 to press 360. In some embodiments, solid/liquid separator 320 receives the slurry from the bottom of extractor 220 via conduit 222 and separates solids from liquids. The solids can be transferred via conduit 322 to press 360. The liquid can be recycled via conduit 321 to mixing 230. Solid/liquid separators (240, 310 and 320) may be any equipment suitable to separate solids from liquids, including, but not limited to, filter, screen, centrifuge, hydrocyclone or any other industrial separation equipment that can separate the spent biomass from the solvent. In some embodiments, the solid/liquid separators comprise a screen capable of letting the solvent through and holding the spent biomass particles. In some embodiments, the solid/liquid separators remove at least 30%, such as at least 40, 50, 60, 70, 80%, or more of the liquids. Press 360 receives all concentrated slurries from the solid/liquid separators. This combined slurry may comprise spent biomass and the remaining loaded solvent. Press 360 further may recover loaded solvent that is transferred to mixing 230 via conduit 361, while the pressed cake is transferred via 362 to drying 370. The vapors released from the spent biomass at drier 370, comprising solvent and water, may be collected, condensed and transferred to liquid/liquid separator 330 via conduit 371. In some embodiments, drier 370 may be a paddle drier. Such driers are commercially available by multiple suppliers.

In certain aspects, the dry spent biomass (W302) is transferred via conduit 372 to a solid waste treatment facility. In some embodiments, dry spent biomass is substantially free of active constituents. In some embodiments, the residual level of each constituent is at most about 20% wt/wt, such as less than 15, 10, 9, 8, 7, 6, 5, 4, 3, 2, 1, 0.1% wt/wt, or less, of the original concentration. In some aspects, when *cannabis* is the plant being extracted, the residual amount of active constituents can be low enough to discard the spent biomass as unregulated dry biomass.

In some aspects, liquid/liquid separator 330 receives the condensed vapors from spent biomass drier 370, as well as from evaporator 350 and stripper 340 via conduits 352 and 341, respectively. In some embodiments, liquid/liquid separator 330 comprises a stationary decanter, a centrifuge, or any appropriate device for separating an organic solvent phase from an aqueous phase. In some embodiments, separator 330 is a decanter. In some embodiments, separator 330 transfers recovered solvent via conduit 301 to solvent tank 250. In some embodiments, the amount of residual water in solvent stream 301 is at most about 10% wt/wt, such about 9, 8, 7, 6, 5, 4, 3% wt/wt, or less. In some embodiments, the amount of water in solvent stream is about 2-4% wt/wt. In some embodiments, separator 330 transfers separated water 331 to stripper 340. In some embodiments, the water stream comprises at most about 30% wt/wt solvent, such about 25, 20, 15, 10, 9, 8, 7, 6%, or less wt/wt solvent. In some embodiments, stripper 340 comprises a distillation unit, suitable to distill the solvent/water azeotrope at the top, while water remains at the bottom of the distillation unit. In some embodiments, the stripper comprises a packed column distillation unit. The top distillate of stripper 340 may be transferred by conduit 341 back to liquid/liquid separator 330. In some embodiments, the temperature of the distillation top is controlled at about 40-95° C., such as about 50-85° C. or about 65-75° C. In some embodiments, the temperature of the distillation top is about 70° C. In some embodiments, the bottom stream comprises at most about 2% wt/wt solvent, such as about 1, 0.1, 0.05% wt/wt, or less solvent. In some embodiments, bottom distillates W301 of stripper 340 are transferred by conduit 342 to a waste water treatment facility.

In some embodiments, the clarified stream of solvent comprising extracted constituents (311) is transferred to evaporator 350. Stream 311 may be characterized as having a light-yellow color. Stream 311 may comprise less than about 2% wt/wt chlorophyll, such as less than about 1, 0.5, 0.1, 0.05, 0.01% wt/wt, or less chlorophyll. Stream 311 may comprise less than about 2% wt/wt wax or gums, such as less than 1, 0.5, 0.1, 0.05, 0.01%, or less wt/wt wax or gums.

In certain aspects, evaporator 350 comprises at least a single effect evaporator. In some embodiments, evaporator 350 comprises a single or double effect evaporator. Such evaporators may be associated with reduced investment cost and require significantly less energy and cost of operation compared to other industrial evaporators, particularly compared to wiped film evaporators. The vapors collected at evaporator 350 top may be condensed and transferred back to liquid/liquid separation 330 via conduit 352. In some embodiments, evaporation is carried out at temperature of at most about 100° C., such as about 90, 80, 70, 60, 50° C., or less in the first effect, such that degradation of extracted excipients is minimized. In some embodiments, at most about 90%, such as about 80, 70, 60, 50, 40, or 30% of the solvent and at least about 50%, such as at least about 60, 70, 80, 90, 95, 99%, or more of the water are removed by evaporation. In some embodiments, solvent and water are removed to the degree that the concentrated solution comprises one phase. In some embodiments, the remaining water after evaporation is at most about 20% wt/wt, such as about 15, 10, 9, 8, 7, 6, 5, 4, 3, 2, or 1% wt/wt, or less when calculated as water/(solvent+water). In a preferred embodiment, stream 351 comprises most about 1% wt/wt, such as about 0.5, 0.4, 0.3, 0.2, 0.1%, or less wt/wt water. In some embodiments, the viscosity of the concentrated solution is at most about 5 mPa·s, such as at most about 3, 2, 1 mPa·s, or less at 25° C. In some embodiments, the concentrated product stream comprises at least about 30% wt/wt, such as 40, 50, 60, 70, 80, 90% wt/wt, or more extracted oil. In some embodiments, the concentrated product stream is transferred from evaporator 350 via conduit 351 to refining unit 400.

Figure 9:
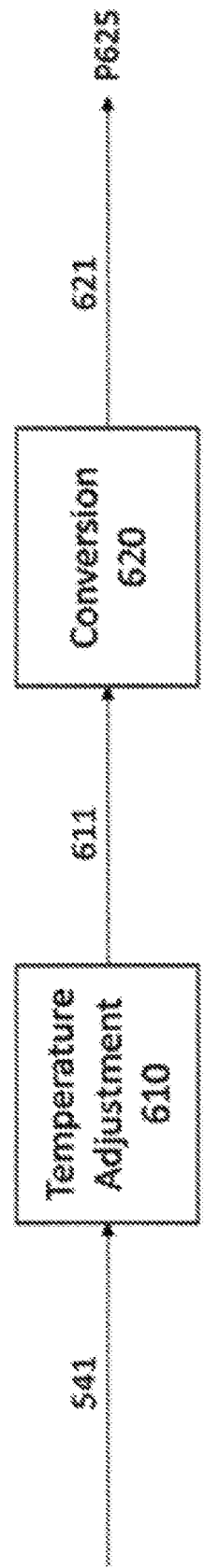
FIG. 9 illustrates a schematic diagram of a process for the conversion of cannabinoids from their carboxylic acid form to the decarboxylated form (e.g. THC, CBD).

FIG. 9 illustrates processes applied in converting unit 600. The temperature of concentrated refined cannabinoid stream 541 may be adjusted in temperature adjustment unit 610, then transferred via conduit 611 to conversion unit 620. The decarboxylated refined cannabinoid stream may be collected as product P625 via conduit 621.

In certain aspects, refined cannabinoids may be contacted with an acid, a base and water at increased temperature. In some embodiments, the acid or the base is dissolved in the aqueous phase. In some embodiments, the acid or the base is provided by contacting with a macroporous strongly acidic resin. In some embodiments, the macroporous strongly acidic resin is Amberlyst 15 (Dow Chemicals). In some embodiments, decarboxylation is carried out under inert gas pressure. In some embodiments, decarboxylation is carried out under vacuum. In some embodiments, decarboxylation is accelerated by heating the solution to at least 40° C., such as at least 50, 60, 70, 80, 90° C., or more. In some embodiments, the temperature of decarboxylation is at most about 150° C., such as about 140, 130, 120, 110, 100° C., or less.

In certain aspects, the refined and fractionated cannabinoid fraction is decarboxylated by heating without additional agents. The refined and fractionated extract can be subjected to heat, optionally under inert gas, optionally under reduced or increased pressure to cause decarboxylation. Since terpenes may have already been separated from this fraction, no loss of terpenes can be expected from such heat treatment. This is a clear advantage of the process over the more traditional processes for decarboxylating phytocannabinoids by heat treatment, as it allows for obtaining high yield of terpenes along with fine tuning of the decarboxylation conditions. In some embodiments, the heating is conducted at a temperature of about 70 to 150° C., such as about 80 to 140° C. or about 110 to 130° C., for a period of about 2 minutes to about 5 hours.

Figure 1C:
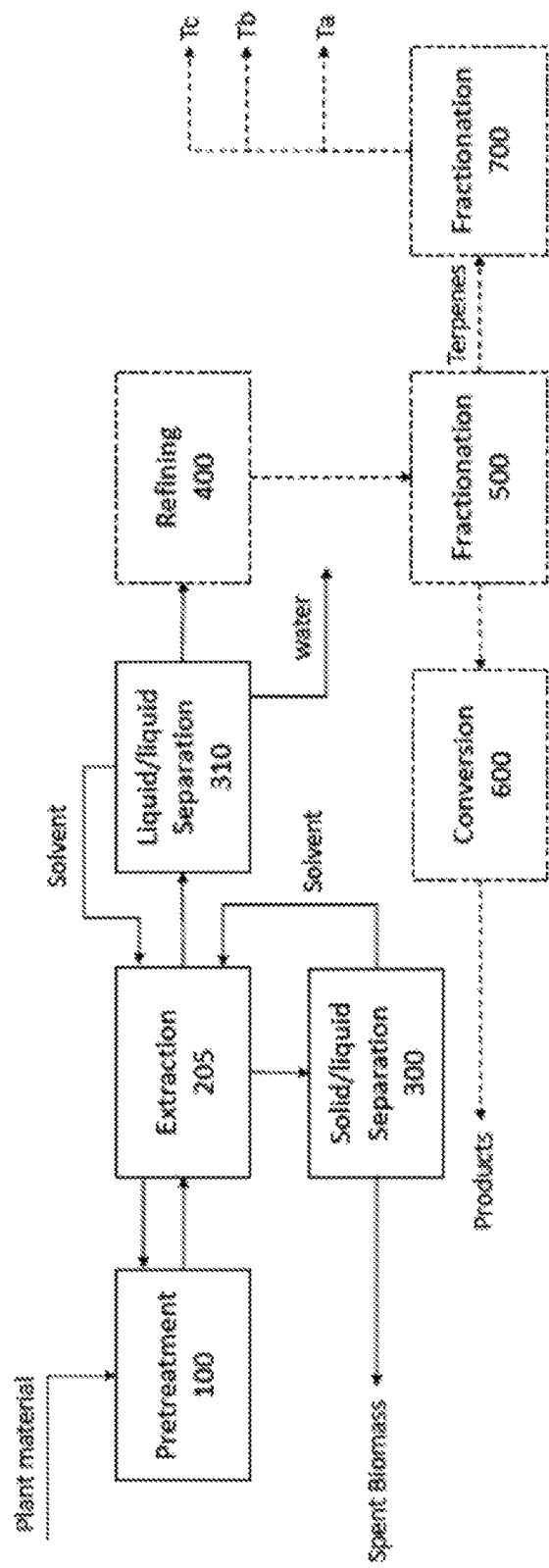
FIG. 1C illustrates a schematic diagram of a process to extract herbal extractives from plant material. The scheme also shows optional downstream process steps for refining, fractionating and converting the crude product of extraction.

A schematic continuous process for providing extracted products from plant material is shown in FIG. 1C. In some embodiments, plant material may be pretreated (100) prior to extraction (205). Pretreatment may comprise separating the different parts of the plants, i.e. buds, leaves, stalk, etc., such that each part can be treated separately. Pretreatment may comprise a reduction in plant material size (e.g. mechanical breaking, milling, grinding). Size reduction may be done on the plant material before adding a solvent, during mixing with the solvent or after adding a solvent. The sized plant material can then extracted in the extraction unit (205) to provide a liquid stream of solvent loaded with extractives and a slurry stream comprising liquid and extracted biomass.

In certain aspects, the liquid stream is separated at the liquid/liquid separation unit 310 to provide a liquid stream comprising solvent that is returned to extraction unit 205, and an aqueous stream comprising solvent. The aqueous stream may be stripped by distillation of solvent residues and may be directed to a waste water treatment plant. The slurry stream may be separated at the solid/liquid separation unit (300) to provide a stream of solvent that can be partially loaded with extractives that may be returned to the extraction unit 205 and a stream of dried, spent biomass.

In certain aspects, solvent and water are removed from the loaded extractant stream by evaporation to provide a crude, concentrated extractives oil product. In some embodiments, before solvent removal, the separated solvent stream is contacted with activated carbon (GAC or PAC).

In certain aspects, the crude product may be further treated by refining (400) and fractionating (500) to provide a first stream comprising terpenes and a second stream comprising cannabinoids. In some embodiments, the cannabinoids may be converted (600) to their decarboxylated form. In some embodiments, the terpenes may be further fractionated (700) to obtain fractions of terpenes separated by their boiling point range or by other physical properties.

Figure 5A:
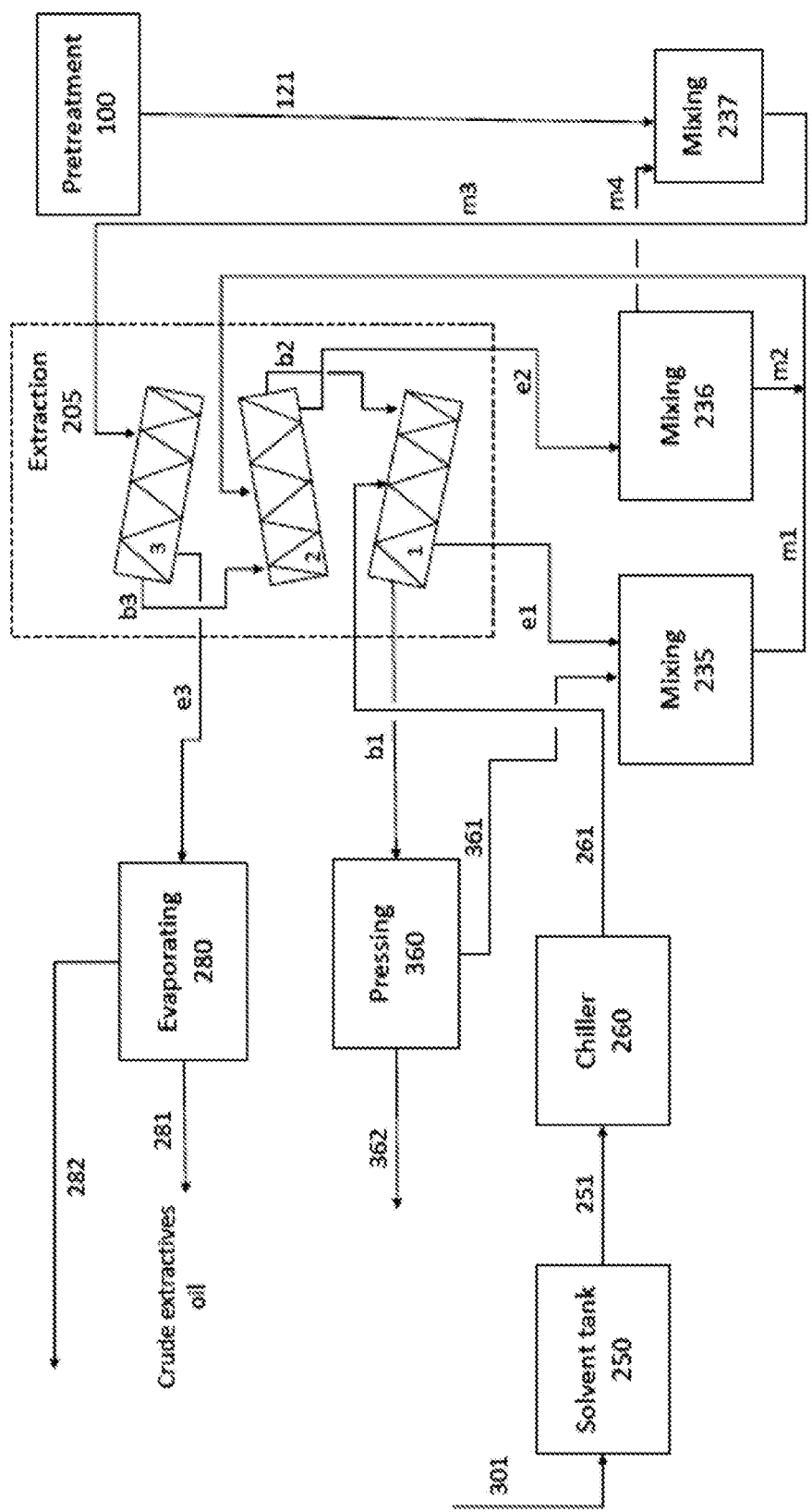
FIG. 5A illustrates a schematic diagram of a continuous process for extracting the constituents of interest from the plant material. The figure shows the configuration of an extractor comprising three extraction conveyor screw units, and three mixing units, wherein each unit operates in a co-current mode, while the flows between different units is in counter-current mode. The scheme presents three units. More units may be added in series or in parallel to any of the three conveyor screw units, to optimize extraction.

FIG. 5A illustrates extraction unit 205 in more detail. U.S. Pat. No. 4,617,177 discloses a system for the solid/liquid extraction of in particular vegetable raw materials, such as oilseeds and oil-yielding plants, with low-boiling solvents, such as gasoline and the like, in continuous co-current manner. The equipment, which is also to be regarded as the actual extraction unit, is formed by the combination of a conveyor screw having a screw flight pitch which widens in the direction of the transport of material, and a screen such as wedge wire provided at a short distance upstream of the discharge of the extracted material. The equipment is closed on all sides and is vapor tight. It can be employed in the solvent extraction of oilseeds and oil-yielding plants, the glyceride constituents (oils and fats) extracted from the predominantly solid raw material passing into the liquid phase, the so-called miscella. It is particularly suitable for extracting oil-yielding plants in industrial operation where the extracting solvent has a low boiling point, in the ranges of 60°-100° C. These relatively low-boiling extracting agents pose stringent requirements on the constructional expense on both the equipment and the processes. The expense relates to the safety of the maintenance and operating personnel coming into contact with the solvents and to optimum operational control, so that the extraction remains within economically acceptable limits.

In certain aspects, extraction unit 205 is formed by the combination of conveyor screws and mixing tanks that provide a simple way to contact effectively the pretreated biomass with the extracting solvent. In some embodiments, the design of the system allows for different ratios of liquid to solvent in its different subunits by means of pumps and buffer volume in the mixing tanks. For clarity, FIG. 5A depicts three conveyor screw units, wherein each unit is operated at co-current mode, while the flow of solvent and biomass is in counter-current mode between the different units. The conveyor screws may be mounted in an alternating inclined arrangement, such that flow from conveyor to conveyor can be driven by gravitation. In some embodiments, the conveyor screw may have a screw flight pitch that widens in the direction of the transport of material. In some embodiments, the screw flight pitch is the same along its whole length, thus reducing the capital expenditure to construct the system.

In some embodiments, flows of slurries comprising biomass from one extractor to the next is gravitational. In some embodiments, flow of biomass slurry from the mixing tanks to the extractors is by means of suitable pumps, thus allowing control of flow rates. The solids discharge end of each conveyor may be fitted with a wedge wire screen, which may allow liquid to pass through while the slurry remains on top of the screen. In some embodiments, the conveyors provide solid/liquid separation at the extraction unit. The conveyor screws may be inclined at a determined angle to control the residence time of material in each conveyor and screening area. The system can be installed such that this angle may be modified.

In some embodiments, extractor 205, mixing tanks 235, 236, 237 and other parts of the system are jacketed for thermal insulation, such that the extraction is conducted at low temperature, such as at most 0° C., −5° C., −10° C., −15° C., −20° C., −25° C., −35° C., −45° C., or less. In some embodiments, the extraction is conducted at about −25° C. In some embodiments, the extraction system comprises a chiller (260), with capacity to cool down the freshly regenerated solvent to the designated temperature while feeding into extractor 205(1) via conduit 261. In some embodiments, extractor 205, mixing tanks 235, 236, 237 and other parts of the system are jacketed for thermal insulation. In some embodiments, the extraction may be conducted at a temperature of about −25° C. to +35° C., −5° C. to +25° C., or +5° C. to +25° C.

Referring to FIG. 5A, pretreated biomass can be mixed in mixing tank 237 with an overflow stream of mixing tank 236 (m4) comprising partially loaded solvent, to provide slurry stream (m3), which is fed into the uppermost conveyor, extractor 205(3). Biomass and liquid may be conveyed up along extractor 205(3), where the initial extraction of fresh biomass takes place into a partially loaded extractant. The loaded solvent may be separated on the screen to provide a through stream comprising the fully loaded extracted stream (e3), and a retained stream of partially extracted stream comprising biomass (b3), which is transferred as feed to the middle conveyor, extractor 205(2). Additional volumes of extracting solvents can be fed into extractor 205(2) by a stream comprising low levels of extractives from mixing tank 235 (m1). In some embodiments, more volumes of extracted solvent comprising low levels of extractives are fed into this stream from mixing tank 236 (m2). In some embodiments, extractor 205(2) is where much of the extraction process occurs, thus it is advantageous to have greater amounts liquid available at this stage. Biomass and liquid may be conveyed up extractor 205(2), and may be separated to a partially loaded liquid stream (e2), which is transferred to mixing tank 236, while the biomass comprising steam (b2) can be transferred to lowermost conveyor, extractor 205(1). The extracted biomass may then be washed in extractor 205(1), which may also be fed with freshly regenerated chilled solvent (261), which may be essentially free of extractives and therefore may have a strong capacity to remove the low levels of extractives remaining with the biomass at that stage. Biomass and liquid may be conveyed up extractor 205(1), and can be separated to a partially loaded extractant at low level of extractives (e1), which may be transferred to mixing tank 235, and a spent biomass slurry that (b1), which is transferred to solid/liquid separation 310 for recovery of the loaded solvent and drying of the spent biomass.

In some aspects, extractor 205(2) comprises more than one conveyor. In some embodiments, additional conveyor(s) are arranged in parallel or in series with respect to conveyor 2 as depicted in FIG. 5A. In some embodiments, the additional conveyor or conveyors are arranged in a countercurrent mode with respect to conveyor 2.

In some aspects, wetting, extraction and solid/liquid separation in each conveyor is controlled by physical attributes of the screw and the wire screen. In some aspects, wetting extraction and solid/liquid separation is optimized by operational parameters of the conveyor screws. In some embodiments, the inclination angle can be controlled to at least about 5, 10, 20, 30, 40, 50, 60, or more degrees with respect to the horizontal. In some embodiments, at the designated angle of inclination, the internal conveyor volume is flooded from the leading edge of the drainage screen to the biomass inlet of the conveyor. In some embodiments, the flight pitch is the same along the conveyor. In some embodiments, the flight pitch is varied along the conveyor to optimize for initial wetting and solvent penetration in the flooded section and drainage in the screening section. In some embodiments, the rotation speed of the screw may be about 0.15-3.0 rpm. In some embodiments, the overall residence time of biomass in extractor 205 is controlled from about 1 and 60 minutes, 5 and 30 minutes, or 10 and 20 minutes.

In certain aspects, the ratio of liquid to solid in each section of extraction 205 is different. In some embodiments, the liquid to solid (L/S) ratio in extractor 205(1) and in extractor 205(3) is controlled at the range of about 1-20 weight parts of liquid to solid. In some embodiments, the L/S ratio in extractor 205(2) is controlled at the range of about 1-60 weight parts liquid to solid. In some embodiments, solvent and/or water can be easily added into the process to conveyor 1 to mixer tank 235.

In certain aspects, extraction unit 205 is designed to extract constituents from plant material at high efficiency. In some embodiments, extraction unit 205 is capable of extracting at least 50, 60, 70, 80, 90, 95%, or more of the amount present of each constituent of interest in the plant material. In some embodiments, it may be preferred to set the extraction yield at different efficiency values for different components. Operation parameters of the extractor can be easily modified to allow for optimal yields.

In certain aspects, the fully loaded extract stream (e3) comprises liquids only. In some embodiments, solvent and water are partially evaporated from this stream at evaporator 280 to provide crude, concentrated extractive oil (281). In some embodiments, evaporation is conducted at temperatures of at most 100° C., such as below 90, 80, 70, 60, 50° C., or less to minimize product degradation. In some embodiments, evaporation is conducted at about 55° C. In some embodiments, the crude concentrated oil comprises at most about 5, 4, 3, 2, 1, 0.5, 0.1%, or less solvent. In some embodiments, the crude concentrated oil comprises at most 1, 0.5, 0.1, 0.05, 0.01%, or less water. In some embodiments, the solution of oil, solvent and water are controlled by evaporation to have a viscosity of about 0.5 to 25 cPs at 25° C. In some aspects, the solvent to oil ratio is from about 1 to 20 wt/wt. In some embodiments, the crude oil may be further refined (400). The refined oil may be fractionated (500).

In some embodiments, prior to evaporating 280, stream e3, comprising crude oil with the solvent, the solution is contacted with activated carbon by flowing the stream through at least one GAC column. In some embodiments, the ratio of solvent to crude oil in stream e3 is from about 100:1 to about 1:1. In some embodiments, the ratio of solvent to crude oil in stream e3 is about 70:1 to 30:1. In some embodiments, the ratio of solvent to crude oil in stream e3 is about 10:1. In some embodiments, the solution is controlled by evaporation to have a viscosity of about 0.5 to 25 cPs at 25° C. In some embodiments, contacting with the GAC is done at about 10 to 60° C., 30 to 55° C., or about 40 to 50° C.

Figure 8B:
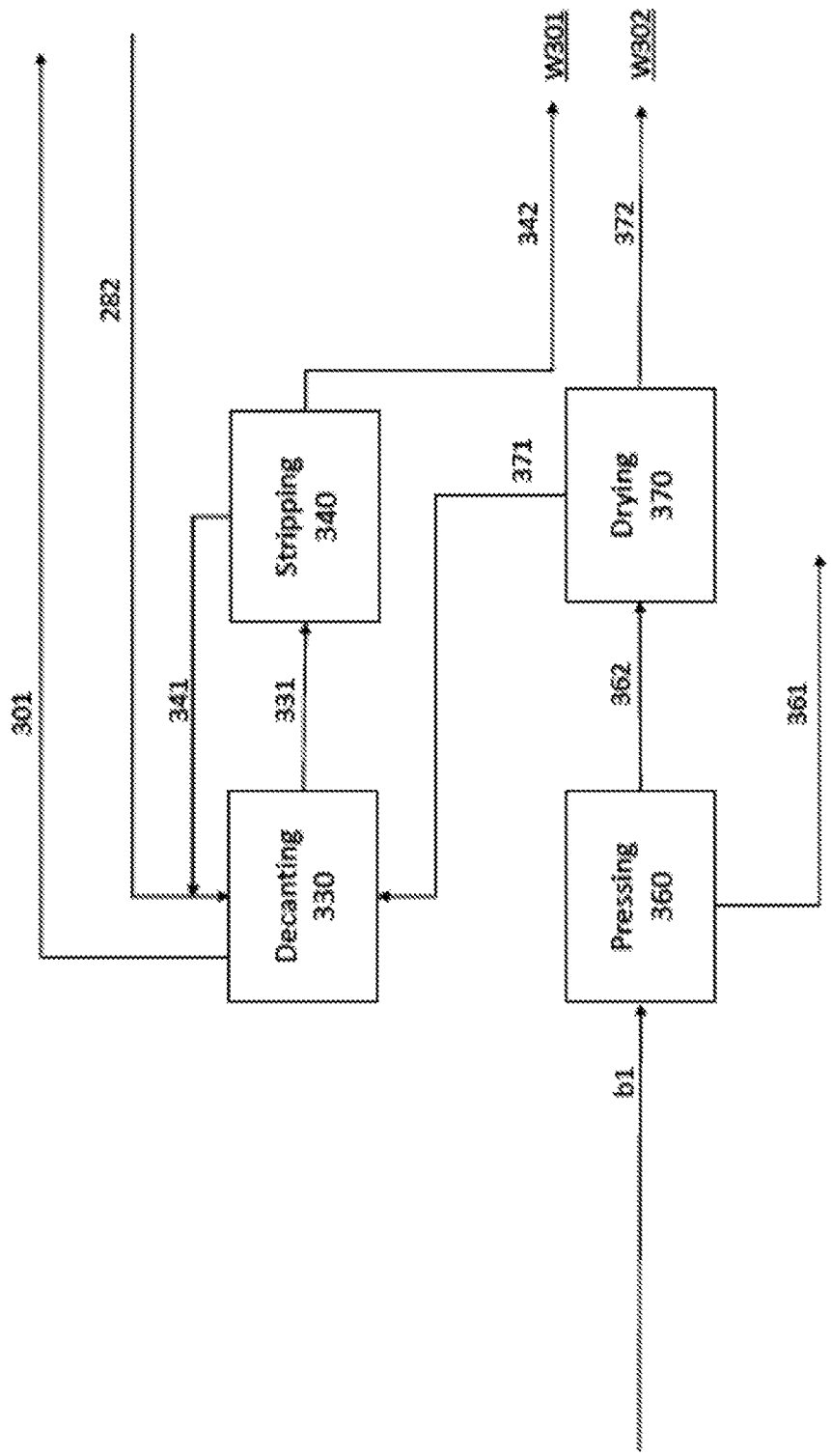
FIG. 8B illustrates a schematic diagram of a continuous process for separating spent biomass and waste water from the solvent and for recovering the solvent.

FIG. 8B illustrates in more detail various parts of solid/liquid separation units 300. The spent biomass slurry may be transferred directly via conduit b1 to press 360. In some embodiments, the spent biomass slurry comprises about 5-15% wt/wt solids. In some embodiments, press 360 recovers loaded solvent that is transferred to mixing 235 via conduit 361, while the concentrated solids stream is transferred via 362 to drying 370. In some embodiments, the press is a screw press (e.g., Vincent Corporation CP-4 press). In some embodiments, the concentrated solids stream comprises about 50-80% wt/wt solids. The vapors released from the spent biomass at dryer 370, comprising solvent and water, may be collected, condensed and transferred to liquid/liquid separator 330 via conduit 371. In some embodiments, dryer 370 is a paddle dryer. Such dryers are commercially available from multiple suppliers, for example, GEA model Rosinaire Paddle dryer. In some embodiments, other spent solid materials used in processing and refining of the extractives (e.g., used PAC, GAC, or other adsorbent materials, such as clays and minerals) can be combined in the paddled dryer with the spent biomass and dried together. In some embodiments, the dried spent solids may be used as solid fuel.

In certain aspects, liquid/liquid separator 330 receives the condensed vapors from spent biomass dryer 370, as well as from evaporator 280 and stripper 340 via conduits 371, 341 and 282, respectively. In some embodiments, liquid/liquid separator 330 comprises a stationary decanter, a centrifuge, or any appropriate device for separating an organic solvent phase from an aqueous phase. In some embodiments, separator 330 is a decanter. In some embodiments, separator 330 transfers recovered solvent via conduit 301 to solvent tank 250. In some embodiments, the amount of residual water in solvent stream 301 is at most about 10% wt/wt, such as about 9, 8, 7, 6, 5, 4, 3% wt/wt, or less. In some embodiments, the amount of water in solvent stream is about 2-4% wt/wt. In some embodiments, separator 330 transfers separated water 331 to stripper 340. In some embodiments, the water stream comprises at most about 30% wt/wt solvent, such as about 25, 20, 15, 10, 9, 8, 7, 6% wt/wt, or less solvent.

In some embodiments, stripper 340 comprises a distillation unit. In some embodiments, the distillation unit may be suitable to distill the solvent/water azeotrope at the top, while water remains at the bottom of the distillation unit. In some embodiments, the stripper comprises a packed column distillation unit. The top distillate of stripper 340 can be transferred by conduit 341 back to liquid/liquid separator 330. In some embodiments, the temperature of the distillation top is controlled from about 40-95° C., such as about 50-85° C. or about 65-75° C. In some embodiments, the temperature of the distillation top is about 70° C. In some embodiments, the bottom stream comprises at most about 2% wt/wt solvent, such as about 1, 0.1, 0.05, 0.01, 0.005% wt/wt, or less solvent. In some embodiments, bottom distillates W301 of stripper 340 are transferred by conduit 342 to a waste water treatment facility.

In some aspects, solid/liquid separation unit 300 is optimized to minimize solvent loss such that solvent loss of the entire extraction operation is at most 10%, such as at most 9, 8, 7, 6, 5, 4, 3, 2, 1, 0.1%, or less of the total solvent capacity of the entire operation. In some aspects, solid/liquid separation unit 300 is optimized to separate water from the solvent at minimal energy costs.

In certain aspects, the dry spent biomass (W302) is transferred via conduit 372 to a solid waste treatment facility. In some embodiments, the dry solid waste may be used for energy production. In some embodiments, the dry solid waste is pelletized. In some embodiments, it comprises only trace amounts of active constituents. In some embodiments, the residual level of each constituent is at most about 20% wt/wt, such as about 15, 10, 9, 8, 7, 6, 5, 4, 3, 2, 1, 0.1% wt/wt, or less, of the original concentration. In some aspects, when *cannabis* is the plant being extracted, the residual amount of active constituents can be low enough to discard the spent biomass as unregulated dry biomass.

In some aspect, the present disclosure provides an extracted *cannabis* plant composition, wherein the composition comprises at least one following characteristics: (i) less than 10% wt/wt dry base cannabinoids compared to the pre-extracted plant; (ii) less than 0.001, 0.01, or 0.1% wt/wt water; and less than 0.01, 0.1, or 1% wt/wt solvent. In some embodiments, the composition comprises at most about 5% wt/wt dry base cannabinoids compared to the pre-extracted plant, such as about 4%, 3%, 2%, 1% wt/wt, or less dry base cannabinoids. In some embodiments, the composition comprises at least about 80% organic matter. In some embodiments, the organic matter can be characterized as spent biomass, comprising predominantly cellulose, hemicellulose pectin and lignin In some embodiments. The spent biomass comprises at least about 90% cellulose, hemicellulose, pectin and lignin in total. In some embodiments, the composition comprises about 0.0001 to about 0.1% wt/wt water and about 0.0001 to about 1% wt/wt solvent. In some embodiments, the composition comprises about 0.001 to about 5% wt/wt dry base cannabinoids, such as about 0.001 to about 1% or about 0.001 to about 0.1% wt/wt dry base cannabinoids.

Figure 1D:
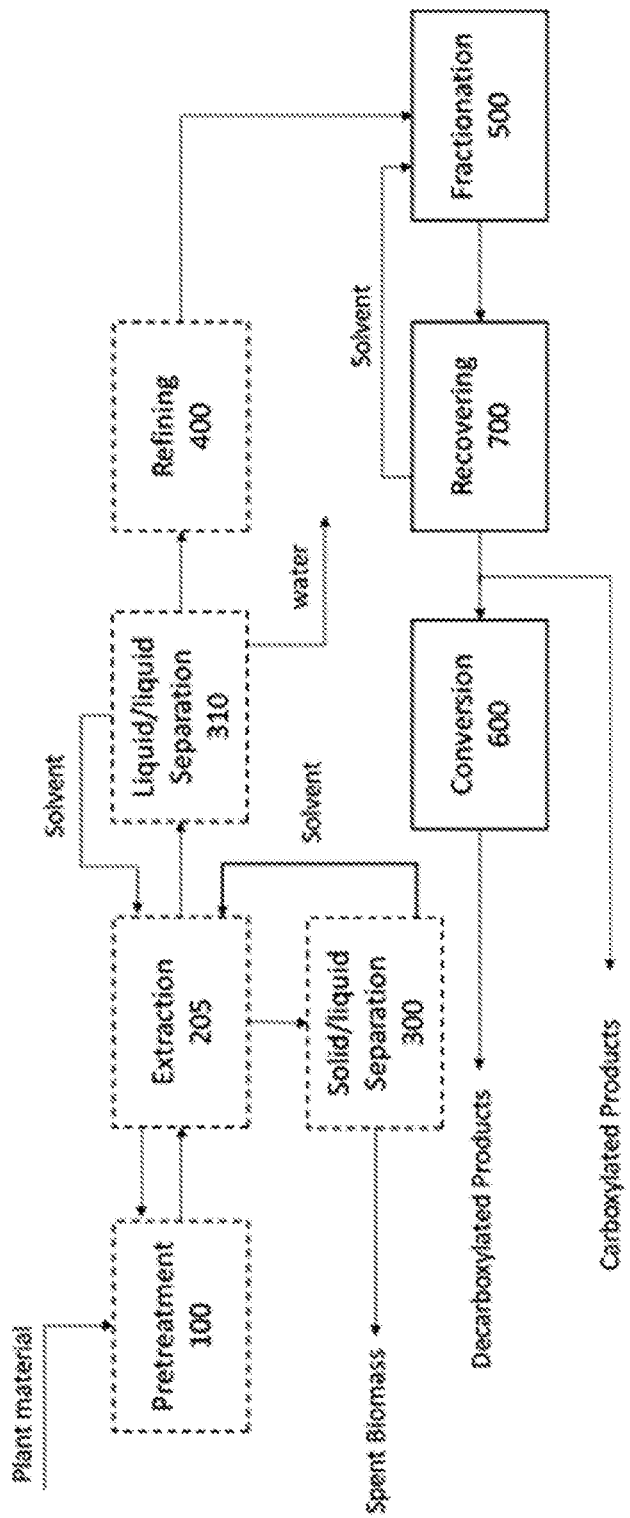
FIG. 1D illustrates a schematic diagram of a process to extract and refine cannabinoids from plant material, to provide products enriched with a certain constituent or group of constituents, and to convert cannabinoids to their active form by decarboxylating them.

A schematic continuous process for providing extracted products from plant material is shown in FIG. 1D. In some aspects, plant material may be pretreated (100) prior to extraction (205). Pretreatment may comprise separating the different parts of the plants, i.e. buds, leaves, stalk, etc., such that each part can be treated separately. Pretreatment may comprise a reduction in plant material size (e.g. mechanical breaking, milling, grinding). Size reduction may be done on the plant material before adding a solvent, during mixing with the solvent or after adding a solvent. The sized plant material may then be extracted in the extraction unit (205) to provide a liquid stream of solvent loaded with extractives and a slurry stream comprising liquid and extracted biomass.

Solvent and water can be removed partially or completely from the loaded extractant stream by evaporation to provide a crude, concentrated extractives oil product. In some embodiments, the liquid stream is further separated at the liquid/liquid separation unit 310, to provide a liquid stream comprising solvent that is returned to extraction unit 205, and an aqueous stream comprising solvent. The aqueous stream may be stripped by distillation of solvent residues and is directed to a waste water treatment plant. The slurry stream may be separated at the solid/liquid separation unit (300) to provide a stream of partially loaded solvent that may be returned to the extraction unit 205 and a stream of dried, spent biomass.

In some embodiments, the crude product may be further treated by refining (400) and fractionating (500) to provide a first stream comprising terpenes and a second stream comprising cannabinoids, mostly still in their carboxylic acid form. In some embodiments, the cannabinoids may be converted (600) to their decarboxylated form.

In certain aspects, as biomass is a complex matrix, the target constituents, e.g. cannabinoids and terpenes, are co-extracted with lipids, phospholipids, waxes and gums, color bodies, as well as residues of pesticides and herbicides, various natural toxins, inorganic elements, including heavy metal ions. In some embodiments, it is critical that all potentially harmful compounds are removed at least below the required regulatory concentration. In some embodiments, at least one constituent that causes high viscosity, stickiness or any other physical property that may hinder downstream processing or adversely affect in any way the quality of the products be substantially removed. In some embodiments, all constituents that cause high viscosity, stickiness or any other physical property that may hinder downstream processing or adversely affect in any way the quality of the products are substantially removed. The relative amount of each undesired compound may change depending on growing conditions, type of the strain, season, geographic location and extraction process. It is expected that various steps of the refining process may be altered to address specific challenges when implementing the process disclosed herein.

Refining steps may include contact with acid, base, enzymes, adsorbent materials, resins or solvents. In some embodiments, the refining process needs to remove to a sufficiently low concentration all compounds that may adversely affect the quality of the product for consumption by humans or animals by any method of delivery, or on the ability to apply refining steps, or the storage life of the product. In some embodiments, the required limit for each impurity that should be removed may change according to the intended method of delivery (i.e. oral, inhaling, smoking, dermal, or any other delivery method). In some embodiments, the refining process may not leave traces of solvents in the refined product. In some embodiments, the refined product may be substantially free of such impurities.

In certain aspects, the sufficiently refined oil from any strain of cannabis plant is suitable to be fractioned by the processes disclosed herein. In some embodiments, the refined oil is a substantially pure product (i.e., the remaining concentration of impurities that need to be eliminated from the starting crude product is well below the relevant limit for each such impurity compound). In some embodiments, the refined oil meets quality requirements with respect to residual amounts of volatile solvents (VOC), heavy metals, pesticides, herbicides, mycotoxins, aflatoxins, total bacteria count, yeast, mold, bacteria, or any combination thereof.

In some embodiments, the refined oil comprises at most about 100,000, 10,000, 1000, or less colony forming units/g (CFU/g) total aerobic bacteria. In some embodiments, the refined oil comprises at most about 10,000, 1000 CFU/g, or less yeast and mold. In some embodiments, the refined oil comprises at most 1,000, 100 (CFU/g), or less bile-tolerant gram-negative bacteria. In some embodiments, the refined oil comprises at most 1,000, 100 (CFU/g), or less total coliforms. In some embodiments, the refined oil comprises at most 100, 10 (CFU/g), or less E. Coli. In some embodiments, the refined oil comprises at most 100, 10 (CFU/g), or less Salmonella.

In some embodiments, the refined oil comprises any of the solvents acetonitrile, benzene, butane, 1-butanol, 2-butanol, 2-butanone (MEK), 1,2-dichloroethane, dichloromethane, 1,2-dimethoxyethane, N,N-dimethylacetamide, 2,2-dimethylbutane (hexanes) 2,3-dimethylbutane (hexanes), N,N-dimethylformamide, 2,2-dimethylpropane (neopentane), dimethylsulfoxide (DMSO), 1,4-dioxane, chloroform, cumene, cyclohexane, ethanol, 2-ethoxyyethanol, ethyl acetate, ethyl ether, ethylene glycol, ethylene oxide, heptane, hexane, isopropyl acetate, methanol, 2-methylbutane (isopentane), 2-methylpentane (hexanes), 3-methylpentane (hexanes), 2-methylpropane (isobutane), naphtha, pentane, 1-pentanol, petroleum ether, propane, 1-propanol, 2-propanol (isopropyl alcohol), 2-propanone (acetone), sulfolane, trichlorethylene, tetrahydrofuran (THF), toluene, xylenes (o-xylene, m-xylene, p-xylene), pyridine, or any combination thereof, at well below the Minimum Required Limit (MRL).

In some embodiments, the refined oil may comprise a solvent that was used in an upstream refining process. In some embodiments, the solvent is a solvent or a mixture of solvents, wherein the solvent or mixture of solvents (i) is categorized as class 3 according to Q3C—Table and Lists Guidance for Industry (US Department of Health and Human Services, FDA, CDER, CBER), June 2017 ICH rev. 3 or (ii) forms a heterogeneous azeotrope with water, wherein the azeotrope has a boiling point lower than the boiling point of water. In some embodiments, the solvent forms a heterogeneous azeotrope with water, wherein the azeotrope has a boiling point lower than the boiling point of the solvent or mixture of solvents. In some embodiments, the ratio of water to solvent, $R_w/R_s$, may be greater in the vapor phase of the azeotrope than in the solvent phase. In some embodiments, the solvent or mixture of solvents is selected to have a Hildebrand solubility parameter of at least about 16.0 $MPa^{1/2}$, 18.0 $MPa^{1/2}$, or more. In some embodiments, the solvent or mixture of solvent is selected to have a Hildebrand solubility parameter of at most about 30.0 $MPa^{1/2}$. In some embodiments, the solvent or mixture of solvent is selected to have a Hildebrand solubility parameter of at most about 26.0 $MPa^{1/2}$. In some embodiments, the solvent or mixture of solvent is selected to have a Hildebrand solubility parameter of at most about 20.0 $MPa^{1/2}$. In some embodiments, the solvent or mixture of solvents is selected to have a Hildebrand solubility parameter in the range of about 18.0 to 20.0 $MPa^{1/2}$. In some embodiment, the solvent may be selected from 1-butanol, ethyl acetate, ethyl formate, 2-methyl-1-butanol, ethanol, heptane, cyclohexane, 2-butanone, 2-propanol, propylene glycol and mixtures thereof, such as ethyl acetate or ethyl formate. In some embodiment, the solvent is dry, or saturated with water, or is present at its water azeotrope composition. In some embodiments, the solvent may be selected from pentanol, hexanol, heptanol, 2-ethyl hexanol, octanol, 2-butanone (MEK), methyl isobutyl ketone (MIBK). The solvent may be present at a ratio of about 2:1, 1:1, 0.5:1, 0.1:1, 0.01:1 wt/wt, or less with respect to the refined oil.

In some embodiments, the solvent is dry, or saturated with water, or is present at its water azeotrope composition. In some embodiments, the solvent comprises a carboxylic acid, e.g. acetic acid, citric acid, formic acid. In some embodiments, the concentration of the carboxylic acid is about 0.01, 0.05, 0.1, 0.2, 0.3, 0.4, 0.5, 0.6, 0.7, 0.8, 0.9, 1%, or more.

In some embodiments, the refined oil comprises less than the maximum allowed limit of any pesticide or herbicide listed by state authorities with respect to the relevant product, e.g. cannabis products. In some embodiments, the refined oil comprises at most about 1, 0.5, 0.5%, or less ash. In some embodiments, the refined oil comprises at most about 0.14 µg/kg Arsenic, or less. In some embodiments, the refined oil comprises at most about 0.09 µg/kg Cadmium. In some embodiments, the refined oil comprises at most about 0.29 µg/kg Lead. In some embodiments, the refined oil comprises at most about 0.29 µg/kg Mercury. In some embodiments, the refined oil comprises less than or equal to the allowed limit for any other heavy metal of potential harming effect. In some embodiments, the refined oil further comprises at most about 0.1% wt/wt Calcium, at most about 0.1% wt/wt Magnesium, at most about 0.1% wt/wt potassium, and at most about 0.05% wt/wt phosphorous.

The current disclosure provides a method and process for fractionating such refined oil comprising a mixture of constituents, where the constituents are of the cannabinoid family. In some embodiments, the disclosed method provides a fraction enriched with CBDA and depleted of the psychoactive constituents THCA and THC. Many states regulate the amount of the psychoactive constituents in final preparations to be less than 1, 0.5 or even less than 0.3% in the preparation. As concentration of all constituents increases through the refining process, that removes undesired components, relying on a hemp strain that is low in producing the psychoactive component by trait is insufficient, and some fractionation process becomes a must to ensure production of "THC-free" products. The fractionating process disclosed herein is a continuous process that is scalable to industrial scale.

In some embodiments, the amount of total cannabinoids comprise at least about 60, 61, 62, 63, 64, 65, 66, 67, 68, 69, 70% of the refined oil. Preferably, CBDA comprises at least 75, 76, 77, 78, 79, 80, 81, 82, 83, 84, 85, 86, 87, 88, 89, 90, 91, 92, 93, 94, 95, 96, 97%, or more of the total cannabinoids. In some embodiments, THC and/or THCA can be about 0.5, 1, 2, 3, 4, 5, 6, 7, 8%, or more of the total cannabinoids. In some embodiments, refined oil obtained from commercially available hemp from commercial hemp growers.

Figure 2C:
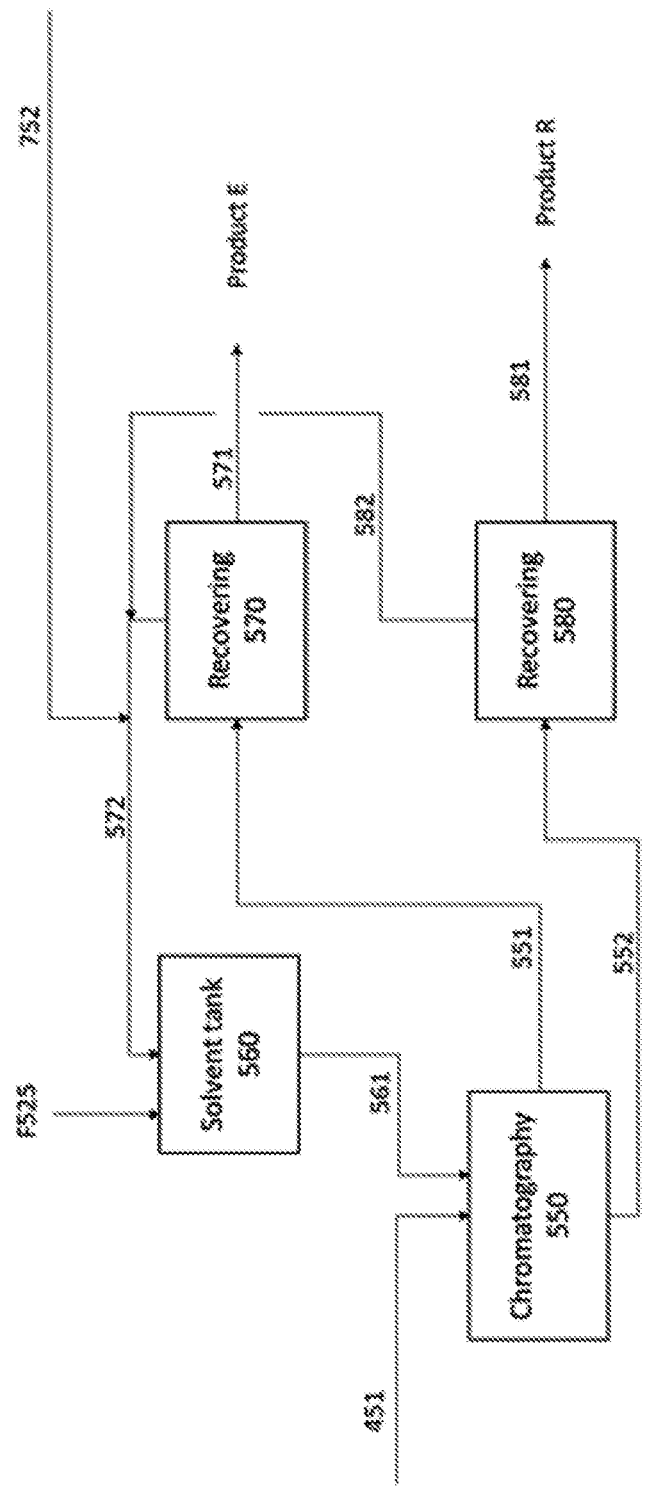
FIG. 2C illustrates a schematic diagram of a process for chromatographically providing a stream enriched with one constituent and a second stream depleted with that constituent, comprising the other constituents.

FIG. 2C illustrates schematically processes applied in fractionating unit 550. In some embodiments, refined oil stream 451 is fractionated to an extract product, enriched with CBDA, and a raffinate product. In some embodiments, the extract product is enriched with THCA and decarboxylated cannabinoids.

Any chromatography method can be used. In some embodiments, the chromatography method is simulated moving bed (SMB) or sequential simulated moving bed (SSMB). Both methods afford a continuous fractionating process that provides at least two streams of products, termed extract stream(s) and raffinate stream. Examples of simulated moving bed processes are disclosed, for instance, in U.S. Pat. Nos. 6,379,554; 5,102,553; 6,093,326; and 6,187,204, and examples of sequential simulated moving bed processes can be found in GB 2,240,053; and U.S. Pat. Nos. 4,332,623; 4,379,751; and 4,970,002, each of which is incorporated herein by reference in its entirety. In some embodiments, the resin bed is divided into a series of discrete vessels, each of which sequence through a series of 4 zones (feed, separation, feed/separation/raffinate and safety) connected by a recirculation loop. A manifold system can connect the vessels and may direct, in appropriate sequence to (or from) each vessel, each of the four media accommodated by the process. In some embodiments, the media is referred to as feed, eluent, extract or raffinate (e.g., a feed can be refined oil mixture 451, the eluent can be a solvent (561), the extract is a solution enriched with CBDA (551), one raffinate is a solution enriched with THCA and decarboxylated cannabinoids (552)).

The chromatographic fractionation can be carried out in a batch mode, a simulated moving bed (SMB) mode or a sequential simulated moving bed (SSMB) mode. The temperature of the chromatographic fractionation is typically in the range from about 5° C. to 90° C. In some embodiments, the chromatographic fractionation can be carried out with a linear flow rate of about 0.25-100 ml/min in the separation column.

A method for medium and large-scale chromatographic separations is the sequential simulated moving bed (SSMB) mode, or alternatively a simulated moving bed (SMB) mode. Both methods use a number of columns packed with a suitable sorbent and connected in series. There are inlet ports for feed and solvent (which may include recycled solvent), and outlet ports for two or more products (or other separated fractions). The injection of the mixture solution to be separated is periodically switched between the columns along the direction of the liquid flow, thereby simulating continuous motion of the sorbent relative to the ports and to the liquid. The SMB is a continuous counter current type operation. SSMB is a more advanced method, requiring a sequential operation. Its advantages over SMB and over other older methods include: fewer columns are needed in the SSMB method versus the SMB, hence less resin is required and associated costs of installation are significantly reduced in large systems; the pressure profile is better controlled, facilitating the use of more sensitive resins; and the achievable recovery/purity is higher than obtained with SMB systems.

In some embodiments, two chromatography processes can be operated in series as schematically shown in FIG. 5A, where the raffinate of the first chromatography system is transferred as feed to the second chromatography process to provide a second extract product and a second raffinate stream. An example of a dual simulated moving bed process is, for instance, in U.S. Pat. No. 6,482,268. In some embodiments, the number of columns, size of columns, flow rate, SSMB sequence of chromatography system 2 are different to those of chromatography system 1. In some embodiments, the resin in chromatography system 2 may be identical or different to chromatography system 1. In some embodiments, eluent composition may be altered between system 1 and 2.

Fractionating of cannabidiolic acid, CBDA, from other cannabinoids present in refined extracted oil can be achieved using a chromatographic media that has mixed hydrophilic and hydrophobic properties, such as silica-based media. In some embodiments, the media is modified silica of mixed hydrophilic—hydrophobic nature. In some embodiments, the chromatographic media comprises particles of size of at least 20 micrometers, or more. In some embodiments, the particles are about 20 to 45 micrometers. U.S. Pat. Nos. 4,048,205; 4,049,688 and 4,066,677 claim processes for the separation of esters of fatty acids of various degrees of unsaturation from mixtures of esters of saturated and unsaturated fatty acids. These processes use adsorbents comprising an X or a Y zeolite containing a selected cation at the exchangeable cationic sites. Such separation is often termed ion exclusion chromatography, utilizing several modes of interactions at the molecular level to achieve effective separation, including size and geometry of pores in the adsorbent structure, charge interaction direct and indirect, i.e. charge interaction of the separated solute with an adsorbed charged layer that forms a "soft" stationary phase, as well as hydrophobic interactions and Wan Der Walls forces (see for example: (i) B. K. Glod, Acta Chromatographica 1997, 7, 72-87; (ii) Hong et. al., Journal of Liquid Chromatography & Related Technologies, 35:2923-2950, 2012). Similarly, separation of fatty acids can be achieved using specific molecular sieve that exhibits selectivity for one unsaturated fatty acid with respect to another unsaturated fatty acid thereby making separation of such fatty acids by solid bed selective retention possible.

In some embodiments, cannabinoids can be fractionated using a cross-linked dextran gel that is commercially available from Amersham Bioscienses (Sephadex® LH20), Biotech GmbH (Zetadex 20-LH), Sorbtech (SorbaDex™ LH20) or equivalent products. Alternatively, a marcroreticular non-ionic aliphatic acrylic polymer can be used as the chromatography media, such media available from Dow (AMBERLITE™ XAD7HP), Purolite (Purosorb™ PAD900RFM or Purosorb™ PAD600RFM), and similar. In some embodiments, a macroreticular strong cation exchange resin in the $Ag^+$ form can fractionate cannabinoids. Such resins are available for example from Dow (Amberlyst XN-1010), Bio-Rad (Bio-Rex™ 70) and others. An amberlyst XN-1010 resin in the Ag+ form was used to separate different rosin acids where separated (S. S. Curran et. al., *JAOCS*, 1981, 58, 980-982).

In some embodiments, the chromatography system comprises at least one packed bed column. In some embodiments, the chromatography system comprises from 1 to about 14 packed bed columns comprising one or more of the above resins. In some embodiments, the number of packed columns is about 2 to 10, about 4 to 8, or about 6.

In some embodiments, the adsorbent and desorbent are dry solvents. In some embodiments, the adsorbent and desorbent comprises a solvent, wherein the solvent is saturated with water. In some embodiments, the adsorbent and/or desorbent comprises the water-saturated solvent, wherein the solvent further comprises about 0.0001 to about 1 M carboxylic acid. In some embodiments, the acid is selected from edible organic acids. In some embodiments, the acid is citric acid, acetic acid, lactic acid, citric acid, malic acid, benzoic acid, ascorbic acid, tartaric acid, oxalic acid, tannic acid, caffeotannic acid, butyric acid, fumaric acid, formic acid, folic acid, adipic acid, alginic acid, galic acid, glutamic acid, sorbic acid, succinic acid, phosphoric acid, and 2-aminoethanesulfonic acid. In some embodiments, the acid is acetic acid.

In some embodiments, the solvent is a solvent or a mixture of solvents, wherein the solvent or mixture of solvents (i) is categorized as class 3 according to Q3C—Table and Lists Guidance for Industry (US Department of Health and Human Services, FDA, CDER, CBER), June 2017 ICH rev. 3 or (ii) forms a heterogeneous azeotrope with water, wherein the azeotrope has a boiling point lower than the boiling point of water. In some embodiments, the solvent or a mixture of solvent forms a heterogeneous azeotrope with water, wherein the solvent and the azeotrope have a boiling point lower than the boiling point of water. In some embodiments, the ratio of water to solvent, $R_w/R_s$, may be greater in the vapor phase of the azeotrope than in the solvent liquid phase. In some embodiments, the solvent or mixture of solvents is selected to have a Hildebrand solubility parameter of at least 16.0 $MPa^{1/2}$, or more. In some embodiments, the solvent or mixture of solvent is selected to have a Hildebrand solubility parameter of at most about 30.0 MPa1/2. In some embodiments, the solvent or mixture of solvent is selected to have a Hildebrand solubility parameter of at most about 26.0 $MPa^{1/2}$. In some embodiments, the solvent or mixture of solvent is selected to have a Hildebrand solubility parameter of at most about 20.0 $MPa^{1/2}$. In some embodiments, the solvent or mixture of solvents is selected to have a Hildebrand solubility parameter from about 18.0 to 20.0 $MPa^{1/2}$. In some embodiments, the solvent may be selected from 1-butanol, ethyl acetate, ethyl formate, 2-methyl-1-butanol, ethanol, heptane, cyclohexane, 2-butanone, 2-propanol, propylene glycol and mixtures thereof. In some embodiments, the solvent is ethyl acetate or ethyl formate. Alternatively, the solvent may be selected from pentanol, hexanol, heptanol, 2-ethyl hexanol, octanol, 2-butanone (MEK), methyl isobutyl ketone (MIBK).

In some embodiments, the method of fractionating refined *cannabis* extract comprises a sequential simulated moving bed chromatography sequence, wherein the sequence comprises: (1) passing a feed stream comprising *cannabis* extract into an adsorbent, thereby flushing a raffinate stream comprising THCA and decarboxylated cannabinoids from the adsorbent; (2) flushing an extract stream enriched in CBDA relative to the feed stream with a desorbent stream; and (3) recycling the desorbent stream back to the adsorbent.

In some embodiments, the extract stream is transferred to recovering 570 (FIG. 2C) to recover the solvent for further use and yield Product E. In some embodiments, the solvent is recovered by evaporating. In some embodiments, Product E comprises at least about 98, 99, 99.5, 99.7, 99.8, 99.9%, or more CBDA of total cannabinoids. In some embodiments, the yield of CBDA is at least about 85, 86, 87, 88, 89, 90%, or more of CBDA in the feed. In some embodiments, Product E comprises at most about 0.3% THC and/or THC out of total cannabinoids.

The disclosure is directed to a method for fractionating at least one cannabinoid. In some embodiments, the solution is subjected to chromatographic fractionation by a continuous or sequential SMB method where the two components are enriched in the same fraction or in separate fractions and either the single fraction or the second fraction is subjected to a second chromatographic fractionation in order to recover CBDA and a second component with an improved yield or purity.

In some embodiments, the second CBDA fraction is combined with the CBDA fraction from the first chromatographic fractionation, and CBDA is recovered from the combined CBDA fractions thus obtained.

In some embodiments, the second CBDA fraction is returned to the feed solution for the first fractionation. In this embodiment, CBDA is recovered from the first CBDA fraction.

In some embodiments, the second dissolved component is recovered from the fraction obtained from the second fractionation, which is enriched with the second dissolved component. The term "second dissolved component" refers to organic compounds commonly present in refined extracted oils, such as THCA, THC, CBC, CBN, CBG, CBND, CBL, other cannabinoids or terpenes. The second chromatographic fractionation, i.e., fractionation of the fraction enriched with the second dissolved component which is obtained from the first fractionation, may be performed either by a batch method or a SMB chromatography method.

In some embodiments, CBDA and/or THCA can be recovered from *cannabis* extract. Therefore, the following description of the invention specifically refers to the recovery of CBDA and THCA, but the invention is not so limited. Instead of, or in addition to CBDA, any other dissolved organic substance may be similarly recovered by adjusting the process conditions and parameters to suit the separation in question.

In some embodiments, the raffinate stream is transferred to recovering 580 (FIG. 2C), to recover the solvent for further use and yield product R. In some embodiments, the solvent is recovered by evaporation. In some embodiments, Product R is enriched with THCA and decarboxylated cannabinoids. In some embodiments, the decarboxylated cannabinoids are THC and CBD. In some embodiments, the enrichment of THCA with respect to the feed is at least about 4, 5, 6, 7, 8, 9, or more fold. In some embodiments, the enrichment of THC in Product R with respect to the feed is at least about 4, 5, 6, 7, 8, 9, or more fold. In some embodiments, Product R comprises at least about 5, 10, 15, 20, 25%, or more THCA. In some embodiments, Product R comprises at least about 2, 3, 4, 5, 6, 7, 8, 9, 10%, or more THC. In some embodiments, Product R comprises at least about 30, 35, 40, 45, 50%, or more THCA.

Figure 2D:
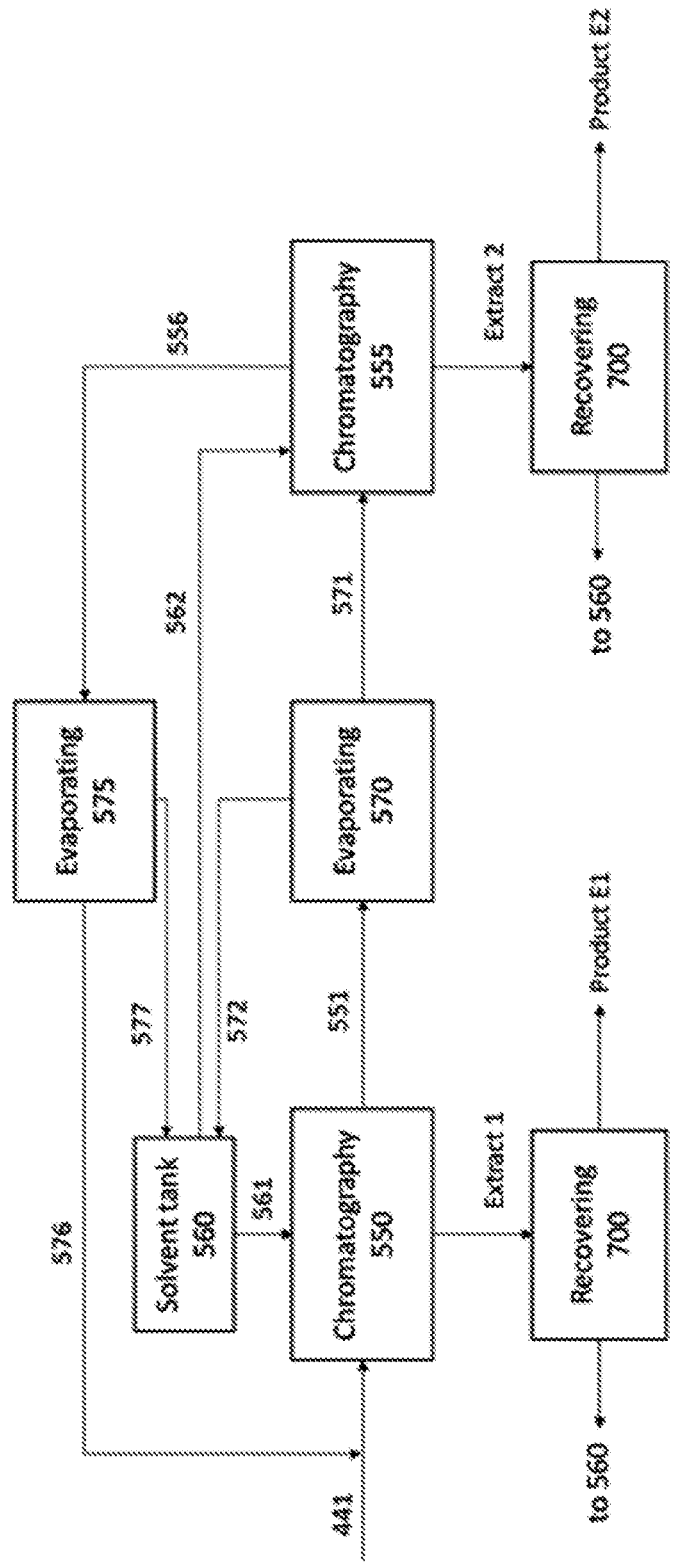
FIG. 2D illustrates a schematic diagram of an process for two sequential chromatography steps, the first one provides a stream enriched with one constituent, the second provides a stream enriched with another constituent, and increases recovery of the first constituent at the first step.

In some embodiments, Product R is fed into a second SSMB process 555 (FIG. 2D), wherein the sequence may comprise: (1) passing a feed stream comprising the raffinate product of the first chromatography into an adsorbent, thereby flushing a second extract stream comprising THCA and decarboxylated cannabinoids from the adsorbent; (2) flushing a second raffinate stream enriched in CBDA relative to the feed stream with a desorbent stream; and (3) recycling the desorbent stream back to the desorbent work tank 560.

In some embodiments, the yield of CBDA in the first extract stream increases to at least about 90, 91, 92, 93, 94, 95, 96, 97%, or more of the CBDA in the feed to the first chromatography system. In some embodiments, the first extract stream is transferred to recovering 700 to yield Product E1.

In some embodiments, extract 2 comprises at least about 10, 15, 20, 25, 30, 35%, or more THCA and at least about 3, 4, 5, 6, 7, 8, 9, 10%, or more THC out of total cannabinoids. In some embodiments, the second extract stream is enriched with THCA and THC (e.g., the relative concentration of THCA and THC is about 1.3 to about 2.5 with respect to the first raffinate). In some embodiments, the second extract is transferred to recovery 700, to recover the solvent for further use and provide Product E2.

In some embodiments, Product E2 comprises about 10 to about 35% CBDA; about 5 to about 55% THCA; about 10 to about 50% CBD; about 3 to about 20% THC and additional decarboxylated cannabinoids. In some embodiment, Product M or product E2 can be used for medicinal purposes where the presence of the psycho active constituents is utilized as the active ingredient. Product M and Product E2 can be handled according to regulatory requirements of handling cannabinoid-related drugs. In some embodiments, the system is equipped with monitors, e.g. flow monitor, weight monitor, optical monitor, to allow for accounting accumulation and movement of this stream of product.

Product E or product E1 are highly enriched with CBDA, e.g. at least 99.7% of total cannabinoid and high purity in general. As such, Product E and Product E1 can be induced to cause crystallization of CBDA. In some embodiments, Product E or Product E1 is concentrated by evaporating or by distillation to remove solvent and water. In some embodiments, concentrating is controlled to a range of about 10:1 to about 0.5:1 solvent to solids, and water concentration is reduced to at most about 3, 2, 1, 0.5, 0.1, 0.05, 0.01%, or less relative to the solvent. In some embodiments, the Hildebrand parameter of the solvent part of the solution is controlled to be lower than 20.1, 20.0, 19.0, 18.0, or less. In some embodiments, the solvent is controlled to have a Hildebrand parameter of 18.2. In some embodiments, the solvent is ethyl acetate. In some embodiments, a solvent having a lower Hildebrand parameter is added to assist control of the solution properties. In some embodiments, the solution is chilled to at most about −10, −15, −20, −25, −30 0C, or less for at least about 1, 2, 3, 4, 5, 6, 7, 8, 9, 10, 12, 24, 48 hours or more to cause precipitation of CBDA crystals. In some embodiments, the crystals are collected by cold filtration, washed and dried under vacuum, to provide high purity CBDA crystals.

Figure 7A:
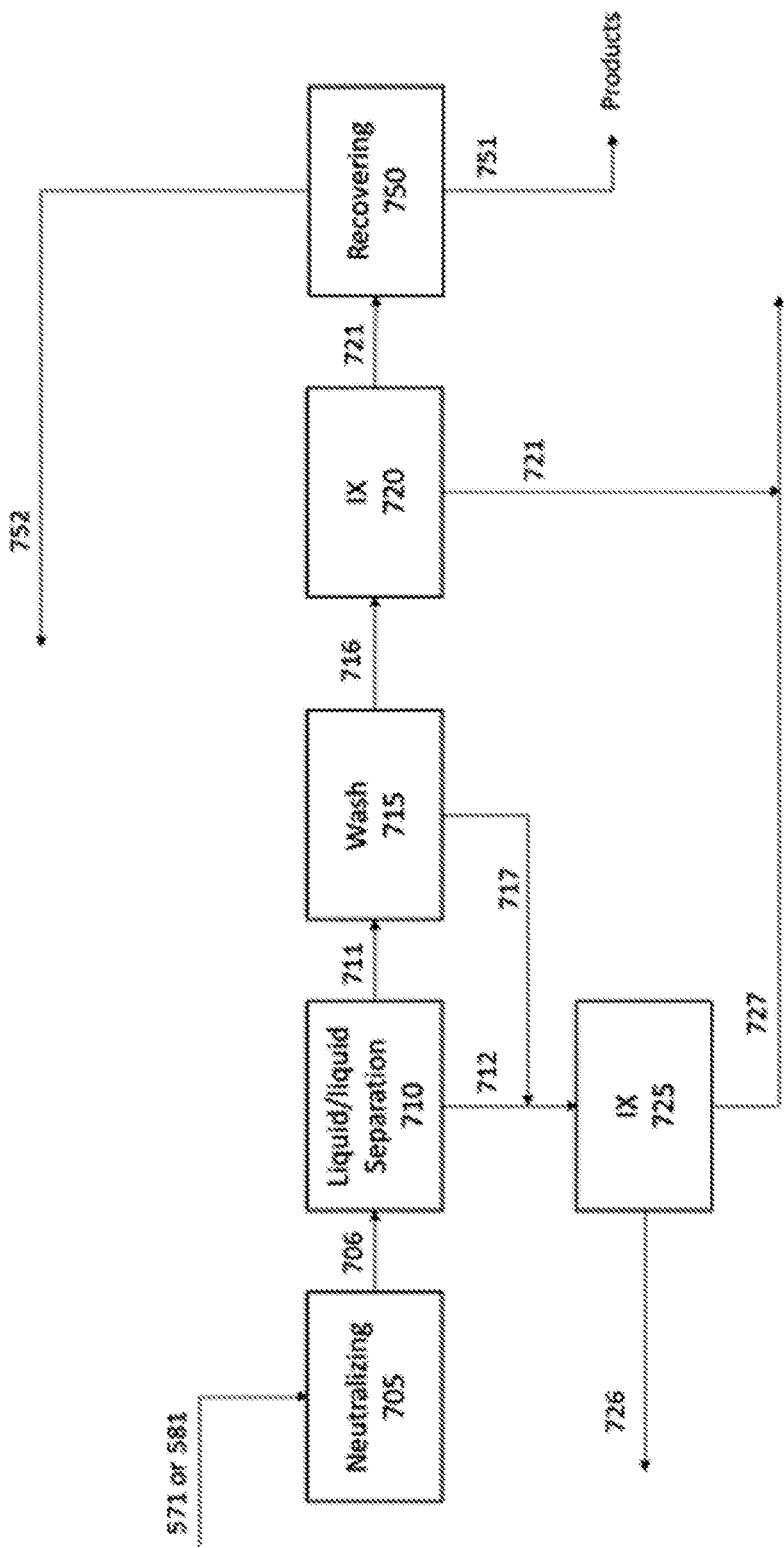
FIG. 7A illustrates a schematic diagram of a process for recovering a carboxylic acid from the product stream, recovering the solvent for further use and optionally decarboxylating a carboxylated cannabinoid.

An aspect disclosed herein is full recovery of all reagents utilized in the separation process for further use. In some embodiments, an additional recovery module for the acid is schematically outlined in the scheme of FIG. 7A. This module may comprise neutralizing 705 of the product streams by mixing the product stream 571 or 581 with an aqueous solution comprising NaOH. In some embodiments, a two phase mixture is provided, wherein the upper phase comprises the product and the solvent. In some embodiments, the upper phase may have a pH of about 5.5. In some embodiments, the lower phase, comprising water and base, may have a pH value of about 7.0. The two phases may then be separated at 710 by decanting. In some embodiments, the upper phase comprising the product is washed by contacted with water 715. In some embodiments the upper phase is further polished to remove any remaining $Na^+$ ions by contacting with a weak acid cation (WAC) exchange resin in the $H^\alpha$ form. In some embodiments, the product is evaporated or distilled (750) to provide a concentrated oil product and recover the solvent for further use. In some embodiments, carboxylated products may be converted (at 750) to decarboxylated product. In some embodiments, the processes may be accelerated by proper selection of temperature and pressure. In some embodiments, this process further comprises a catalyst. In some embodiments, the aqueous streams that were separated at 710 and 715 are combined, and are contacted with strong acid cation exchange resin in the $H^\alpha$ form, to obtain stream 726, comprising dilute acetic acid for further use, and waste stream 727 comprising sodium ions. In some embodiments, waste stream 727 is combined with waste stream 721 generated when the WAC resin is periodically regenerated. In some embodiments, aqueous waste streams are stripped by distillation to remove and recover any solvent, and are then directed to a waste water treatment plant according to local regulations.

Depending on the extraction method and solvent, crude extracted product can have high viscosity at room temperature and feel "tacky". In some embodiments, it appears as a resinous material, which can be almost solid at room temperature or may not tend to flow well. When mixing it at a ratio of about 1:1 with a solvent, filtration can be very difficult and slow. To allow refining of the crude oil it is essential to remove upfront the compounds that contribute to high viscosity and "stickiness" of the crude oil, e.g. phospholipids, gums and waxes, by a "degumming" process.

Figure 7B:
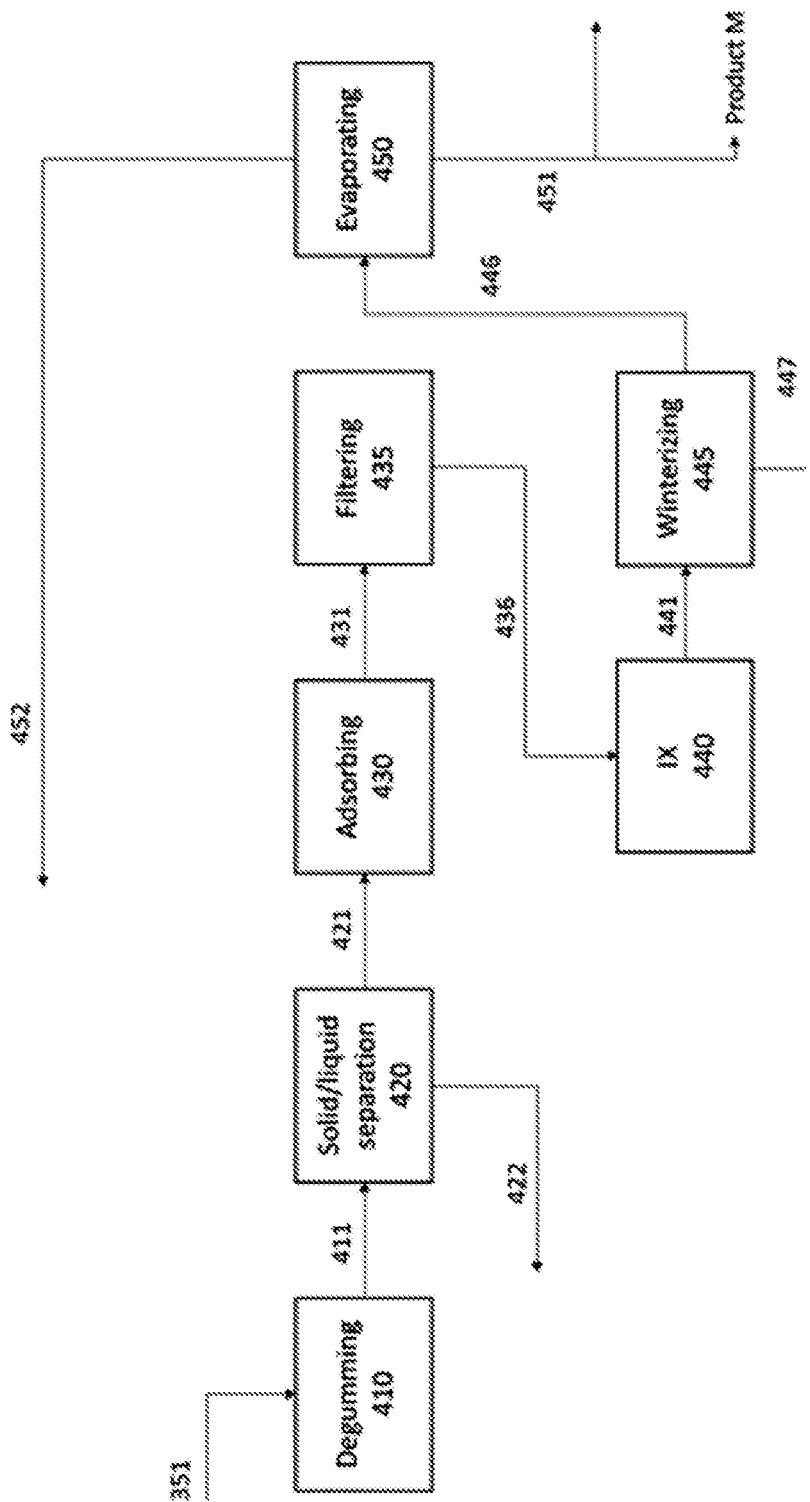
FIG. 7B illustrates a schematic diagram of a process for refining of crude extracted oil.

FIG. 7B illustrates schematically continuous processes for removing the undesired co-extracted compounds and for providing refined extracted oil. The process may comprise the degumming (410), solid/liquid separation (420) (i.e., where the precipitates produced in the degumming step and excess water are removed) contacting with at least one adsorbent (430), filtering to remove particulate solids (435), contacting with an ion exchange resin (430). In some embodiment, the process may further comprise a "winterizing" step (445) (i.e., where the extracted oil is chilled sufficiently for a specific maturation time to cause precipitation of waxes). In some embodiments, solvent and water are removed by evaporation to recycle the solvent for further use and provide concentrated refined oil.

In some embodiments, degumming 410 comprises treating the crude extracted oil with an organic acid, such as citric, acetic acid or formic acid. In some embodiments, the acid is added with vigorous mixing to the crude extracted oil as about a 30-50% solution in water. In some embodiments, the treatment with acid is conducted at a temperature of at most about 80, 70, 60, 55, 50, 45° C., or less. In some embodiments, the process is conducted at about 45° C. to 55° C. or about 40° C. to about 45° C. In some embodiments, water is added to the biphasic mixture. In some embodiments, the water comprises base at an amount sufficient to bring the pH of the aqueous of the biphasic mixture to at least about pH 4.5 to 5.5. In some embodiments, the base is sodium hydroxide. In some embodiments, the aqueous phase is separated by centrifuge to remove gums. In some embodiments, the oil is washed with warm water at temperature of about 40 to about 60° C. In some embodiments, degumming is further enhanced by enzyme degumming. In some embodiments, the enzyme is a phospholipase $A_1$, a phospholipase $A_2$, a phospholipase C, a phospholipase D, or combination thereof. Such enzymes are commercially available and applied in the edible oil industry and the biodiesel industry from Novozymes (Lecitase®), AB Enzymes (Rohalase® MPL), Danisco) (Lysomax®, Verenium (Purifine™) and DSM (Gumzyme®).

In some embodiments, the loss of the target constituents to the aqueous phase with the entrained oil is at most about 5, 4, 3, 2, 1%, or less of the amount present in the crude extracted oil. In some embodiments, the degumming process does not cause decarboxylation or other degradation to at least about 0.1, 0.5, 1, 2%, or more of the cannabinoids present in the crude extracted oil.

In some embodiments, the viscosity of the degummed oil is such that continuous filtration is possible. In some embodiments, the viscosity of the degummed oil is at most about 10 cPs at 25° C., or at most about 5 cPs at 25° C.

In some embodiments, prior to the acid treatment, the crude extracted oil is mixed at a ratio in the range of about 20:1 to about 1:2 with a solvent. In some embodiments, the solvent may be the same or different than the solvent used during extracting. In some embodiments, the ratio is about 10:1. In some embodiments, the ratio of solvent to extract is about 1:1.

In some embodiments, the solvent may comprise a solvent or a mixture of solvents, wherein the solvent or mixture of solvents (i) is categorized as class 3 according to Q3C—Table and Lists Guidance for Industry (US Department of Health and Human Services, FDA, CDER, CBER), June 2017 ICH rev. 3 or (ii) forms a heterogeneous azeotrope with water, wherein the azeotrope has a boiling point lower than the boiling point of water. In some embodiments, the solvent or a mixture of solvent forms a heterogeneous azeotrope with water, wherein the solvent and the azeotrope have a boiling point lower than the boiling point of water. In some embodiments, the ratio of water to solvent, $R_w/R_s$, may be greater in the vapor phase of the azeotrope than in the solvent liquid phase. In some embodiments, the solvent or mixture of solvents is selected to have a Hildebrand solubility parameter of at least 16.0 $MPa^{1/2}$, 18.0 $MPa^{1/2}$, or more. In some embodiments, the solvent or mixture of solvent is selected to have a Hildebrand solubility parameter of at most 30.0 $MPa^{1/2}$, or less. In some embodiments, the solvent or mixture of solvent has a Hildebrand solubility parameter of at most 26.0 $MPa^{1/2}$, or less. In some embodiments, the solvent or mixture of solvent has a Hildebrand solubility parameter of less than about 20.0 $MPa^{1/2}$, or less. In some embodiments, the solvent or mixture of solvents has a Hildebrand solubility parameter from about 18.0 to 20.0 $MPa^{1/2}$. In some embodiments, the solvent may be selected from 1-butanol, ethyl acetate, ethyl formate, 2-methyl-1-butanol, ethanol, heptane, cyclohexane, 2-butanone, 2-propanol, propylene glycol and mixtures thereof. In some embodiments, the solvent is ethyl acetate or ethyl formate. In some embodiments, the solvent may be selected from pentanol, hexanol, heptanol, 2-ethyl hexanol, octanol, 2-butanone (MEK), methyl isobutyl ketone (MIBK).

In some embodiments, the solvent is dry, or saturated with water, or is present at its water azeotrope composition. In some embodiments, the solvent comprises a carboxylic acid, e.g. acetic acid, citric acid, formic acid. In some embodiments, the concentration of the carboxylic acid is at least about 0.01, 0.05, 0.1, 0.2, 0.3, 0.4, 0.5, 0.6, 0.7, 0.8, 0.9, 1%, or more. In some embodiments, degumming is carried at a temperature of at most 50, 45, 30° C., or less. In some embodiments, the solvent is added to the extracted oil after the degumming step 410. In some embodiments, the a ratio is in the from 2:1 to 1:2 solvent to extract. In some embodiment, the ratio of solvent to extract is about 1:1.

Figure 8C:
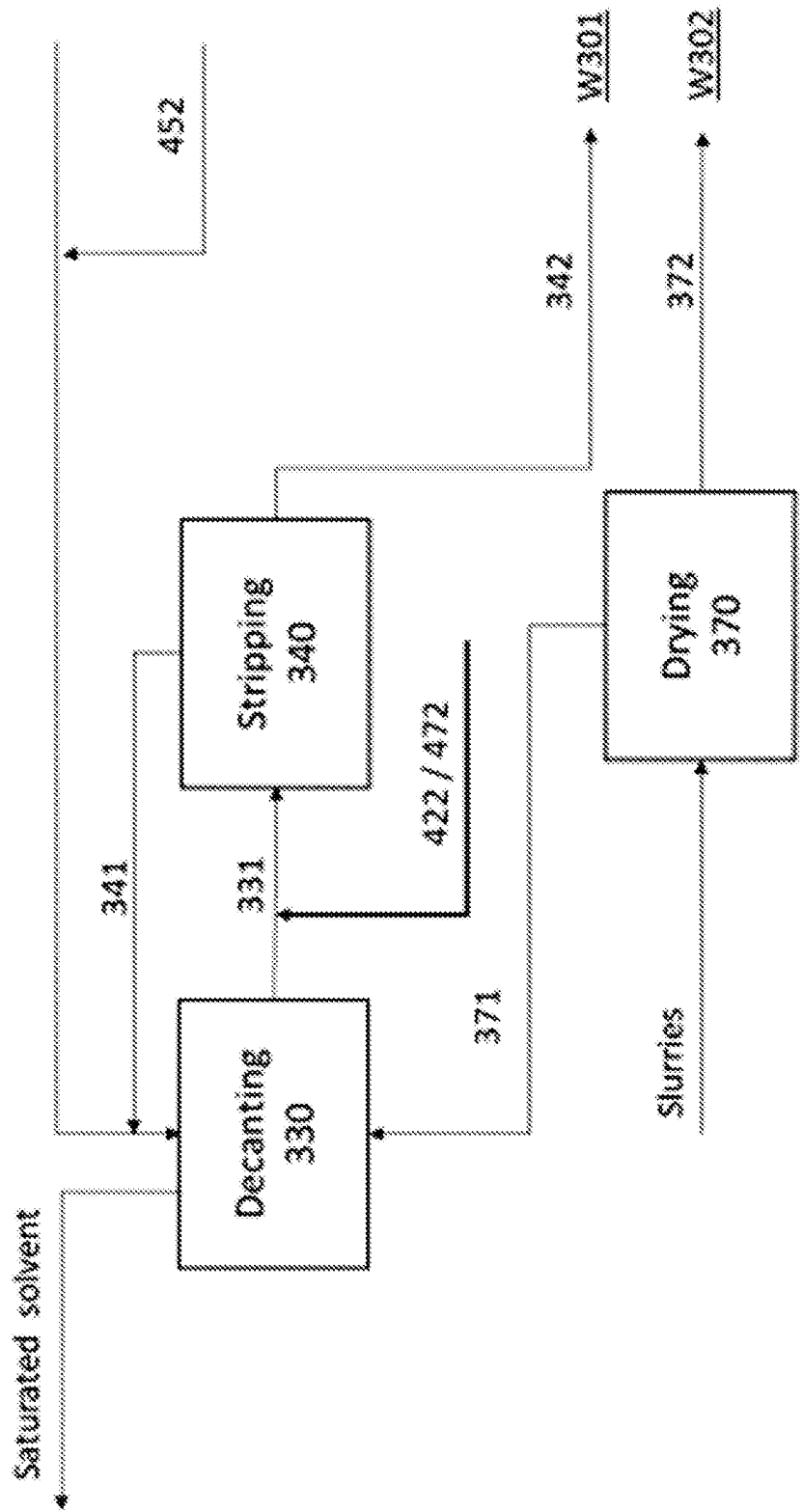
FIG. 8C illustrates a schematic diagram of a process for recovering solvent from the refining process.

In some embodiments, the solution comprises the degummed oil, solvent, water, and solids. In some embodiments, the degummed oil is transferred via conduit 411 to solid/liquid separation 420. Separation 420 may be conducted by a suitable centrifuge to provide degummed oil stream 421. In some embodiments, degummed oil stream 421 comprises the degummed oil and solvent, and stream 422, comprises water and precipitates. Stream 422 may be directed to a stripping 340 (FIG. 8C), comprising a distillation column. In some embodiments, the solvent for 340 is evaporated and recycled back to the process. In some embodiments, the bottom phase, comprising water and precipitates, can be directed to a waste water treatment plant.

In some embodiments, the water stream comprises at most about 30% wt/wt, 25, 20, 15, 10, 9, 8, 7, 6% wt/wt, or less solvent. In some embodiments, stripper 340 comprises a distillation unit. In some embodiments, the distillation unit is suitable to distill the solvent/water azeotrope at the top, while water remains at the bottom of the distillation unit. In some embodiments, the stripper comprises a packed column distillation unit. The top distillate of stripper 340 can be transferred by conduit 341 back to liquid/liquid separator 330. In some embodiments, the temperature of the distillation top is about 40-95° C., such as about 50-85° C. or 65-75° C. In some embodiments, the temperature of the distillation top is about 70° C. In some embodiments, the bottom stream comprises at most 2%, 1, 0.1, 0.05% wt/wt, or less solvent. In some embodiments, bottom distillates W301 of stripper 340 are transferred by conduit 342 to a waste water treatment facility.

In some embodiments, adsorbing 430 comprises contacting the degummed oil stream 351 with activated carbon. In some embodiments, the activated carbon is acid-washed activated carbon. In some embodiments, the contacting may be done by stirring and filtration, or by flowing the degummed oil stream through a loaded column. In some embodiments, the ratio of activated carbon to extracted oil is about 0.01-2% wt/wt, or about 0.5-1.5% wt/wt. In some embodiments, contacting is conducted at at least about 30, 35, 40, 45, 50, 55, 60° C., or more. In some embodiments, contacting is conducted from about 30-60° C. In some embodiments, adsorbing 430 also comprises mixing of the degummed oil with clays. In some embodiments, the clays comprise Fuller's Earth, Kaolin clay, bentonite, diatomaceous earth, or mixtures thereof. In some embodiments, the clay or clays are acid activated or partially activated by washing them with a suitable acid. In some embodiments, the ratio of clay mixture to extracted oil is about 0.01-1.5% wt/wt, or about 0.05-0.5% wt/wt. In some embodiments, contacting is conducted at least about 30, 35, 40, 45, 50, 55, 60° C., or more. In some embodiments, contacting is conducted at about 30-60° C. by pressure filtration. In some embodiments, the contacting is conducted under reduced pressure (e.g. 50-350 mm Hg, 50-125 mm Hg, or 300-760 mm Hg). In some embodiments, filtering 435 removes all solids from stream 431.

In some embodiments, adsorbing 430 is conducted by flowing degummed oil stream through a column packed with granular activated carbon (GAC). In some embodiments, the effluent of the GAC column is mixed with Fullers earth or with Perlite filter aid. In some embodiments, the effluent contacted with the GAC column is filtered 435 to provide a partially refined oil stream 436.

Some pesticides that are in current use are strong or weak bases in character or comprise a nitrogen atom that can be protonated under acidic conditions, for example Microbutanil, Paclobutrazol, Fenoxycarb, Befenazate, Spirotetramat, Spinosad, Imidacloprid, Thiacloprid, Spiroxamine, Propoxur, Paclobutrazol, Methyl parathion, Imazalil, Fenoxycarb, Aldicarb, Abamectin. Analytical methods for their analysis at low level, where pre-concentration is required, utilize their protonated nitrogen functionality for capturing them on PTFE membranes having a strong cation exchange functionality, such membranes are commercially available from 3M (Empore™ SPE).

In some embodiments, pesticides can be effectively removed from the solution comprising the solvent and the partially refined extracted oil by weak acid cation exchange resin (WAC). In some embodiments, the WAC can be regenerated under milder conditions. WAC resins are commercially available from several suppliers including for example Purolite, Dow, Sorbtech, GE and more. In some embodiments, WAC can remove trace amounts of heavy metals. In some embodiments, a strong acid cation exchange (SAC) resin may be used to adsorb many pesticides.

In some embodiments, contacting with WAC resin is performed by flowing the partially refined stream 436 through a column packed with the resin (440). In some embodiments, the resin is in the $H^+$, $Na^+$, $K^+$, $Rb^+$, or $Cs^+$ form. In some embodiments, the resin is in a mixed $Na^+$ and $H^+$ form. In some embodiments, two sequential columns are used, wherein the first is in the $Na^+$ form and the second is in the $H^+$ form. In some embodiments, contacting with the resin is done at about 10 to about 60° C. In some embodiments, the temperature is about 20° C. to about 50° C. In some embodiments, the temperature is about 35° C. to about 45° C. In some embodiments, the contacting with WAC resin provides stream 441, comprising reduced amounts of pesticides and herbicides compared to the feed stream 436. In some embodiments, at least about 70, 80, 90%, 95%, or more of the residual pesticides and herbicides present in stream 436 is removed by contacting with the WAC resin. In some embodiments, contacting with the WAC can remove divalent or trivalent metallic cations. In some embodiments, contacting with the WAC resin efficiently removes heavy metal cations.

In some embodiments, stream 441 comprises metals other than Na, K, Rb or Cs of at most about 6000, 5000, 4000, 3000, 2000, 1000, 500, 100, 50 µg/kg, or less (solvent removed base, SRB). In some embodiments, stream 441 comprises at most about 0.29 µg/kg SRB, or even less than 0.14 µg/kg SRB As. In some embodiments, stream 441 comprises at most about 0.09 µg/kg SRB, or at most about 0.05 µg/kg SRB Cd. In some embodiments, stream 441 comprises at most about 0.29 SRB µg/kg, or at most about 0.15 µg/kg SRB Pb. In some embodiments, stream 441 comprises at most about 0.29 µg/kg SRB, or at most about 0.15 µg/kg SRB Hg. In some embodiments, stream 441 comprises at most about 500 µg/kg SRB Ca. In some embodiments, stream 441 comprises at most about 500 µg/kg SRB Mg. In some embodiments, stream 441 comprises at most about 100 µg/kg SRB Zn. In some embodiments, stream 441 comprises at most about 100 µg/kg SRB Fe. In some embodiments, stream 441 comprises at most about 50 µg/kg SRB Cu. In some embodiments, stream 441 comprises at most about 50 µg/kg SRB, or at most about than 25 µg/kg SRB Cr.

In certain aspects, stream 441 is "winterized" (445) (e.g., chilled for at least about 0.5, 1, 2, 3, 4, 5, 6, 8, 10, 12, 14, 16, 18, 20, 22, 24, or more hours to cause precipitation of fatty acids, gums and waxes). In some embodiments, winterizing comprises chilling the solution to a temperature of about −25° C. to 0° C., or about 0° C. to 8° C., or about 4° C. to 15° C. In some embodiments, Perlite filter aid or Fuller's earth is added to the solution while chilling. In some embodiments, the ratio Perlite filter aid or Fuller's earth is from about 0-2% wt/wt. In some embodiments, the solution may be stirred for part of the chilling time and allowed to stand in part of the chilling time. In some embodiments, winterizing also comprises filtering or centrifuging the chilled solution to remove a precipitate stream 447 and a clarified stream of refined extract 446. In some embodiments, the precipitate stream is dried (FIG. 8C, 370) with other waste solids (e.g. spent biomass, fully loaded adsorbing media) in a paddle dryer. In some embodiments, the vapors of solvent are collected and recycled for further use to provide solid waste comprising at most 1, 0.5, 0.01%, or less solvent. Such paddle dryers are commercially available from multiple suppliers. In some embodiments, refined extract stream 446, comprising solvent and refined extract, is fed into evaporating 450 to provide concentrated refined extract and to recover the solvent for further use. In some embodiments, the vapors are collected and condensed, and transferred via conduit 452 to be recycled.

Figure 7C:
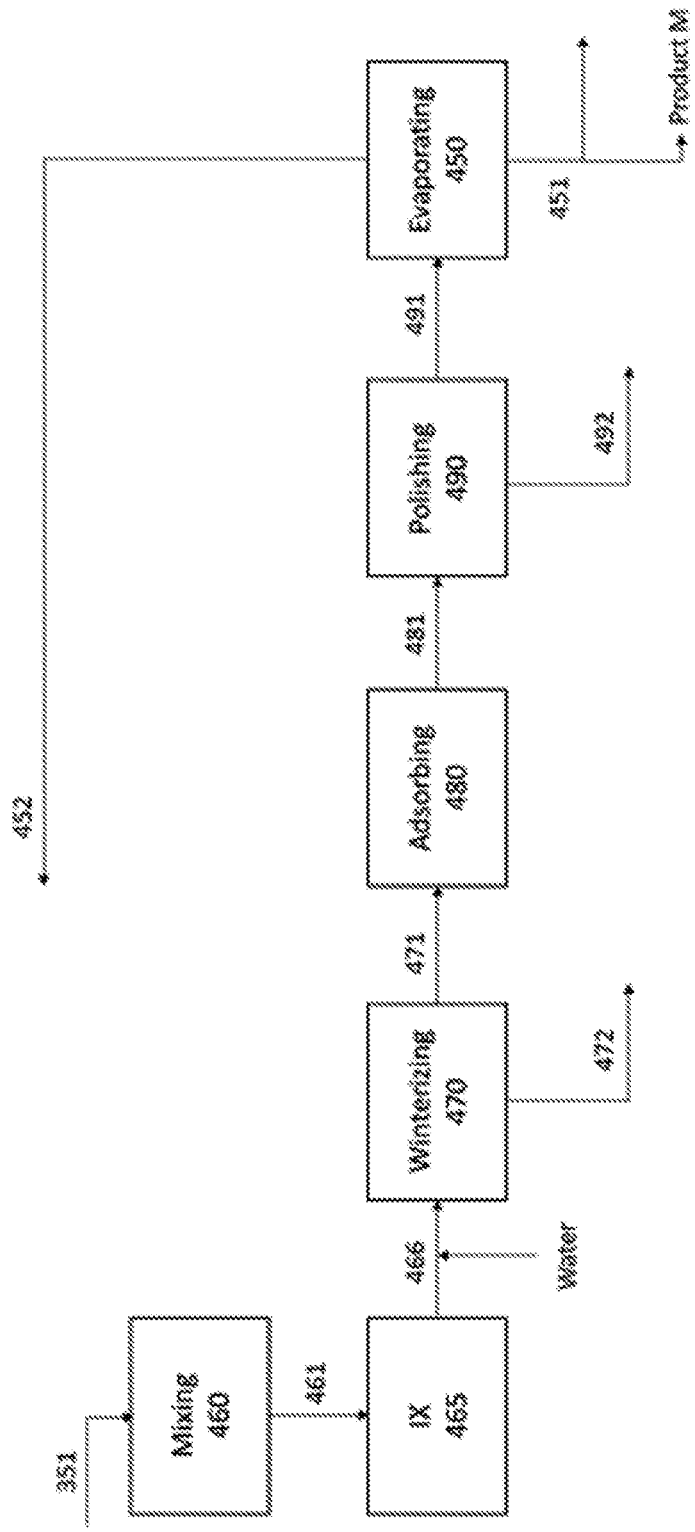
FIG. 7C illustrates a schematic diagram of an alternative process for refining of crude extracted oil.

An alternative scheme of a continuous process for removing the undesired co-extracted compounds and for providing refined extracted oil is illustrated in FIG. 7C. The process may comprise the steps of mixing (460), contacting with an ion exchange resin (465), optionally "winterizing" (470), followed by contacting with at least one adsorbent (480), final polishing (490), and eventually the refined stream is concentrated at evaporating (450) to provide a refined mixed cannabinoids Product M and recover the solvent for further use. The refined mixed cannabinoids Product M may be transferred to fractionating (500) in order to provide products enriched with specific constituent or group of constituents.

In some embodiments, crude extracted oil is provided as a semi solid as a product of any extraction process as described herein above, comprising at most about 5, 2, 1, 0.5, 0.1, 0.01%, or less solvent. In some embodiments, the crude extracted oil is first mixed with a solvent (460) to provide a low viscosity and easy to handle solution. In some embodiments, the crude extracted oil is mixed at a ratio in the range of about 20:1 to 1:2 with a solvent, wherein the solvent may be the same one used for extracting or a different solvent. In some embodiments, the ratio is about 10:1. In some embodiments, the ratio of solvent to extract is about 1:1. In some embodiments, extraction can be conducted with the same solvent, in which case the crude extracted oil is provided as a solution comprising the solvent. In some embodiments, mixing step 460 can be eliminated. In some embodiments, solvent can be removed by evaporation to bring the ratio to the desired solvent to extract range.

In some embodiments, the solvent may comprise a solvent or a mixture of solvents, wherein the solvent or mixture of solvents (i) is categorized as class 3 according to Q3C— Table and Lists Guidance for Industry (US Department of Health and Human Services, FDA, CDER, CBER), June 2017 ICH rev. 3; or (ii) forms a heterogeneous azeotrope with water, wherein the azeotrope has a boiling point lower than the boiling point of water. In some embodiments, the solvent or a mixture of solvent forms a heterogeneous azeotrope with water, wherein the solvent and the azeotrope have a boiling point lower than the boiling point of water. In some embodiments, the ratio of water to solvent, $R_w/R_s$, may be greater in the vapor phase of the azeotrope than in the solvent liquid phase. In some embodiments, the solvent or mixture of solvents is selected to have a Hildebrand solubility parameter of at least 16.0 $MPa^{1/2}$, 18.0 $MPa^{1/2}$, or more. In some embodiments, the solvent or mixture of solvent is selected to have a Hildebrand solubility parameter of at most 30.0 MPa½. In some embodiments, the solvent or mixture of solvent is selected to have a Hildebrand solubility parameter of less than 26.0 MPa$^{1/2}$. In some embodiments, the solvent or mixture of solvent is selected to have a Hildebrand solubility parameter of less than 20.0 MPa$^{1/2}$. In some embodiments, the solvent or mixture of solvents is selected to have a Hildebrand solubility parameter in the range of 18.0 to 20.0 MPa$^{1/2}$. The solvent may be selected from 1-butanol, ethyl acetate, ethyl formate, 2-methyl-1-butanol, ethanol, heptane, cyclohexane, 2-butanone, 2-propanol, propylene glycol and mixtures thereof. In some embodiments, the solvent is ethyl acetate or ethyl formate. Alternatively, the solvent may be selected from pentanol, hexanol, heptanol, 2-ethyl hexanol, octanol, 2-butanone (MEK), methyl isobutyl ketone (MIBK).

In some embodiments, the solvent is dry, or saturated with water, or is present at its water azeotrope composition. In some embodiments, the solvent comprises a carboxylic acid, e.g. acetic acid, citric acid, formic acid. In some embodiments, the concentration of the carboxylic acid is about 0.01, 0.05, 0.1, 0.2, 0.3, 0.4, 0.5, 0.6, 0.7, 0.8, 0.9, 1%, or more.

In some embodiments, the mixed solution 461, comprising solvent and the crude extracted oil, is contacted with a WAC resin. In some embodiments, mixed solution 461 is contacted with a SAC resin. In some embodiments, contacting with WAC resin is performed by flowing the crude stream 461 through a column packed with the resin (465). In some embodiments, the resin is in the H$^+$, Na$^+$, K$^+$, Rb$^+$, or Cs$^+$ form. In some embodiments, the resin is a mixed Na$^+$ and H$^+$ form. In some embodiments, two sequential columns are used, wherein the first is in the Na$^+$ form and the second is in the H$^+$ form. In some embodiments, contacting with the resin is done at about 10° C. to about 60° C., 30 to 55° C., or about 40 to 50° C. In some embodiments, a SAC or a SBA resin may be used to adsorb many pesticides. In some embodiments, prior to contacting with a WAC resin, stream 461, comprising crude oil with the solvent, the solution is contacted with activated carbon by flowing the stream through a GAC column. In some embodiments, the ratio of solvent to crude oil in stream 461 is 100:1 to 1:1. In some embodiments, the ratio of solvent to crude oil in stream 461 is 70:1 to 40:1. In some embodiments, the ratio of solvent to crude oil in stream 461 is 10:1. In some embodiments, the solution is controlled to have a viscosity of 0.5 to 25 cPs at 25° C.

In some embodiments, the contacting with WAC or SAC resin provides stream 466, comprising reduced amounts of pesticides and herbicides compared to the feed stream 461. In some embodiments, at least about 70, 80, 90%, 95%, or more of the residual pesticides and herbicides present in stream 461 is removed by contacting with the resin. In some embodiments, contacting with the WAC or SAC removes divalent or trivalent metallic cations. In some embodiments, contacting with the WAC resin removes heavy metal cations.

In some embodiments, stream 441 comprises metals other than Na, K, Rb or Cs of less than about 6000, 5000, 4000, 3000, 2000, 1000, 500, 100, 50 µg/kg, or less (solvent removed base, SRB). In some embodiments, stream 441 comprises at most 0.29 µg/kg SRB, or at most 0.14 µg/kg SRB As. In some embodiments, stream 441 comprises at most 0.09 µg/kg SRB, or at most 0.05 µg/kg SRB Cd. In some embodiments, stream 441 comprises at most 0.29 SRB µg/kg, or at most 0.15 µg/kg SRB Pb. In some embodiments, stream 441 comprises at most 0.29 µg/kg SRB, or at most 0.15 µg/kg SRB Hg. In some embodiments, stream 441 comprises at most 500 µg/kg SRB Ca. In some embodiments, stream 441 comprises at most 500 µg/kg SRB Mg. In some embodiments, stream 441 comprises at most 100 µg/kg SRB Zn. In some embodiments, stream 441 comprises at most 100 µg/kg SRB Fe. In some embodiments, stream 441 comprises at most 50 µg/kg SRB Cu. In some embodiments, stream 441 comprises at most 50 µg/kg SRB, or at most 25 µg/kg SRB Cr.

In some embodiments, ion-exchanged stream 446 is "winterized" (470). In some embodiments, winterizing comprises mixing with cold water. In some embodiments, the temperature of the water is about 2° C. to 10° C. or about 4° C. to 7° C. In some embodiments, the ratio of water to the ion-exchanged stream is about 5:1 to about 20:1, or about 12:1 volume/volume. In some embodiments, winterizing further comprises at least one step of mixing and chilling. In some embodiments, mixing and chilling may be conducted in a temperature controlled stirred tank. In some embodiments, mixing and chilling may be conducted in other industrial devices for mixing and chilling (e.g., heat exchangers). In some embodiments, mixing and chilling comprises at least two steps of mixing and chilling, wherein the first temperature is higher than the second temperature. For example, the first mixing and chilling temperature may be done at about 15° C., while the second mixing and chilling may be done at about 5° C. In some embodiments, mixing and chilling is conducted at each step for about 0, 0.75, 1, 1.5, 2, 3, 4, 5, 10, 15, 20, or about 24 hours. In some embodiments, the winterized mixture is centrifuged to provide a light phase, comprising solvent and semi-refined extracted oil, and a heavy phase 472, comprising water and precipitates, wherein the precipitates comprise gums, waxes and fatty acids. Stream 472 is directed to a stripping 340 (FIG. 4), comprising a distillation column, where solvent is evaporated and recycled back to the process, and the bottom phase comprising water and precipitates can be directed to a waste water treatment plant.

In some embodiments, the water stream comprises at most 30% wt/wt solvent, such as at most about 25, 20, 15, 10, 9, 8, 7, or 6% wt/wt solvent. In some embodiments, stripper 340 comprises a distillation unit. In some embodiments, the distillation unit is suitable to distill the solvent/water azeotrope at the top, while water remains at the bottom of the distillation unit. In some embodiments, the stripper comprises a packed column distillation unit. The top distillate of stripper 340 can be transferred by conduit 341 back to liquid/liquid separator 330. In some embodiments, the temperature of the distillation top is about 40-95° C., such as 50-85° C. or 65-75° C. In some embodiments, the temperature of the distillation top is about 70° C. In some embodiments, the bottom stream comprises at most about 2% wt/wt solvent, such as less than 1, 0.1, or even less than 0.05% wt/wt solvent. In some embodiments, bottom distillates W301 of stripper 340 are transferred by conduit 342 to a waste water treatment facility.

In some embodiments, the organic stream is transferred via conduit 471 to adsorbing 480. In some embodiments, adsorbing 480 comprises controlling the temperature of the solution to about 30-60° C., or about 40-50° C., or about 45° C. In some embodiments, adsorbing 480 further comprises flowing the solution through at least one column packed with GAC. In some embodiments, the solution is flowed through at least two or three or more columns packed with GAC. In some embodiments, the solution is contacted in a stirred tank with PAC and filtered. In some embodiments, the solution is transferred to further polishing via conduit 481 to polishing.

In some embodiments, polishing comprises cooling the solution to about 10-30° C., or about 20° C. in a stirred tank for about 5, 10, 15, 20, 25, 30, 35, 40 min, 60 min, or more. In some embodiments, polishing further comprises the solution to about 4-15° C., or about 10° C. in a stirred tank for about 5, 10, 15, 20, 25, 30, 35, 40 min, or more. In some embodiments, polishing further comprises adding to the cooled solution Fuller's earth, Perlite filter aid, or mixtures thereof. In some embodiments, the amount added is about 0.1 to about 2% wt/wt. In some embodiments, polishing further comprises filtering all the particulate solids to provide a clarified polished solution 491 and solid waste stream 492. In some embodiments, solid waste is dried with other wastes (e.g. spent biomass, fully loaded adsorbing media, solid waste stream 472) in a paddle dryer, where vapors of solvent are collected and recycled for further use, to provide solid waste comprising less than 1, 0.5, 0.01% solvent. Such paddle dryers are commercially available from multiple suppliers.

In some embodiments, polishing comprises contacting the solution with Fuller's earth, Perlite filter aid, or mixtures thereof at about 10-60° C., or about 40-50° C. in a stirred tank for about 5, 10, 15, 20, 25, 30, 35, 40 min, 60 min, or more. In some embodiments, the amount added is about 0.1 to about 2% wt/wt. In some embodiments, polishing further comprises filtering all the particulate solids to provide a clarified polished solution 491 and solid waste stream 492. In some embodiments, solid waste is dried with other wastes (e.g. spent biomass, fully loaded adsorbing media, solid waste stream 472) in a paddle dryer, where vapors of solvent are collected and recycled for further use to provide solid waste comprising less than 1, 0.5, 0.01% solvent. Such paddle dryers are commercially available from multiple suppliers. In some embodiments, the polished solution is characterized as colorless or slightly yellow.

In some embodiments, the polished solution 491, comprising solvent and refined extract, is fed into evaporating 450, to provide concentrated refined extract and to recover the solvent for further use. In some embodiments, the vapors are collected and condensed, and transferred via conduit 452 to be recycled.

In some embodiments, the refined extract, Product M, is pure enough to be consumed as a mixed cannabinoid product and can be transferred via conduit 451 to packing and selling. In some embodiments, the refined product is transferred via conduit 451 to fractionating 500.

In some embodiments, Product M is an essentially pure product with respect to non-cannabinoids components with the exception of terpenes, i.e. the remaining concentration of impurities that must to be eliminated from the starting crude product is well below the relevant regulatory limit for each such impurity compound. In some embodiments, the total cannabinoids concentration of Product M is at least 80, 82, 84, 86, 88, 90, 92, 94, 95% wt/wt, or more. In some embodiments, the ratio of CBDA to total cannabinoids in Product M is substantially the same as this ratio in the crude product. In some embodiments, the ratio of THCA to total cannabinoids in Product M is substantially the same as this ratio in the crude product.

In some embodiments, when the process is applied for the refining of crude extract of a *cannabis* plant, including a hemp plant, Product M can be tested according to the requirements of various regulators and proven suitable for human consumption. In the US, the authorities of various states have put in place such requirements with respect to residual amounts of volatile solvents (VOC), heavy metals, pesticides and herbicides, mycotoxins and aflatoxins, as well as total bacteria count, yeast & mold and some specific bacteria.

In some embodiments, implementation of processes disclosed herein in equipment designed to be cleaned and sterilized if needed by good manufacturing practices can routinely ensure Product M can meet all standards related to microbiology, particularly since much of the processing is conducted in a solvent that does not generally support microbiological contamination. In some embodiments, Product M comprises at most about 100,000, 10,000, 1000, or less colony forming units/g (CFU/g) total aerobic bacteria. In some embodiments, Product M comprises at most about 10,000, 1000 CFU/g, or less yeast and mold. In some embodiments, Product M comprises at most 1,000, 100 (CFU/g), or less bile-tolerant gram-negative bacteria. In some embodiments, Product M comprises at most 1,000, 100 (CFU/g), or less total coliforms. In some embodiments, Product M comprises at most 100, 10 (CFU/g), or less *E. Coli*. In some embodiments, Product M comprises at most 100, 10 (CFU/g), or less *Salmonella*.

In some embodiments, Product M comprises any of the solvents acetonitrile, benzene, butane, 1-butanol, 2-butanol, 2-butanone (MEK), 1,2-dichloroethane, dichloromethane, 1,2-dimethoxyethane, N,N-dimethylacetamide, 2,2-dimethylbutane (hexanes) 2,3-dimethylbutane (hexanes), N,N-dimethylformamide, 2,2-dimethylpropane (neopentane), dimethylsulfoxide (DMSO), 1,4-dioxane, chloroform, cumene, cyclohexane, ethanol, 2-ethoxyethanol, ethyl acetate, ethyl ether, ethylene glycol, ethylene oxide, heptane, hexane, isopropyl acetate, methanol, 2-methylbutane (isopentane), 2-methylpentane (hexanes), 3-methylpentane (hexanes), 2-methylpropane (isobutane), naphtha, pentane, 1-pentanol, petroleum ether, propane, 1-propanol, 2-propanol (isopropyl alcohol), 2-propanone (acetone), sulfolane, trichlorethylene, tetrahydrofuran (THF), toluene, xylenes (o-xylene, m-xylene, p-xylene), pyridine, or any combination thereof, at well below the Minimum Required Limit (MRL).

In some embodiments, Product M comprises at most about 5000 µg/g ethanol. In some embodiments, Product M comprises at most about 3000 µg/g methanol. In some embodiments, Product M comprises at most about 5000 µg/g ethyl acetate. In some embodiments, Product M comprises at most about 5000 µg/g butane. In some embodiments, Product M comprises at most about 290 µg/g hexane. In some embodiments, Product M comprises at most about 60 µg/g chloroform. In some embodiments, Product M comprises at most about 600 µg/g dichloromethane. In some embodiments, Product M comprises at most about 5 µg/g 1,2-dichloroethane. In some embodiments, Product M comprises at most about 5000 µg/g acetone. In some embodiments, Product M comprises at most about 410 µg/g acetonitrile. In some embodiments, Product M comprises at most about 2 µg/g benzene. In some embodiments, Product M comprises at most about 5000 µg/g ethyl ether. In some embodiments, Product M comprises at most about 50 µg/g ethylene oxide. In some embodiments, Product M comprises at most about 5000 µg/g heptane. In some embodiments, Product M comprises at most about 5000 µg/g 2-propanol. In some embodiments, Product M comprises at most about 400 µg/g naphtha. In some embodiments, Product M comprises at most about 5000 µg/g pentane. In some embodiments, Product M comprises at most about 400 µg/g petroleum ether. In some embodiments, Product M comprises at most about 5000 µg/g propane. In some embodiments, Product M comprises at most about 80 µg/g trichloroethylene. In some embodiments, Product M comprises at most about 890 µg/g toluene. In some embodiments, Product M comprises at most about 2170 µg/g total xylenes.

In some embodiments, Product M comprises at most about the maximum allowed limit of any pesticide or herbicide listed by state authorities with respect to the relevant product, e.g. *cannabis* products. In some embodiments, Product M comprises at most about 1, 0.5, or even less than 0.5% ash. In some embodiments, Product M comprises at most about 0.14 µg/kg Arsenic. In some embodiments, Product M comprises at most about 0.09 µg/kg Cadmium. In some embodiments, Product M comprises at most about 0.29 µg/kg Lead. In some embodiments, Product M comprises at most about 0.29 µg/kg Mercury. In some embodiments, Product M comprises at most about the allowed limit for any other heavy metal of potential harming effect. In some embodiments, Product M further comprises at most about 0.1% wt/wt Calcium, at most about 0.1% wt/wt Magnesium, at most about 0.1% wt/wt potassium, at most about 0.05% wt/wt phosphorous.

Each unit is described below in more details.

Extraction Unit

Figure 3:
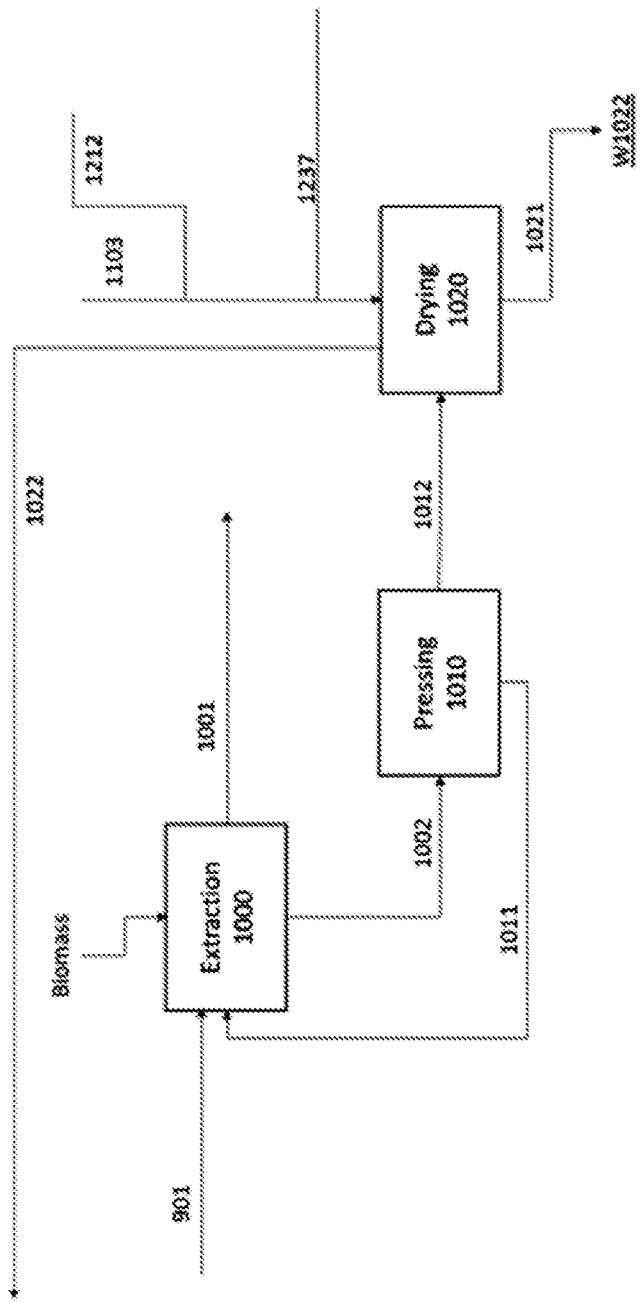
FIG. 3 illustrates a schematic diagram of a process unit for extracting plant material.

FIG. 3, shows a schematic process for extracting plant material. Plant material is fed into the extracting system (1000), where it is extracted with solvent that is transferred via conduit 901 from the solvent recovery unit (900), to provide loaded extractant stream 1001, that is transferred to refining, and a slurry of extracted plant material, that is transferred via conduit 1002 to pressing 1010. The liquid collected by pressing is recycled back to extracting via conduit 1011, the pressed biomass is transferred via conduit 1012 to a drying (1020). The drying system 1020 receives additional streams of moist solids from the refining units further downstream. All solids are dried together at dryer 1020, where all vapors are collected and returned via conduit 1022 to solvent recovery (900). The dry solids are collected as solid waste stream 1021, and can be dispensed off according to local regulations. Further details of the extraction system are provided in FIG. 4 and FIG. 5B and disclosed herein.

Figure 4:
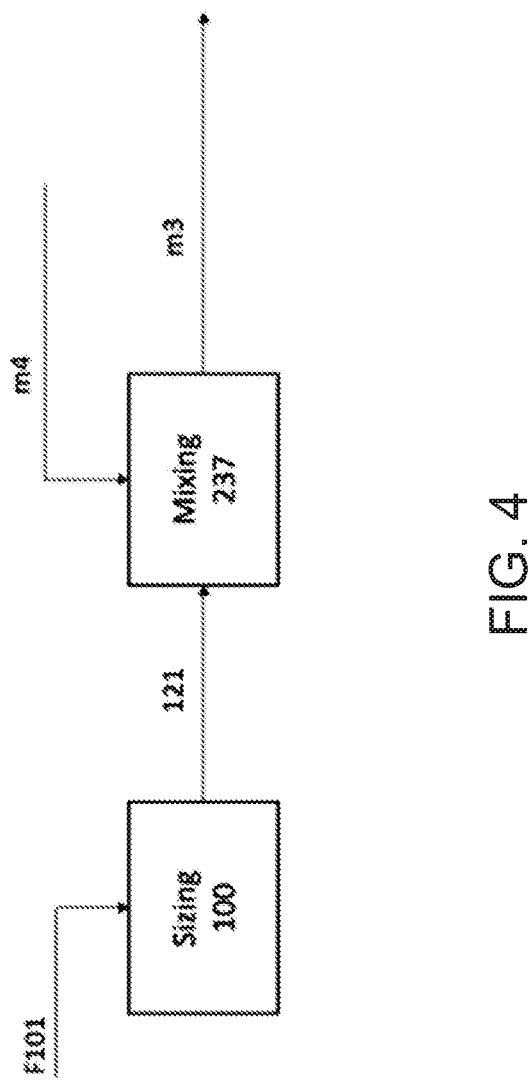
FIG. 4 illustrates a schematic diagram of a pretreating process of plant material by sizing the plant material and mixing it with a solvent or a partially loaded solvent.

In some embodiments, plant material may be pretreated prior to extraction. Pretreatment may comprise separating the different parts of the plants, i.e. buds, leaves, stalk, etc., such that each part can be treated separately. Pretreatment may comprise a reduction in plant material size (e.g. mechanical breaking, milling, grinding), or disintegrating or breaking up if the plant material is provided as pellets. Size reduction may be done on the plant material before adding a solvent, during mixing with the solvent or after adding a solvent. In some embodiments, different parts of the plant may separate at or after sizing by density. In some embodiments, sized particles of low density, i.e. density lower than the extractant solvent density, are separated by floatation. In some embodiments, a stream of floated low density slurry is transferred directly to pressing (1010). FIG. 4 illustrates a schematic pretreatment process, comprising a sizing operation (100) and a mixing operation (237), wherein F101 denotes the feed of plant material and 121 denotes the sized plant material stream. Stream m4, comprising partially loaded solvent (e.g. comprising some extracted constituents), transfers liquid from the extraction unit (1000) via a conduit. The slurry of plant material and solvent is fed into extraction 1000 (FIG. 5B) via conduit m3. Alternatively, stream m4 and stream 121 may be feed directly to extraction 1000, and mixed in the first extractor to contact biomass in extraction 1000.

Figure 5B:
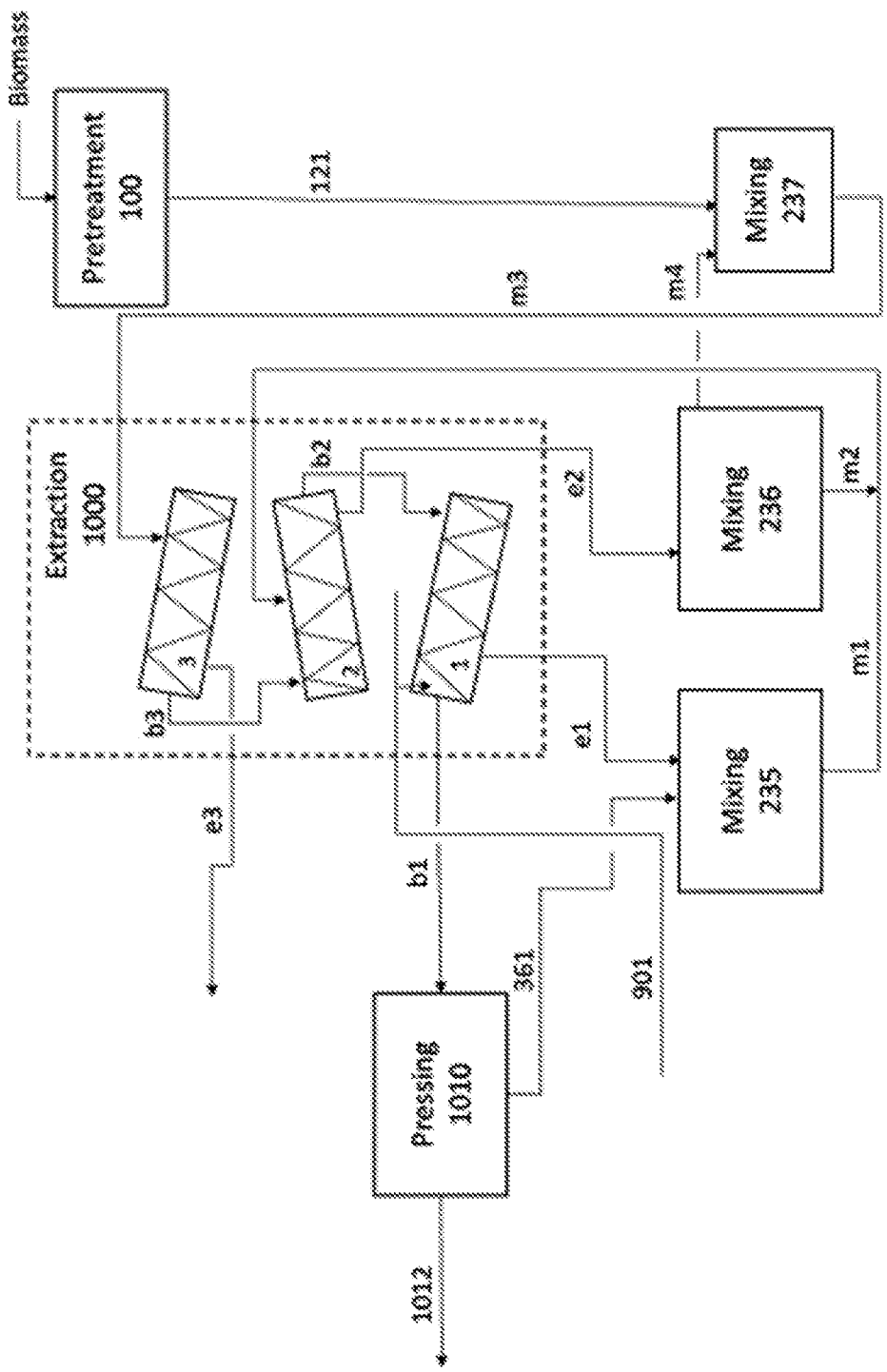
FIG. 5B illustrates an alternative schematic diagram of a continuous process for extracting the constituents of interest from the plant material. The figure shows the configuration of an extractor comprising three extraction conveyor screw units, and three mixing units, wherein each unit operates in a co-current mode, while the flows between different units is in counter-current mode. The scheme presents three units. More units may be added in series or in parallel to any of the three conveyor screw units, to optimize extraction.

FIG. 5B illustrates extraction unit 1000 in more detail. U.S. Pat. No. 4,617,177 discloses a system for the solid/liquid extraction of in particular vegetable raw materials, such as oilseeds and oil-yielding plants, with low-boiling solvents, such as gasoline and the like, in continuous co-current manner. The equipment, which is also to be regarded as the actual extraction unit, is formed by the combination of a conveyor screw having a screw flight pitch which widens in the direction of the transport of material, and a screen such as wedge wire provided at a short distance upstream of the discharge of the extracted material. The equipment is closed on all sides and is vapor tight. It can be employed in the solvent extraction of oilseeds and oil-yielding plants, the glyceride constituents (oils and fats) extracted from the predominantly solid raw material passing into the liquid phase, the so-called miscella. It is particularly suitable for extracting oil-yielding plants in industrial operation where the extracting solvent has a low boiling point, in the ranges of 60°-100° C. These relatively low-boiling extracting agents pose stringent requirements on the constructional expense on both the equipment and the processes. The expense relates to the safety of the maintenance and operating personnel coming into contact with the solvents and to optimum operational control, so that the extraction remains within economically acceptable limits.

Extraction unit 1000 is formed by the combination of conveyor screws and mixing tanks that provide a simple way to contact effectively the pretreated biomass with the extracting solvent. The design of the system allows for different ratios of liquid to solvent in its different subunits by pumps and buffer volume in the mixing tanks. For clarity, FIG. 5B depicts three conveyor screw units, wherein each unit is operated at co-current mode, while the flow of solvent and biomass is in counter-current mode between the different units. The conveyor screws are mounted in an inclined arrangement, optionally at an angle of about 30 degree to about 60 degree, or about 40 to about 50 degrees, or at about 45 degrees, such that flow from conveyor to conveyor can be driven by gravitation. In some aspects, the conveyor screw has a combination of screw flight pitches to mix, compress and transport the solid material. In some aspects, the screw flight pitch is the same along its whole length, thus reducing the capital expenditure to construct the system.

In some embodiments, flows of slurries comprising biomass from one extractor to the next one is gravitational. In some embodiments, flow of biomass slurry from the mixing tanks to the extractors is by suitable pumps, thus allowing control of flow rates. The solids discharge end of each conveyor is fitted with a wedge wire screen, which allows liquid to pass through while the slurry remains on top of the screen. Thus, the conveyors provide solid/liquid separation at the extraction unit. The conveyor screws can be inclined at a determined angle, wherein the angle is about 30 degrees to about 60 degrees, or about 40 degrees to about 50 degrees, or about 45 degrees to control the residence time of material in each conveyor and screening area. The angle may be about 60 degrees or more. The angle may be about 30 degrees, or less. The system in installed such that this angle may be modified.

In some aspects, extractor 1000, mixing tanks 235, 236, 237 and other parts of the system are jacketed for thermal insulation, such that the extraction is conducted at low temperature, such as lower than about 0° C., lower than about −5° C., lower than about −10° C., lower than about −15° C., lower than about −20° C., lower than about −25° C., lower than about −35° C., lower than about −45° C., or lower. In some aspects, the extraction is conducted at about −25° C. In some aspects, the extraction system disclosed herein comprises a chiller (260), with capacity to cool down the freshly regenerated solvent to the designated temperature while feeding into extractor 1000(1) via conduit 261. In some aspects, extractor 1000, mixing tanks 235, 236, 237 and other parts of the system are jacketed for thermal insulation, such that the extraction is conducted at a temperature of about 35° C. or more. In some aspects, extractor 1000, mixing tanks 235, 236, 237 and other parts of the system are jacketed for thermal insulation, such that the extraction is conducted at a temperature of about −25° C., or less. In some aspects, extractor 1000, mixing tanks 235, 236, 237 and other parts of the system are jacketed for thermal insulation, such that the extraction is conducted at a temperature of about −25° C. (minus 25° C.) to about +35° C. (plus 35° C.), about −5° C. (minus 5° C.) to about +25° C. (plus 25° C.), or about +5° C. (plus 5° C.) to about +25° C. (plus 25° C.). In some embodiments, extraction is conducted at a temperature of about +10° C. to (plus 10° C.) to about +25° C. (plus 25° C.), or at a temperature of about +15° C. to (plus 15° C.) to about +20° C. (plus 20° C.).

Referring to FIG. 5B, pre-treated biomass can be mixed in mixing tank 237 with an overflow stream of mixing tank 236 (m4) comprising partially loaded solvent, to provide slurry stream (m3), which is fed into the uppermost conveyor, extractor 1000(3). Biomass and liquid are conveyed up along extractor 1000(3), where the initial extraction of fresh biomass takes place into a partially loaded extractant. The loaded solvent is separated on the screen to provide a through stream comprising the fully loaded extracted stream (e3), and a retained stream of partially extracted stream comprising biomass (b3), which is transferred as feed to the middle conveyor, extractor 1000(2). Additional volumes of extracting solvents are fed into extractor 1000(2) by a stream comprising low levels of extractives from mixing tank 235 (m1). In some embodiments, more volumes of extracted solvent comprising low levels of extractives are feed into this stream from mixing tank 236 (m2). Extractor 1000(2) is where much of the extraction process occurs, thus it is advantageous to have greater amounts liquid available at this stage. Biomass and liquid are conveyed up extractor 1000 (2), and are separated to a partially loaded liquid stream (e2), which is transferred to mixing tank 236, while the biomass comprising steam (b2) is transferred to the lower-most conveyor, extractor 1000(1). The extracted biomass is then washed in extractor 1000(1) that is fed also with freshly regenerated chilled solvent (261), which is essentially free of extractives and therefore has strong capacity to remove the low levels of extractives remaining with the biomass at that stage. Biomass and liquid are conveyed up extractor 1000 (1), and are separated to a partially loaded extractant at low level of extractives (e1), which is transferred to mixing tank 235, and a spent biomass slurry that (b1), which is transferred to solid/liquid separation 310 for recovery of the loaded solvent and drying of the spent biomass.

In some embodiments, extractor 1000(2) comprises more than one conveyor (e.g., additional conveyor(s) are arranged in parallel or in series with respect to conveyor 2 as depicted in FIG. 5B). In some embodiments, the additional conveyor or conveyors are arranged in a counter-current mode with respect to conveyor 2.

In some aspects, wetting, extraction and solid/liquid separation in each conveyor is controlled by physical attributes of the screw and the wire screen. In some aspects, wetting extraction and solid/liquid separation is optimized by operational parameters of the conveyor screws. In some aspects, the inclination angle can be controlled to about 10, 20, 30, 40, 50, 60, or more degrees with respect to the horizontal. In some aspect, the inclination angle can be controlled to about 45 degrees. In some aspects, at the designated angle of inclination the internal conveyor volume is flooded from the leading edge of the drainage screen to the biomass inlet of the conveyor. In some aspects, the flight pitch is the same along the conveyor. In some aspects, the flight pitch is varied along the conveyor to optimize for initial wetting and solvent penetration in the flooded section and drainage in the screening section. In some aspects, the rotation speed of the screw is about 0.15-20 rpm, or about 0.5 to 5 rpm, depending on the pitch of the flights. In some aspects, the overall residence time of biomass in extractor 1000 is controlled to be about 60 minutes or more. In some aspects, the overall residence time of biomass in extractor 1000 is controlled to be about 1 minute, or less. In some aspects, the overall residence time of biomass in extractor 1000 is controlled to be between about 1 minute to about 60 minutes, between about 5 minutes to about 30 minutes, or between about 10 minutes to about 20 minutes.

In some embodiments, the ratio of liquid to solid in each section of extraction 1000 is different. In some aspects, the liquid to solid (L/S) ratio in extractor 1000(1) and in extractor 1000(3) is controlled at the range from about 1 to about 50 weight parts of liquid to solid, while the L/S ratio in extractor 1000(2) is controlled at the range from about 1 to about 100 weight parts liquid to solid. In some aspects, the liquid to solid (L/S) ratio in extractor 1000(1) and in extractor 1000(3) is controlled at the range from about 5 to about 20 weight parts of liquid to solid, while the L/S ratio in extractor 1000(2) is controlled at the range from about 20 to about 60 weight parts liquid to solid. In some embodiments, the solvent, water, or mixture thereof can be easily added into the process via fresh solvent to conveyor 1 to mixer tank 235.

In some aspects, extraction unit 1000 is designed to extract constituents from plant material at high efficiency. In some aspects, extraction unit 1000 is capable of extracting at least about 50%, such as at least about 60, 70, 80, 90, 95%, or more, of the amount present of each constituent of interest in the plant material. Provided the different chemical character of multiple extracted constituents, the extraction yield can be set at different efficiency values for different components, which may allow production of variable combinations of extracted constituents. Operation parameters of the extractor can be easily modified to allow for optimal yields.

In some aspects, the fully loaded extract stream (e3) comprises the liquids, due to solid/liquid separation that is performed within the conveyors. In some embodiments, the fully loaded extract stream (e3) is transferred via conduit 1001 to the first refining (1100).

In some aspects, the extraction unit further comprises a solid/liquid separation unit comprising a press 1010 and a dryer 1020 (FIG. 3, FIG. 5B). The spent biomass slurry is transferred directly via conduit b1 (FIG. 5B) to press 1010. In some aspects, the spent biomass slurry comprises about 5-20% wt/wt solids. Press 1010 recovers loaded solvent that is transferred to mixing 235 via conduit 361, while the concentrated solids stream is transferred via 362 to drying 370. Optionally, the press is a screw press, for example, such as Vincent Corporation CP-4 press, or larger units. In some aspects, the concentrated solids stream comprises about 35-75% wt/wt solids. The vapors released from the spent biomass at dryer 370, comprising solvent and water, are collected, condensed in a barometric condenser, and transferred to the solvent recovery unit 900. In some aspects, dryer 370 is a paddle dryer (e.g., GEA model Rosinaire Paddle dryer). In some embodiments, other spent solid materials used in processing and refining of the extractives, for example, use PAC or GAC, and, optionally, other adsorbent materials that may be used in refining of biomass extractives, such as clays and minerals, can be combined in the paddled dryer with the spent biomass and dried together. In some embodiments, the dried spent solids may be used as solid fuel.

The dry spent biomass (W1022) is transferred via conduit 1021 to a solid waste treatment facility, where it is treated according to local regulations. In some aspects, the dry solid waste may be used for energy production. In some embodiments, the dry solid waste can be pelletized. Since the spent biomass has been effectively extracted, it comprises trace amounts of active constituents. In some aspects, the residual level of each constituent is less than 20% wt/wt, such as less than or equal to about 15, 10, 9, 8, 7, 6, 5, 4, 3, 2, 1, or even less than or equal to about 0.1% wt/wt, of the original concentration. In some aspects, when *cannabis* is the plant being extracted, the residual amount of active constituents can be low enough to discard the spent biomass as unregulated dry biomass.

In some aspect, the present disclosure provides an extracted *cannabis* plant composition, wherein the composition comprises one or more of the following characteristics: (i) less than or equal to about 10% wt/wt dry base cannabinoids compared to the pre-extracted plant; (ii) less than or equal to about 0.001, 0.01, or 0.1% wt/wt water; and less than or equal to about 0.01, 0.1, or 1% wt/wt solvent. In some embodiments, the composition comprises less than or equal to about 5% wt/wt dry base cannabinoids compared to the pre-extracted plant, such as less than or equal to about 4%, less than or equal to about 3%, less than or equal to about 2%, or less than or equal to about 1% wt/wt dry base cannabinoids. In some embodiments, the composition comprises at least about 80%, or more, organic matter. In some embodiments, the organic matter can be characterized as spent biomass, comprising predominantly cellulose, hemicellulose pectin and lignin, such as comprising at least about 90% cellulose, hemicellulose, pectin and lignin, or more, in total. In some embodiments, the composition comprises about 0.0001 to 0.1% wt/wt water and about 0.0001 to 1% wt/wt solvent. In some embodiments, the composition comprises about 0.001 to about 5% wt/wt dry base cannabinoids, such as about 0.001 to about 1% or about 0.001 to about 0.1% wt/wt dry base cannabinoids.

Refining Units

In some aspects, as biomass may be a complex composition of constituents, the target constituents, e.g. cannabinoids and terpenes, are co-extracted with lipids, phospholipids, waxes and gums, color bodies, as well as residues of pesticides and herbicides, various natural toxins, inorganic elements including heavy metal ions. Aiming to provide a well-controlled extract, it is critical that all potentially harmful compounds are removed at least below the required regulatory concentration, and that all compounds that cause high viscosity, stickiness or any other physical property that may hinder downstream processing or adversely affect in any way the quality of the products, be removed. The relative amount of each undesired compound may change depending on growing conditions, type of the strain, season, geographic location and extraction process. It is an important aspect of the current disclosure to provide refining processes that can be successfully applied to crude products of diverse biomass feeds, extracted by different processes.

Various degumming processes for the refining of edible oils can be used, which is usually categorized as "water degumming", "acid degumming", and "enzymatic degumming". Such processes are commonly used in the production of edible oil from crude extracted oils of many grains, seeds, nuts, olives, palm fruit and so on, as well as in the biodiesel industry (*Edible Oil Processing*, Second Edition. Edited by Wolf Hamm, Richard J. Hamilton and Gijs Calliauw. 2013 by John Wiley & Sons, Ltd.). Crude vegetable oils obtained from either pressing or solvent extraction methods can be a complex mixture of triacylglycerols, phospholipids, sterols, tocopherols, free fatty acids, trace metals, and other minor compounds. In some embodiments, the phospholipids, free fatty acids and trace metals can be removed in order to produce a quality oil with a blend taste, light color, and a long shelf life.

In some aspects, adoption of these methods for the refining of crude extracted oil when the target constituents are not the triglycerides but rather constituents, such as cannabinoids and terpenes, which are soluble in triglycerides but are different in their molecular structure and are typically more sensitive to temperature and pH conditions, requires a careful design of the process. Moreover, some constituents of edible oil can be removed in the refining process, e.g. some of the tocopherols (Food Fats and Oils, 2016 Institute of Shortening and Edible Oils); thus, the refining process can be designed to avoid losses of the target constituents. In one aspect, as described herein, methods and processes suitable for refining the crude extract of the *cannabis* genre and hemp, such that phytocannabinoids, i.e. the cannabinoids as produced in the plant and extracted, are preserved to a large extent through the process and are not chemically modified or removed.

Removal of pesticides and herbicides from the extracted oil can be a challenge, and multiple such agents may be present at trace amounts depending on the method of growth of the biomass, e.g. indoors in a shielded area or outdoors in a field, the geography, the season, neighboring fields where other crops may be grown and treated in different ways and so on. Moreover, pesticides and herbicides are organic pollutants can persist in soil in many parts of the world (A. Marican et. al., A review on pesticide removal through different processes, Environmental Science and Pollution Research (2018) 25:2051-2064), and thus may be found in growing plants even if not used at the growing season, or due to their use in neighboring fields for different crops. In some aspects, as described herein, multiple steps for the removal of trace amounts of pesticides and herbicides can be accomplished while maintaining the level of the target constituents. In some embodiments, pesticides and herbicides may be cationic, anionic or non-ionic in nature, some may be protonated or deprotonated depending on acidity of the solution.

It may be essential to ensure removal of heavy metals to very low levels, as required by regulations already in place in some states. For example, Nevada state Division of Public and behavioral Health Policy # MME005 titled *Medical Marijuana Establishment Heavy Metals Testing Standards*, effective as of 18 Feb. 2015 requires that the limits of the following heavy metals for medical marijuana are: Arsenic less than or equal to about 0.14; Cadmium less than or equal to about 0.09; Lead less than or equal to about 0.29; Mercury less than or equal to about 0.29 µg/kg. A study by P. Atkins and J. Akers of SPEX CertiPrep, titled *Analysis of Cannabis and Hemp Products for Heavy Metals*, details the analysis of heavy metals in 18 samples of commercial oil prepared by different methods and sold in different forms in the USA. The samples can vary significantly in their profile, but most samples have been shown to contain some Arsenic, Cadmium and Lead, while Mercury was below level of detection for all but one sample. In addition, most samples contained some level of Chromium. The level measured in some of the products can be of concern if used to treat a child, having inherently lower body mass, and particularly child with health concern. Furthermore, the challenge in ensuring removal of heavy metals from cannabinoids products is aggravated by inherent properties of the plant: the *cannabis* genre can accumulate heavy metals and are sometimes used to reclaim contaminated soils (V. Angelova et. al., *Bioaccumulation and distribution of heavy metals in fibre crops (flax, cotton and hemp)*, Industrial Crops and Products 19(3):197-205, 2004). In some aspects, the current disclosure provides multiple steps for the effective removal of heavy metals.

Depending on the extraction method and solvent, crude extracted product can have high viscosity at room temperature and feel "tacky". In certain cases it appears as a resinous material, which can be almost solid at room temperature or may not flow well. When mixing it at a ratio of about 1:1 with a solvent, filtration can be very difficult and slow. To allow refining of the crude oil, it is essential to remove initially the compounds that contribute to high viscosity and "stickiness" of the crude oil, e.g. phospholipids, gums and waxes, by a "degumming" process.

In some aspects, design of various refining steps where concentration, temperature, viscosity and flow rate to be optimal and specific for different classes of impurities, allow the construction of an integrated process for the stepwise refining of the crude extracted oil to a degree that makes plant extracted constituents suitable for human consumption.

First Refining Unit

FIG. 6A, shows a schematic process for a first refining of a loaded extractant. The loaded extractant comprising solvent, water, extracted constituents and extracted impurities, is transferred via conduit 1001 to the first refining (1100). The first refining unit comprises at least one adsorbing unit 1101, also, optionally, comprises at least a second adsorbing unit 1102. The stream is then transferred via conduit 1111 to evaporating unit 1105. Fully loaded adsorbing media can be transferred via conduit 1103 to drying (FIG. 3, 1020) or regenerated for reuse. At evaporating 1105 solvent and water are partially evaporated from the stream at to provide a first refined oil, which can be transferred to the second refining unit via conduit 1006. Vapors are collected, condensed in a barometric condenser and transferred via conduit 1107 to solvent recovery unit 900.

When extracting thermally sensitive extractives, it is often desired to maintain low temperature. Moreover, low temperature can provide better selection of target extractives, e.g. cannabinoids and terpenes, while minimizing extraction of undesired species, such as gums, waxes, chlorophyll, such selection is sometimes termed "winterizing". Alternatively, extraction can be performed at higher temperatures to achieve faster kinetics of extraction and higher yield, such as about −5° C. to +25° C., or even about +5° C. to +25° C., or even about +10° C. to +25° C. Such higher temperature of extraction can cause higher extraction of various undesired compounds from biomass, such as chlorophyll, color bodies, and other impurities. Surprisingly in was found that the additional undesired compounds can be removed efficiently from the extract by contacting the loaded solvent, comprising all extracts (i.e. target constituents and impurities), with activated carbon (e.g., PAC or GAC). In some aspect, when the extracted plant is a *cannabis* plant, contact with activated carbon can also reduce the amount of THC and THCA in the extracted constituents. In some aspects, at least 10, 20, 30, 40 or even at least 50% of the THC and THCA are removed from the loaded solvent. In some aspects, contacting is conducted by flowing the loaded solvent through at least one column packed with GAC. In some embodiments, the loaded solvent flows through at least two sequential GAC columns 1101 and 1102 (FIG. 6A).

In some aspects, the ratio of solvent to loaded extractant in stream 1001 is about 100:1 to 1:1. In some aspects, the ratio of solvent to crude oil in stream 1001 is about 70:1 to 20:1. In some aspects, the ratio of solvent to crude oil in stream 1001 is about 20:1. In some aspects, the solution is controlled to have a viscosity of about 0.5 to 25 cPs at 25° C. In some aspects, contacting with the GAC is done at about 50° C., or more. In some aspects, contacting with the GAC is done at about 10° C., or less. In some aspects, contacting with the GAC is done at about 10° C. to about 60° C., at about 30° C. to about 55° C., or at about 40° C. to about 50° C.

Solvent and water can be partially evaporated from this stream at evaporating 1105 to provide a first refined oil. In some aspects, evaporation can be conducted at temperatures at all stages below 100° C., such as below 90, 80, 70, 60, or even below 50° C., to minimize product degradation. In some aspects, evaporation is conducted at about 45° C. to about 50° C. In some aspects, the ratio of solvent to oil in stream 1106 is about 12:1, or more. In some embodiments, the ratio of solvent to oil in stream 1106 is about 5:1, or less. In some aspects, the ratio of solvent to oil in stream 1106 is about 5:1 to about 12:1, or about 6:1 to about 10:1. In some embodiments, stream 1106 comprises about 15%, or more, extracted oil. In some embodiments, stream 1106 comprises about 5%, or less, extracted oil. In some aspects, stream 1106 comprises about 5% to about 15% extracted oil. In some embodiments, stream 1106 comprises about 30%, or more, water. In some embodiments, stream 1106 comprises about 3%, or less, water. In some embodiments, stream 1106 comprises about 90%, or more, solvent. In some embodiments, stream 1106 comprises about 60%, or less, solvent. In some aspects, stream 1106 comprises about 3% to 30% water, and about 60% to about 95% solvent. In some embodiments, stream 1107 comprises about 0.1%, or less, oil. In some embodiments, stream 1107 comprises about 85%, or less, solvent and water. In some aspects, stream 1107 comprises about 0.1%, or less, oil, and about 85%, or more, solvent and water.

Second Refining Unit

Figure 7D:
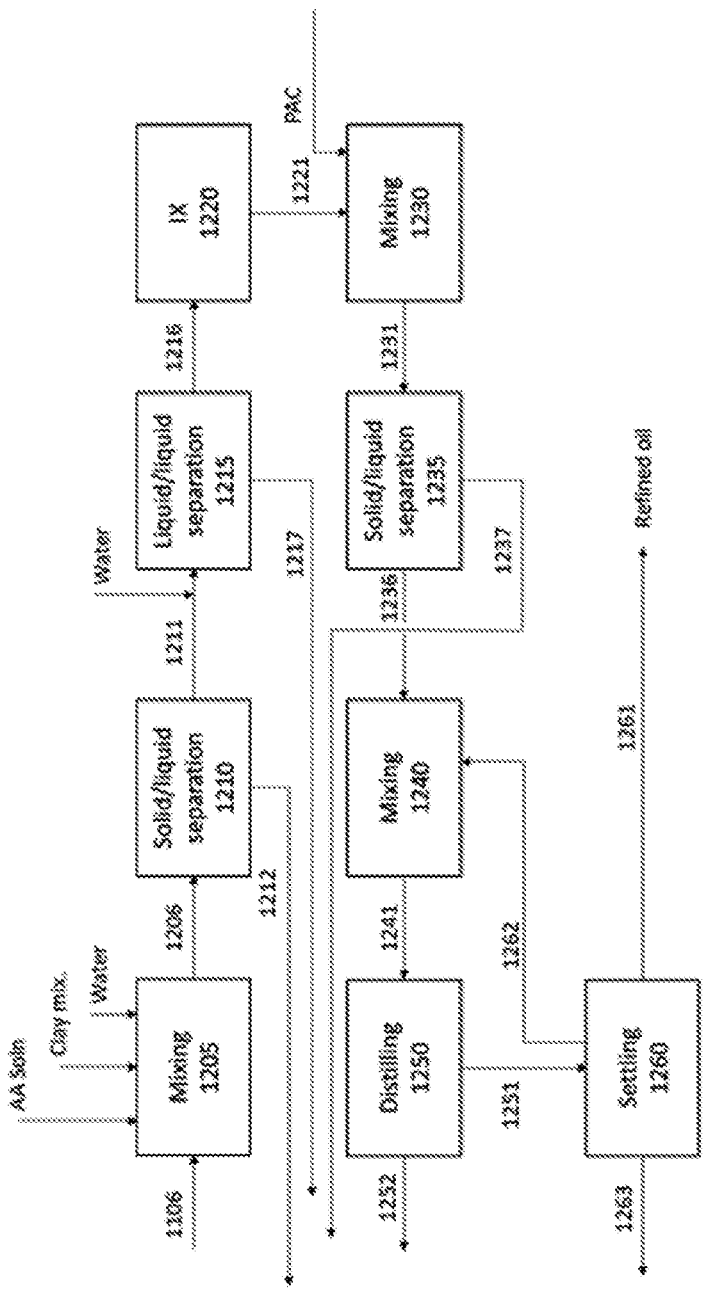
FIG. 7D illustrates a schematic diagram of a process module for a second refining of the first refined oil to provide a second refined oil.

FIG. 7D illustrates schematically a process for a second refining method, process and system. The first refined oil can be transferred via conduit 1106 to mixing 1205. In some embodiments, mixing 1205 may be a temperature-controlled mixing tank, comprising at least one additional feeding port that facilitates dosing refining agents as solution or suspension in water and/or solvent, or as solids. In some aspects, the temperature in mixing 1205 may be controlled to be about 10° C. to 80° C., or about 30° C. to 70° C., or about 60° C. In some aspects, the refining agents include at least one of a basic amino acid or a solution of a protamine, at least one clay or a clay mixture, a filter aid such as diatomaceous earth, and optionally additional amount of water.

Basic amino acids or a protamine can form salts with certain fatty acids that have solubility in water and low solubility in certain solvents (T. H. Jukes and C. L. A. Schmidt, *The Combination of Certain Fatty Acids with Lysine, Arginine and Salmine,* J. Biol. Chem. 1935, 110). In some aspects, this property is utilized to reduce the concentration of fatty acids present in the first refined oil by adding an aqueous solution comprising at least one of lysine, arginine or salmine, and stirring for about 2 minutes to 20 minutes, or about 10 minutes to cause the formation of a combination salt of low solubility in the mixing tank. In some aspects, an aqueous solution comprising 1 mole lysine is added per mole fatty acid present in first refined crude oil. In some aspects, about 0.1, 0.2, 0.3, 0.4, 0.5, 0.6, 0.7, 0.8, 0.9, 1.0, 1.5, 2.0, 2.5, 3.0, 4.0, 5.0, 6.0, 7.0, 8.0, 9.0, 10.0%, or more wt/wt lysine is added. In some aspects, about 10.0, 9.0, 8.0, 7.0, 6.0, 5.0, 4.0, 3.0, 2.5, 2.0, 1.5, 1.0, 0.5, 0.1%, or less wt/wt lysine is added. In some aspects, further agents are added to mixing 1205, comprising at least one of Fuller's Earth, Kaolin clay, bentonite, diatomaceous earth, magnesium silicate (such as Florisil) or mixtures thereof. In some embodiments, about 5% to about 20% wt/wt of a refining agent mixture is added, where the mixture comprises perlite, aluminum silicate and magnesium silicate. In some embodiments, the mixture comprises about 50% perlite, about 40% aluminum silicate and about 10% magnesium silicate. In some aspects, the mixing is continued for about 15 minutes at about 60° C. In some aspects, some of the impurities precipitate with the added mixture on the walls of the mixing tank. In some embodiments, additional water is added to the mixture to solubilize the percipitate, such as about 5%, 10%, 15%, 20%, 25%, 30%, 35%, 40%, or more, wt/wt. In some embodiments, about 5% water wt/wt, or less, is added to the mixture.

In some aspects, the solution is transferred to solid/liquid separation 1210 via conduit 1206. In some aspects, solid/liquid separation 1210 is a filter (e.g. a rotary vacuum filter with an adjustable knife system). In some embodiments, additional water is applied to wash the solids; the additional filtrate is added to the first filtrate. In some embodiments, the added water can be about equal to the amount of water added in mixing 1205, or can be about double or about triple the amount added in mixing 1205. The liquid phase can be transferred via conduit 1211 to liquid/liquid separation 1215. In some embodiments, liquid/liquid separation is a decanting tank or centrifuge. The organic phase can be transferred via conduit 1216 for further refining, while the aqueous phase 1217 can be collected and transferred to the solvent recovery unit 900. The solids collected at the solid/liquid separation may be transferred via conduit 1212 to drying 1020 to recover the solvent.

In some aspects, the filtrate is visually much clearer than the first refined oil. In some aspects, at least about 50%, 60%, 70%, 80%, or more of the fatty acids are removed. In some aspects, at most about 80%, 70%, 60%, 50%, or less of the fatty acids are removed. In some aspects, at least about 30%, 40%, 50%, 60%, 70%, 80%, 90%, or more of sterols present in the oil are still present in the filtrate. In some aspects, at most about 90%, 80%, 70%, 60%, 50%, 40%, 30%, or less of sterols present in the oil are still present in the filtrate. In some aspects, additional impurities are washed out at this stage, including, for example, sugars, salts or any other water-soluble impurity.

In certain aspects, the organic phase 1216 can be contacted by an ion exchange resin, (i.e., contacting can be conducted by flowing the stream through at least one column packed with an ion exchange resin, 1220).

Some pesticides are strong or weak bases, or comprise a nitrogen atom that can be protonated under acidic conditions, for example, Microbutanil, Paclobutrazol, Fenoxycarb, Befenazate, Spirotetramat, Spinosad, Imidacloprid, Thiacloprid, Spiroxamine, Propoxur, Paclobutrazol, Methyl parathion, Imazalil, Fenoxycarb, Aldicarb, Abamectin. Analytical methods for their analysis at low levels, where pre-concentration is required, utilizes the protonated nitrogen functionality for capturing them on PTFE membranes having a strong cation exchange functionality, such membranes are commercially available from 3M (Empore™ SPE).

Such compounds can be effectively removed from the solution comprising the solvent and the first refined extracted oil by weak acid cation exchange resin (WAC), which advantageously can be regenerated under milder conditions than a strong acid or base resin (SAC or SBA, respectively). When regenerating an SBA or SAC resin ensuring that no regenerating agents (e.g. strong base) remain in the resin is difficult and costly. WAC resin can be applied for softening water, as it is effective in capturing divalent cations from aqueous solutions. WAC resins are commercially available from several suppliers, including, for example, Purolite, Dow, Sorbtech, GE and more. Contacting with a WAC resin may remove trace amounts of heavy metals. Alternatively, a SAC resin may be used to adsorb pesticides.

In some aspects, contacting with WAC resin is performed by flowing the partially refined stream 1216 through a column packed with the resin (1220). In some embodiments, the resin is controlled to be in the $H^+$, $Na^+$, $K^+$, $Rb^+$, or $Cs^+$ form. In some aspects, the resin is controlled to be in a mixed $Na^+$ and $H^+$ form. Alternatively, two sequential columns are used, wherein the first is in the $Na^+$ form and the second is in the $H^+$ form. In some embodiments, the resin is contacted at about 60° C., or more. In some aspects, contacting with the resin is done at about 10° C. to 60° C., about at 20° C. to 50° C., about at 35° C. to 45° C. In some aspects, the contacting with WAC resin provides the purified oil, comprising reduced amounts of pesticides and herbicides compared to the feed stream 1216. In some embodiments, about 70%, 80%, 90%, 95%, or more of the residual pesticides and herbicides present in the purified oil is removed by contacting with the WAC resin, as can be tested in stream 1216. In some embodiments, contacting with the WAC is also efficient at removing divalent or trivalent metallic cations. In some aspects, contacting with the WAC resin efficiently removes heavy metal cations.

Referring to FIG. 7D, the deionized the purified oil is transferred to mixing 1230, where it is contacted with PAC for polishing, by mixing for about 5 minutes to about 30 minutes, or about 10 minutes to about 20 min at temperature of about 10° C. to 60° C. In some embodiments, the mixing with PAC is for about 30 minutes, or more. In some embodiments, the mixing with PAC is for about 5 minutes, or less. In some embodiments, the mixing with PAC is at a temperature of about 60° C., or more. In some embodiments, the mixing with PAC is at a temperature of about 10° C., or less. The slurry can be transferred via conduit 1231 to solid/liquid separation 1235. The filtrate can be transferred to mixing tank 1240 via conduit 1236, the solid can be collected and transferred via conduit 1237 to the dryer, to recover the solvent. The liquid can be mixed in mixing tank with an aqueous salt solution, and transferred via conduit 1241 to distilling 1250. The solvent can be removed by azeotropic distillation. The solvent-removed liquid, comprising refined oil and an aqueous solution, can be transferred via conduit 1251 to settling 1260. The vapors may be collected and condensed in a barometric condenser, and transferred via conduit 1252 to solvent recovery 900. In some embodiments, the phases separate in settling 1260 to provide an upper phase comprising the refined oil and a bottom phase comprising the aqueous salt solution. The refined oil can be transferred via conduit 1261 to converting 1300. The aqueous salt solution may be recycled back into mixing 1240. The aqueous salt solution may comprise a salt such as sodium chloride, sodium acetate or sodium formate. In some embodiments, the salt comprises sodium acetate.

Third Refining Unit

Figure 8D:
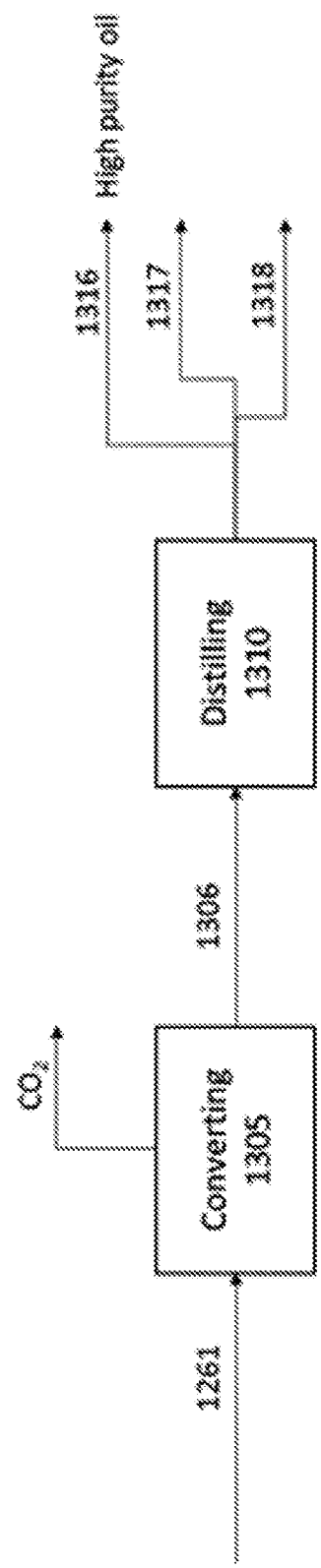
FIG. 8D illustrates a schematic diagram of a process unit for converting carboxylic acid constituents to their decarboxylated constituents and further refining in a third refining unit to provide a purified oil.

FIG. 8D illustrates schematically a process for a third refining method, process and system. The second refined oil may be transferred via conduit 1261 to converting 1305, wherein carboxylic acid constituents can be converted to their de-carboxylated constituents. In some embodiments, the refined oil is heated to about 150° C. or more. In some embodiments, the refined oil is heated to about 45° C. or less. In some embodiments, the refined oil is heated from about 45° C. to about 170° C., or from about 130° C. to about 160° C. for 0.5 to 4 h. In some embodiments, heating is conducted under vacuum. In some embodiments, 95% or less of carboxylic acid constituents are converted to their respective de-carboxylated constituents. In some embodiments, at least about 95%, 96%, 97%, 98%, 99%, or more of carboxylic acid constituents are converted to their respective de-carboxylated constituents. In some embodiments, when the extracted plant is a *cannabis* plant, at least some of the THC and THCA present in the refined oil is oxidized to CBN. In some embodiments, at least 10, 20, 30, 40, 50% of the THC/THCA present in the oil is oxidized to CBN. The de-carboxylated purified oil can be transferred via conduit 1306 to distilling 1310.

Distilling 1310 may comprise a short path distillation. In some embodiments, distilling 1310 comprises a wiped film distillation system. Such systems are commercially available from multiple suppliers at all scales from lab to industrial, for example Pope Scientific Inc., Root Sciences, UIC GmbH and others. In some embodiments, the distillation temperature is 250° C. or more. In some embodiments, the distillation temperature is 100° C. or less. In some embodiments, the distillation temperature is about 100° C. to about 250° C. In some embodiments, the distillation pressure is at most about 10 Torr, or less. In some embodiments, the distillation pressure is at least about 450 Torr, or more. In some embodiments, the distillation pressure is from about 10 Torr to about 450 Torr. In some embodiments, the distillation pressure is from about 150 Torr to about 450 Torr. In some embodiments, the distillation pressure is from about 10 Torr to about 250 Torr. In some embodiments, at least about 1, 2, 3, 4, or more fractions are collected. In some embodiments, a first fraction comprises monoterpenes hydrocarbons and oxygenated monoterpenes (e.g., α-pinene, myrcene and terpinolene); a second fraction comprises Sesquiterpene hydrocarbons, Oxygenated sesquiterpenes (e.g., (E)-caryophyllene, α-humulene and caryophyllene oxide) and residual fatty acids; a third fraction comprises cannabinoids. In some aspects, the purified oil is transferred via conduit 1316 to extracting fractionating 1400 (FIG. 1A).

Fractionating Unit

Chromatography can be carried out by any chromatographic technique (e.g., using a simulated moving bed (SMB) or sequential simulated moving bed (SSMB) process). Some chromatographic methods afford a continuous fractionating process that provide at least two streams of products, termed extract stream(s) and raffinate stream. Examples of simulated moving bed processes are disclosed, for instance, in U.S. Pat. Nos. 6,379,554; 5,102,553; 6,093,326; and 6,187,204, and examples of sequential simulated moving bed processes can be found in GB 2,240,053; and U.S. Pat. Nos. 4,332,623; 4,379,751; and 4,970,002, each of which is incorporated herein by reference in its entirety. In an SMB or SSMB setup, the resin bed can be divided into a series of discrete vessels, each of which sequence through a series of 4 zones (feed, separation, feed/separation/raffinate and safety) connected by a recirculation loop. A manifold system can connect the vessels and directs, in appropriate sequence to (or from) each vessel, each of the four media accommodated by the process. Those media may be referred to as feed, eluent, extract and raffinate. For example, a feed can be the purified oil mixture 1316, the eluent can be the solvent, the extract is a solution enriched with CBD, one raffinate is a solution enriched with THC.

The chromatographic fractionation can be carried out in a batch mode, a simulated moving bed (SMB) mode or a sequential simulated moving bed (SSMB) mode, which is a form of batch operation. The temperature of the chromatographic fractionation can be in the range of 5° C. to 90° C. The chromatographic fractionation can be carried out with a linear flow rate of about 0.25-100 ml/min in the separation column.

A method for medium and large-scale chromatographic separations can be the sequential simulated moving bed (SSMB) mode, or alternatively a simulated moving bed (SMB) mode. Both methods may use a number of columns packed with a suitable sorbent and connected in series. There can be inlet ports for feed and solvent (which may include recycled solvent), and outlet ports for two or more products (or other separated fractions). The injection of the mixture solution to be separated may be periodically switched between the columns along the direction of the liquid flow, thereby simulating continuous motion of the sorbent relative to the ports and to the liquid. The SMB may be a continuous counter current type operation. SSMB may be a more advanced method, requiring a sequential operation. Its advantages over SMB and over other older methods can include: fewer columns can be used in the SSMB method versus the SMB, hence less resin is required and associated costs of installation are significantly reduced in large systems; the pressure profile is better controlled, facilitating the use of more sensitive resins; and the achievable recovery/purity is higher than obtained with SMB systems. In some embodiments, the chromatography system may comprise more than or equal to 14 packed bed columns comprising one or more of the above resins. In some aspects, the chromatography system comprises 1 to 14 packed bed columns comprising one or more of the above resins. In some embodiments, the number of packed columns is about 2 to 10, or 4 to 8 or about 6.

In some embodiments, cannabinoids can be fractionated using a cross-linked dextran gel that is commercially available from Amersham Biosciences (Sephadex® LH20), Biotech GmbH (Zetadex 20-LH), Sorbtech (SorbaDex™ LH20) or equivalent products. In some embodiments, a marcroreticular nonionic aliphatic acrylic polymer can be used as the chromatography media, such media available from Dow (AMBERLITE™ XAD7HP), Purolite (Purosorb™ PAD900RFM or Purosorb™ PAD600RFM), and similar. In some embodiments, a macroreticular strong cation exchange resin in the $AS^+$ form can fractionate cannabinoids. Such resins are available, for example, from Dow (Amberlyst XN-1010), Bio-Rad (Bio-Rex™ 70) and others. An amberlyst XN-1010 resin in the $AS^+$ form was used to separate different resin acids where separated (S. S. Curran et. al., *JAOCS*, 1981, 58, 980-982). Other chromatographic media can also be modified to be in the $Ag^+$ form to achieve separation, such modification is also termed "argentation" or Immobilized Metal Affinity Chromatography (IMAC) or Metal Chelate Affinity Chromatography (MCAC). For example, U.S. Pat. No. 4,961,881 disclosed the separation of polyunsaturated triglycerides from monounsaturated triglycerides and polyunsaturated fatty acids from monounsaturated fatty acids is performed by an adsorptive chromatographic process in liquid phase using silver- or copper-exchanged aluminosilicates as the adsorbent. In another example, U.S. Pat. No. 4,305,882 disclosed mixtures containing polyunsaturated fatty esters are fractionated by partial argentation resin chromatography, in which the mixture is eluted through a column packed with a partially silvered sulfonic acid ion exchange resin. In some aspects, the silverized chromatography media can be chitosan, spherical highly pure silica of defined particle size and defined pore size, wherein the defined pore size may be in the range of about 10 Angstroms to 100 Angstroms, or irregular silica having a size range of from about 60-200 microns and a defined pore size, wherein the pore size may be in the range of about 10 Angstroms to about 100 Angstroms, such as available from SiliCyle, Quebec City. In some embodiments, a different metal cation or mixture of metal cation can be used to modify the chromatographic media, for example $K^+$, $Na^+$, $Ag^+$, $Cs^+$, $Rb^{30}$, $Li^+$, $Mn^{2+}$, $Cu^{2+}$, $Ca^{2+}$, $Mg^{2+}$, $Ba^{2+}$, $Be^{2+}$, $Sr^{2+}$, $Fe^{3+}$, $La^{3+}$, $Ce^{3+}$, $Sc^{3+}$, $Y^{3+}$, as well as organic cations such as $NH_4^+$, $CH_3\ NH_3^+$, $(CH_3)_2\ NH_2^+$, $C_2H_5\ NH_3^+$, etc., and mixtures thereof.

In some aspect, the adsorbent and desorbent is a dry solvent, wherein the solvent may be the same solvent used in extraction and refining or a different solvent. In some aspects, the adsorbent and desorbent comprises a solvent, wherein the solvent is saturated with water or wherein the composition is the azeotrope composition of solvent and water. In some aspects, the adsorbent and/or desorbent comprises the water-saturated solvent, wherein the solvent further comprises about 0.0001 M, or more, carboxylic acid. In some aspects, the adsorbent and/or desorbent comprises the water-saturated solvent, wherein the solvent further comprises about 1 M, or less, carboxylic acid. In some aspects, the adsorbent and/or desorbent comprises the water-saturated solvent, wherein the solvent comprises about 0.0001 to 1 M carboxylic acid.

In some aspects, the solvent is a mixture of ethanol and ethyl acetate at a ratio of about 1:5, or less. In some aspects, the solvent is a mixture of ethanol and ethyl acetate at a ratio of about 5:1, or more. In some aspects, the solvent is a mixture of ethanol and ethyl acetate at a ratio of about 1:5 to 5:1, or the azeotrope ratio of ethanol and water and the resin is Purosorb™ PAD900RFM or Purosorb™ PAD600RFM.

In some aspects, the method of fractionating a high purity *cannabis* extract comprises a sequential simulated moving bed chromatography sequence, wherein the sequence comprises: (1) passing a feed stream comprising high purity *cannabis* oil into an adsorbent, thereby flushing a raffinate stream comprising THC and additional cannabinoids from the adsorbent; (2) flushing an extract stream enriched in CBD and additional cannabinoids relative to the feed stream with a desorbent stream; and (3) recycling the desorbent stream back to the adsorbent.

In some aspects, resolution and yield of the chromatography process is enhanced by feeding a purified oil, comprising at least about 85, 86, 87, 88, 89, 90, 91, 92, 93, 94, 95%, or more wt/wt pure cannabinoids. In some aspects, resolution and yield of the chromatography process is enhanced by feeding a purified oil, comprising at most about 95, 90, 85%, or less wt/wt pure cannabinoids. In some aspects, the purified oil fed to chromatography comprises less than or equal to about 5, 4, 3, 2, 1% wt/wt sterols, terpenes and fatty acids. In some aspects, the purified oil fed to chromatography comprises more than or equal to about 1, 2, 3, 4, 5%, or more wt/wt sterols, terpenes and fatty acids.

In some aspects, a fraction of THC-depleted is collected, that is characterized as having about 0.3%, or less, or not more than about 0.001% THC. In some aspects, a second fraction is collected, which as characterized as having more than or equal to about 1, 2, 3, 4, 5, 6, 7, 8, 9, 10%, or more, THC.

Solvent Recovery and Recycling Unit and Systems

In some aspects, full recovery and recycling of solvent used in the extraction and refining methods and processes is accomplished. In some aspects, the system is designed such that all vapors are collected from all process stages where vapors are generated in an evaporation, drying or distillation process. In some aspects, the system is further designed to condense vapor in a simple set up at minimal energy requirements by employing barometric condenser systems, also referred to as atmospheric evaporators, at all relevant stages in the extraction and refining processes disclosed herein, such systems are described in U.S. Pat. No. 6,254,734 and are commercially available from multiple vendors, for example, Poly Products Inc., Condorchem Envitech, Aqua Logic Inc., Schutte & Koerting and others. An important aspect to being able to fully recover and recycle the solvent for further use is the selection of a solvent as disclosed in the next section below. Another important aspect of the solvent recovery system is that while solvent is recycled, water that was introduced into the solvent with the plant material is efficiently and effectively stripped off solvent, such that it can be directed to a waste water treatment facility, while complying with regulations with respect to volatile organics and solvents.

In some aspects, the solvent recycling system comprises: (i) at least one decanting tank for separating solvent phase and aqueous phase; (ii) evaporating systems equipped with barometric condensers for removing solvent and water from process streams, wherein the vapors are collected and transferred to the decanting tank; (iii) at least one stripper distillation for stripping solvent residues from waste water stream, wherein the distillate is collected and transferred to the decanting tank; (iv) decanting systems for separating process streams into an aqueous phase and organic phase, wherein the aqueous phase is transferred to the stripper to recover the solvent; (v) a press for separating depleted biomass from liquids, wherein the pressed depleted biomass is transferred to a dryer and the liquids are transferred for further refining; (vi) a dryer for drying solids, wherein the vapors are collected and transferred to the decanting tank, and wherein the solids comprise depleted plant material after extraction and loaded solid adsorbents; (vii) a chiller, wherein the solvent is chilled to a designated temperature; and, (viii) pumps and piping systems operated under a controller to continuously collect streams from operation units and transfer recycled stream of chilled solvent to the extraction unit and the barometric evaporators.

In some aspects, at least 99% of the solvent is recovered as freshly regenerated solvent for further extraction. In some aspects, the aqueous stream comprises less than or equal to about 0.1, 0.01 or even less than or equal to about 0.005% solvent and is suitable to be treated in industrial waste water plants. In some aspects, the solids comprise less than or equal to about 0.5, 0.1 or even less than or equal to about 0.01% solvent, and less than or equal to about 0.1% water.

Solvent

In some aspects, the solvent may comprise a solvent or a mixture of solvents, wherein the solvent or mixture of solvents (i) is categorized as class 3 according to Q3C—Table and Lists Guidance for Industry (US Department of Health and Human Services, FDA, CDER, CBER), June 2017 ICH rev. 3; and/or (ii) forms a heterogeneous azeotrope with water, wherein the azeotrope has a boiling point lower than the boiling point of water. In some embodiments, the solvent or a mixture of solvent forms a heterogeneous azeotrope with water, wherein the solvent and the azeotrope have a boiling point lower than the boiling point of water. In some embodiments, the ratio of water to solvent, $R_w/R_s$, may be greater in the vapor phase of the azeotrope than in the solvent liquid phase. In some aspects, the solvent or mixture of solvents is selected to have a Hildebrand solubility parameter of at least about 10.0 $MPa^{1/2}$, or more. In some aspects, the solvent or mixture of solvent is selected to have a Hildebrand solubility parameter of about 40.0 $MPa^{1/2}$, or less. In some aspects, the solvent or mixture of solvent is selected to have a Hildebrand solubility parameter of about 26.0 $MPa^{1/2}$, or less. In some embodiments, the solvent or mixture of solvent is selected to have a Hildebrand solubility parameter of about 20.0 $MPa^{1/2}$, or less. In some embodiments, the solvent or mixture of solvents is selected to have a Hildebrand solubility parameter in the range of about 18.0 to about 20.0 $MPa^{1/2}$. The solvent may be selected from 1-butanol, ethyl acetate, ethyl formate, 2-methyl-1-butanol, ethanol, heptane, cyclohexane, 2-butanone, 2-propanol, propylene glycol and mixtures thereof. In some aspects, the solvent is ethyl acetate or ethyl formate. Alternatively, the solvent may be selected from pentanol, hexanol, heptanol, 2-ethyl hexanol, octanol, 2-butanone (MEK), methyl isobutyl ketone (MIBK).

In some aspects, the solvent is dry, or saturated with water, or is present at its water azeotrope composition. In some embodiments, the solvent comprises a carboxylic acid, e.g. acetic acid, citric acid, formic acid. In some embodiments, the concentration of the carboxylic acid is about 0.01, 0.05, 0.1, 0.2, 0.3, 0.4, 0.5, 0.6, 0.7, 0.8, 0.9, 1%, or more.

In some aspects, the water stream comprises less than 30% wt/wt solvent, such as less than 25, 20, 15, 10, 9, 8, 7, or 6%, or less wt/wt solvent. In some embodiments, stripper 340 comprises a distillation unit, suitable to distill the solvent/water azeotrope at the top, while water remains at the bottom of the distillation unit. In some aspects, the stripper comprises a packed column distillation unit. The top distillate of stripper 340 may be transferred by conduit 341 back to liquid/liquid separator 330. In some aspects, the temperature of the distillation top can be controlled at about 40-95° C., such as about 50-85° C. or about 65-75° C. In some aspects, the temperature of the distillation top is about 70° C. In some aspects, the bottom stream comprises about 2% wt/wt, or less, solvent, such as less than or equal to about 1, 0.1, or even less than or equal to about 0.05% wt/wt solvent. in some embodiments, bottom distillates W301 of stripper 340 are transferred by conduit 342 to a waste water treatment facility.

System Controls

In certain aspects, the system is equipped with various sensors and human interface reporting points, all data is continuously collected, monitored and archived at a central computer.

Efficiency of extraction can be optimized by controlling parameters, such as particle size of the extracted biomass, contact time with the extractant, liquid to solid ratio, conveyor speed. concentration of extractives in the extracting solvent at each step and temperature.

In some aspects of this disclosure, contact time between biomass and the extracting solvent is controlled at each conveyor by the inclination angle of the conveyor, the rotational speed of the screw, and the pumping rate of the feeding pump.

In some aspects, feed weights of biomass and solvent are constantly monitored and logged in the data historian of the process control computer(s). Feed biomass can be analyzed for constituents composition by an online monitoring system, which may comprise NIR or a UV-VIS spectrometer. The output of extracted oil can also be analyzed by similar spectrometers and by flow meter, such that full mass control of specific constituents is facilitated.

Refined Oil

In some aspects, the refined oil may be sufficiently pure for some applications. In some aspects, the color of the purified oil is colorless to light yellow-brown. In some aspects, the UV-VIS absorption of the purified oil when diluted 1:10 to 1:100 with water-saturated ethyl acetate is less than 0.1 OD at 640-670 nm. In some aspects, the concentration of chlorophyll is less than or equal to about $10^{-5}$ or even less than or equal to about $10^{-6}$ M. In some aspect, the total cannabinoids concentration of the refined oil is at least about 50, 60, 70% or more wt/wt. In some aspect, the total cannabinoids concentration of the refined oil is at most about 70, 60, 50, 40% or less wt/wt. In some aspects, at least about 20, 30, 40 50, 60, 70, 80%, or more of the cannabinoids are carboxylated cannabinoids. In some aspects, at most about 80, 70, 60, 50, 40, 30, 20%, or less of the cannabinoids are carboxylated cannabinoids. In some aspects, the refined oil comprises more than or equal to about 0.1, 0.5, 1, 2, 3, 4, 5, 6%, or more wt/wt terpenes and sesquiterpenes. In some aspects, the refined oil comprises less than or equal to about 6, 5, 4, 3, 2, 1, 0.5, 0.1%, or less wt/wt terpenes and sesquiterpenes. In some aspects, the refined oil comprises more than or equal to about 0.5, 1, 2, 4, 5%, or more sterols. In some aspects, the refined oil comprises less than or equal to about 5, 4, 3, 2, 1, 0.5%, or less sterols.

In some aspects, the refined oil comprises less than or equal to about 5, 4, 3, 2, 1%, or less wt/wt sugars. In some aspects, the refined oil comprises more than or equal to aboutl, 2, 3, 4, 5%, or more wt/wt sugars. In some aspects, the refined oil comprises less than or equal to about 5, 4, 3, 3, 1, 0.6, 0.4%, or less wt/wt fatty acids. In some aspects, the refined oil comprises more than or equal to about 0.3, 0.5, 1, 2, 3, 4, 5%, or more wt/wt fatty acids. In some aspects, the refined oil comprises less than or equal to about 1, 0.9, 0.8, 0.7, 0.6, 0.5, 0.4, 0.3, 0.2, 0.1%, or less palmitic acid. In some aspects, the refined oil comprises more than or equal to about 0.1, 0.2, 0.3, 0.4, 0.5, 0.6, 0.7, 0.8, 0.9, 1%, or more palmitic acid. In some aspects, the refined oil comprises less than or equal to about 0.5, 0.4, 0.3, 0.2, 0.1%, or less linoleic acid. In some aspects, the refined oil comprises more than or equal to about 0.1, 0.2, 0.3, 0.4, 0.5%, or more linoleic acid. In some aspects, the refined oil comprises less than or equal to about 0.5, 0.4, 0.3, 0.2, 0.1%, or less oleic acid. In some aspects, the refined oil comprises more than or equal to about 0.1, 0.2, 0.3, 0.4, 0.5%, or more oleic acid.

Purified Oil

In some aspects, the purified oil is an essentially pure product, i.e. the remaining concentration of impurities that are eliminated from the starting crude product is well below the relevant regulatory limit for each such impurity compound. In some aspects, the color of the purified oil is colorless to light yellow-brown. In some aspects, the UV-VIS absorption of the purified oil when diluted 1:10 to 1:100 with water-saturated ethyl acetate is less than 0.1 OD at 640-670 nm. In some aspects, the concentration of chlorophyll is less than or equal to about $10^{-5}$ or even less than or equal to about $10^{-6}$ M. In some aspects, the total cannabinoids concentration of the purified oil is at least about 70, 80, 82, 84, 86, 88, 90, 92, 94 95%, or more wt/wt. In some aspect, the total cannabinoids concentration of the purified oil is at most about 70, 60, 50, 40% or less wt/wt. In some aspects the purified oil comprises at least about 85, 86, 87, 88, 89, 90, 91, 92, 93, 94, 95%, or more wt/wt de-carboxylated cannabinoids. In some aspects, at most about 80, 70, 60, 50, 40, 30, 20%, or less of the cannabinoids are carboxylated cannabinoids.

In some aspects, the purified oil comprises at least about 0.1, 0.2, 0.3, 0.4, 0.5, 0.6, 0.7, 0.8, 0.9, 1, 1.1, 1.2, 1.3, 1.4, 1.5%, or more wt/wt terpenes. In some aspects, the purified oil comprises less than or equal to about 6, 5, 4, 3, 2, 1, 0.5, 0.1%, or less wt/wt terpenes. In some aspects, terpenes that are collected separately at distillation are added back to the purified oil fraction that comprises the cannabinoids.

In some aspects, the purified oil comprises less than or equal to about 5, 4, 3, 2, 1%, or less wt/wt sugars. In some aspects, the purified oil comprises more than or equal to about 1, 2, 3, 4, 5%, or more wt/wt sugars. In some aspects, the purified oil comprises less than or equal to about 5, 4, 3, 3, 1, 0.6, 0.4%, or less wt/wt fatty acids. In some aspects, the purified oil comprises more than or equal to about 0.3, 0.5, 1, 2, 3, 4, 5%, or more wt/wt fatty acids. In some aspects, the purified oil comprises less than or equal to about 1, 0.9, 0.8, 0.7, 0.6, 0.5, 0.4, 0.3, 0.2, 0.1%, or less palmitic acid. In some aspects, the purified oil comprises more than or equal to about 0.1, 0.2, 0.3, 0.4, 0.5, 0.6, 0.7, 0.8, 0.9, 1%, or more palmitic acid. In some aspects, the purified oil comprises less than or equal to about 0.5, 0.4, 0.3, 0.2, 0.1%, or less linoleic acid. In some aspects, the refined oil comprises more than or equal to about 0.1, 0.2, 0.3, 0.4, 0.5%, or more linoleic acid. In some aspects, the purified oil comprises less than or equal to about 0.5, 0.4, 0.3, 0.2, 0.1%, or less oleic acid. In some aspects, the refined oil comprises more than or equal to about 0.1, 0.2, 0.3, 0.4, 0.5%, or more oleic acid.

In some aspects, when the process is applied for the refining of crude extract of a *cannabis* plant, including a hemp plant, the purified oil can be tested according to the requirements of various regulators and proven suitable for human consumption. In the US, the authorities of various states have put in place such requirements with respect to residual amounts of volatile solvents (VOC), heavy metals, pesticides and herbicides, mycotoxins and aflatoxins, as well as total bacteria count, yeast & mold and some specific bacteria.

In some aspects, implementation of processes disclosed herein in equipment designed to be cleaned and sterilized if needed by proper manufacturing practices can routinely ensure the purified oil can meet all standards related to microbiology, particularly since much of the processing is conducted in a solvent that does not generally support microbiological contamination. In some aspects, the purified oil comprises less than or equal to about 100,000, less than or equal to about 10,000, or even less than or equal to about 1000 colony forming units/g (CFU/g) total aerobic bacteria. In some aspects, the purified oil comprises less than or equal to about 10,000, or even less than or equal to about 1000 (CFU/g) yeast and mold. In some aspects, the purified oil comprises less than or equal to about 1,000, or even less than or equal to about 100 (CFU/g) bile-tolerant gram-negative bacteria. In some aspects, the purified oil comprises less than or equal to about 1,000, or even less than or equal to about 100 (CFU/g) total coliforms. In some aspects, the purified oil comprises less than or equal to about 100, or even less than or equal to about 10 (CFU/g) *E. Coli*. In some aspects, the purified oil comprises less than or equal to about 100, or even less than or equal to about 10 (CFU/g) *Salmonella.*

In some aspects, the purified oil comprises any of the solvents acetonitrile, benzene, butane, 1-butanol, 2-butanol, 2-butanone (MEK), 1,2-dichloroethane, dichloromethane, 1,2-dimethoxyethane, N,N-dimethylacetamide, 2,2-dimethylbutane (hexanes) 2,3-dimethylbutane (hexanes), N,N-dimethylformamide, 2,2-dimethylpropane (neopentane), dimethylsulfoxide (DMSO), 1,4-dioxane, chloroform, cumene, cyclohexane, ethanol, 2-ethoxyyethanol, ethyl acetate, ethyl ether, ethylene glycol, ethylene oxide, heptane, hexane, isopropyl acetate, methanol, 2-methylbutane (isopentane), 2-methylpentane (hexanes), 3-methylpentane (hexanes), 2-methylpropane (isobutane), naphtha, pentane, 1-pentanol, petroleum ether, propane, 1-propanol, 2-propanol (isopropyl alcohol), 2-propanone (acetone), sulfolane, trichlorethylene, tetrahydrofuran (THF), toluene, xylenes (o-xylene, m-xylene, p-xylene), pyridine, at well below the Minimum Required Limit (MRL).

In some aspects, the purified oil comprises less than or equal to about 5000 μg/g ethanol. In some aspects, the purified oil comprises less than or equal to about 3000 μg/g, or less, methanol. In some aspects, the purified oil comprises about 5000 μg/g, or less ethyl acetate. In some aspects, the purified oil comprises about 5000 μg/g, or less, butane. In some aspects, the purified oil comprises about 290 μg/g, or less hexane. In some aspects, the purified oil comprises about 60 μg/g, or less, chloroform. In some aspects, the purified oil comprises about 600 μg/g, or less dichloromethane. In some aspects, the purified oil comprises about 5 μg/g, or less, 1,2-dichloroethane. In some aspects, the purified oil comprises about 5000 μg/g, or less, acetone. In some aspects, the purified oil comprises about 410 μg/g, or less, acetonitrile. In some aspects, the purified oil comprises about 2 μg/g, or less, benzene. In some aspects, the purified oil comprises about 5000 μg/g, or less, ethyl ether. In some aspects, the purified oil comprises about 50 μg/g, or less, ethylene oxide. In some aspects, the purified oil comprises about 5000 μg/g, or less, heptane. In some aspects, the purified oil comprises about 5000 μg/g, or less, 2-propanol. In some aspects, the purified oil comprises about 400 μg/g, or less, naphtha. In some aspects, the purified oil comprises about 5000 μg/g, or less pentane. In some aspects, the purified oil comprises about 400 μg/g, or less, petroleum ether. In some aspects, the purified oil comprises about 5000 μg/g, or less, propane. In some aspects, the purified oil comprises about 80 μg/g, or less, trichloroethylene. In some aspects, the purified oil comprises about 890 μg/g, or less, toluene. In some aspects, the purified oil comprises about 2170 μg/g, or less, total xylenes.

In some aspects, the purified oil comprises less than or equal to the maximum allowed limit of any pesticide or herbicide listed by state authorities with respect to the relevant product, e.g. *cannabis* products. In some aspects, the purified oil comprises about 1%, 0.5%, or even less than about 0.5% ash. In some aspects, the purified oil comprises about 0.14 μg/kg, or less, Arsenic. In some aspects, the purified oil comprises about 0.09 μg/kg, or less, Cadmium. In some aspects, the purified oil comprises about 0.29 μg/kg, or less, Lead. In some aspects, the purified oil comprises about 0.29 μg/kg, or less, Mercury. In some aspects, the purified oil comprises less than or equal to the allowed limit for any other heavy metal of potential harming effect. In some aspects, the purified oil further comprises about 0.1% wt/wt, or less, Calcium, about 0.1% wt/wt, or less Magnesium, about 0.1% wt/wt, or less, potassium, about 0.05% wt/wt, or less, phosphorous.

In some aspects, the purified oil comprises total metals other than Na, K, Rb or Cs of less than or equal to about 6000, 5000, 4000, 3000, 2000, 1000, 500, 100, or even less than about 50 µg/kg (solvent removed base, SRB). In some aspects, the purified oil comprises less than or equal to about 0.29 µg/kg SRB, or even less than about 0.14 µg/kg SRB As. In some aspects, the purified oil comprises less than or equal to about 0.09 µg/kg SRB, or even less than or equal to about 0.05 µg/kg SRB Cd. In some aspects, the purified oil comprises less than or equal to about 0.29 SRB µg/kg, or even less than about 0.15 µg/kg SRB Pb. In some aspects, the purified oil comprises less than or equal to about 0.29 µg/kg SRB, or even less than about 0.15 µg/kg SRB Hg. In some aspects, the purified oil comprises less than or equal to about 500 µg/kg SRB Ca. In some aspects, the purified oil comprises less than or equal to about 500 µg/kg SRB Mg. In some aspects, the purified oil comprises less than or equal to about 100 µg/kg SRB Zn. In some aspects, the purified oil comprises less than or equal to about 100 µg/kg SRB Fe. In some aspects, the purified oil comprises less than or equal to about 50 µg/kg SRB Cu. In some aspects, the purified oil comprises less than or equal to about 50 µg/kg SRB, or even less than about 25 µg/kg SRB Cr.

Fractionated Oil

In some aspects, fractionated oil comprises at least about 70, 80, 82, 84, 86, 88, 90, 92, 94 or 95%, or more wt/wt cannabinoids, and maintains all other purity attributes of the purified oil. Different purified oil may be collected as fractionated oil, for example THC oil, comprising not more than about 0.001% wt/wt THC. In some aspects, the fractionated oil can comprise about 0.001 to 0.3% THC. In some aspects, the fractionated oil comprises at least about 10, 15, 20, 25, 30, 35%, or more wt/wt THC. In some aspects, the fractionated oil comprises at most about 35, 30, 25, 20, 15, 10%, or less wt/wt THC. In some aspects, the fractionated oil comprises at least about about 1, 2, 3, 4, 5, 6 7, 8, 9, 10, 20, 30%, or more wt/wt CBN. In some aspects, the fractionated oil comprises at most about 10, 9, 8 7, 6, 5, 4, 3, 2, 1%, or less wt/wt CBN. In some aspects, the fractionated oil comprises at least about 1, 2, 3, 4, 5, 6 7, 8, 9, 10%, or more wt/wt CBG. In some aspects, the fractionated oil comprises at most about 10, 9, 8 7, 6, 5, 4, 3, 2, 1%, or less wt/wt CBG.

EMBODIMENTS

The following are example embodiments of the invention, and should not be construed as limiting.

Embodiment 1

An integrated modular system for extracting, refining, and fractionating plant constituents, comprising:
a) a biomass feeding unit;
b) at least one solvent extraction unit;
c) a first refining unit;
d) a second refining unit;
e) at least one chemical conversion unit; and
f) a third refining unit.

Embodiment 2

The system of Embodiment 1, wherein the biomass feeding unit further comprises a biomass grinding unit, sizing unit, sorting unit, or any combination thereof.

Embodiment 3

The system of Embodiment 2, wherein the sizing unit comprises a screen that the plant material passes through.

Embodiment 4

The system according to Embodiment 2 or 3, wherein the screen comprises a plurality of openings that are at least ⅛ inches wide.

Embodiment 5

The system of Embodiment 4, wherein the plurality of openings are about ¼ inches wide.

Embodiment 6

The system of any of Embodiments 2-5, wherein the sorting unit separates the plant material by density.

Embodiment 7

The system of Embodiment 6, wherein at least one solvent is used to separate the plant material by density.

Embodiment 8

The system of Embodiment 7, wherein the plant material with a density lower than the solvent floats to the surface of the at least one solvent.

Embodiment 9

The system of Embodiment 8, wherein the plant material that floats to the surface of the at least one solvent is substantially free of cannabinoids.

Embodiment 10

The system of any of Embodiments 2-9, wherein the sorting unit is adjacent to the sizing unit.

Embodiment 11

The system of any of Embodiments 1-10, further comprising at least one solvent recycling unit.

Embodiment 12

The system of any of Embodiments 1-11, wherein the system further comprises pumps, pipes, and conveyors for transferring the biomass.

Embodiment 13

The system of any of Embodiments 1-12, wherein the system is designed and constructed for continuous extracting, refining and fractionating high purity constituents from plant material.

Embodiment 14

The system of any of Embodiments 1-13, wherein the system further comprises:
g) a central computer control;
h) control valves; and
i) monitors and sensors for continuously monitoring temperature, pressure, or flow.

Embodiment 15

The system of Embodiment 14, wherein the monitors continuously monitor mass balance of incoming material and outflowing products.

Embodiment 16

The system of any of Embodiments 11-15, wherein the at least one solvent recycling unit comprises:
- i) at least one decanting tank;
- ii) at least one evaporating system equipped with barometric condensers, wherein solvent and, optionally, water vapors are collected and transferred to the decanting tank;
- iii) at least one stripper distillation system, wherein a distillate is collected and transferred to the decanting tank;
- iv) at least one decanting system, wherein an aqueous phase is transferred to the at least one stripper distillation system to recover a solvent;
- v) at least one press, wherein a pressed depleted biomass is transferred to a dryer, wherein subsequent liquids are transferred for further refining;
- vi) at least one dryer, wherein solvent and, optionally, water vapors are collected and transferred to the decanting tank, wherein the solids comprise (a) depleted plant material after extraction and (b) loaded solid adsorbents;
- vii) at least one chiller, wherein a solvent is chilled to a temperature; and,
- viii) at least one pump and piping system.

Embodiment 17

The system of Embodiments 16, wherein the at least one decanting tank separates an aqueous phase and an organic phase.

Embodiment 18

The system according to Embodiment 16 or 17, wherein the at least one evaporating system equipped with barometric condensers removes solvent and water from a process stream(s).

Embodiment 19

The system of any of Embodiments 16-18, wherein the at least one stripper distillation system removes solvent residues from at least one waste water stream.

Embodiment 20

The system of any of Embodiments 16-19, wherein the at least one decanting system separates a process stream(s) into an aqueous phase and an organic phase.

Embodiment 21

The system of any of Embodiments 16-20, wherein the at least one press separates depleted biomass from a liquid(s).

Embodiment 22

The system of any of Embodiments 16-21, wherein the at least one pump or piping system is operated under a controller to continuously collect a stream(s) from operation units and transfers a recycled stream(s) of chilled solvent to the extraction unit and the barometric evaporator(s).

Embodiment 23

The system of any of Embodiments 1-22, wherein the plant biomass comprises *cannabis*.

Embodiment 24

The system of any of Embodiments 1-23, wherein the *cannabis* comprises cannabinoids and terpenes.

Embodiment 25

The system of any of Embodiments 1-24, wherein the first refining unit comprises:
- i) at least one column of granulated activated carbon (GAC); and
- ii) at least one barometric evaporator.

Embodiment 26

The system of any of Embodiments 1-25, wherein the second refining unit comprises:
- i) at least one temperature-controlled stirring tank;
- ii) at least one filter;
- iii) at least one decanting tank;
- iv) at least one buffering tank;
- v) at least one ion exchange column;
- vi) at least one barometric evaporator;
- vii) at least one decanter tank; and
- viii) at least one settler.

Embodiment 27

The system of Embodiments 26, further comprising at least a second temperature-controlled stirring tank, at least a second filter, or any combination thereof.

Embodiment 28

The system of Embodiments 27, further comprising a third temperature-controlled stirring tank.

Embodiment 29

The system of any of Embodiments 26-28, wherein the filter separates solid adsorbents from a liquid.

Embodiment 30

The system of any of Embodiments 26-29, wherein at least one decanting tank separates an aqueous phase from an organic phase.

Embodiment 31

The system of any of Embodiments 26-30, wherein a second filter separates solid adsorbents from a liquid.

Embodiment 32

The system of any of Embodiments 26-31, wherein the at least one settler separates an aqueous phase from a refined oil phase.

Embodiment 33

The system of any of Embodiments 1-32, wherein the at least one chemical conversion unit comprises a stirred heating tank.

Embodiment 34

The system of any of Embodiments 1-33, wherein the third refining unit comprises distillation unit.

Embodiment 35

The system of Embodiment 34, wherein the distillation unit comprises a short path distillation unit.

Embodiment 36

The system of Embodiment 35, wherein the short path distillation unit comprises a wiped film evaporator.

Embodiment 37

A method of preparing at least one plant-extracted constituent, the method comprising:
(i) extracting a constituent from the plant material with a first solvent to obtain a first loaded extractant;
(ii) contacting the first loaded extractant with an adsorbent, a desorbant, or a combination thereof to obtain a first refined extractant;
(iii) concentrating the first refined extractant to obtain a first refined oil;
(iv) contacting the first refined oil with at least one substance selected from the group consisting of a basic amino acid, a protamine, clay, water, activated carbon, filter aid, and ion exchange resin, or a combination thereof to obtain a second refined extractant; and
(v) concentrating the second refined extractant to obtain a second refined oil.

Embodiment 38

The method of Embodiment 37, wherein, prior to (iv), the first refined oil is contacted with a second solvent to obtain a second loaded extractant, wherein the second loaded extractant is subsequently contacted with at least one substance selected from the group consisting of a basic amino acid, a protamine, clay, water, activated carbon, filter aid, and ion exchange resin, or a combination thereof to obtain a second refined extractant.

Embodiment 39

The method according to Embodiment 37 or 38, further comprising distilling the second refined oil to obtain a purified oil

Embodiment 40

The method of any one of Embodiments 37-39, further comprising fractionating the purified oil by chromatography to obtain at least one fractionated plant-extracted constituent.

Embodiment 41

The method of Embodiment 40, wherein the chromatography is simulated moving bed (SMB) chromatography.

Embodiment 42

The system of Embodiment 41, wherein the SMB chromatography is a continuous process.

Embodiment 43

The method of any of Embodiments 37-42, further comprising treating the second refined oil with heat, thereby de-carboxylating at least one carboxylic acid containing constituent of the second refined oil.

Embodiment 44

The method of any of Embodiments 37-43, further comprising treating the second refined oil with a catalyst, thereby de-carboxylating at least one carboxylic acid containing constituent of the second refined oil.

Embodiment 45

The method of any of Embodiments 37-44, further comprising treating the second refined oil with (a) heat and (b) a catalyst, thereby de-carboxylating at least one carboxylic acid containing constituent of the second refined oil.

Embodiment 46

The method according to Embodiment 43 or 45, wherein treating the second refined oil is under vacuum.

Embodiment 47

The method of any of Embodiments 43, 45, or 46, wherein the second refined oil is heated at a temperature ranging from 105° C. to 170° C.

Embodiment 48

The method of Embodiment 47, wherein the second refined oil is heated at a temperature ranging from 135° C. to 160° C.

Embodiment 49

The method of any of Embodiments 43, 45-48, wherein the second refined oil is heated for 0.5 hours to 4 hours.

Embodiment 50

The method of any of Embodiments 44-49, wherein the catalyst is a dicarboxylic acid, a tricarboxylic acid, an ion exchange resin, or any combination thereof.

Embodiment 51

The method of Embodiment 50, wherein the catalyst is selected from the group consisting of citric acid, oxalic acid, malic acid, ascorbic acid, tartaric acid, Amberlite, Amberlyst, Smopex, or Dowex.

Embodiment 52

The method of Embodiment 45, wherein (a) the second refined oil is heated at a temperature ranging from 105° C.

to 170° C., and (b) the catalyst is a dicarboxylic acid, tricarboxylic acid, an ion exchange resin, or any combination thereof.

Embodiment 53

The method of Embodiment 52, wherein (a) the second refined oil is heated at a temperature ranging from 135° C. to 160° C., and (b) the catalyst is selected from the group consisting of citric acid, oxalic acid, malic acid, ascorbic acid, tartaric acid, Amberlite, Amberlyst, Smopex, or Dowex.

Embodiment 54

The method of any of Embodiments 37-53, wherein at least 85% (% mol) of the cannabinoid constituents of the plant material are de-carboxylated in the purified oil.

Embodiment 55

The method of any of Embodiments 39-54, wherein the distillation comprises a short path distillation.

Embodiment 56

The method of Embodiment 55, wherein the short path distillation comprises a wiped film evaporator.

Embodiment 57

The method of any of Embodiments 37-56, further comprising, prior to (i), feeding a plant material into a biomass feeding unit.

Embodiment 58

The method of Embodiment 57, wherein the biomass feeding unit further comprises a biomass grinding or sizing unit.

Embodiment 59

The method according to claim 57 or 58, wherein the biomass feeding unit processes the plant material, thereby producing a homogenized plant material.

Embodiment 60

The method of any of Embodiments 37-59, wherein the plant material is fed into at least one solvent extraction unit.

Embodiment 61

The method of any of Embodiments 37-60, wherein extracting a constituent from the plant material with a first solvent is performed by the at least one solvent extraction unit, thereby obtaining the first loaded extractant.

Embodiment 62

The method of any of Embodiments 37-61, wherein the first loaded extractant is transferred to a first refining unit.

Embodiment 63

The method of any of Embodiments 37-62, wherein, in the first refining unit, the first loaded extractant is contacted with an adsorbent, a desorbant, or a combination thereof to obtain a first refined extractant.

Embodiment 64

The method of any of Embodiments 37-63, wherein the first refined extractant is transferred to at least one evaporating system.

Embodiment 65

The method of any of Embodiments 37-64, wherein the first refined oil is produced by concentrating the first refined extractant in the at least one evaporating system.

Embodiment 66

The method of any of Embodiments 37-65, wherein the first refined oil is transferred to a second refining unit.

Embodiment 67

The method of any of Embodiments 37-66, wherein the first refined oil is contacted with the second solvent after concentration in the at least one evaporating system, thereby obtaining a second loaded extractant.

Embodiment 68

The method of any of Embodiments 38-67, wherein the second loaded extractant is transferred to a second refining unit.

Embodiment 69

The method of any of Embodiments 37-68, wherein the second refined extractant is produced by contacting the first refined oil with a substance of (iv) in the second refining unit.

Embodiment 70

The method of any of Embodiments 38-68, wherein the second refined extractant is produced by contacting the second loaded extractant with a substance of (iv) in the second refining unit.

Embodiment 71

The method of any of Embodiments 38-70, wherein the second refined extractant is transferred to at least one evaporating system.

Embodiment 72

The method of any of Embodiments 37-71, wherein the second refined oil is produced by concentrating the second refined extractant in the at least one evaporating system.

Embodiment 73

The method of any of Embodiments 37-72, wherein the second refined extractant is transferred to at least one chemical conversion unit.

Embodiment 74

The method of Embodiments 73, wherein carboxylic acid-containing constituents within the second refined extractant are de-carboxylated using the at least one chemical conversion unit.

Embodiment 75

The method of Embodiments 74, wherein the second refined extractant comprising at least one de-carboxylated constituent is transferred to at least one extracting unit.

Embodiment 76

The method of Embodiments 75, wherein the second refined extractant comprising at least one de-carboxylated constituent is transferred to a third refining unit.

Embodiment 77

The method of Embodiments 76, wherein a purified oil is obtained upon distilling the second refined extractant comprising at least one de-carboxylated constituent using the third refining unit.

Embodiment 78

The method of any one of Embodiments 37-77, further comprising fractionating the refined oil or the purified oil by chromatography to obtain at least one fractionated plant-extracted constituent.

Embodiment 79

The method of Embodiment 78, wherein the chromatography is simulated moving bed (SMB) chromatography.

Embodiment 80

The method of Embodiment 79, wherein the SMB chromatography is a continuous process.

Embodiment 81

The method of Embodiment 79, wherein the SMB chromatography is a sequential process.

Embodiment 82

The method of Embodiment 81, wherein the sequential SMB chromatography process comprises a sequence of batch separations.

Embodiment 83

The method of any one of Embodiments 37-82, wherein the first loaded extractant comprises at least one extracted constituent and water.

Embodiment 84

The method of any one of Embodiments 37-83, wherein the adsorbent is selected from the group consisting of silica gel, alumina, zeolites, polymers, resins, clay, clay minerals, ores, charcoal, activated carbon, or metals, such as Ni, Cu, Ag, Pt and colloids.

Embodiment 85

The method of Embodiment 84, wherein the adsorbent is selected from the group consisting of polymers, resins, clays, charcoal, activated carbon, or metals, such as Ni, Cu, Ag, Pt and colloids.

Embodiment 86

The method of Embodiment 85, wherein the adsorbent is activated carbon.

Embodiment 87

The method of Embodiment 86, wherein the activated carbon is granulated activated carbon (GAC).

Embodiment 88

The method of Embodiment 87, wherein contacting with the GAC column occurs at temperature of 40° C. to 55° C.

Embodiment 89

The method of Embodiment 88, wherein contacting with GAC removes at least 10% of the tetrahydrocannabinoids present in the loaded extractant.

Embodiment 90

The method of Embodiment 89, wherein contacting with GAC removes at least 40% of the tetrahydrocannabinoids present in the loaded extractant.

Embodiment 91

The method according to Embodiment 89 or 90, wherein the tetrahydrocannabinoids is selected from the group consisting of THC, (−)-Δ-9-trans-tetrahydrocannabinol (Δ9-THC), (−)-delta-8-trans-tetrahydrocannabinol (Δ8-THC), or THCA.

Embodiment 92

The method of any one of Embodiments 37-91, wherein the desorbent is selected from the group consisting of 1-butanol, ethyl acetate, ethyl formate, 2-methyl-1-butanol, ethanol, heptane, cyclohexane, 2-butanone, 2-propanol, or propylene glycol.

Embodiment 93

The method of any one of Embodiments 37-92, wherein the first refined oil of (iii) is obtained by evaporating at least one solvent from the first refined extractant.

Embodiment 94

The method of any one of Embodiments 37-92, wherein the first refined oil of (iii) is obtained by evaporating at least one solvent and water from the first refined extractant.

Embodiment 95

The method of any one of Embodiments 37-94, wherein the first refined oil comprises extracted oil, solvent, and water, having a ratio of about 6 to 12 parts (solvent+water) to about 1 part extracted oil wt/wt.

Embodiment 96

The method of any one of Embodiments 37-95, wherein the second loaded extractant is contacted with activated carbon.

Embodiment 97

The method of any one of Embodiments 37-96, further comprising:
a) contacting the first refined oil or the second loaded extractant with a solution of the basic amino acid, the protamine, or a combination thereof;
b) further contacting the first refined oil or the second loaded extractant with the clay, thereby obtaining a first slurry;
c) filtering at least one solid from the first slurry, thereby obtaining a first mother liquor comprising an aqueous phase and an organic phase;
d) separating the aqueous phase and the organic phase;
e) contacting the organic phase with an ion exchange resin, thereby obtaining a deionized organic phase;
f) contacting the deionized organic phase with activated carbon, thereby obtaining a second slurry;
g) filtering at least one solid from the second slurry, thereby obtaining a second mother liquor comprising an aqueous phase and an organic phase;
h) adding brine to the second mother liquor;
i) concentrating the second mother liquor, thereby obtaining an aqueous phase and a concentrated organic phase; and
j) separating the aqueous phase and the concentrated organic phase, thereby obtaining the second refined extract.

Embodiment 98

The method of Embodiment 97, further comprising, adding water to the first slurry.

Embodiment 99

The method of any one of Embodiments 37-98, wherein the basic amino acid is selected from the group consisting of arginine, lysine, and histidine.

Embodiment 100

The method of any one of Embodiments 37-99, wherein the protamine is an arginine rich, nuclear protein.

Embodiment 101

The method of any one of Embodiments 92-100, wherein (a) and (b) are conducted (A) in one mixing tank, and (B) the temperature is from 55° C. to 65° C.

Embodiment 102

The method of any one of Embodiments 92-101, further comprising contacting the loaded extractant with water.

Embodiment 103

The method of any one of Embodiments 37-102, wherein the clay is selected from the group consisting of Fuller's Earth, Kaolin clay, bentonite, diatomaceous earth, magnesium silicate (such as Florisil®), or a mixture thereof.

Embodiment 104

The method of any one of Embodiments 37-103, wherein the ion exchange resin is a strong acid ion exchange resin (SAC) or a weak acid ion exchange resin (WAC), and the temperature is from 45° C. to 60° C.

Embodiment 105

The method of Embodiment 104, wherein the ion exchange resin is a WAC resin.

Embodiment 106

The method of Embodiment 105, wherein the WAC resin is in an $Na^+$ form, $H^+$ form, or a mixture thereof.

Embodiment 107

The method of any of Embodiments 92-104, wherein the deionized organic phase is contacted with powdered activated carbon (PAC) at a temperature from 35° C. to 65° C.

Embodiment 108

The method of Embodiment 107, wherein the deionized organic phase is contacted with powdered activated carbon (PAC) at a temperature from 40° C. to 50° C.

Embodiment 109

The method of any of Embodiments 92-108, wherein at least a portion of the separated aqueous phase is further combined with the second refined extractant prior to evaporating.

Embodiment 110

The method of any of Embodiments 92-109, wherein the brine is a solution of a salt that is selected from the group consisting of sodium chloride, sodium acetate, sodium formate, or any mixture thereof.

Embodiment 111

The method of Embodiment 110, wherein the brine is a solution of salt that comprises sodium acetate at a concentration from 0.5% to 4% wt/wt.

Embodiment 112

The method of any of Embodiments 37-111, wherein solvent and water are evaporated in (v) to obtain the second refined oil.

Embodiment 113

The method of any of Embodiments 92-112, wherein separating the aqueous phase and the organic phase is accomplished by decantation.

Embodiment 114

The method of any of Embodiments 37-113, wherein the plant material comprises *cannabis*.

Embodiment 115

The method of any of Embodiments 37-114, wherein the extracted constituents comprise cannabinoids and terpenes.

Embodiment 116

The method of any of Embodiments 37-115, wherein the plant material comprises green, dried, or pelletized material.

Embodiment 117

The method of any of Embodiments 37-116, wherein the solvent:
(a) is categorized as class 3 according to Q3C—Table and Lists Guidance for Industry (US Department of Health and Human Services, FDA, CDER, CBER), June 2017 ICH rev. 3; and/or
(b) forms a heterogeneous azeotrope with water, wherein the solvent and the azeotrope have a boiling point lower than the boiling point of water.

Embodiment 118

The method of any of Embodiments 37-117, wherein the first solvent comprises a mixture of solvents.

Embodiment 119

The method of any of Embodiments 37-118, wherein the second solvent comprises a mixture of solvents.

Embodiment 120

The method of any of Embodiments 37-119, wherein the first solvent is the same as the second solvent.

Embodiment 121

The method of any of Embodiments 37-120, wherein the solvent forms a heterogeneous azeotrope with water, wherein the heterogeneous azeotrope has a boiling point lower than the boiling point of the solvent.

Embodiment 122

The method of any of Embodiments 37-121, wherein the solvent has a ratio of water to solvent, $R_w/R_s$, that is greater in the vapor phase of the azeotrope than in the solvent liquid phase.

Embodiment 123

The method of any of Embodiments 37-122, wherein the solvent comprises a Hildebrand solubility parameter ranging from 10 MPa to 40.0 MPa$^{1/2}$.

Embodiment 124

The method of Embodiment 123, wherein the solvent comprises a Hildebrand solubility parameter ranging from 18 MPa to 20.0 MPa$^{1/2}$.

Embodiment 125

The method of any of Embodiments 37-124, wherein the solvent is selected from the group consisting of 1-butanol, ethyl acetate, ethyl formate, 2-methyl-1-butanol, ethanol, heptane, cyclohexane, 2-butanone, 2-propanol, or propylene glycol.

Embodiment 126

The method of Embodiment 125, wherein the solvent is ethyl acetate or ethyl formate.

Embodiment 127

The method of any of Embodiments 37-126, wherein the solvent comprises a carboxylic acid.

Embodiment 128

The method of Embodiment 127, wherein the carboxylic acid is a dicarboxylic acid or a tricarboxylic acid.

Embodiment 129

The method of Embodiment 128, wherein the dicarboxylic acid or tricaboxylic acid is selected from the group consisting of citric acid, oxalic acid, malic acid, ascorbic acid, or tartaric acid.

Embodiment 130

The method of any of Embodiments 37-129, wherein the method is a continuous process at industrial or semi-industrial scale.

Embodiment 131

The method of any of Embodiments 37-130, wherein the method is an integrated process for preparing at least one plant-extracted constituent.

Embodiment 132

The method of any of Embodiments 37-131, wherein extracting the constituent from the plant material of (i) is conducted from 10° C. to 45° C.

Embodiment 133

The method of any of Embodiments 37-132, wherein an evaporation device selected from the group consisting of an evaporator, a stripper, or a dryer is used for concentrating, wherein the evaporation device further comprises a barometric condenser.

Embodiment 134

The method of any of Embodiments 37-133, wherein concentrating occurs at temperature from 40° C. to 85° C. at a pressure from 100 mmHg to 760 mmHg.

Embodiment 135

The method of Embodiment 134, wherein concentrating occurs at a temperature from 40° C. to 60° C. at a pressure of 200 mmHg to 400 mmHg.

Embodiment 136

The method of Embodiment 134, wherein concentrating occurs at a temperature from 60° C. to 85° C. at a pressure of 150 mmHg to 300 mmHg.

Embodiment 137

The method of any of Embodiments 37-136, wherein the constituents of the purified oil comprises any of the characteristics, or any combination thereof, selected from:
i) at least 85% wt cannabinoids;
ii) at most 1% wt/wt fatty acids
iii) at most 30 ppm heavy metals;
iv) at most 5000 µg/g ethanol;
v) at most 3000 µg/g methanol;
vi) at most 5000 µg/g ethyl acetate;
vii) at most 5000 µg/g butane; and
viii) at most 290 µg/g hexane

Embodiment 138

The method of Embodiment 137, wherein the heavy metals are selected from the group consisting of mercury, arsenic, cadmium, lead, or any combination thereof.

Embodiment 139

The method of any of Embodiments 37-138, wherein the concentration of THC in the purified oil is controlled to at most about 0.001% wt/wt, or less.

Embodiment 140

The method of any of Embodiments 37-138, wherein the concentration of THC in the purified oil is controlled to about 0.001% to about 0.3% wt/wt.

Embodiment 141

The method of any of Embodiments 37-138, wherein the concentration of THC in the purified oil is controlled to at least about 0.3% wt/wt, or more.

Embodiment 142

The method of Embodiment 141, wherein the concentration of THC in the purified oil is controlled to at least about 30% wt/wt, or more.

Embodiment 143

The method of Embodiment 142, wherein the concentration of THC in the purified oil is controlled to at least about 50% wt/wt, or more.

Embodiment 144

The method of Embodiment 143, wherein the concentration of THC in the purified oil is controlled to at least about 60% wt/wt, or more.

Embodiment 145

The method of any of Embodiments 40-144, wherein at least one fractionated plant-extracted constituent comprises at least about 95%, or more, of the THC present in the purified oil, thereby forming a THC-enriched fraction.

Embodiment 146

The method of Embodiment 145, wherein the THC-enriched fraction comprises at least about 99%, or more, of the THC present in the purified oil.

Embodiment 147

The method according to Embodiment 145 or 146, wherein the THC-enriched fraction comprises at most about 25%, or less, of the CBD present in the purified oil.

Embodiment 148

The method of Embodiment 147, wherein the THC-enriched fraction comprises at most about 15%, or less, of the CBD present in the purified oil.

Embodiment 149

The method of Embodiment 148, wherein the THC-enriched fraction comprises at most about 5%, or less, of the CBD present in the purified oil.

Embodiment 150

The method of any of Embodiments 40-149, wherein the at least one fractionated plant-extracted constituent comprises at most about 0.300%, or less, THC in the purified oil, thereby forming a THC-depleted fraction.

Embodiment 151

The method of Embodiment 150, wherein the THC-depleted fraction comprises at most about 0.001%, or less, THC in the purified oil.

Embodiment 152

The method of any of Embodiments 37-151, wherein the concentration of CBN in the purified oil can be controlled to at most about 2% wt/wt, or less.

Embodiment 153

The method of any of Embodiments 37-151, wherein the concentration of CBN in the purified oil can be controlled to at least about 2% wt/wt, or more.

Embodiment 154

The method of Embodiment 153, wherein the concentration of CBN in the purified oil can be controlled to at least about 20% wt/wt, or more.

Embodiment 155

The method of Embodiment 154, wherein the concentration of CBN in the purified oil can be controlled to at least about 30% wt/wt, or more.

Embodiment 156

The method of any of Embodiments 40-155, wherein the concentration of THC in the at least one fractionated plant-extracted constituent is controlled to at most about 0.001% wt/wt, or less.

Embodiment 157

The method of any of Embodiments 40-155, wherein the concentration of THC in the at least one fractionated plant-extracted constituent is controlled to about 0.001% to 0.3% wt/wt.

Embodiment 158

The method of any of Embodiments 40-155, wherein the concentration of THC in the at least one fractionated plant-extracted constituent is controlled to at least about 0.3% wt/wt, or more.

Embodiment 159

The method of Embodiment 158, wherein the concentration of THC in the at least one fractionated plant-extracted constituent is controlled to at least about 30% wt/wt, or more.

Embodiment 160

The method of Embodiment 159, wherein the concentration of THC in the at least one fractionated plant-extracted constituent is controlled to at least about 50% wt/wt, or more.

Embodiment 161

The method of Embodiment 160, wherein the concentration of THC in the at least one fractionated plant-extracted constituent is controlled to at least about 60% wt/wt, or more.

Embodiment 162

The method of any of Embodiments 40-161, wherein the concentration of CBN in the at least one fractionated plant-extracted constituent is controlled to at most about 2% wt/wt, or less.

Embodiment 163

The method of any of Embodiments 40-161, wherein the concentration of CBN in the at least one fractionated plant-extracted constituent is controlled to at least about 2% wt/wt, or more.

Embodiment 164

The method of Embodiment 163, wherein the concentration of CBN in the at least one fractionated plant-extracted constituent is controlled to at least about 20% wt/wt, or mmore.

Embodiment 165

The method of Embodiment 164, wherein the concentration of CBN in the at least one fractionated plant-extracted constituent is controlled to at least about 30% wt/wt, or more.

Embodiment 166

The method of any of Embodiments 37-165, wherein the purified oil further comprises any of the characteristics, comprises any characteristics, or a combination thereof, selected from:
i) at most about 0.14 μg/kg, or less, Arsenic;
ii) at most about 0.09 μg/kg, or less, Cadmium;
iii) at most about 0.15 μg/kg, or less, Lead;
iv) at most about 0.29 μg/kg, or less, Mercury; and
v) at most about 0.05% wt/wt, or less, phosphorous.

Embodiment 167

The method of any of Embodiments 37-166, wherein the purified oil further comprises at most about 0.05 mg/kg, or less, pesticides as analyzed by Official Methods of Analysis, AOAC Official Method 2007.01, Pesticide Residues in Foods by Acetonitrile Extraction and Partitioning with Magnesium Sulfate, AOAC INTERNATIONAL (modified) or CEN Standard Method EN 15662: Food of plant origin—Determination of pesticide residues using GC-MS and/or LC-MS/MS following acetonitrile extraction/partitioning and clean-up by dispersive SPE-QuEChERS method.

Embodiment 168

A system for continuously extracting herbal constituents from a plant material, wherein the system comprises at least two conveyors and at least two mixing tanks, wherein each conveyor comprises:
a) an internal screw for propagating plant material and at least one solvent from an upstream end to a downstream end of at least one of the conveyors of the at least two conveyors;
b) a wire screen for separating liquids from the plant material; and
c) an inlet for the plant material comprising at least one inlet for solvent, wherein the inlet is adjacent to at least one of the at least two conveyors, wherein a flow direction for each conveyor is co-current.

Embodiment 169

The system of Embodiment 168, wherein each conveyor is inclined, such that the plant material is fed at the downstream end and propagated out of the upstream end.

Embodiment 170

The system according to Embodiment 168 or 169, wherein the plant material is propagated by the internal screw.

Embodiment 171

The system of any of Embodiments 166-170, wherein the at least two conveyors are arranged in a substantially opposing arrangement such that a stream of solvent can flow between the at least two conveyors.

Embodiment 172

The system of any of Embodiments 168-171, where in the flow is assisted by gravitation.

Embodiment 173

The system of any of Embodiments 168-172, wherein the at least two mixing tanks are connected with the at least two conveyors via conduits equipped with pumps for pumping a plant material slurry and a partially loaded extractant to the at least two conveyors, wherein the overall flow of the system is in counter-current orientation.

Embodiment 174

The system of any of Embodiments 168-173, wherein the mixing tanks and pumps process the plant material in the at least two conveyors.

Embodiment 175

The system of any of Embodiments 168-174, wherein the processing in a first conveyor is with at most about 20 parts, or less, of solvent to plant material (wt/wt).

Embodiment 176

The system of any of Embodiments 168-174, wherein the processing in a first conveyor is with at least about 20 parts, or more, of solvent to plant material (wt/wt).

Embodiment 177

The system of any of Embodiments 168-176, wherein the processing in a second conveyor is with at most about 60 parts, or less, of solvent to plant material (wt/wt).

Embodiment 178

The system of any of Embodiments 168-176, wherein the processing in a second conveyor is with at least about 60 parts, or more, of solvent to plant material (wt/wt).

Embodiment 179

The system of any of Embodiments 168-176, wherein the ratio of liquid to plant material in the system is about 1 to 20 (wt/wt).

Embodiment 180

The system of any of Embodiments 166-179, wherein the residence time of plant material in the extractor and the ratio of liquid to plant material in each conveyor is controlled by the angle of inclination, the pitch of the screw, the turning speed of the screw, the pumping speed of the solvent and plant material.

Embodiment 181

The system of any of Embodiments 168-180, wherein the residence time of plant material in the extractor and the ratio of liquid to plant material in at least one conveyor is distinct from each conveyor in the system.

Embodiment 182

The system of any of Embodiments 168-181, wherein the residence time of plant material in the extractor and the ratio of liquid to plant material in each conveyor is distinct from each conveyor in the system.

Embodiment 183

The system of any of Embodiments 168-182, wherein the angle of inclination is altered to control the residence time of plant material and liquid in each conveyor.

Embodiment 184

The system of any of Embodiments 168-183, wherein the turning speed of the screw is altered to control the residence time of plant material and liquid in each conveyor.

Embodiment 185

The system of any of Embodiments 168-184, wherein the pumping speed is altered to control the liquid to plant material ratio in each conveyor.

Embodiment 186

The system of any of Embodiments 168-185, wherein the cumulative residence time of plant material in the system is at least about 1 minute, or more.

Embodiment 187

The system of Embodiment 186, wherein the cumulative residence time of plant material in the system is at least about 60 minutes, or more.

Embodiment 188

The system of any of Embodiments 168-185, wherein the cumulative residence time of plant material in the system is at most about 60 minutes, or less.

Embodiment 189

The system of Embodiment 188, wherein the cumulative residence time of plant material in the system is at most about 1 minute, or less.

Embodiment 190

The system of any of Embodiments 168-185, wherein the cumulative residence time of plant material in the system is from about 1 minute to about 60 minutes.

Embodiment 191

The system of Embodiment 190, wherein the cumulative residence time of plant material in the system is from about 5 minutes to about 30 minutes.

Embodiment 192

The system of Embodiment 191, wherein the cumulative residence time of biomass in the system is from about 10 minutes to about 20 minutes.

Embodiment 193

The system of any of Embodiments 168-192, wherein the wire screen is a wedge wire screen.

Embodiment 194

The system of any of Embodiments 168-193, wherein the conveyors are insulated and/or jacketed for temperature control.

Embodiment 195

The system of any of Embodiments 168-194, wherein the operating temperature is at most about −10° C., or less.

Embodiment 196

The system of Embodiment 195, wherein the operating temperature is at most about −25° C., or less.

Embodiment 197

The system of any of Embodiments 168-194, wherein the operating temperature is at least about −10° C., or more.

Embodiment 198

The system of Embodiment 197, wherein the operating temperature is at least about 35° C., or more.

Embodiment 199

The system of any of Embodiments 168-194, wherein the operating temperature is from about −25° C. to about 35° C.

Embodiment 200

The system of Embodiment 199, wherein the operating temperature is from about −5° C. to about 25° C.

Embodiment 201

The system of Embodiment 200, wherein the operating temperature is from about 5° C. to about +25° C.

Embodiment 202

The system of any of Embodiments 168-201, comprising at least three conveyors, at least three tanks, at least three pumps, and any combination thereof.

Embodiment 203

The system of any of Embodiments 168-202, wherein:
a) an uppermost conveyor or a plurality of uppermost conveyors is fed with plant material and at least one solvent, thereby producing a loaded extractant;
b) a middle conveyor or a plurality of middle conveyors is fed with partially extracted plant material from the uppermost conveyor or the plurality of uppermost conveyors and at least one solvent; and
c) the lowermost conveyor or a plurality of lowermost conveyors is fed with extracted biomass from the middle conveyor the plurality of middle conveyors and freshly regenerated solvent.

Embodiment 204

The system of Embodiment 203, wherein the plurality of middle converters comprises at least two conveyors in parallel.

Embodiment 205

The system of Embodiment 204, wherein the plurality of middle converters comprises two conveyors in parallel.

Embodiment 205

The system of Embodiment 203, wherein the plurality of middle converters comprises at least two conveyors in series.

Embodiment 206

The system of Embodiment 205, wherein the plurality of middle converters comprises two conveyors in series.

Embodiment 207

The system according to Embodiment 205 or 206, wherein the conveyors in series are operated in a counter-current mode with respect to each other.

Embodiment 208

The system of any of Embodiments 203-207, wherein the ratio of liquid to solid is:
a) from about 1 to about 20 (wt/wt) in the uppermost conveyor or the plurality of uppermost conveyors;
b) From about 1 to about 60 (wt/wt) in the middle conveyor or the plurality of middle conveyors; and
c) from 1 about to about 20 (wt/wt) in the lowermost conveyor or the plurality of lowermost conveyors.

Embodiment 209

The system of any of Embodiments 168-208, wherein plant material and liquids are separated in the conveyor over the wire screen, wherein the through stream comprises a loaded extractant and water and the retained stream comprises a loaded extractant, water and plant material.

Embodiment 210

The system of any of Embodiments 168-209, wherein the plant material is separated by density.

Embodiment 211

The system of Embodiment 210, wherein at least one solvent is used to separate the plant material by density.

Embodiment 212

The system of Embodiment 211, wherein the plant material with a density lower than the solvent floats to the surface of the at least one solvent.

Embodiment 213

The system of Embodiment 212, wherein the plant material that floats to the surface of the at least one solvent is substantially free of cannabinoids.

Embodiment 214

The system of any of Embodiments 168-213, further comprising at least one granulated activated carbon (GAC) column.

Embodiment 215

The system of Embodiment 214, wherein the separated liquid phase is contacted with GAC by flowing through the at least one column.

Embodiment 216

The system according to Embodiment 214 or 215, wherein the contact with the GAC column is conducted at least about 10° C., or more.

Embodiment 217

The system of Embodiment 216, wherein the contact with the GAC column is conducted at least about 60° C., or more.

Embodiment 218

The system according to Embodiment 214 or 215, wherein the contact with the GAC column is conducted at most about 60° C., or less.

Embodiment 219

The system of Embodiment 218, wherein the contact with the GAC column is conducted at most about 10° C., or less.

Embodiment 220

The system of Embodiment 219, wherein the contact with the GAC column is conducted from about 10° C. to about 60° C.

Embodiment 221

The system of Embodiment 220, wherein the contact with the GAC column is conducted from about 30° C. to about 55° C.

Embodiment 222

The system of Embodiment 221, wherein the contact with the GAC column is conducted from about 40° C. to about 50° C.

Embodiment 223

The system of any of Embodiments 168-222, wherein the separated liquid phase is contacted with an adsorbent.

Embodiment 224

The system of any of Embodiments 168-223, further comprising an evaporator.

Embodiment 225

The system of Embodiment 224, wherein the evaporator receives the through stream and evaporates the solvent and water to provide a concentrated oil stream.

Embodiment 226

The system of Embodiment 225, wherein the concentrated oil stream comprises solvent and extractants at a ratio of about 10:1.

Embodiment 227

The system according to Embodiment 225 or 226, wherein the concentrated oil stream comprises less than about 5% solvent and less than about 1% water.

Embodiment 228

The system of Embodiment 227, wherein the concentrated oil stream comprises less than about 0.5% solvent and less than about 0.1% water.

Embodiment 229

The system of any of Embodiments 168-228, wherein the retained stream from the upper extraction conveyor comprises at least about 7% solids.

Embodiment 230

The system of any of Embodiments 166-229, further comprising a system for solid/liquid separation and a system for liquid/liquid separation, wherein the separation systems receive a plurality of effluent streams from the extracting system.

Embodiment 231

The system of Embodiment 230, wherein the separation systems separate the streams to provide: (i) concentrated extractives stream; (ii) freshly regenerated solvent stream; and (iii) an aqueous stream.

Embodiment 232

The system according to Embodiment 230 or 231, wherein the efficiency of separation such that:
a) at least about 90%, or more, of the solvent is recovered as freshly regenerated solvent for further extraction;
b) the aqueous stream comprises at most about 0.1%, or less, solvent and is suitable to be treated in industrial waste water plants; and,
c) the solids comprise at most about 0.5% solvent, at most about 0.1% water, and at most about 5% of the starting extractable constituents.

Embodiment 233

The system of Embodiment 232, wherein at least about 99%, or more, of the solvent is recovered as freshly regenerated solvent for further extraction.

Embodiment 234

The system of Embodiment 232, wherein the aqueous stream comprises at most about 0.005%, or less, solvent.

Embodiment 235

The system of any of Embodiments 168-234, comprising a screw press, wherein the screw press receives the retained stream from the uppermost conveyor and removes liquids to provide a concentrated plant material stream, comprising about 50 to about 80% solids.

Embodiment 236

The system of any of Embodiments 168-235, wherein the separated liquid is returned to a mixing tank of Embodiment 168.

Embodiment 237

The system of any of Embodiments 168-236, further comprising a paddle dryer, wherein the paddle dryer dries the concentrated solid stream to provide dry solids.

Embodiment 238

The system of Embodiment 237, wherein the vapors are collected, condensed, and returned to the liquid/liquid separation system.

Embodiment 239

The system according to Embodiment 237 or 238, wherein the dried solids comprise at most about 0.5% solvent, or less, and at most about 0.1% water, or less.

Embodiment 240

The system of any of Embodiments 237-239, wherein the dried solids comprise spent plant material and spent adsorbents.

Embodiment 241

The system of any of Embodiments 230-240, wherein the liquid/liquid separation unit receives condensates of vapors comprising solvent and water from the evaporator from a striping distillation column and from the paddle dryer.

Embodiment 242

The system of any of Embodiments 230-241, wherein the liquid/liquid separation unit further comprises a decanting unit and a stripping distillation column.

Embodiment 243

The system of Embodiment 242, wherein the decanting unit comprises a decanting tank or a decanting centrifuge, and wherein the decanting unit provides a water-saturated solvent stream and a solvent-saturated aqueous stream.

Embodiment 244

The system of any of Embodiments 230-243, wherein the water-saturated solvent stream is returned to the extraction system as freshly regenerated solvent stream.

Embodiment 245

The system of any of Embodiments 230-244, wherein the solvent saturated solvent stream is fed into the stripping distillation column to provide an aqueous stream comprising at most about 0.1% solvent.

Embodiment 246

The system of any of Embodiments 230-245, wherein the aqueous stream is sent to a waste water treatment plant.

Embodiment 247

A method of extracting cannabinoids and terpenes from plant material, the method comprising:
i. feeding plant material, wherein the plant is a *Cannabis* plant;
ii. extracting the plant material with a solvent to obtain a loaded extractant, wherein the loaded extractant comprises extractives and water;
iii. evaporating the solvent and the water as a heterogeneous azeotrope to provide a concentrated extractant stream, a recycle solvent stream and a water stream;
iv. refining the concentrated extractant stream to provide a high purity extract;

Embodiment 248

The method of Embodiment 247, further comprising fractionating the high purity extract to provide a terpene stream and a cannabinoid stream.

Embodiment 249

The method according to Embodiment 247 or 248, further comprising decarboxylating cannabinoid compounds in the cannabinoid stream, wherein at any stage of the process is conducted at a temperature of at least about 100° C., or more.

Embodiment 250

The method according to Embodiment 247 or 248, further comprising decarboxylating cannabinoid compounds in the cannabinoid stream, wherein at any stage of the process is conducted at a temperature of at most about 100° C., or less.

Embodiment 251

The method of Embodiment 250, wherein the temperature is at most about 90° C., or less.

Embodiment 252

The method of Embodiment 251, wherein the temperature is at most about 80° C., or less.

Embodiment 253

The method of Embodiment 252, wherein the temperature is at most about 70° C., or less.

Embodiment 254

The method of Embodiment 253, wherein the temperature is at most about 60° C., or less.

Embodiment 255

The method of Embodiment 254, wherein the temperature is at most about 50° C., or less.

Embodiment 256

The method of any of Embodiments 247-255, wherein the plant material is not dried prior to extraction.

Embodiment 257

The method of any of Embodiments 248-256, wherein the terpene stream is further fractionated to at least two fractions by fractional distillation.

Embodiment 258

The method of any of Embodiments 249-257, wherein the decarboxylating comprises heating the cannabinoids under reduced or increased pressure.

Embodiment 259

The method of any of Embodiments 249-258, wherein the decarboxylating is conducted in the presence of a catalyst.

Embodiment 260

The method of Embodiment 259, wherein the catalyst is a strongly acidic cation (SAC) exchange resin or a carboxylic acid.

Embodiment 261

The method of Embodiment 260, wherein the SAC is a microporous exchange resin.

Embodiment 262

The method of Embodiment 260, wherein the carboxylic acid is a dicarboxylic acid or a tricarboxylic acid.

Embodiment 263

The method of any of Embodiments 247-263, wherein the solvent comprises a solvent or a mixture of solvents, wherein the solvent or mixture of solvents:
i. is categorized as class 3 according to Q3C—Table and Lists Guidance for Industry (US Department of Health and Human Services, FDA, CDER, CBER), June 2017 ICH rev. 3;
ii. forms a heterogeneous azeotrope with water, wherein the azeotrope has a boiling point lower than the boiling point of water; and/or
iii. forms a heterogeneous azeotrope with water, wherein the azeotrope has a boiling point lower than the boiling point of the solvent or mixture of solvents.

Embodiment 264

The method of any of Embodiments 247-264, wherein the ratio of water to solvent, Rw/Rs, is greater in the vapor phase of the azeotrope than in the solvent phase.

Embodiment 265

The method of any of Embodiments 247-264, wherein the solvent is selected from 1-butanol, ethyl acetate, ethyl formate, 2-methyl-1-butanol, ethanol, heptane, cyclohexane, 2-butanone, 2-propanol, propylene glycol and mixtures thereof

Embodiment 266

The method of any of Embodiments 247-265, wherein the solvent is ethyl acetate or ethyl formate.

Embodiment 267

A system for extracting herbal constituents from a plant material, wherein the system comprises at least one pulse column and wherein the stream of plant material and the stream of extraction liquid are fed in a counter-current mode.

Embodiment 268

The system of Embodiment 267, comprising at least two columns, wherein the stream of plant material and the stream of extraction liquid are fed in a counter-current mode over the at least two columns.

Embodiment 269

The system according to Embodiment 267 to 268, wherein the feed ratio of extraction liquid to plant material is at least about 10:1 wt/wt, or more.

Embodiment 270

The system according to Embodiment 269, wherein the feed ratio of extraction liquid to plant material is at least about 40:1 wt/wt, or more.

Embodiment 271

The system according to Embodiment 267 to 268, wherein the feed ratio of extraction liquid to plant material is most about 40:1 wt/wt, or less.

Embodiment 272

The system of Embodiment 271, wherein the feed ratio of extraction liquid to plant material is most about 10:1 wt/wt, or less.

Embodiment 273

The system according to Embodiment 267 or 268, wherein the feed ratio of extraction liquid to plant material is from about 40:1 to about 10:1 wt/wt.

Embodiment 274

The system of any one of Embodiment 267-273, wherein the temperature of extraction is controlled by pre-cooling or pre-heating the extraction liquid.

Embodiment 275

A method of fractionating a *cannabis* extract, the method comprising (1) fractionating a *cannabis* extract using an ion-exchange resin, (2) collecting a fraction enriched in terpenes relative to the *cannabis* extract and (3) collecting a fraction enriched in cannabinoids relative to the *cannabis* extract.

Embodiment 276

The method of Embodiment 275, wherein the ion-exchange resin is a strongly basic anion (SBA) exchange resin.

Embodiment 277

The method of Embodiment 276, further comprising washing the SBA exchange resin with an acid to maintain it in an acidic form.

Embodiment 278

The method according to Embodiment 276 or 277, wherein the anion exchange resin has a particle size of at least about 300 µm, or more.

Embodiment 279

The method of Embodiment 278, wherein the anion exchange resin has a particle size of at least about 1200 µm, or more.

Embodiment 280

The method according to Embodiment 276 or 277, wherein the anion exchange resin has a particle size of most about 1200 µm, or less.

Embodiment 281

The method of Embodiment 280, wherein the anion exchange resin has a particle size of at most about 300 µm, or less.

Embodiment 282

The method according to Embodiment 276 or 277, wherein the anion exchange resin has a particle size from about 300 µm to about 1200 µm.

Embodiment 283

The method of Embodiment 282, wherein the anion exchange resin has a particle size from about 200 µm to about 400 µm.

Embodiment 284

The method of Embodiment 283, wherein the anion exchange resin has a particle size from about 280 µm to about 320 µm.

Embodiment 285

The method of any of Embodiments 275-284, wherein the particle size of the ion-exchange resin is uniform.

Embodiment 286

The method of Embodiment 285, wherein the ion-exchange resin has a uniformity coefficient of at most 1.7, or less.

Embodiment 287

The method of any of Embodiments 275-286, wherein the fractionating is carried out in a simulated moving bed mode.

Embodiment 288

The method of any of Embodiments 275-287, wherein the fractionating is carried out in a sequential simulated moving bed mode.

Embodiment 289

The method of Embodiment 288, wherein the sequential simulated moving bed chromatography mode further comprises: (1) passing a feed stream comprising *cannabis* extract into an adsorbent, thereby flushing a first raffinate stream comprising terpenes from the adsorbent; (2) flushing an extract stream enriched in cannabinoids relative to the feed stream with a desorbent stream; and (3) recycling the desorbent stream back to the adsorbent.

Embodiment 290

The method of Embodiment 289, further comprising flushing a second raffinate stream comprising decarboxylated cannabinoids from the adsorbent during step (1).

Embodiment 291

The method according to Embodiment 289 or 290, wherein the desorbent stream comprises low amounts of acid, and wherein the acid is the same acid used to wash the ion-exchange resin to maintain it in acidic form.

Embodiment 292

The method of any of Embodiments 289-291, wherein the acid is selected from citric acid, acetic acid, lactic acid, malic acid, benzoic acid, ascorbic acid, tartaric acid, oxalic acid, tannic acid, caffeotannic acid, butyric acid, fumaric acid, formic acid, folic acid, adipic acid, alginic acid, galic acid, glutamic acid, sorbic acid, succinic acid, phosphoric acid, and 2-aminoethanesulfonic acid.

Embodiment 293

The method of Embodiment 292, wherein the acid is acetic acid or citric acid.

Embodiment 294

The method of any of Embodiments 289-293, further comprising mixing the fraction enriched in terpenes with the fraction enriched in cannabinoids in a terpene to cannabinoid ratio that is different that the ratio of the *cannabis* extract.

Embodiment 295

The method of any of Embodiments 289-294, wherein the refining further comprises contacting with a bleaching agent, wherein the bleaching agent comprises at least one of activated carbon, Fuller's Earth, Kaolin clay, bentonite, diatomaceous earth or mixtures thereof.

Embodiment 296

The method of Embodiment 295, wherein the bleaching agent is acid-washed.

Embodiment 297

A method of fractionating a *cannabis* extract, the method comprising (1) fractionating a *cannabis* extract using a continuous simulated moving bed method (2) collecting a fraction enriched in a first cannabinoid relative to the *cannabis* extract and (3) collecting a fraction enriched in at least a second cannabinoid relative to the *cannabis* extract.

Embodiment 298

The method of Embodiment 297, wherein the first cannabinoid is CBDA, and the second cannabinoid is THCA.

Embodiment 299

The method according to Embodiment 297 or 298, wherein the fractionating is carried out in a sequential simulated moving bed mode.

Embodiment 300

The method of Embodiment 299, wherein the sequential simulated moving bed chromatography sequence comprises: (1) passing a feed stream comprising *cannabis* extract into an adsorbent, thereby flushing a first raffinate stream comprising THCA and decarboxylated cannabinoids from the adsorbent; (2) flushing an extract stream enriched in CBDA relative to the feed stream with a desorbent stream; and (3) recycling the desorbent stream back to the adsorbent.

Embodiment 301

The method of any of Embodiments 297-300, wherein the solvent comprises a solvent or a mixture of solvents, wherein the solvent or mixture of solvents:
i is categorized as class 3 according to Q3C—Table and Lists Guidance for Industry (US Department of Health and Human Services, FDA, CDER, CBER), June 2017 ICH rev. 3; and/or
ii. forms a heterogeneous azeotrope with water, wherein the azeotrope has a boiling point lower than the boiling point of water.

Embodiment 302

The method of any of Embodiments 297-301, wherein the solvent or a mixture of solvents form a heterogeneous azeotrope with water, wherein the azeotrope has a boiling point lower than the boiling point of the solvent or mixture of solvents.

Embodiment 303

The method of any of Embodiments 297-302, wherein the ratio of water to solvent, $R_w/R_s$, is greater in the vapor phase of the azeotrope than in the solvent phase.

Embodiment 304

The method of any of Embodiments 297-303, wherein the solvent or a mixture of solvent is characterized as having a Hildebrand solubility parameter in the range of 18.0 to 20.0 $MPa^{1/2}$.

Embodiment 305

The method of any of Embodiments 297-304, wherein the solvent is selected from 1-butanol, ethyl acetate, ethyl formate, 2-methyl-1-butanol, ethanol, heptane, cyclohexane, 2-butanone, 2-propanol, propylene glycol and mixtures thereof.

Embodiment 306

The method of any of Embodiments 297-305, wherein the solvent is ethyl acetate or ethyl formate.

Embodiment 307

The method of any of Embodiments 297-306, wherein the desorbent comprises a dry solvent.

Embodiment 308

The method of any of Embodiments 297-306, wherein the desorbent comprises a water-saturated solvent.

Embodiment 309

The method of any of Embodiments 297-308, wherein the solvent comprises low amounts of acid, and wherein the acid is the same acid used to wash the chromatography media to maintain it in acidic form.

Embodiment 310

The method of any of Embodiments 297-308, wherein the acid is selected from citric acid, acetic acid, lactic acid, malic acid, benzoic acid, ascorbic acid, tartaric acid, oxalic acid, tannic acid, caffeotannic acid, butyric acid, fumaric acid, formic acid, folic acid, adipic acid, alginic acid, galic acid, glutamic acid, sorbic acid, succinic acid, phosphoric acid, and 2-aminoethanesulfonic acid.

Embodiment 311

The method of any of Embodiments 297-310, wherein the acid is acetic acid, formic acid or citric acid.

Embodiment 312

The method of any of Embodiments 297-311, wherein the chromatography media is a cross-linked dextran polymer.

Embodiment 313

The method of any of Embodiments 297-311, wherein the chromatography media is a non-ionic acrylic polymer.

Embodiment 314

The method of any of Embodiments 297-311, wherein the chromatography media is macroporous resin such as a strong acid cation resin (SAC), a weak base anion resin (WBA) or a strong base anion resin (SBA).

Embodiment 315

The method of any of Embodiments 297-314, wherein the *cannabis* extract is a refined *cannabis* extract.

Embodiment 316

A method of refining a crude plant extract to provide refined extract, the method comprising:

i. contacting a crude solution comprising a solvent and the crude extract with a weak acid cation exchange resin;
ii. mixing the solution with cold water;
iii. chilling the mixture;
iv. separating the chilled mixture by centrifuge to provide a light phase and a heavy phase, wherein the light phase comprises solvent and extract, and wherein the heavy phase comprises water and precipitates;
v. contacting the light phase with activated carbon;
vi. cooling the contacted solution;
vii. filtering the cooled solution to provide a refined solution; and
viii. evaporating the solvent to provide a concentrated refined extract.

Embodiment 317

The method of Embodiment 316, wherein the plant is a *cannabis* plant, and the extract comprises cannabinoids and terpenes.

Embodiment 318

The method according to Embodiment 316 or 317, wherein the crude solution comprises the crude extract and an added solvent at a ratio of at least about 1:2, or more.

Embodiment 319

The method of Embodiment 318, wherein the crude solution comprises the crude extract and an added solvent at a ratio of at least about 20:1, or more.

Embodiment 320

The method according to Embodiment 316 or 317, wherein the crude solution comprises the crude extract and an added solvent at a ratio of at most about 20:1, or less.

Embodiment 321

The method of Embodiment 320, wherein the crude solution comprises the crude extract and an added solvent at a ratio of at most about 1:2, or less.

Embodiment 322

The method according to Embodiment 316 or 317, wherein the crude solution comprises the crude extract and an added solvent at a ratio from about 20:1 to about 1:2.

Embodiment 323

The method of any of Embodiments 316-321, further comprising contacting the solution with a clay, bleached clay, a filtering aid, or a combination thereof, before filtering.

Embodiment 324

The method of any of Embodiments 316-323, wherein the solvent comprises a solvent or a mixture of solvents, wherein the solvent or mixture of solvents:
i is categorized as class 3 according to Q3C—Table and Lists Guidance for Industry (US Department of Health and Human Services, FDA, CDER, CBER), June 2017 ICH rev. 3; and/or
ii. forms a heterogeneous azeotrope with water, wherein the solvent and the azeotrope have a boiling point lower than the boiling point of water.

Embodiment 325

The method of any of Embodiments 316-324, wherein the solvent or a mixture of solvents form a heterogeneous azeotrope with water, wherein the azeotrope has a boiling point lower than the boiling point of the solvent or mixture of solvents.

Embodiment 326

The method of any of Embodiments 316-325, wherein the ratio of water to solvent, $R_w/R_s$, is greater in the vapor phase of the azeotrope than in the solvent liquid phase.

Embodiment 327

The method of any of Embodiments 316-326, wherein the solvent or a mixture of solvent is characterized as having a Hildebrand solubility parameter in the range of 18.0 to 20.0 $MPa^{1/2}$.

Embodiment 328

The method of any of Embodiments 316-327, wherein the solvent is selected from 1-butanol, ethyl acetate, ethyl formate, 2-methyl-1-butanol, ethanol, heptane, cyclohexane, 2-butanone, 2-propanol, propylene glycol and mixtures thereof.

Embodiment 329

The method of any of Embodiments 316-328, wherein the solvent is ethyl acetate or ethyl formate.

Embodiment 330

The method of any of Embodiments 316-329, wherein the solvent comprises a carboxylic acid.

Embodiment 33

The method of any of Embodiments 316-330, wherein the refined extract comprises any of the following characteristics, or a combination thereof:
i. at least about 80% wt cannabinoids;
ii. about the same ratio of CBDA to total cannabinoids as in the crude extract;
iii. about the same ratio of THCA to total cannabinoids as in the crude extract;
iv. at most about 5000 µg/g ethanol;
v. at most about 3000 µg/g methanol;
vi. at most about 5000 µg/g ethyl acetate;
vii. at most about 5000 µg/g butane;
viii. at most about 290 µg/g hexane Embodiment 332

The method of any of Embodiments 316-331, wherein at least 88% of the cannabinoids is CBDA.

Embodiment 333

The method of any of Embodiments 316-332, further comprising any of the following characteristics, or a combination thereof:

i. at most about 0.14 µg/kg Arsenic;
ii. at most about 0.09 µg/kg Cadmium;
iii. at most about 0.29 µg/kg Lead;
iv. at most about 0.29 µg/kg Mercury; and
v. at most about 0.05% wt/wt phosphorous.

Embodiment 334

An extracted *cannabis* plant, wherein an extracted plant comprises not more than 1% wt/wt dry base cannabinoids compared to the pre-extracted plant.

Embodiment 335

The extracted *cannabis* plant of Embodiment 334, further comprising at most about 1%, 0.1%, 0.01%, 0.001%, or less wt/wt water and at most 1%, 0.1%, 0.01%, or less wt/wt solvent.

Embodiment 336

A composition of a *cannabis*-derived extract substantially free of heavy metals.

Embodiment 337

A composition of Embodiment 336, comprising:
i) at least about 85% wt cannabinoids;
ii) at most about 1% wt/wt fatty acids
iii) at most about 30 ppm heavy metals;
iv) at most about 5000 µg/g ethanol;
v) at most about 3000 µg/g methanol;
vi) at most about 5000 µg/g ethyl acetate;
vii) at most about 5000 µg/g butane; and
viii) at most about 290 µg/g hexane Embodiment 338

The composition of Embodiment 337, wherein the heavy metals are selected from the group consisting of mercury, arsenic, cadmium, lead, or any combination thereof.

Embodiment 339

The composition according to Embodiment 337 or 338, wherein the concentration of THC is at most about 0.001% wt/wt, or less.

Embodiment 340

The composition according to Embodiment 337 or 338, wherein the concentration of THC is about 0.001% to 0.3% wt/wt.

Embodiment 341

The composition according to Embodiment 337 or 338, wherein the concentration of THC is at least 0.3% wt/wt, or more.

Embodiment 342

The composition of Embodiment 341, wherein the concentration of THC is at least about 30% wt/wt, or more.

Embodiment 343

The composition according to Embodiment 341 or 342, wherein the concentration of THC is at least about 50% wt/wt, or more.

Embodiment 344

The composition of any of Embodiments 341-343, wherein the concentration of THC is at least about 60% wt/wt, or more.

Embodiment 345

The composition of any of Embodiments 341-344, wherein the concentration of THC is about 100% wt/wt.

Embodiment 346

The composition of any of Embodiments 337-345, wherein the concentration of CBD, CBDA, or a combination thereof is at most about 0.001% wt/wt, or less.

Embodiment 347

The composition of any of Embodiments 337-344, wherein the concentration of CBD, CBDA, or a combination thereof is about 0.001% to 0.3% wt/wt.

Embodiment 348

The composition of any of Embodiments 337-344, wherein the concentration of CBD, CBDA, or a combination thereof is at least 0.3% wt/wt, or more.

Embodiment 349

The composition of Embodiment 348, wherein the concentration of CBD, CBDA, or a combination thereof is at least about 30% wt/wt, or more.

Embodiment 350

The composition of any of Embodiments 337-343, wherein the concentration of CBD, CBDA, or a combination thereof is at least about 50% wt/wt, or more.

Embodiment 351

The composition of any of Embodiments 337-342, wherein the concentration of CBD, CBDA, or a combination thereof is at least about 60% wt/wt, or more.

Embodiment 352

The composition of any of Embodiments 337-339, wherein the concentration of CBD, CBDA, or a combination thereof is about 100% wt/wt.

Embodiment 353

The composition of any one of Embodiments 337-352, wherein the concentration of CBN is at most about 2% wt/wt, or less.

Embodiment 354

The composition of any one of Embodiments 337-344 and 346-351, wherein the concentration of CBN is at least about 2% wt/wt, or more.

Embodiment 355

The composition of any one of Embodiments 337-344, 346-351, and 354, wherein the concentration of CBN is at least about 20% wt/wt, or more.

Embodiment 356

The composition of any one of Embodiments 337-344, 346-351, 354, and 355, wherein the concentration of CBN is least about 30% wt/wt, or more.

Embodiment 357

The composition of any one of Embodiments 337-356, wherein the composition further comprises any of the characteristics, comprises any of the characteristics, or any combination thereof, selected from:
 i) at most about 0.14 µg/kg Arsenic, or less;
 ii) at most about 0.09 µg/kg Cadmium, or less;
 iii) at most about 0.15 µg/kg Lead, or less;
 iv) at most about 0.29 µg/kg Mercury, or less; and
 v) at most about 0.05% wt/wt phosphorous, or less.

Embodiment 358

The composition of any one of Embodiments 337-357, wherein composition further comprises at most about 0.05 mg/kg pesticides, or less, as analyzed by Official Methods of Analysis, AOAC Official Method 2007.01, Pesticide Residues in Foods by Acetonitrile Extraction and Partitioning with Magnesium Sulfate, AOAC INTERNATIONAL (modified) or CEN Standard Method EN 15662: Food of plant origin—Determination of pesticide residues using GC-MS and/or LC-MS/MS following acetonitrile extraction/partitioning and clean-up by dispersive SPE-QuEChERS method.

EXAMPLES

Example 1: HPLC Method for the Analysis of Cannabinoids

Figure 10:
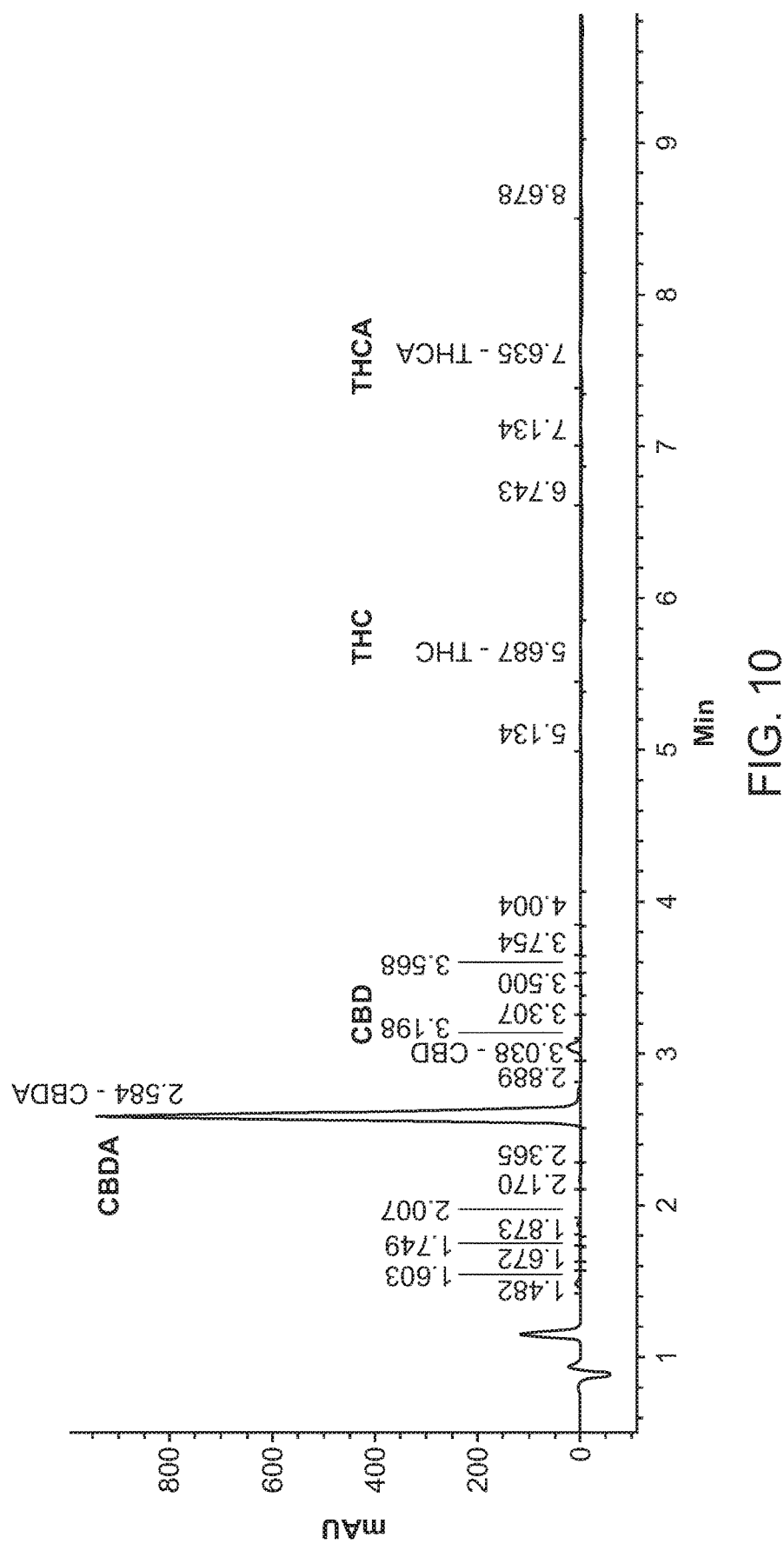
FIG. 10 depicts a HPLC chromatogram of a refined extract, detecting cannabinoids.

Process samples are diluted 1000 fold with 25:75 v/v methanol:acetonitrile, filtered and injected (5 µL) onto a Raptor ARC-18 column (cat. #9314A65), 150 mm×4.6 mm ID. Elution done at 30° C., using isocratic mixture of 25% A:75% B, where A comprises 5 mM ammonium formate, 0.1% formic acid in water; B comprises Acetonitrile, 0.1% formic acid. CBDA, CBD, THCA and THC are calibrated against their standards, purchased from Restek. A typical chromatogram shown in FIG. 10.

Example 2: Extraction of Hemp Biomassdc

Hemp whole plants (as received from a US supplier) were ground in a coffee grinder (Hamilton Beach Fresh-Grind Coffee Grinder). 563 g of biomass was added to 5500 g of precooled to −10° C. water-saturated ethyl acetate. The biomass slurry was stirred with $N_2$ bubbling and occasionally with a spoon at −7° C. for 20 min. The slurry was vacuum filtered through a 25 µm ceramic filter. The filtrate was extracted a second time with a fresh portion of 5500 g of precooled water-saturated ethyl acetate. Both extracts had yellow-green color. The fractions were pulled together and evaporated to remove all solvent at 40° C., to obtain 112 g of dark brown concentrated crude extract.

Example 3: Extraction of Hemp Biomass 24.6 gr of ground hemp was mixed with 237 gr of water-saturated ethyl acetate or with azeotropic ethanol at 16-17° C. under $N_2$ bubbling for 20 min. The solids were filtered and extracted once more with 228.4 g water-saturated ethyl acetate or with azeotropic ethanol under the same conditions. The two extracts were combined. The combined solution was passed through a series of 2 GAC columns (5 ml BV, acid washed) at a rate of 4-14 BV/h. The effluent was evaporated under vacuum to remove the solvent, to obtain 5.2 g of brown oil. Table 1 summarizes the amounts of cannabinoids analyzed in the oil in several preparations.

TABLE 1

| | cannabinoid analysis of extracted samples | | | | | | | |
|---|---|---|---|---|---|---|---|---|
| Sam- | % wt cannabinoid/biomass | | | | % wt/cannabionoids | | | |
| ple | CBDA | CBD | THC | THCA | CBDA | CBD | THC | THCA |
| EtOH ext. 1 | 13.84 | 0.69 | 0.09 | 0.48 | 91.7 | 4.7 | 0.5 | 5.3 |
| EtAc ext. 1 | 13.82 | 0.66 | 0.10 | 0.48 | 91.8 | 4.4 | 0.7 | 3.2 |
| EtAc ext. 2 | 12.58 | 0.64 | 0.08 | 0.43 | 91.6 | 4.7 | 0.6 | 3.1 |

Example 4: Refining of Crude Extract 5 g of the crude extract prepared according to example 2 were heated to 40° C. with agitation, 0.025 g of an aqueous solution comprising either citric acid or acetic acid was added (2500 ppm acid), the sample was mixed on a vortex mixer for 1 min. 0.1 g water was added and mixed for 1 min at high speed. The mixture was agitated for another 20 min, after which 5 g of ethyl acetate and 2 g of water were added. The phases were separated by centrifuge, the lighter phase comprising solvent and extract was drawn, aqueous phase with precipitated gums removed. The solution was passed through an acid-washed granulated activated carbon column, the effluent of the column was visibly much lighter. 0.1% wt/wt mixture of Fuller's earth and Perlite filter aid (1:1) was added to the solution, and the solution was filtered. The solvent was removed by evaporating at 40° C. The sample was analyzed by HPLC for cannabinoid content by the method of example 1. The refined sample contained 76.6% cannabinoids, the relative amount of the major cannabinoids was: 92.1% CBDA, 5.1% CBD, 2.3% THCA, 0.6% THC.

Example 5: Refining of Crude Extract 112 g of concentrated crude extract were mixed with 112 g water-saturate ethyl acetate, the solution was heated to 35° C. and passed through a column packed with WAC resin in a 1:1 $H^+/Na^+$ form (Purolite C115E) at a flow rate of 4 BV/h. 212 g of the ion-exchanged solution was mixed with 14 g of cool water (6-7° C.). The sample was mixed for a period of time, then kept overnight in a refrigerator. The sample was centrifuged to obtain a yellow-orange light phase, an aqueous phase and a white precipitate. The upper phase was drawn for further refining. 180 g of the light phase were passed through a column packed with acid-washed GAC at 40° C., flow of 4 BV/h. 160 g of the effluent were mixed with 1 g Fuller's earth and 1 g Perlite, chilled to 7° C. and kept in the refrigerator overnight. The sample was filtered, the clarified liquid collected. The solvent was evaporated at 40-45° C. Bright yellow/orange viscous oil was obtained. Table 2 summarizes the concentration of cannabinoids at various steps of the refining sequence. The overall purity with respect to cannabinoids increased from 78% in the crude extract, to 90% in the sample.

under conditions similar to the first round. The slurry is filtered through a fresh 25 micron filtering bag and the bag is squeezed to drain as much liquid as possible, or if using a wire mesh strainer, a plunger is applied to press the biomass to allow maximal drainage of miscella. The spent biomass is collected for further analysis of residual constituents, after removal of about 20% wt of extracted constituents. The liquid miscellas are and the solution is pumped through two SS columns filled with acid-washed GAC that has been preconditioned with ethyl acetate, at flow rate of about 4 BV/h, 15-20° C. The effluent of the GAC columns is colorless to yellow. About 40 L solvent and water are removed by evaporating at 45-50° C. under reduced pres-

TABLE 2 cannabinoid analysis of samples at various refining steps

| | Mass % of oil | | | | | | Individual cannabinoid/total cannabinoids | | | |
|---|---|---|---|---|---|---|---|---|---|---|
| Sample | CBDA | CBD | THC | THCA | Total Cannainoids | Waxes, Gums, Terpenes, Solvent | CBDA | CBD | THC | THCA |
| Feed | 70.9% | 3.9% | 0.7% | 2.4% | 77.8% | 22.2% | 91.2% | 5.0% | 0.8% | 3.0% |
| After WAC | 74.4% | 3.8% | 0.5% | 4.3% | 83.1% | 16.9% | 89.6% | 4.6% | 0.6% | 5.2% |
| After centrifuge | 74.8% | 3.9% | 0.5% | 2.5% | 81.7% | 18.3% | 91.5% | 4.8% | 0.7% | 3.1% |
| After final filtration | 80.2% | 4.3% | 0.5% | 2.2% | 87.1% | 12.9% | 92.1% | 4.9% | 0.5% | 2.5% |
| Final 50 gr | 82.2% | 4.61% | 0.53% | 2.39% | 89.7% | 10% | 91.6% | 5.1% | 0.6% | 2.7% |

Example 6: Refining of Crude Extract 52 g solvent were added to the oil of example 3, the solution was passed through a Purolite C115E column (5 ml BV, 1:1 $H^+/Na^+$ form) at 40° C., flow rate of 4 BV/h. Then, the collected solution was passed through 2 sequential GAC columns (acid washed, 5 ml BV) at 40° C., 4 BV/h. The resulting solution was stirred at 40° C. for 15 min. with 0.1% wt/wt mixture of Fuller's earth and Perlite (1:1), and filtered to provide a colorless solution. The solvent was evaporated under vacuum to provide a yellow-orange clear oil. The results of cannabinoid composition of several runs are summarized in table 3.

TABLE 3 cannabinoid analysis of refined samples

| | % wt/cannabionoids | | | |
|---|---|---|---|---|
| Sample | CBDA | CBD | THC | THCA |
| EtOH ext. 1 | 94.0 | 5.0 | 0.4 | 0.7 |
| EtAc ext. 1 | 93.0 | 5.2 | 0.5 | 1.3 |
| EtAc ext. 2 | 93.4 | 5.9 | 0.3 | 0.5 |

Example 7: Extraction of Hemp and Refining of Crude Extract 2.5 kg of hemp is ground in coffee grinders in small portions. The ground biomass is mixed in a tank with 27 L of water-saturated ethyl acetate for 20 minutes, at 15-20° C. by nitrogen bubbling and gentle agitation. The slurry is filtered through a 25 micron filtering bag or a wire mesh. The collected solids are returned to the mixing tank, and mixed with a fresh amount of 25 L water-saturated ethyl acetate sure. About 5 L of concentrated brown solution is obtained, comprising crude extract and solvent at a ratio of about 10:1 to 12:1. Small amount of water is added to re-saturate the solvent. The solution is heated to 45-50° C., and is pumped (~4 BV/h) through a SS vessel loaded with a WAC resin in a mixed form (50:50 $Na^+:H^+$), which is dehydrated with saturated ethyl acetate, and then through two SS vessels loaded with acid-washed GAC, preconditioned with water-saturated ethyl acetate. The columns are flushed with saturated ethyl acetate. The liquids are combined to provide about 10-11 L of light brown color. The solution is agitated for 10 min. at 45-50° C. with 10 g mixture of Perlite and Fuller's Earth (1:1), and finally filtered. The clear solution is evaporated at 45-50° C. under reduced pressure to provide about 500 g of refined product of yellow color. The product is packed in dark plastic bottles, optionally, under inert gas.

Example 8: Extraction and Refining of Hemp 0.5 kg of fresh hemp or hemp pellets were ground in a grinder. The ground biomass was mixed with x10 wt of water-saturated ethyl acetate for 20 at 15-20° C. The slurry was filtered, the filtrate was collected and the solids were extracted once more by mixing again with a second portion of fresh solvent under the same conditions. Both filtrates were combined. The solution was warmed to ~45° C. and passed through two sequential GAC columns at flow rate of about 4 BV/h. The solvent was removed by evaporation to about 0.07 kg crude oil. The crude oil was mixed with x10 water-saturated ethyl acetate. About 0.02 g of lysine were added per kg crude oil, the solution was stirred for about 20 min. at 60° C. Clay mixture was added as 10% wt of the crude oil wt, the mixture comprising 50% wt perlite; 40% bentonite; 10% Florisil, the slurry was stirred for another 15 min. at 60° C. Water was added to the mixture, 20% wt/wt, optionally with 1-2% NaCl or sodium acetate, mixed for about 2 min. at 60° C. and filtered. The filtrate was allowed to separate to phases, the aqueous phase was removed. The organic phase was passed through a column loaded with Purolite C115E, 1:1 Na⁺:H⁺ at 45° C., 4 BV/h. Activated carbon was added to the solution and mixed at 45° C. for 15 min. The slurry was filtered, the filtrated evaporated at 60-70° C. under vacuum, a solution of 1-2% sodium acetate was added while evaporating to ensure full removal of the solvent. The remaining hot solution was collected, allowed to separate into phases, the aqueous phases was removed and the refined oil collected.

Example 9: Characterization of Refined Extract by GCMS

Figure 11:
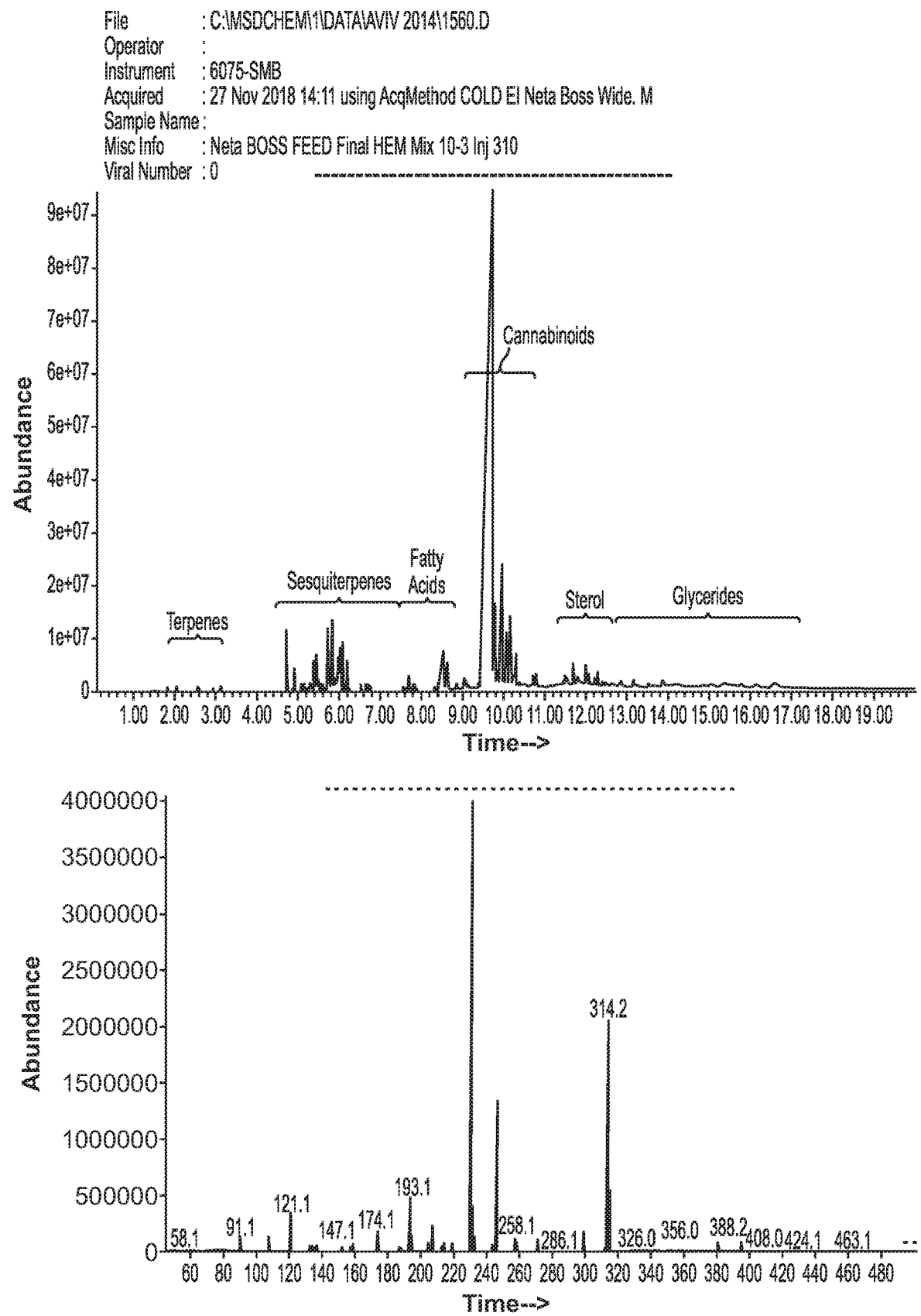
FIG. 11 depicts a chromatogram obtained by GCMS with Cold EI detector of a refined extract of hemp, which was refined according to a method of this disclosure. The lower panel depicts the MS spectrum of the major peak, identified as CBD.

A sample of refined hemp extract, prepared according to example 4, was characterized by 5977-SMB GC-MS with Cold EI detector, which enables the detection of species having molecular weight in the range 400-1000 as their molecular ions (A. Amirav et. al., Rapid Communications in Mass Spectrometry 29(21):1954-1960, 2015). This method is highly suitable for identifying unknowns against the NIST library. The chromatogram of the sample is depicted in FIG. 11. Cannabinoids are decarboxylated at the injector, thus all cannabinoids are present in their decarboxylated form. The sample was injected at a concentrated where the CBD signal was over saturated to allow detection of other species present at much lower concentration, and is therefore under estimated in concentration. The MS analysis suggested the presence of the following cannabinoids at low concentrations: cannabidiverol CBDV (0.55%), cannabinol CBL (0.1%) and several other cannabinoids that were not identified at sufficient certainty. Vitamin E (alpha tocopherol) was clearly identified. Multiple terpenes including carene, limonene, pinene, linalool and others were identified, mounting to about 0.5%; multiple sesquiterpenes and oxidized sesquiterpenes mounting to about 2-3% was also identified. The sample also showed the presence of multiple fatty acids, including stearic, oleic and linoleic acids (total about 2%). The samples also showed the presence of ethylhexyl terpthalate, attributed to contact of the sample with plastic labware in the lab (no attempt was made to avoid such contact in this preparation). No chlorophyll residues were found at the amount injected, nor was some specific pesticides found.

Example 10: Characterization of Refined Extract by HPLC

Figure 12:
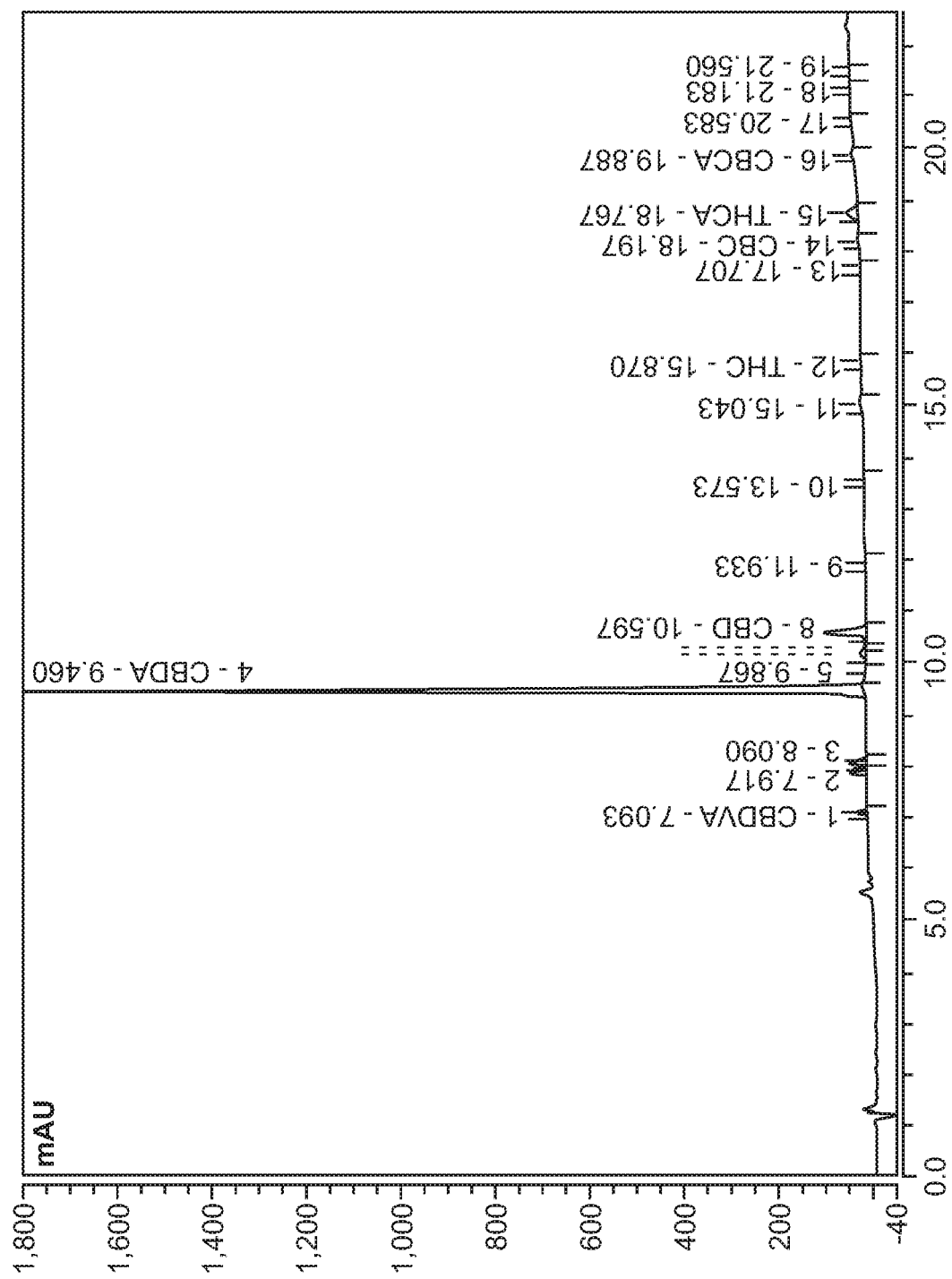
FIG. 12 depicts a HPLC chromatogram of a refined extract, detecting cannabinoids.

A sample of refined hemp extract, prepared according to example 4, was characterized by UPLC with UV detection. The method is suitable for quantification of multiple cannabinoids. The chromatogram is depicted in FIG. 12, the quantitative results are summarized in Table 4. The analysis quantified a total of 81.6% of the sample weight as cannabinoids. As expected, the cannabinoids comprised predominantly CBDA (89.1%), with small amounts of CBD, THCA, THC, CBCA, CBC, CBGA, CBG and CBDVA. While being highly refined, the sample has too high THCA and THC to comply with "THC free" limit of 0.3%, as regulations of many states require. To comply with such regulations further processing is performed, for example crystallizing the CBDA or chromatographic separation to enrich the composition with CBDA and lower THCA/THC concentration.

TABLE 4 cannabinoid analysis of refined samples

| Cannbinoid | % wt/wt | % wt/TC |
|---|---|---|
| THCA | 1.61 | 1.97 |
| THC | 0.40 | 0.49 |
| CBDA | 72.70 | 89.11 |
| CBD | 4.29 | 5.26 |
| CBGA | 0.65 | 0.80 |
| CBG | 0.18 | 0.22 |
| CBDVA | 0.44 | 0.54 |
| CBDV | ND | ND |
| THCV | ND | ND |
| CBNA | ND | ND |
| CBN | ND | ND |
| CBCA | 1.08 | 1.32 |
| CBC | 0.23 | 0.28 |
| CBL | ND | ND |
| CBCV | ND | ND |
| D8-THC | ND | ND |
| Cannbicitran | ND | ND |
| TC | 81.58 | |

Example 11: Characterization of the Extracted Crude Oil

The starting biomass, the spent biomass after extraction and the crude oil were evaluated for terpene concentration by a certified service laboratory, Eurofins Food Integrity and Innovation, the results are summarized in Table 5.

TABLE 5 determination of terpenes in the raw biomass, spent biomass at the extract.

| | mg/100 g | | |
|---|---|---|---|
| | Raw Biomass | Spent Biomass | Extract 2 Biomass |
| (−)-alpha-Bisabolol | 42 | <1.0 | 150 |
| Camphene | <1.0 | <1.0 | 4.2 |
| (1S)-(+)-3-Carene | <1.0 | <1.0 | <1.0 |
| beta-Caryophyllene | 69 | 7.7 | 950 |
| p-Cymene | <1.0 | <1.0 | <1.0 |
| Eucalypton | <1.0 | <1.0 | <1.0 |
| alpha-Humulene (alpha-Caryophyllene) | 28 | <5.0 | 320 |
| (−)-Isopulegol | <1.0 | <1.0 | <1.0 |
| (R)-(+)-Limonene | 4.6 | 1.4 | 180 |
| Linallol | 10 | <1.0 | 120 |
| beta-Myrcene | 27 | 13 | 1100 |
| (E)-b-Ocimene | 2.2 | <0.60 | 28 |
| (Z)-b-Ocimene | 0.51 | <0.30 | 8 |
| alpha-Pinene | 6.8 | 1.8 | 66 |
| beta-Pinene | 3.7 | 1 | 58 |
| alpha-Terpinene | <1.0 | <1.0 | 1.3 |
| gamma-Terpinene | <1.0 | <1.0 | 1 |
| Terpinolene | <1.0 | <1.0 | 2.3 |

It is observed that ~85% of the terpenes present in the feed biomass are effectively extracted into the extracted oil. Terpenes comprise about 3% wt/wt of the refined oil.

Example 12: Characterization of Refined Oil

Figure 13:
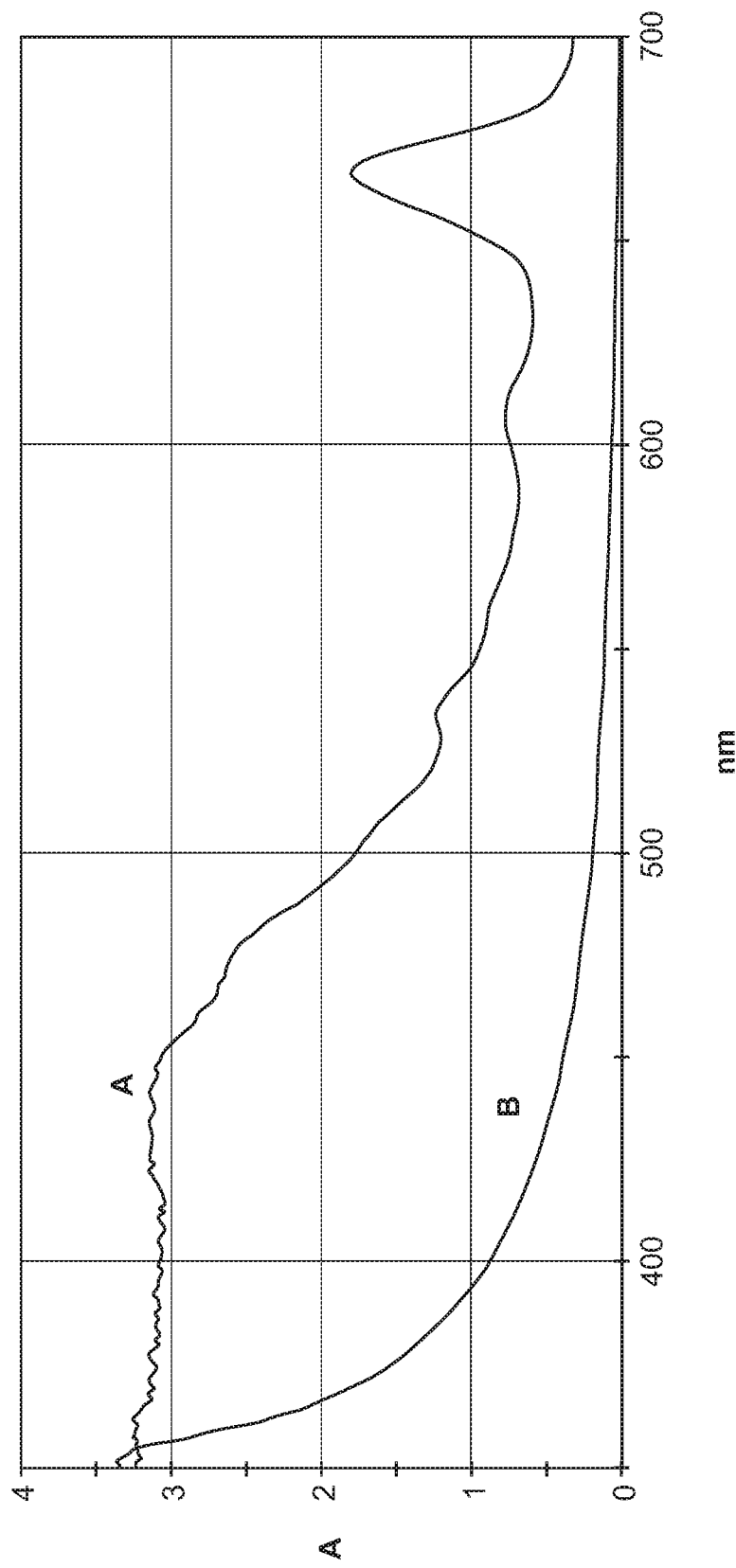
FIG. 13 depicts the UV-VIS spectrum of crude oil (A) and refined oil (B).

A qualitative measure to the purity of the refined oil is provided by its appearance—light yellow solution. FIG. 13 depicts the UV-VIS of the crude oil (A) and the refined oil (B). The composition and purity were further characterized by several methods.

Figure 14:
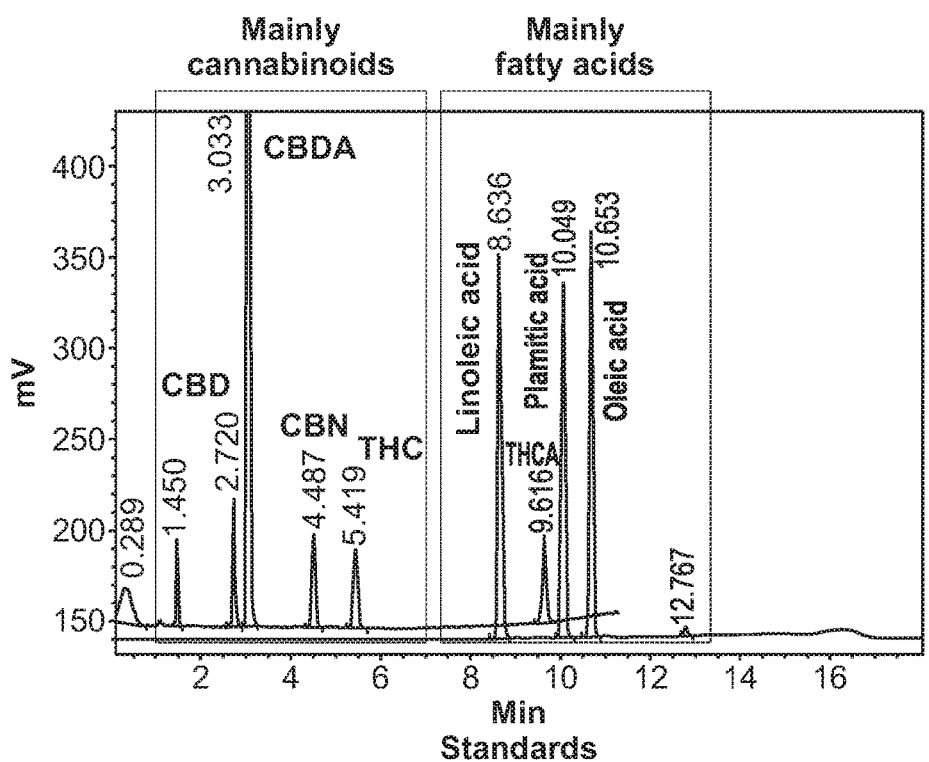
FIG. 14 depicts HPLC chromatograms of standards and refined extract, detecting cannabinoids and fatty acids.
Figure 14:
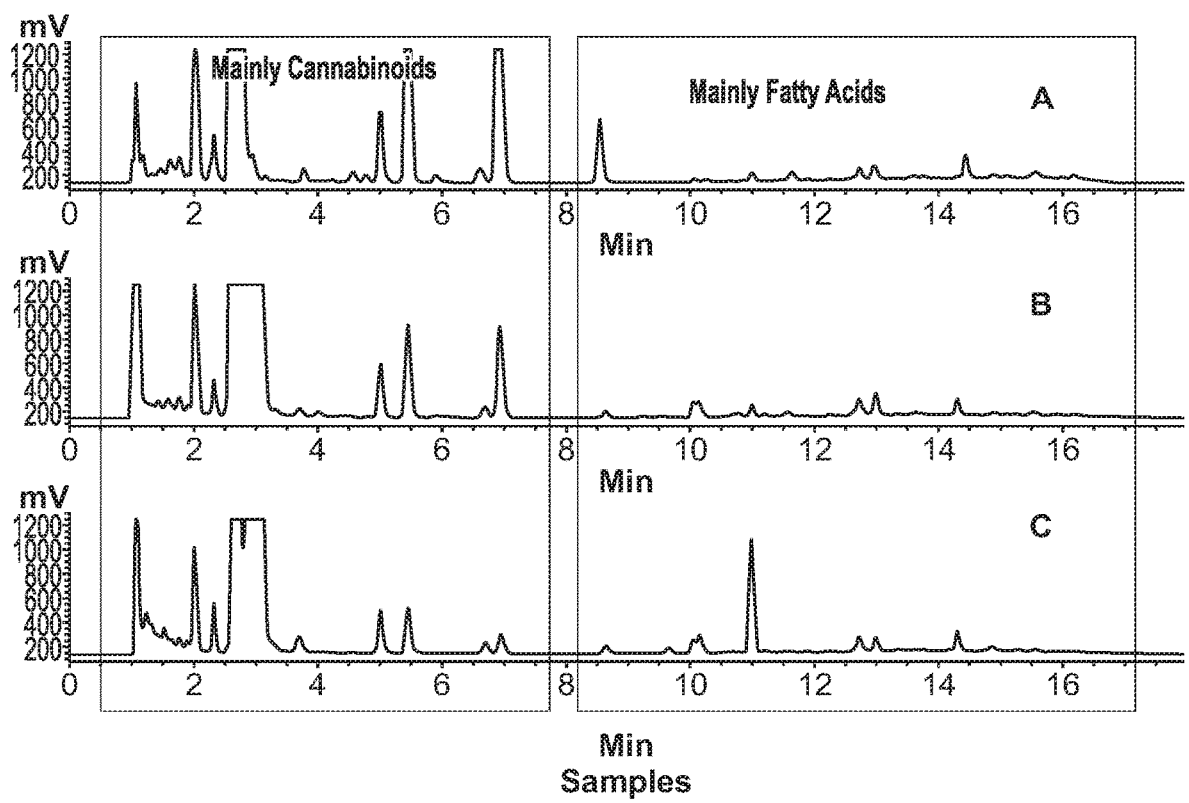

Fatty Acid Content:

FA content was evaluated by HPLC (Varian Prostar, RI detector), using a Thermo Scientific ODS Hypersil column, 150×4.6 mm, 3 μLeluent: 80:20 acetonitrile: 0.1% acetic acid/water, 0.5 ml/min, 25° C. The oil sample was diluted ×1000 with methanol, filtered through a 0.22 μm Nylon filter, 10 μL injected. FIG. 14 depicts comparative chromatograms: A is a typical oil obtained by a comparative ethanol extraction process; B is a sample of refined oil prepared according to example 8; C is a sample prepared according to example 8 but omitting the step of adding lysine in the refining sequence. The chromatograms demonstrate the efficiency of removing FA by adding lysine in the refining process. The amount of residual FA in sample B was determined to be 0.25% wt/wt linoleic acid; 0.23% wt/wt palmitic acid; 0.16% oleic acid, which is about 0.5 to 0.25 of the residue remaining without this refining step.

Figure 15:
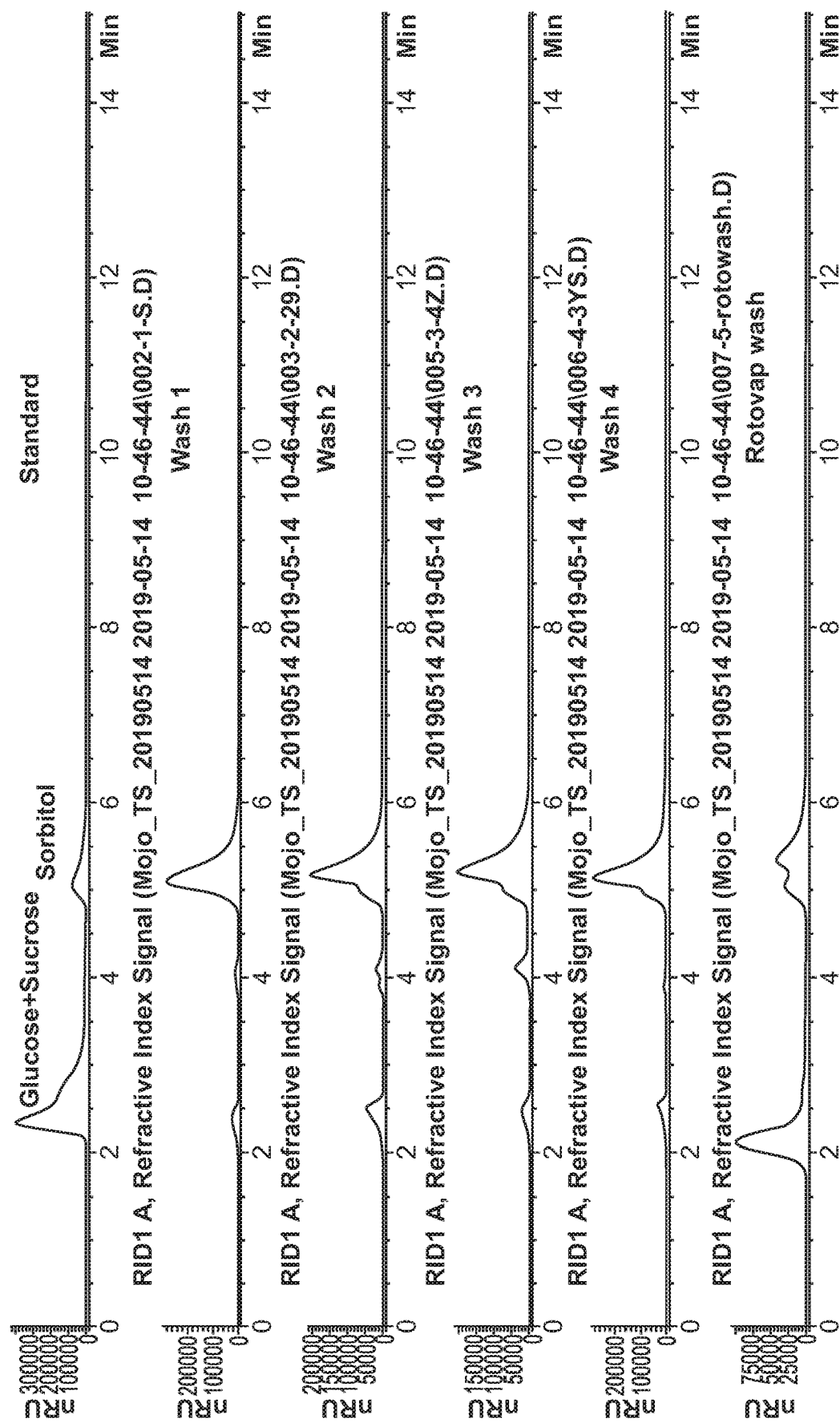
FIG. 15 depicts HPLC chromatograms of refined extract, detecting saccharides.

Sugar Removal:

the effectiveness of sugars removal from the oil was evaluated by determining the amount of sugars extracted into the separated aqueous phases in the course of the refining process. Sugars were analyzed by HPLC, using a Bio-Rad Fast Carbohydrate Analysis column—HPAP, 100× 7.8 mm, using water as eluent, 0.6 ml/min, 80° C., 10 μL injected. FIG. 15 depicts chromatograms of sugar analysis: The top chromatograph is a standards injection (glucose, sucrose, sorbitol, ~1% each); the chromatograms below are runs of aqueous solutions separated at liquid/liquid phase separation steps of example 8, the bottom chromatogram is the aqueous phase separated at the evaporation of the refined oil. It is clear that each contact with an aqueous phase removes some sugars from the oil.

Heavy Metals:

samples of feed biomass, spent biomass and refined oil were analyzed by Eurofins Food Integrity and Innovation according to Official Methods of Analysis, Method 2011.19 and 993.14, AOAC INTERNATIONAL, (Modified). Pequette, L. H., Szabo, A., Thompson, J. J., "Simultaneous Determination of Chromium, Selenium, and Molybdenum in Nutritional Products by Inductively Coupled Plasma/Mass Spectrometry: Single-Laboratory Validation," Journal of AOAC International, 94(4): 1240-1252 (2011), the results are summarized in Table 6.

TABLE 6 analysis of heavy metals in biomass and refined oil

| metal | parts per billion (ppb) | | |
|---|---|---|---|
| | Raw Biomass | Spent Biomass | Final oil |
| Arsenic | 75.3 | 48.2 | <10 |
| Cadmium | 384 | 280 | <5 |
| Lead | 105 | 72.1 | 26.1 |
| Mercury | 6.2 | <5 | <5 |

The results indicate ~30% extraction of the heavy metals from the biomass, with removal of ~97%. It is expected that this value can be further optimized to bring all heavy metals to bellow the regulatory requirements.

Microbiology:

the refined oil was characterized by the same laboratory for yeast and mold according to UMN2K-Yeast-BAM Chapter 18, Method Reference: FDA BAM Chapter 18 to show Yeast <10 cfu/g; Mold <10 cfu/g.

Pesticides:

raw biomass, spent biomass and the refined oil was characterized by the same laboratory according to Multi-Residue Analysis for hemp products of 60+ compounds: Official Methods of Analysis, AOAC Official Method 2007.01, Pesticide Residues in Foods by Acetonitrile Extraction and Partitioning with Magnesium Sulfate, AOAC INTERNATIONAL (modified). CEN Standard Method EN 15662: Food of plant origin—Determination of pesticide residues using GC-MS and/or LC-MS/MS following acetonitrile extraction/partitioning and clean-up by dispersive SPE—QuEChERS method. No residual pesticides were found in any of the samples, all were indicates as <0.05 mg/kg.

Cannabinoids:

cannabinoids were analyzed according to example 1. The results are summarized in Table 7.

TABLE 7 cannabinoids concentration in feed biomass, spent biomass and refined oil

| | % weight | | | |
|---|---|---|---|---|
| Cannabinoid | Raw Biomass | Spent Biomass | Final oil | Final oil carboxylation |
| CBCA | 0.38 | ND | 1.27 | ND |
| CBL | ND | ND | ND | 0.10 |
| CBD | 0.22 | ND | 3.89 | 65.5 |
| CBDA | 6.03 | 0.13 | 60.83 | 0.60 |
| CBDV | ND | ND | 0.70 | 0.29 |
| CBDVA | 0.05 | ND | 0.64 | 0.06 |
| CBG | ND | ND | ND | 0.90 |
| CBGA | 0.21 | 0.05 | 1.24 | ND |
| CBC | 0.04 | ND | 0.57 | 0.70 |
| CBN | ND | ND | ND | ND |
| CBNA | ND | ND | 0.58 | ND |
| Δ9-THC | 0.07 | ND | ND | 1.0 |
| Δ8-THC | ND | ND | ND | ND |
| THCA | 0.15 | ND | 0.97 | 0.10 |
| THCV | ND | ND | 0.08 | ND |
| THCVA | ND | ND | 0.17 | ND |
| Total cannabinoids | 7.16 | 0.17 | 70.94 | 69.27 |
| Total THC | 0.20 | ND | 0.85 | 1.07 |
| Total CBD | 5.51 | 0.11 | 57.24 | 66.01 |

The results indicate about 100% extraction efficiency of cannabinoids by the extraction method of example 8.

Figure 16:
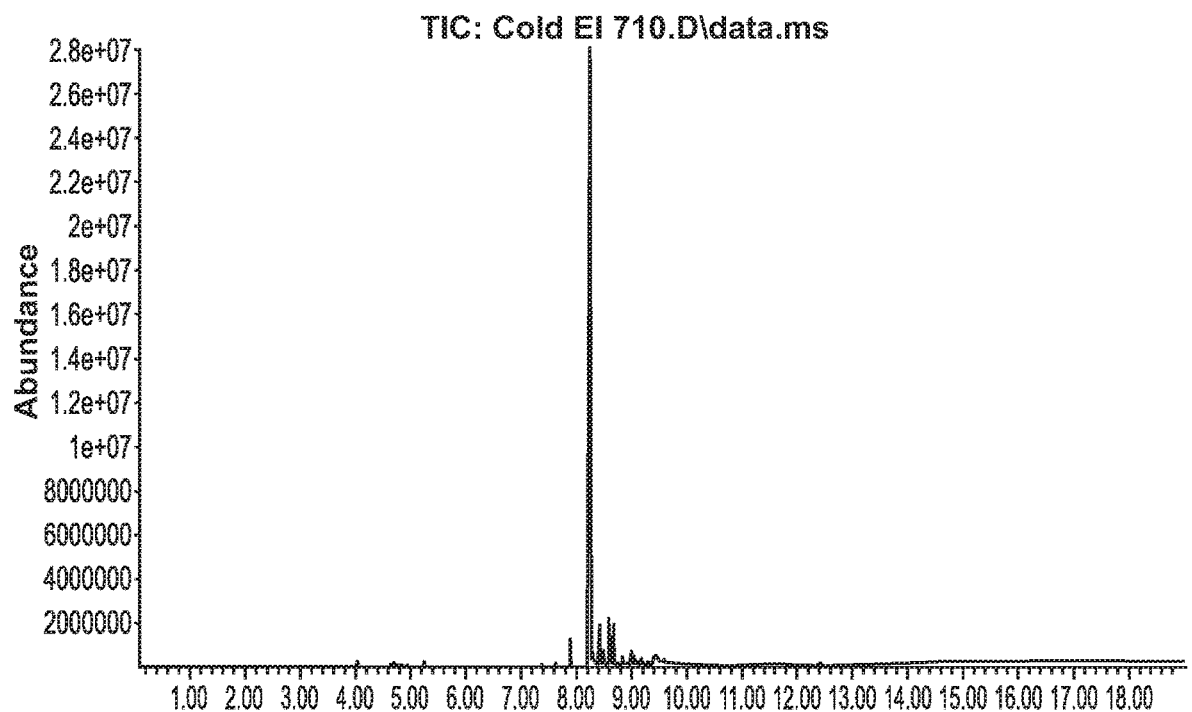
FIG. 16 depicts a chromatogram obtained by GCMS with Cold EI detector of a refined extract of hemp, which was refined according to a method of this disclosure, the major peak identified as CBD.
Figure 16:
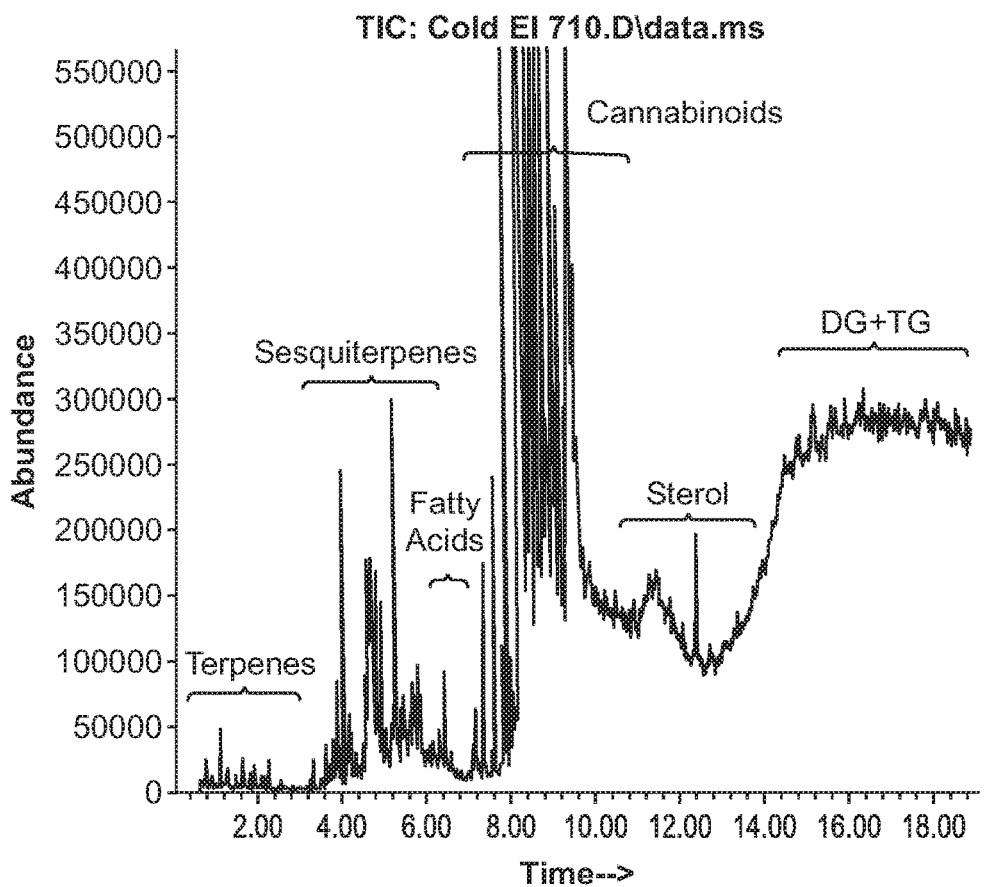

Characterization by GCMS:

the refined oil was characterized by GCMS according to example 9. The chromatogram is depicted in FIG. 16. The sample comprises predominantly CBD, with small amounts of other cannabinoids estimated as 90.8% of the sample, terpenes and sesquiterpenes (~1% and 3.7% respectively), reduced amounts of fatty acids (~0.5%), sterols (~4.1%) and small amount diglycerides and triglycerides.

Example 13: HPLC Analysis of the Crude Extract

A sample of the *cannabis* plant and samples of crude extract (i.e. without further refining) NS3 and NS4 were analyzed at CannaSoul Ltd. for cannabinoid content. The results are summarized in Table 2. It is observed that THCA is the major cannabinoid detected both in the feed plant material and in the crude extracted product. As expected, the mild conditions applied cause very little decarboxylation, hence the extract composition virtually mirrors the plant composition with respect to cannabinoids.

TABLE 8

HPLC analysis* of the feed cannabis plant and crude extracted samples

| Sample | THCA (wt/wt %) | THC (wt/wt %) | CBDA (wt/wt %) | CBGA (wt/wt %) | CBG (wt/wt %) | Total cannabinoids/extract |
|---|---|---|---|---|---|---|
| Feed plant | 9.724 | 0.338 | 0.042 | 0.332 | 0.045 | |
| NS3 | 53.047 | 1.776 | 0.228 | 1.638 | 0.236 | 57 |
| NS3 % extracte | 107 | 103 | 106 | 96 | 103 | |
| NS4 | 45.626 | 1.881 | 0.197 | 1.477 | 0.216 | 49 |
| NS4 % extracte | 99 | 117 | 98 | 93 | 101 | |

*CBD, CBDV, THCV, CBN, CBC, CBL, D8-THC were not detected in this plant.

Example 14: Co-Extraction of Terpenes from *Cannabis* Plants

Figure 17:
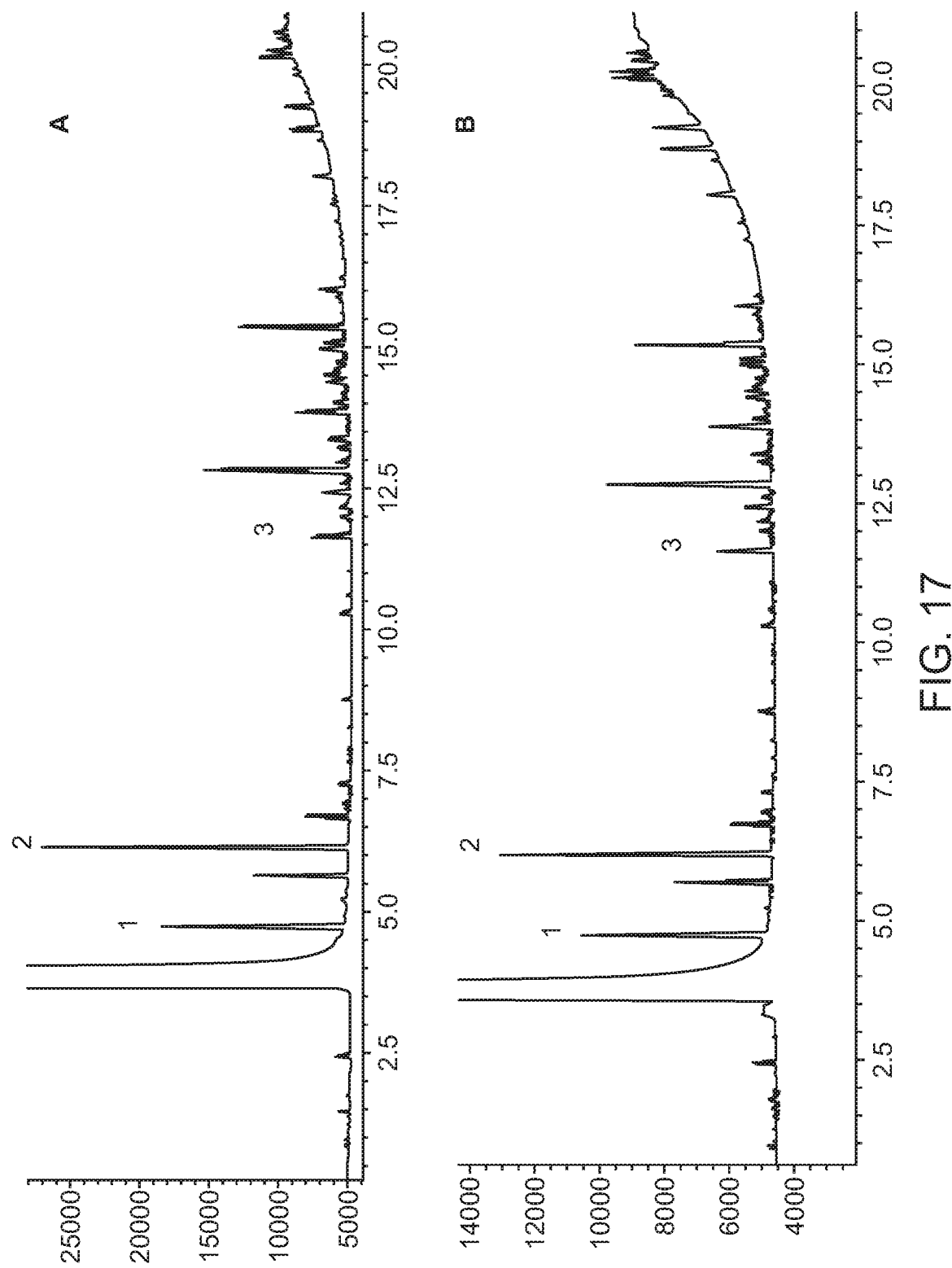
FIG. 17 depicts a typical GC FID chromatogram of *cannabis* extract. (A) depicts extraction by ethanol, and (B) depicts extraction by isopropanol (IPA). Identified species include (1) a-Pinene; (2) 3-Carene; and (3) THC.

Samples NS1 and NS2 were qualitatively characterized by GC FID chromatography. 1 µL of the extract before solvent evaporation was injected to the GC (Agilent 5890 Series II; Column: DB-WAX GC Column, 30 m, 0.25 mm, 0.50 am, 7 inch cage. Temperature gradient: 120° C.—2 min, 120° C.-240° C.—5 min (10° C./min), 250° C.—18 min). The chromatograms are shown in FIG. 17: A—NS1; B—NS2. Some of the observed peaks were identified by injecting standards: (1) a-Pinene; (2) 3-Carene; (3) THC. It should be noted that under the GC injection conditions all THC species (including THCA) are expected to be observed as THC. The chromatogram indicates the presence of a myriad of terpenes both at the lower boiling ranges (similar to the identified species pinene and carene) and at the higher boiling range. Cannabinoids are expected to elute at the middle range.

Figure 18:
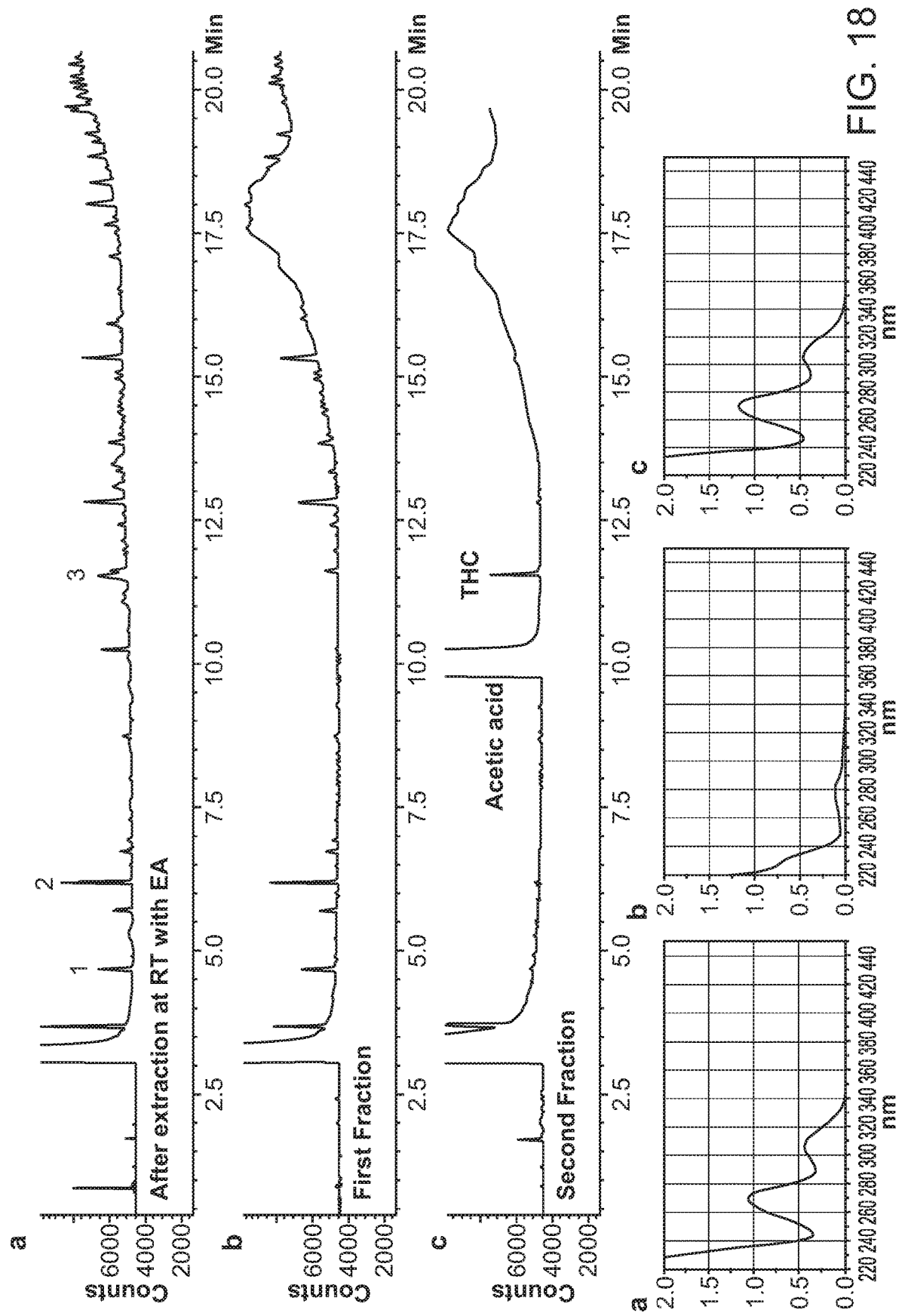
FIG. 18 depicts a GC FID chromatogram of *cannabis* extract. (a) depicts extraction by ethyl acetate, with the corresponding UV-Vis absorbance spectrum of the sample shown on the right (220-400 nm). (b) depicts the raffinate fraction eluted by chromatographic separation using a strong base anion exchange resin (SBA, acetic acid form) with the corresponding UV-Vis spectrum shown on the right. (c) depicts the extract fraction eluted by increasing acidity of the solvent, with the corresponding UV-Vis spectrum shown on the right. Identified species include (1) a-Pinene; (2) 3-Carene; and (3) THC.

Example 15: Fractionation of the Extract to Cannabinoid-Enriched Fraction and Terpenes-Enriched Fraction by Chromatography A strongly basic anion exchange resin (SBA) was washed with ethyl acetate comprising about 1% wt/wt (~0.2M) acetic acid. A sample of NS5 was loaded onto the resin. The GC chromatogram of the loaded phase shows the presence of terpenes and THC (FIG. 18, part a). The column was washed with the same eluent as the pre-wash. The fraction that was eluted showed very low absorbance at $2_{,max}$ 260 and 300 nm. The GC chromatogram shows peaks that are typical to terpenes (FIG. 18, part b). The acidity of the eluent was increased to ~0.4M by more acetic acid to the eluent. The eluted sample showed UV absorbance at $2_{,max}$ 260 and 300 nm, indicating the presence of THCA. The GC chromatogram (FIG. 18, part c) shows no terpene peak and a clear THC peak (note: THCA is decarboxylated to THC when injected to the GC, so all species are detected as THC). This test demonstrates the feasibility of fractionating cannabinoids from terpenes by chromatography.

Example 16: Fractionation of the Extract to Cannabinoid-Enriched Fraction and Terpenes-Enriched Fraction by Chromatography An SBA resin (such as Dowex Type I 1×4-400, Dowex Type I 1×8-400, Dowex Type II 2×8400) is washed with ethyl acetate comprising 0.05-0.3M acetic acid (adsorbant eluent). In step 1, a refined extract of *cannabis* is loaded as a low viscosity oil. In step 2, the column is washed with 4-6 bed volumes of adsorbent eluent and raffinate fractions are collected. The fractions are analyzed by GC to identify the presence of terpene enriched or cannabinoid enriched fractions, which are then pulled together according to their profile. It is anticipated that two types of raffinates should elute at different bed volumes. The order of elution may depend on resin type, as selection is based on molecular size and "soft interactions" with the solvated layer of the resin: (i) a terpene fraction; (ii) a decarboxylated cannabinoid fraction. In step 3, the column is washed with a desorbant eluent comprising 0.4M acetic acid to extract the carboxylated cannabinoid species as the extract.

Example 18: Pulse Test of Cannabinoids Separation

Figure 19A:
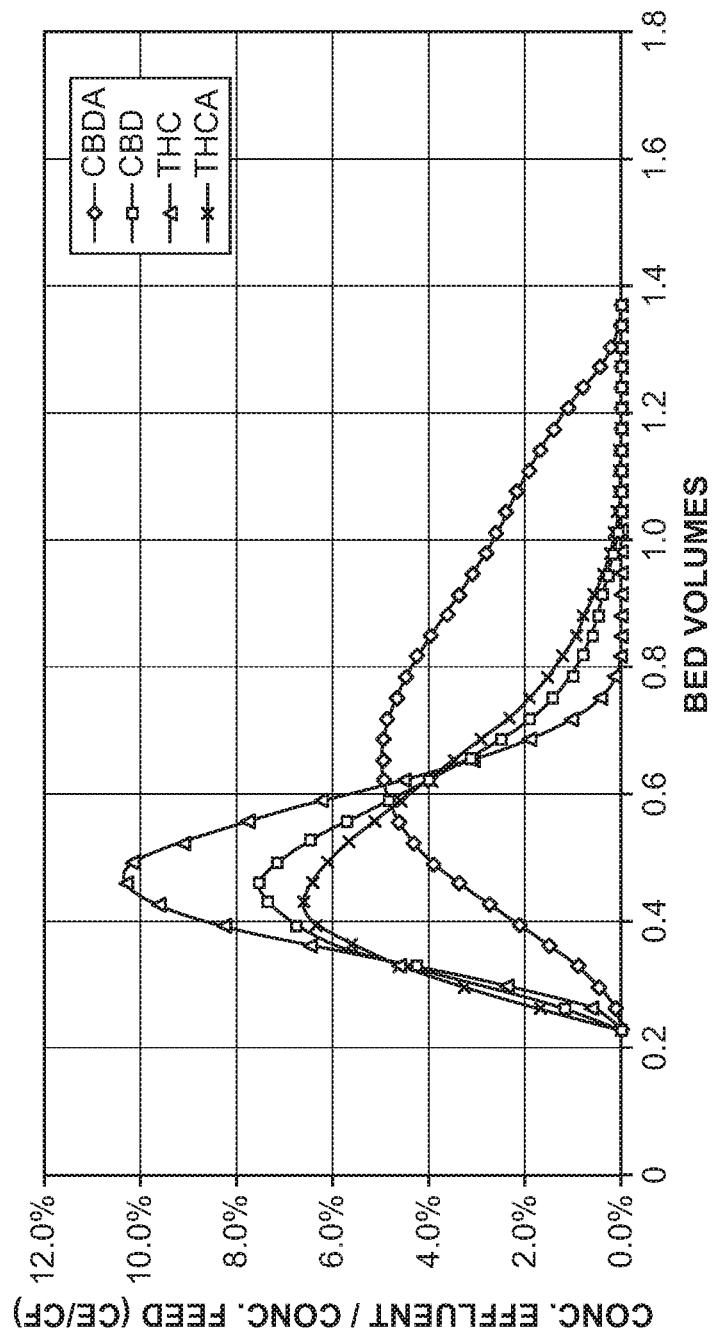
FIG. 19A-C are pulse tests demonstrating fractionation of CBDA from other cannabinoids.

The ability to fractionate CBDA from a refined extract of hemp was evaluated by a pulse test. The refined extract was evaporated to remove solvents used in the refining process to provide a light yellow oil of low viscosity. Analysis of the sample indicated 68.4% of the mass were cannabinoids. The cannabinoids were identified as: 90.6% CBDA, 4.0% CBD, 0.4% THC, 4.0% THCA, 0.9% other cannaibanoids. 7.4 ml of the oil sample were loaded onto a column of 1.6 cm diameter and 100 cm height, containing 125 g Sephadex® LH20 gel, which was pre-washed with ethyl acetate. Bed volume was 198 ml. The column was then washed with ethyl acetate at a rate of 6.6 ml/min, at 55° F. Effluent samples were collected and analyzed for cannabinoids by HPLC. A plot of effluent concentration/feed concentration of each sample against the bed volume is presented in FIG. 19A, showing that THCA and decarboxylated cannabinoids are eluted first, while CBDA is retained by the gel and elute later. The separation demonstrated is sufficient for developing a continuous SSMB method.

Example 19: Pulse Test of Cannabinoids Separation

Figure 19B:
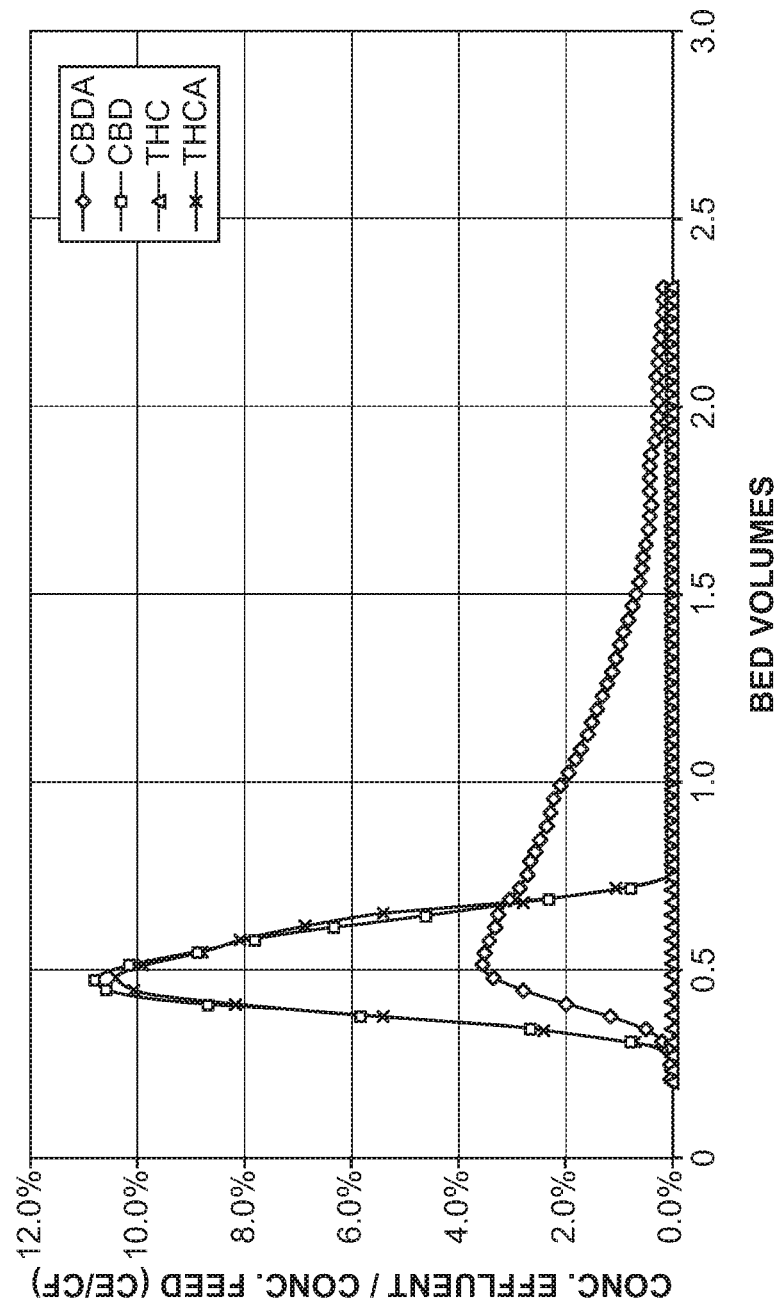

The ability to fractionate CBDA from a refined extract of hemp was evaluated by a pulse test. The refined extract was evaporated to remove solvents used in the refining process to provide a light yellow oil of low viscosity. Analysis of the sample indicated 68.4% of the mass were cannabinoids. The cannabinoids were identified as: 90.6% CBDA, 4.0% CBD, 0.4% THC, 4.0% THCA, 0.9% other cannaibanoids. 6.4 ml of the oil sample were loaded onto a column of 1.6 cm diameter and 100 cm height, containing 125 g Sephadex® LH20 gel, which was pre-washed with water-saturated ethyl acetate. Bed volume was 198 ml. The column was then washed with water-saturated ethyl acetate at a rate of 6.6 ml/min, at 68° F. Effluent samples were collected and analyzed for cannabinoids by HPLC. A plot of effluent concentration/feed concentration of each sample against the bed volume is presented in FIG. 19B, showing that THCA and decarboxylated cannabinoids are eluted first, while CBDA is retained by the gel and elute later. The separation demonstrated is sufficient for developing a continuous SSMB method.

Example 20: Pulse Test of Cannabinoids Separation

Figure 19C:
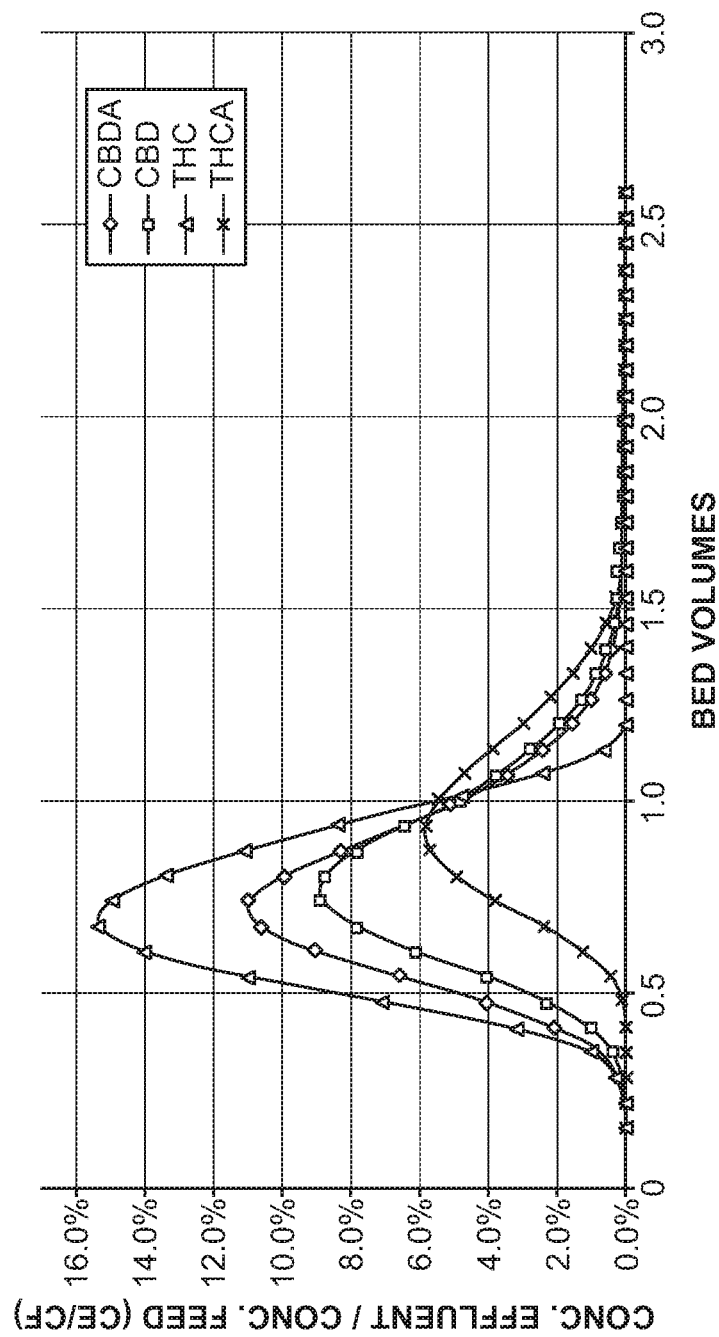

The ability to fractionate CBDA from a refined extract of hemp was evaluated by a pulse test. The refined extract was evaporated to remove solvents used in the refining process to provide a light yellow oil of low viscosity. Analysis of the sample indicated 68.4% of the mass were cannabinoids. The cannabinoids were identified as: 90.6% CBDA, 4.0% CBD, 0.4% THC, 4.0% THCA, 0.9% other cannaibanoids. 6.8 ml of the oil sample were loaded onto a column of 1.60 cm diameter and 100 cm height Purosorb™ PAD600RFM resin, which was pre-washed with water-saturated ethyl acetate. Bed volume was 198 ml. The column was then washed with water-saturated ethyl acetate at a rate of 6.6 ml/min, at 68° F. Effluent samples were collected and analyzed for cannabinoids by HPLC. A plot of effluent concentration/feed concentration of each sample against the bed volume is presented in FIG. 19C, showing that THCA and decarboxylated cannabinoids are eluted first, while CBDA is retained by the gel and elute later. The separation demonstrated is sufficient for developing a continuous SSMB method.

Example 21: Continuous Fractionating of CBDA by a SSMB Method

The fractionating is performed using a system equipped with 6 columns of dimensions 25 mm diameter 100 cm height, loaded with Sephadex® LH20 or equivalent media and equilibrated with water-saturated ethyl acetate and connecting pipes, all suitable for working with solvents. The system is positioned in a class II controlled space, and is controlled by a computerized control unit positioned outside the controlled space and connected by suitable cables. Fractionating is effected by a repeated sequence that periodically feeds refined *cannabis* extract, comprising about 91% CBDA, about 4% THCA, about 0.5% THC, about 4% CBD and about 0.5% other cannabinoids (% out of total cannabinoids); elutes the raffinate enriched THCA and decarboxylated cannabinoids, and depleted of about half the CBDA; desorbing the extract comprising not more than 0.3% THCA and THC, and at least 99.7% CBDA; and collecting the raffinate stream and the extract stream separately for the recovery of products. A Step 1 Recycle, Step 2 Desorbent to Extract, Step 3 Feed to raffinate Step 4 Desorbent to Raffinate. The yield of extracted CBDA product with respect to the feed is 90.0%.

Example 22: Continuous Fractionating of CBDA by a SSMB Method

The fractionating is performed using a system of example 5 connected to a second system, comprising 6 columns of dimensions 25 mm diameter 100 cm height, loaded with Sephadex® LH20 or equivalent media and equilibrated with water-saturated ethyl acetate and connecting pipes, all suitable for working with solvents. The overall system further comprises between SSMB 1 and SSMB 2 an evaporator, suitable for evaporating ethyl acetate. The systems are connected such that the raffinate stream of SSMB1 is evaporated, and used as feed to SSMB 2. The extract stream of SSMB 2 is directed to a second evaporator and through to the feed stream of SSMB 1, Both systems are controlled by the control unit. Fractionating is effected by a repeated sequence that periodically feeds refined *cannabis* extract, comprising about 91% CBDA, about 4% THCA, about 0.5% THC, about 4% CBD and about 0.5% other cannabinoids (% out of total cannabinoids); elutes the raffinate enriched THCA and decarboxylated cannabinoids, and depleted CBDA; transferring the raffinate to evaporating; feeding the concentrated raffinate to SSMB 2; desorbing raffinate 2; and, recycling extract 2 to a second evaporator; and combining the concentered extract 2 to the feed of SSMB1. The yield of extracted CBDA product with respect to the feed is 97.3%.

Example 23: Recovering of Acetic Acid from Products

Fractions collected in a pulse test according to example 3, wherein the solvent comprised 0.1% acetic acid was adjusted carefully in an agitated vessel with 1 molar NaOH to pH of about 5.5 and an aqueous layer having pH of about 7. The two phases were separated. The light phase was washed with water and the aqueous wash phase was separated from the organic phase and combined with the original aqueous phase. The washed organic phase was passed over the WAC and then evaporated to recover the oil product and recovered solvent. The aqueous phase was passed over a SAC ($H^+$ form), to recover dilute acetic acid for further use.

Example 24: Crystallization of CBDA from Enriched Extract Product

The extract stream comprising CBDA at concentration of at least 99.7% is concentrated by evaporation or distillation to provide a solution comprising solvent and CBDA at a ratio of about 1:1, and the water concentration is reduced to minimum (water and solvent removed as azeotrope). The composition of the solvent part of the solution is controlled to have a Hildebrand parameter of less than 20 $MPa^{1/2}$. The solution is chilled to −16° C. or less, to cause precipitation of CBDA as crystals. The crystals are filtered cold, washed with chilled water or solvent and dried under vacuum.

What is claimed is:

1. A system for isolating at least one constituent from a biomass feed, comprising:
    three or more refining units configured to receive a feed stream derived from said biomass feed and to produce, from said feed stream, a refined oil, wherein said refined oil comprises one or more cannabinoid at a total concentration of at least 60% weight by weight percentage (wt/wt %), and wherein one of said three or more refining units is refining unit comprising an ion exchange resin; and
    a sequential simulated moving bed (SSMB) chromatography unit in fluid communication with said three or more refining units, which SSMB chromatography unit is configured to receive at least a portion of said refined oil and separate said at least one constituent from said at least said portion of said refined oil, thereby isolating said at least one constituent from said biomass feed.

2. The system of claim 1, wherein said at least one constituent is selected from the group consisting of cannabidiolic acid (CBDA), cannabichromenic acid (CBCA), cannabicyclol (CBL), cannabidiol (CBD), cannabidivarin (CBDV), cannabidivarinic acid (CBDVA), cannabigerol (CBG), cannabigerolic acid (CBGA), cannabichromene (CBC), cannabinol (CBN), cannabinolic acid (CBNA), Δ9-tetrahydrocannabinol (THC), Δ8-THC, tetrahydrocannabinolic acid (THCA), tetrahydrocannabivarin (THCV), and tetrahydrocannabivarinic acid (THCVA).

3. The system of claim 1, wherein said refined oil comprises a plurality of constituents.

4. The system of claim 3, wherein said plurality of constituents comprises at least two members selected from the group consisting of a terpene, a fatty acid, a sterol, CBDA, CBCA, CBL, CBD, CBDV, CBDVA, CBG, CBGA, CBC, CBN, CBNA, Δ9-THC, Δ8-THC, THCA, THCV, and THCVA.

5. The system of claim 3, wherein each constituent of said plurality of constituents is separated in said SSMB chromatography unit.

6. The system of claim 1, wherein at least 80 (wt/wt %) of said at least one constituent comprised in said refined oil is collected from said refined oil.

7. The system of claim 6, wherein at least 95 (wt/wt %) of said at least one constituent comprised in said refined oil is collected from said refined oil.

8. The system of claim 1, wherein at least 90 (wt/wt %) of said at least one constituent originally comprised in said biomass feed is collected from said biomass feed.

9. The system of claim 1, wherein said SSMB chromatography unit is configured to recycle a solvent, or a mixture of solvents, which has been subjected to said SSMB chromatography unit, thereby producing a recycled solvent, or a mixture of recycled solvents.

10. The system of claim 1, wherein said refined oil comprises at most 2 (wt/wt %) of a fatty acid, at most 2 (wt/wt %) of a terpene, at most 2 (wt/wt %) of a sterol, or any combination thereof.

11. The system of claim 1, wherein said refined oil comprises a total cannabinoid concentration of at least 80 wt/wt %.

12. The system of claim 1, wherein said three or more refining units comprise a refining unit comprising one or more refining agents selected from a basic amino acid and a protamine.

13. The system of claim 12, wherein said one or more refining agents comprise lysine, histidine, arginine, salmine, or any combination thereof.

14. The system of claim 1, wherein said three or more refining units are in fluid communication with one another and said SSMB chromatography unit.

15. The system of claim 1, wherein said three or more refining units comprise a refining unit comprising a bleaching agent.

16. The system of claim 1, wherein said three or more refining units comprise a distillation unit.

17. The system of claim 1, wherein said feed stream is a loaded extractant extracted from said biomass feed in at least one extraction unit in fluid communication with said three or more refining units, which at least one extraction unit is configured to receive said biomass feed and extract said loaded extractant from said biomass feed using at least one solvent.

18. A method for isolating at least one constituent from a biomass feed, comprising:

a) directing a feed stream derived from said biomass feed into three or more refining units to produce a refined oil, wherein said refined oil comprises one or more cannabinoid at a total concentration of at least 60% weight by weight percentage (wt/wt %), and wherein one of said three or more refining units is a refining unit comprising an ion exchange resin; and b) directing at least a portion of said refined oil to a sequential simulated moving bed (SSMB) chromatography unit, which is in fluid communication with said three or more refining units, to separate said at least one constituent from said at least said portion of said refined oil, thereby isolating said at least one constituent from said biomass feed.

19. The method of claim 18, wherein said at least one constituent is selected from the group consisting of cannabidiolic acid (CBDA), cannabichromenic acid (CBCA), cannabicyclol (CBL), cannabidiol (CBD), cannabidivarin (CBDV), cannabidivarinic acid (CBDVA), cannabigerol (CBG), cannabigerolic acid (CBGA), cannabichromene (CBC), cannabinol (CBN), cannabinolic acid (CBNA), Δ9-tetrahydrocannabinol (THC), Δ8-THC, tetrahydrocannabinolic acid (THCA), tetrahydrocannabivarin (THCV), and tetrahydrocannabivarinic acid (THCVA).

20. The method of claim 18, wherein b) comprises separating a first constituent and a second constituent from said refined oil using said SSMB chromatography unit.

21. The method of claim 18, further comprising recycling a solvent, or a mixture of solvents, which has been subjected to said SSMB chromatography unit, thereby generating a recycled solvent, or a mixture of recycled solvents.

22. The method of claim 21, further comprising directing and subjecting said recycled solvent, or said mixture of recycled solvents, to said SSMB chromatography unit.

23. The method of claim 18, wherein said refined oil comprises a total cannabinoid concentration of at least 80 wt/wt %.

24. The method of claim 18, wherein said three or more refining units comprise a refining unit comprising one or more refining agents selected from a basic amino acid and a protamine.

25. The method of claim 24, wherein said one or more refining agents comprise lysine, histidine, arginine, salmine, or any combination thereof.

* * * * *